US009987309B2

(12) United States Patent
Dzau et al.

(10) Patent No.: US 9,987,309 B2
(45) Date of Patent: Jun. 5, 2018

(54) DIRECT REPROGRAMMING OF CELLS TO CARDIAC MYOCYTE FATE

(75) Inventors: Victor J. Dzau, Durham, NC (US); Maria Mirotsou, Durham, NC (US); Tilanthi Jayawardena, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 437 days.

(21) Appl. No.: 13/808,311

(22) PCT Filed: Jul. 8, 2011

(86) PCT No.: PCT/US2011/043438

§ 371 (c)(1), (2), (4) Date: Jul. 17, 2013

(87) PCT Pub. No.: WO2012/006577

PCT Pub. Date: Jan. 12, 2012

(65) Prior Publication Data

US 2014/0011281 A1 Jan. 9, 2014

Related U.S. Application Data

(60) Provisional application No. 61/399,178, filed on Jul. 8, 2010.

(51) Int. Cl.

| | |
|---|---|
| ***A61K 31/7105*** | (2006.01) |
| ***C12N 15/113*** | (2010.01) |
| ***C12N 5/07*** | (2010.01) |
| ***A61K 35/33*** | (2015.01) |
| ***A61L 27/38*** | (2006.01) |
| ***A61L 27/54*** | (2006.01) |
| ***A61L 29/16*** | (2006.01) |
| ***A61L 31/16*** | (2006.01) |
| ***C12N 5/077*** | (2010.01) |

(52) U.S. Cl.

CPC .......... *A61K 35/33* (2013.01); *A61L 27/3804* (2013.01); *A61L 27/3839* (2013.01); *A61L 27/54* (2013.01); *A61L 29/16* (2013.01); *A61L 31/16* (2013.01); *C12N 5/0657* (2013.01); *C12N 15/113* (2013.01); *C12N 2310/141* (2013.01); *C12N 2320/31* (2013.01); *C12N 2501/65* (2013.01); *C12N 2501/999* (2013.01); *C12N 2506/1307* (2013.01); *C12N 2510/00* (2013.01)

(58) Field of Classification Search

None

See application file for complete search history.

(56) References Cited

U.S. PATENT DOCUMENTS

2009/0215879 A1* 8/2009 Diprimio et al. ........... 514/44 R
2011/0196017 A1* 8/2011 Olson ................ A61K 31/7088 514/44 A

FOREIGN PATENT DOCUMENTS

| | | | | |
|---|---|---|---|---|
| WO | WO 2007070483 A2 * | 6/2007 | | |
| WO | WO-2009/018492 A2 | 2/2009 | | |
| WO | WO-2009/018492 A3 | 2/2009 | | |
| WO | WO-2009/092005 A2 | 7/2009 | | |
| WO | WO-2009/092005 A3 | 7/2009 | | |
| WO | WO 2010036111 A1 * | 4/2010 | ......... | C12N 15/1136 |
| WO | WO-2011/154553 A2 | 12/2011 | | |
| WO | WO-2011/154553 A3 | 12/2011 | | |

OTHER PUBLICATIONS

Ikeda et al., "MicroRNA-1 negatively regulates expression of the hypertrophy-associated calmodulin and Mef2a genes" Molecular and Cellular Biology, vol. 29, No. 8, pp. 2193-2204 (Apr. 2009).
Cordes et al., "MicroRNA regulation of cardiovascular development" Circulation Research, vol. 104, pp. 724-732 (Mar. 27, 2009).
Liu et al., "MicroRNA-133a regulates cardiomyocyte proliferation and suppresses smooth muscle gene expression in the heart" Genes and Development, vol. 22, pp. 3242-3254 (Nov. 17, 2008).
Chen et al., "The role of microRNA-1 and microRNA-133 in skeletal muscle proliferation and differentiation" Nature Genetics, vol. 38, No. 2, pp. 228-233 (Feb. 2006).
Anderson et al., "MIR-206 regulates connexin43 expression during skeletal muscle development" Nucleic Acid Research, vol. 34, No. 20, pp. 5863-5871 (Oct. 24, 2006).
Ieda, M. et al. (Aug. 6, 2010). Direct Reprogramming of Fibroblasts into Functional Cardiomyocytes by Defined Factors, *Cell* 142(3):375-386.
Jayawardena, T. M. et al. (May 25, 2012, e-published Apr. 26, 2012). "MicroRNA-Mediated in vitro and in vivo Direct Reprogramming of Cardiac Fibroblasts to Cardiomyocytes," *Circulation Research* 110(11):1465-1473.
Muraoka, N. et al. (2014, e-published Sep. 20, 2013). "Direct Reprogramming of Fibroblasts into Myocytes to Reverse Fibrosis," *Annu. Rev. Physiol.* 76:21-37.
Takeuchi, J.K. et al. (Jun. 4, 2009, e-published Apr. 26, 2009). "Directed Transdifferentiation of Mouse Mesoderm to Heart Tissue by Defined Factors," *Nature* 459(7247):708-711.
Hattori et al., "Strategies for Ensuring that Regenerative Cardiomyocytes Function Properly and in Cooperation with the Host Myocardium" Experimental and Molecular Medicine, vol. 42, No. 3, pp. 155-165 (Mar. 2010).

* cited by examiner

*Primary Examiner* — Tracy Vivlemore
(74) *Attorney, Agent, or Firm* — Mintz Levin Cohn Ferris Glovsky and Popeo P.C.

(57) ABSTRACT

A method for promoting conversion of cells into cardiomyocytic tissue is carried out by contacting fibrotic tissue (e.g., scar tissue) with a microRNA oligonucleotide or combination of microRNA oligonucleotides. The methods lead to direct reprogramming of fibroblasts to cardiomyocytes or cardiomyoblasts.

18 Claims, 9 Drawing Sheets
(4 of 9 Drawing Sheet(s) Filed in Color)

SEQUENCE LISTING

```
<160> NUMBER OF SEQ ID NOS: 31

<210> SEQ ID NO 1
<211> LENGTH: 77
<212> TYPE: DNA
<213> ORGANISM: Artificial Sequence
<220> FEATURE:
<223> OTHER INFORMATION: Mmu-miR-1 stem loop

<400> SEQUENCE: 1

gcuugggaca cauacuucuu uauaugccca uaugaaccug cuaagcuaug gaauguaaag      60

aaguauguau uucaggc                                                     77


<210> SEQ ID NO 2
<211> LENGTH: 22
<212> TYPE: DNA
<213> ORGANISM: Artificial Sequence
<220> FEATURE:
<223> OTHER INFORMATION: Mmu-miR-1 mature

<400> SEQUENCE: 2
```

uggaauguaa agaaguaugu au 22

<210> SEQ ID NO 3
<211> LENGTH: 68
<212> TYPE: DNA
<213> ORGANISM: Artificial Sequence
<220> FEATURE:
<223> OTHER INFORMATION: Mmu-miR-133a stem loop

<400> SEQUENCE: 3
gcuaaagcug guaaaaugga accaaaucgc cucuucaaug gauuuggucc ccuucaacca 60
gcuguagc 68

<210> SEQ ID NO 4
<211> LENGTH: 22
<212> TYPE: DNA
<213> ORGANISM: Artificial Sequence
<220> FEATURE:
<223> OTHER INFORMATION: Mmu-miR-133a mature

<400> SEQUENCE: 4
uuuggucccc uucaaccagc ug 22

<210> SEQ ID NO 5
<211> LENGTH: 73
<212> TYPE: DNA
<213> ORGANISM: Artificial Sequence
<220> FEATURE:
<223> OTHER INFORMATION: Mmu-miR-206 stem loop

<400> SEQUENCE: 5
ccaggccaca ugcuucuuua uauccucaua gauaucucag cacuauggaa uguaaggaag 60
ugugugguuu ugg 73

<210> SEQ ID NO 6
<211> LENGTH: 22
<212> TYPE: DNA
<213> ORGANISM: Artificial Sequence
<220> FEATURE:
<223> OTHER INFORMATION: Mmu-miR-206 mature

<400> SEQUENCE: 6
uggaauguaa ggaagugugu gg 22

<210> SEQ ID NO 7
<211> LENGTH: 83
<212> TYPE: DNA
<213> ORGANISM: Artificial Sequence
<220> FEATURE:
<223> OTHER INFORMATION: Mmu-miR-208a stem loop

<400> SEQUENCE: 7
uuccuuugac gggugagcuu uuggcccggg uuauaccuga cacucacgua uaagacgagc 60
aaaaagcuug uuggucagag gag 83

<210> SEQ ID NO 8
<211> LENGTH: 22
<212> TYPE: DNA
<213> ORGANISM: Artificial Sequence
<220> FEATURE:
<223> OTHER INFORMATION: Mmu-miR-208a mature

<400> SEQUENCE: 8
auaagacgag caaaaagcuu gu 22

<210> SEQ ID NO 9
<211> LENGTH: 71
<212> TYPE: DNA
<213> ORGANISM: Artificial Sequence
<220> FEATURE:
<223> OTHER INFORMATION: Human miR-1-1 stem loop

<400> SEQUENCE: 9
ugggaaacau acuucuuuau augcccauau ggaccugcua agcuauggaa uguaaagaag 60
uauguaucuc a 71

<210> SEQ ID NO 10
<211> LENGTH: 85
<212> TYPE: DNA
<213> ORGANISM: Artificial Sequence
<220> FEATURE:
<223> OTHER INFORMATION: Human miR-1-2 stem loop

<400> SEQUENCE: 10
accuacucag aguacauacu ucuuuaugua cccauaugaa cauacaaugc uauggaaugu 60
aaagaaguau guauuuuugg uaggc 85

<210> SEQ ID NO 11
<211> LENGTH: 22
<212> TYPE: DNA
<213> ORGANISM: Artificial Sequence
<220> FEATURE:
<223> OTHER INFORMATION: Human miR-1-1 and Human miR-1-2 mature

<400> SEQUENCE: 11
uggaauguaa agaaguaugu au 22

<210> SEQ ID NO 12
<211> LENGTH: 88
<212> TYPE: DNA
<213> ORGANISM: Artificial Sequence
<220> FEATURE:
<223> OTHER INFORMATION: Human miR-133a-1 stem loop

<400> SEQUENCE: 12
acaaugcuuu gcuagagcug guaaaaugga accaaaucgc cucuucaaug gauuuggucc 60
ccuucaacca gcuguagcua ugcauuga 88

<210> SEQ ID NO 13
<211> LENGTH: 102
<212> TYPE: DNA
<213> ORGANISM: Artificial Sequence
<220> FEATURE:
<223> OTHER INFORMATION: miR-133a-2 stem loop

<400> SEQUENCE: 13
gggagccaaa ugcuuugcua gagcugguaa aauggaacca aaucgacugu ccaauggauu 60
ugguccccuu caaccagcug uagcugugca uugauggcgc cg 102

<210> SEQ ID NO 14
<211> LENGTH: 22
<212> TYPE: DNA
<213> ORGANISM: Artificial Sequence
<220> FEATURE:
<223> OTHER INFORMATION: Human miR-133a-1 and miR-133a-2 mature

<400> SEQUENCE: 14
uuuggucccc uucaaccagc ug 22

<210> SEQ ID NO 15
<211> LENGTH: 86
<212> TYPE: DNA
<213> ORGANISM: Artificial Sequence
<220> FEATURE:
<223> OTHER INFORMATION: Human miR-206

<400> SEQUENCE: 15
ugcuucccga ggccacaugc uucuuuauau ccccauaugg auuacuuugc uauggaaugu 60
aaggaagugu gugguuucgg caagug 86

<210> SEQ ID NO 16
<211> LENGTH: 22
<212> TYPE: DNA
<213> ORGANISM: Artificial Sequence
<220> FEATURE:
<223> OTHER INFORMATION: miR-206 mature

<400> SEQUENCE: 16
uggaauguaa ggaagugugu gg 22

<210> SEQ ID NO 17
<211> LENGTH: 71
<212> TYPE: DNA
<213> ORGANISM: Artificial Sequence
<220> FEATURE:
<223> OTHER INFORMATION: Human miR-208a stem loop

<400> SEQUENCE: 17
ugacgggcga gcuuuuggcc cggguuauac cugaugcuca cguauaagac gagcaaaaag 60
cuuguugguc a 71

<210> SEQ ID NO 18
<211> LENGTH: 22
<212> TYPE: DNA
<213> ORGANISM: Artificial Sequence
<220> FEATURE:
<223> OTHER INFORMATION: miR-208 mature

<400> SEQUENCE: 18
auaagacgag caaaaagcuu gu 22

<210> SEQ ID NO 19
<211> LENGTH: 99
<212> TYPE: DNA
<213> ORGANISM: Artificial Sequence
<220> FEATURE:
<223> OTHER INFORMATION: Human miR-138-1 stem loop

<400> SEQUENCE: 19
cccuggcaug gugugguggg gcagcuggug uugugaauca ggccguugcc aaucagagaa 60
cggcuacuuc acaacaccag ggccacacca cacuacagg 99

<210> SEQ ID NO 20
<211> LENGTH: 84
<212> TYPE: DNA
<213> ORGANISM: Artificial Sequence
<220> FEATURE:
<223> OTHER INFORMATION: Human miR-138-2 stem loop

<400> SEQUENCE: 20
cguugcugca gcugguguug ugaaucaggc cgacgagcag cgcauccucu uacccggcua 60
uuucacgaca ccaggguugc auca 84

<210> SEQ ID NO 21
<211> LENGTH: 23
<212> TYPE: DNA
<213> ORGANISM: Artificial Sequence
<220> FEATURE:
<223> OTHER INFORMATION: Human miR-138-1 and miR-138-2 mature

<400> SEQUENCE: 21
agcugguguu gugaaucagg ccg 23

<210> SEQ ID NO 22
<211> LENGTH: 3727
<212> TYPE: DNA
<213> ORGANISM: Homo sapiens

<400> SEQUENCE: 22
tgtacatgga gatcttgctg ggaaaatccg cttgctcccc tcacgtcgtc cagcccagga 60
gaaccaccgc cgtcaccccg gagcttcctc ggccaccgcg cagagccctc cgagagcccg 120
agccgcggtc ttcgagctcc aaggctcatt cagggcccca gatccttgcc ccgaaaggag 180
aggatctgag aaaatggatg cactgagacc tctctgaaaa ccctccgaga gagcgcgaga 240
ggagcgagga cacgttactc gcagctaaaa tcacatttaa ggaccaaaac aacaacaacc 300
aaaaatttca ttaaaacaat aagcgcccaa gaacccagat cggctggtg gggggagggg 360 aagaggcggg aaggggaggg tcgcacggag gtagctttgc agtgagcagt cgaccccgcc 420
gccccccggc acagctggac cggctcctcc agccgcggct cagactcgcc cctggattcc 480
gggttagctt cggtgccagg accgcggccc gggcttggat tcccgagact ccgcgtacca 540
gcctcgcggg agccccggca cctttgtatg agcacgagag gattctgcct ccgcgcagca 600
gcccgggaag caggagccga agcgcgggcc gtggagcaag gcgggaaccg gaggcggcgg 660
cggcggcggc caggggcgca cggtgccagg accagctcgc cgcgccccat ggggagccgg 720
cggccgcagc gctgctgagg cgggcccggc tggccaggcg gggggacggg gcccgggctg 780
cagcagcccc ctctgcggct gccgggcggg cccgggcgcc cgggggctgg ggggtggggg 840
gtgggggagg acgccgagcg ctgaggcagg ggcccgggcc gagggcgcgg cggggctgcg 900
cgcacgctgg ggcgcgtgga ggggcgcgga gggcgaaatg agtctggtag gtggttttcc 960
ccaccacccg gtggtgcacc acgagggcta cccgtttgcc gccgccgccg ccgcagctgc 1020
cgccgccgcc gccagccgct gcagccatga ggagaacccc tacttccatg gctggctcat 1080
cggccacccc gagatgtcgc cccccgacta cagcatggcc ctgtcctaca gccccgagta 1140
tgccagcggc gccgccggcc tggaccactc ccattacggg ggggtgccgc cgggcgccgg 1200
gcccccgggc ctgggggggc cgcgcccggt gaagcgccga ggcaccgcca accgcaagga 1260
gcggcgcagg actcagagca tcaacagcgc cttcgccgaa ctgcgcgagt gcatccccaa 1320
cgtacccgcc gacaccaaac tctccaaaat caagaccctg cgcctggcca ccagctacat 1380
cgcctacctc atggacctgc tggccaagga cgaccagaat ggcgaggcgg aggccttcaa 1440
ggcagagatc aagaagaccg acgtgaaaga ggagaagagg aagaaggagc tggtcagtac 1500 caggggggcgg caggcggtgg ggctgagggg gtcagggaac tggtgctccc ggcctctttc 1560
caattgggct gagaaatggc atctcgtgtt ctttggctgc gtcccgcttc aaggttgttt 1620
gcaccaggtt gtgtaaggat ggcttccggc ataagcagag agttgagggg agggtgtcag 1680

```
caggaggagg agaaggttag ggatgctttg cgctggtgat cttacctccg ggttatcgct   1740
gctcccctag tacttaggac ggaccttgaa aactctgggt cgcgatcgat cgcgatcgca   1800
ctggtctgga tgcctcaccc cgtctctgtt agacccttct tttggcctcc aatccaatct   1860
tgctttcaga tgtttccaga ataagtctcg aagaagccct tgattccaat tatttcacta   1920
ttgatcgcac cccctacccc actcccagaa ggaggctgcc agagactgag ccctgagttt   1980
tgtggttgtt ctcatactat gcccggaaaa cgtaatggta aacataaaat aagtactttt   2040
gacttcaaaa tacagctcca atttttcctt ggctatgacg ttaaaatgta atttcccaga   2100
tgagtatatt ccattggcat ttctaatttt atttgaataa gcctgtacat tttaaggggg   2160
aaaaggcatt actatggtca ttgttattaa aaataacacg aaagtaaatt gagccgctta   2220
aaatttctc agattcctac caagtgccca cagggcagtg gtgcaggata gagctatgtc    2280
cacgaagggc ccggaaaata attgcatttg tcgaattttt cttctttggc ccctgcagcc   2340
ctttggtggc tgcataatcg agtgacctcc cgaataacca gagatttcag aagccttgga   2400
ggagaggcac tgctgagctg gaggccgaga gcctctggcc gagaggccca ggccgaaaca   2460
gaggctcctt cgccctattt ttcctagatg tggatctagg attgctaatg aaaacagaga   2520
aaccagactt agcgccgact ccagctcccg cccctacatc tggagtaaga gaaaaggccc   2580
cccgctcctc cataaacgac tcgaaaacgg gcggttgttt ataaacttgt ggatccggtt   2640
gttgagcgct gcagcgccga ggcctccccg ccggctaggg tagcgctaac cttggtagct   2700
tctctgcagg ggctgggact cccccatcgt atcctttcct ctctggttca ctgtctcctc   2760
cggcgcagga agctccgggt tggtgtggaa ccaggtatcc tctctgaatt tctctttcca   2820
cttttctcgc cctcgccttt cctctgtcca gaacgaaatc ttgaaaagca cagtgagcag   2880
caacgacaag aaaaccaaag gccggacggg ctggccgcag cacgtctggg ccctggagct   2940
caagcagtga ggaggaggag aaggaggagg aggagagcgc gagtgagcag gggccaaggc   3000
gccagatgca gacccaggac tccggaaaag ccgtccgcgc tccgctctga ggactccttg   3060
catttggaat catccggttt atttatgtgc aatttccttc ccctctcttt gacccccttt   3120
gaggcatctg ctccccgtct cccccctccaa aaaaaaagtg gatatttgaa gaaaagcatt  3180
ccatatttta atacgaagag gacactcccg tgtggtaagg gatcccgtcg tctcatagat   3240
tctgtgtgcg tgaatgttcc ctcttggctg tgtagacacc agcgttgccc cccgccaacc   3300
tactcaaccc cttccagata aagacagtgg gcactagtgc gtttgtgaag tgtatcttta   3360
atacttggcc tttggatata aatattcctg ggtattataa agttttattt caaagcagaa   3420
aacagggccg ctaacatttc cgttggggtc ggtatctagt gctatccatt catctgtggt   3480
cgttccctct ttgaagatgt ttccaacagc cacttgtttt gtgcacttcc gtcctctaaa   3540
actaaatgga atttaattaa tattgaaggt gtaaacgttg taagtattca ataaaccact   3600
gtgttttttt tttacaaaaa ccttaatctt ttaatggctg atacctcaaa agagttttga   3660
aaacaaagct gttatacttg ttttcgtaat atttaaaata ttcagaagta aactaaatta   3720
tcatgat                                                             3727
```

<210> SEQ ID NO 23
<211> LENGTH: 11607
<212> TYPE: DNA
<213> ORGANISM: Homo sapiens

<400> SEQUENCE: 23

```
agaaggaaga ggaagaggag gagagggagg ccagagccag aacagcccgg cagcccgagc     60
```

```
ttcgggggag aacggcctga gccccgagca agttgcctcg ggagccctaa tcctctcccg    120
ctggctcgcc gagcggtcag tggcgctcag cggcggcgag gctgaaatat gataatcaga    180
acagctgcgc cgcgcgccct gcagccaatg ggcgcggcgc tcgcctgacg tccccgcgcg    240
ctgcgtcaga ccaatggcga tggagctgag ttggagcaga gaagtttgag taagagataa    300
ggaagagagg tgcccgagcc gcgccgagtc tgccgccgcc gcagcgcctc cgctccgcca    360
actccgccgg cttaaattgg actcctagat ccgcgagggc gcggcgcagc cgagcagcgg    420
ctctttcagc attggcaacc ccaggggcca atatttccca cttagccaca gctccagcat    480
cctctctgtg ggctgttcac caactgtaca accaccattt cactgtggac attactccct    540
cttacagata tgggagacat gggagatcca ccaaaaagta agaggctatt ttaccttgtg    600
gggctcggtg tgctgttctt gtgcggggtt ctctctcagg cacaggctga ggtgccaagg    660
gctctttgga gttggagtca ttgcctggag aaagagaaaa ggtggctttt tcttgttgcc    720
gccacgcctg catgcttact gtcggttctt atcttcggga aactgattgt accttgtgtg    780
tgaattcgcc tgtgtgccct ccaaagctct agctttctgg tgctaagcgg tgatttcctc    840
ctggggaatc ctgagctctc cgagaaggtt attatgttgc aaaggtctgc ctgcacagtc    900
aatgcccaga gatgtgaatt agcattagac ttgcaaaaga gaacgagtga caactgtatt    960
tatgcctgct cttgctaaca atatccagtc ctgtgtgcta tttaagagcg cgcttcacgg   1020
aaaatataga catccctgcg ttcacttaac gcttctagtc aaaacctttt ctttgacttg   1080
acttatccat aatctttccc aatgattata gcaaagagga aggggggggg gagaaataca   1140
aaatgagcgg gtttgattgc gtgctaggcg tacaaatgta gactattcca atctgcattt   1200
tacatatatt ccacctcctt ttaaaaatga gtcaaggttt tgatggcaca tttcaattac   1260
catcccaaag tgcaatgctc taaaaaaaaa aaaaaagaaa gaaagaaaga aagaaaaaaa   1320
cctcccagag tacgccctat aagagaacga cactaaaagt gtgtttatct ctgtaggaag   1380
taaacggtta gtcaatcatg tatttatttt catttcagaa aaacgtctga tttccctatg   1440
tgttggttgc ggcaatcaga ttcacgatca gtatattctg agggtttctc cggatttgga   1500
atggcatgcg gcatgtttga aatgtgcgga gtgtaatcag tatttggacg agagctgtac   1560
atgctttgtt agggatggga aaacctactg taaaagagat tatatcaggt atggcattta   1620
cacttctttc ttaattttgt gggatttccc tgaatctccc cactctttat gtattatttg   1680
gtgtggcttt gtctttttgt gaagtttgcc tcagtgtagt catacaagcc aaagttaccc   1740
tgtacatgtg ttaaaaaaat caagctatgc tgttcatttc attctttagt tgagaaaaac   1800
aaaaaccctt aacagtggta ttcataattc cggggtattg aggcttgttt aattactctt   1860
ggagtttatg atgcacaaat tattttcctc tttcaccctc cccttacaa aacaaaattt   1920
taaaaagatg gagaagtttg gatttttagc tttaaaatag ggttgatttt tgttgtatag   1980
tgcagtgttc tgtttgtttt agtccttttt aaaattagta gcttacaaat tctttggtgg   2040
catcaatgca ataggtgaaa taaaagtttg accgaagcat gtttagagat gtactttgaa   2100
agagcgagta caggtattgc tccttttatt tttggggtaa gacctccttc tgagaaaaat   2160
ttaaaaccaa cctaaatatt ccttggaaaa aacaccggaa acttaatctt tttaaatatt   2220
aaccctttgg tgacatctaa ctgtctcttc tttcttatct tatctgagct gatgaattag   2280
agcagatcaa attgcccatc atctgtctac gaacaattgg tatatttaga taattgaaca   2340
gcttcctttc tcacattaaa atctggtaac tgataaaatg agcgaattgt ccaaattgac   2400
```

-continued

```
aagactgaaa caacatagga actttctgag tttggttttg ttgttttgga gagtttttgt   2460
ttttttttc ctccaattta ttctgcaaca cgttttgcta atctcaagtt tcctctgact   2520
tgtgtgtatg tatcagaaac tttgttttct gccttagaaa gccagtagtc tctaaagaaa   2580
attgtattca ttttattaac aaacagaaga gacatcagca tcattattat gttaaataat   2640
agcaaaatat cactttttaa atgtccggtg gctattaaca agtaattaat tagcttttgt   2700
taggcaaatg gtttctggag cttgagaact tttattaaag tttagttaag atttaatata   2760
cagtcacagt ttgctcctgc tcacttagta tccagcattt ttttcttctt ttttaaaaat   2820
catgacacag agagtataat cttggtagat aaaattaacc tggttgggg aggttaatac   2880
ttcggagagg gagtgaaagg aagtaaggga agtcggggta caggaagggg gagggatttt   2940
ctaaattgtt tggtcaccgc caaagtcaag tcttcaccct atgaaatgga agatctcaca   3000
ttgagtaggc ggagggagga aaaacttttg agtccacctt ctaacctctg acaaatgagc   3060
gttttcattg tttactagat tggtgtgtaa acgcaagatt ctagagaagg agagcccact   3120
tcaggagtat ctttactgct atggaaatag tattttgctc aattgcacac aggcttgcat   3180
gtgcctaatt ctggatacac acatgtgtag aaggaactaa tcatttttac cttctcttca   3240
ctctctctca actctgtgtg tgtgtgtgtg tgtgtgtgtg tgtgtgtgtg taatcttgta   3300
gttgtaaaag cagaacagac tggacagtta gatttccaca tctctccttg gagaagcagg   3360
atgcctcctc ctgttatgtg gatcttttcc tctctcttcc attctttctg ttcgtaggaa   3420
tgccccagct tctgttattc ctgaaagatg gagaaggggc cagggaagtg cagcctagat   3480
ggaacctata aagattgtcc cttggtaagg aaaggccagg agtgagaaag accttagaag   3540
cgggtctttg catttttttc attctggtca tggttttcaa gaaaattgaa atgaggtaga   3600
tgattcagca acttgaaaaa gattgaggga acagacgcag attttttaa aaaaataata   3660
atacaaggaa gaatggagag gaaattttct gttaacattg ctgcctgaag aaaatcttta   3720
gttggagaaa gactggaaag tacttgtgca aaaggagatg tggaaactct cagaggtttc   3780
attttgttat tctgcttgtt tatttgtgag tgtttgcaaa ccgagtgggg tgacaatccc   3840
cttctcctac ctccttttt cttggaagga ggactttttg ttgcagtttt agacatttct   3900
agcagcagaa attgtgggat agggaagtga aagtgttggt gtcggtggcc accagagtct   3960
ttctggattc cttcctgcca agatctgcaa gatcaacact gggattgatt gctagagcag   4020
cagcccgagt ttggaaccca tcaatacatt ttctgtggta caagctaggt gttttgagct   4080
aagagttacc aactaagaca gaggttcatc ggaaaggaaa cgggagtaaa agaaagggag   4140
gagggaggga ggggaaaaga gagatggggg aaggaagaga gacagggaag gagagagcag   4200
ggtttcattt ctgtccttct gtttccaact tctgtttgga aatgctgttt acttggggcg   4260
tcttgcccgg gatcttgggc cagggaagtg ccggcctgaa gtgacccccct cttcctgtac   4320
ttctctcccc gctctgggcc gcctccgctc ccccctcccc cgcacaggtt gtacgggatc   4380
aaatgcgcca agtgcagcat cggcttcagc aagaacgact tcgtgatgcg tgcccgctcc   4440
aaggtgtatc acatcgagtg tttccgctgt gtggcctgca gccgccagct catccctggg   4500
gacgaatttg cgcttcggga ggacggtctc ttctgccgag cagaccacga tgtggtggag   4560
agggccagtc taggcgctgg cgacccgctc agtcccctgc atccagcgcg gccactgcaa   4620
atggcaggta ctcctctgcc cggctcgggt aggcaggcgc caggttaagc cagcctgtgt   4680
gccagcggcc acaacaacta tggtagctac aggggtggtc gtagtgtttg cctgcagtta   4740
aatgaagtgt tctgtatgca atttgcgctg tgctctgctc ctttgcagca aggttcaatg   4800
```

```
cactcactgt ctcccttgat tccccgagca cacctacacc gtctgtgtgt ctctatatgg   4860
ttacacataa atgtacacca cttgtgtaca cgtgtataca cacgcccaaa cattacttcc   4920
agttcgctct ggcctccaaa ccttggcttg ctgaaaacgg gcttcagctc ccagccaggt   4980
attctcctgc tgcctaatta aaggggcgga gccccgggtc cctggagctt catcctttaa   5040
cccaatgaag gaagcttagg tggcctgaag tcatttagtc tcccaaatcc tttttccttg   5100
tgagttgctt cacactcgaa attttttttt taattttttt atctttctgt gagagaacag   5160
gactgaaaag atacagtttt aaaaactgca ggccattgca cagagttgta atataaaact   5220
gtcaacaagc ttatctgcag taattgcctt ttaaagggag cctgcttctt taaatcattc   5280
attctatatg atttggtgag aatttcatct tcaggcccat ggttgtagct ctaaattgac   5340
cccataggtg ttggcctgac cctagggggt tgtagaaggt gcaggatttg tatcatgtag   5400
ataagaggac tcattcccaa ggaagaggag tggaaacaca gcaaggttgg ccgggaccaa   5460
agcagtgggt tagaaggtgg acagtgtttc caaacctgac ttcctgccat gaatagatct   5520
acccctttgc agttttaaag tatcaattcc cactaaacac tgaaggtgag gaaactatag   5580
ccctccctta cccttctgcc ttctggcagc tctaagaatt ctgttcaggg ggatttgtga   5640
ctagtttgca ccggggcacg gctggggtgg tgctcctgtt cagtggagcc tgcactctgc   5700
ttgtggggaa gcacagagga agctaaaata ccgagaggga ggcgggggac atctcccagc   5760
caccgtttat ctagagccta ggcagctcaa cagagtttcc gttttccact gcttgggatc   5820
agcccatctc aggaacatcc atgtattacc ttagatttaa tactaagagc agggattgga   5880
gatatggcag aaatagcgaa tctcttcagc cccttcacat gactgtcctc tcggactgaa   5940
gttcaaggcg ttctggcaga gttctcgacc ttccccttgc agaagtccct gctggtgtag   6000
tatttatggc tgtcactgaa gtgctctgcg ttcctttccc tggtaccctc tgtggccttg   6060
gcccaagaga aaattctgat cctggagagg gtggtaatca atgtaactgg ggcccagtct   6120
gggcacaagg aaaggtgaga atggaggaga aacagtgctg aaaaatgcca cccctgctgt   6180
gaacaggggg acagactttg agacctgctt cccttggcta acactttgtt gacacgagga   6240
ggggcgagtg ctgcgtttca ggccgggatt actcagcaaa gacctctgca gattagagag   6300
gaagatttta ttctcccttt caccctcttc gcccccacct ctgccgcccc ctgctttgtg   6360
tgctgaggct gcaaacccta gccattgtcc tgagtatctc gggcgggcga gcaagtaagc   6420
gggcgggcgg gcgggcaagc gagcgagcga gcgagcgcgc gaccgcgggc gggccggcaa   6480
gcgagcctcc agcccagcgc tcacggcgct ccttgccccg cagcggagcc catctccgcc   6540
aggcagccag ccctgcggcc ccacgtccac aagcagccgg agaagaccac ccgcgtgcgg   6600
actgtgctga acgagaagca gctgcacacc ttgcggacct gctacgccgc aaacccgcgg   6660
ccagatgcgc tcatgaagga gcaactggta gagatgacgg gcctcagtcc ccgtgtgatc   6720
cgggtctggt ttcaaaacaa gcggtgcaag gacaagaagc gaagcatcat gatgaagcaa   6780
ctccagcagc agcagcccaa tgacaaaact gtgagtggct ctggggccgg gcagggaatg   6840
cgagggggaa ggagacgcag cgtgcgaggt gcgttcctgg tacgcaggat cgcacggttt   6900
tcaatcctgc tcctgggcag gagtttggcc ggggctgccc ctcatcctta ccccccctacc  6960
catgccccgg gggacaggct acccggcgcc ggccgccagc tgagggcggg gaagctggga   7020
ggctccgtgc gccgggggag cagcatccag gtcccaacct cgtgggtggg ctcatgccct   7080
tccacctcgc ctgtacctgt gaaccggaga aacgccgtcc tcccctctga gggcaggcgg   7140
```

-continued

```
caacgaggtt tggcccgggt tttgccaaca ttcagatcgt cagttcctca cgtacacaag   7200
aagagggagg gataatacct tggattcctg cctacatcca ggggttccgt gggcaggtca   7260
ccctgtgagc ccccagggcg caccgcactt ctaagtaagg tcggccgctg cgccttcagg   7320
ctggcgagtt cccccaaggt gacccgcatg cccagatcac cctctgctcc aggtgaagcc   7380
caggcctcca cagaggcatc aggcccctcg caccagtatc cactgttatc ttggtcccac   7440
ggaagcaccc actctgcagg cctcctggtg aagttaagct agagtttctt ttcttccttt   7500
ttttcttttc tttcttttc ttttttttt ttttttttt ttttttttt ttttttttac        7560
tgctttggac ctatttttaa atgccataaa atctgctgtc attaaacttg gcaggctggc   7620
caagattggg ccagggcact ttctgagttg gttagtgcat aatagcacaa taggaaccag   7680
acccaaatgc tttgggggga tggagtgggg ggctggctct tccttgagga gaacggcttg   7740
gaaaaaatct gcagctaact gaaactgctc agaaaaccac cctgtctaga ggctgaaggg   7800
aagccctgct tacctcagct ttttagttct gggaagctat ggtctgagaa ggcagagggg   7860
aggaattggg ctgagctgtg aaggtaaggg ggaagaagaa aatcaaagta gaatttggtt   7920
taataaggtc catgcagacc taatagtcca gcccacagag gcagaaaaac aaaacaataa   7980
aacaaattga attctaacta atatccgtag gtacggcgga ttaactgagt caataaagac   8040
cactatatag ataagataat accagggtat atttgcttag cctgtgcaga caacggaggg   8100
agggaatttg ctcattaaca tgttgggatt ggttgggggg cctattcaca gaatatccag   8160
gggatgacag gaactcccat ggtggctgcc agtccagaga gacacgacgg tggcttacag   8220
gctaacccag tggaagtaca aagttaccag ccaccttgga aagtactgag cgacttcgcc   8280
ttgcagagtg acatagatca gcctgctttt cagcaactgg taagtgtcag ctcccagatg   8340
gaagaggctg aattcccaac aggagactct ggtttaactg tcacacattg aaagattcag   8400
tggggagggt gccttcttgg gctcagggtt ggggagaaac caaggaggtg ggtaatgaag   8460
agaagggaga caaatgcagg gaaaacgaac ctcttggcat cttttttttt ttaatgagac   8520
tgcataattt gaccatatag gttgaatttt ctatcaatca ggccttcttt gaaggattaa   8580
tttcaaggta cctaactcta ggtagcatgt gccagaagat gtacagtgtt ggagaatcat   8640
acatcttaga attttagagt tgtcaaggac ttcaggaaat cgtcttggca tttcaatcag   8700
caattagtaa gtttatcctt cctgagcatc tagagaatgg gatatatagg acccaaatca   8760
aggcgattgt agtatataat caatgctata atacacaatc agtgttgtta tcaataaaca   8820
gcaggcatgt gtctgggtac aattttcaaa tatattaata aagattattc aaatagatga   8880
atacttttg ttacagtatc ccttgctggg aatgtcttaa tctaaaatgt aggaccgttt    8940
aaatgtttc aagtgtatga gttcaaatgt catagagaca cacagtgtgt accatgtata    9000
gcaaaaggga catgagctct accaatcaga agtaaagtgt ttaatctgtg aaaaccttaa   9060
catgttttcc acatccagag aggagaaaat taattcactt tttgcctaca aaaggcttaa   9120
ggggtcaaga taaataagaa caataaatat atgtcctttg taatatgcta tatttatata   9180
gatgatttt ttttcttaaa gagtaatcag ccttatagaa tcttgtttta taaaatgtaa    9240
agatctatcc tgaaaccttg ttcccttttt tggaaatgaa gctttagttg aggttagctt   9300
tttaccctca tatttacctg gagggcattt gctttctcaa tgtcaacagt taggtaattg   9360
gccagaggca agtggttaaa agggcttggc cccaggcttg tgtttgcaaa tgctaagtgg   9420
gtgcagaggc tagaagtccc ttaatctcat attggaaaaa tttactgtag aaagaaatgt   9480
aggctctaga actaggaaaa aaaaattatt ctaagctcat taatctgttg agttatttga   9540
```

```
gcgaatcctg aatcacagga ggaaggtaag gggaggcttc agggcagcca aatgtttgca   9600
ctttctgaaa ctttagtgtc agatgagagc agtggaaggg aagctgaggc aggagtgggc   9660
atagttagag aaggtttaca acagcagtac aatgcgttta gggttaaaag aaggagtcag   9720
atatttaaga aggagtcaga tattagggtt aaaagaagga gtcagaatgg gatgatgtca   9780
taatatatgg gtctcatttt ggaaggaaga gcctgattta aagagagaga gagagaaagg   9840
ccaagaggca gcaggaccaa caaggaagaa tgcccaagct gtgagcctgc tgaggagtta   9900
atctttgttc tgtggagcct cctctcaatc tcctgtcaaa ggatctgagc ctgttacgga   9960
ttttccaact gaagaagaga gtctttgatg cctagagact gagagctcac ctactcccag  10020
ggcaacatgt agccagcagg ataattttat ttcgagcatg catagtagag ttgtgatgcc  10080
attttacagt gggaaacaca tttgttctta aataatttaa tgcaacataa tgttgggaat  10140
tcagtttcag ttaaaacaga gatcttttgg aagatgggaa agtgagagga tttcttccca  10200
agtttttctc ctctaggctt tctctaagcc tgttaaaatt cagttatcta tgtgaatatc  10260
tttacatatc tatctacaca aacatttcta catatacaat atgatgagtt tataatcttt  10320
ttatgaatac tattccagtg tcctttattt atttctcaac cttctatgca ggtcaatttt  10380
tcagaaggag gaccgggctc taattccact ggcagtgaag tagcatcaat gtcctctcaa  10440
cttccagata cacctaacag catggtagcc agtcctattg aggcatgagg aacattcatt  10500
ctgtattttt tttccctgtt ggagaaagtg ggaaattata atgtcgaact ctgaaacaaa  10560
agtatttaac gacccagtca atgaaaactg aatcaagaaa tgaatgctcc atgaaatgca  10620
cgaagtctgt tttaatgaca aggtgatatg gtagcaacac tgtgaagaca atcatgggat  10680
tttactagaa ttaaacaaca aacaaaacgc aaaacccagt atatgctatt caatgatctt  10740
agaagtactg aaaaaaaaag acgtttttaa aacgtagagg atttatattc aaggatctca  10800
aagaaagcat tttcatttca ctgcacatct agagaaaaac aaaaatagaa aattttctag  10860
tccatcctaa tctgaatggt gctgtttcta tattggtcat tgccttgcca aacaggagct  10920
ccagcaaaag cgcaggaaga gagactggcc tccttggctg aaagagtcct ttcaggaagg  10980
tggagctgca ttggtttgat atgtttaaag ttgactttaa caaggggtta attgaaatcc  11040
tgggtctctt ggcctgtcct gtagctggtt tattttttac tttgcccccct ccccactttt  11100
tttgagatcc atcctttatc aagaagtctg aagcgactat aaaggttttt gaattcagat  11160
ttaaaaacca acttataaag cattgcaaca aggttacctc tattttgcca caagcgtctc  11220
gggattgtgt ttgacttgtg tctgtccaag aacttttccc ccaaagatgt gtatagttat  11280
tggttaaaat gactgttttc tctctctatg gaaataaaaa ggaaaaaaaa aaaggaaact  11340
ttttttgttt gctcttgcat tgcaaaaatt ataaagtaat ttattattta ttgtcggaag  11400
acttgccact tttcatgtca tttgacattt tttgtttgct gaagtgaaaa aaaaagataa  11460
aggttgtacg gtggtctttg aattatatgt ctaattctat gtgttttgtc tttttcttaa  11520
atattatgtg aaatcaaagc gccatatgta gaattatatc ttcaggacta tttcactaat  11580
aaacatttgg catagataaa taaataa                                      11607
```

<210> SEQ ID NO 24
<211> LENGTH: 185812
<212> TYPE: DNA
<213> ORGANISM: Homo sapiens

<400> SEQUENCE: 24

```
aactgggggg tttctcttca aagccagctg gtctggcttt attctgcagg aatttttttta    60
cctgtcaggg tttggacaac aaagccctca gcaggtgctg acgggtacaa cttcctggag   120
aagcagaaag gcactggtga gtttcaattg ccaaaatata tttttaatc tctaaaagtt   180
aattttgttg tcttgaaaga ggcaccactg aggtacctgt gttcacaaag ttgatgagac   240
cattggaatc agagccaact cactcaacag tgggtttgcc ttgtgtgaaa gtaaagctgt   300
taccatataa caatttttta ggttttttt ttaggtttaa aacaagattc tattttttaaa   360
tattggtctc tttcattact gttttcaata tttggaagat gaagagttaa ttacatttat   420
aatattacac gatttaacac acattttagt ctcctttta tctaattctg tcataatctt   480
ttctgaataa aaagttattt tctaataaat ctcccaaata aaaaggtgta atggtacata   540
ctattttcaa aaattacatg tactgggttt tttaaaatgt gtgcatgcta caagaacatg   600
attagagaga acatgcaatt aactttattt taatacattt ttaaagcata cattgcatgt   660
ataattaaat aatttaaaat atattgcatg tttaataatt aaataaaagt aaattgtatt   720
gtagtaaata ttatttaata attaaaagtg gcaatatttt ctcattactt tacaaagagc   780
gtcttttgag aaaaatcttt gaaattaaca accaagacgg tattaaagca tgtttttaca   840
tcactgattt ccaaaattcg tatatttata tatttttat ttttattttg ttaattcaaa   900
agtttaggca aaaatatttt tttcagaata ggactttaat taatgcaaaa catgaaaaaa   960
tgagaccaca tgttaggaca tatttttaaa aagtgactct atttcaggga ttcattcttt  1020
taactatgct tcacagcatt tctctacaaa ttgttgtatt atagtaaatt gaaaacattt  1080
atttaagcaa gtaagcagct caaagctaga gcctatacgt agtaaacata tgaaaccatt  1140
ttaataacca aattccatat tcacaagcaa catgggctaa tgaatttaaa agaaacaaca  1200
gtatacattg atgaagaatg ctataaatta ttatggataa aatcaatttt ctgggctgtg  1260
gggggtagaa ttggtgctta agaaagaaaa gactcctacc aatataaatt actaatacta  1320
tgaggcaatt gttttattct gatgatccca taaataactt taaatctaca tccttaacac  1380
atgattgtat agtggaaaaa aaataaggtc tgactttttt aatgaccact gtacctgaaa  1440
tgatttttaa atcagtgacg acatggatat gccacaaatg tataactaac atactctttt  1500
aaactgttgt aattgctgtt gaaaattatg aaacatttgt ggtttaaaaa attatcagaa  1560
atactccacc caaacaaaat agctaatatt ttaaaaacat aacgttaccc acaaacattt  1620
taatgaaccc ctattttaaa acattaaaac ccaaatatac tttttattat aaattgttac  1680
atatatattt caaatgatta aaacatttaa aaatatatgt gtatttattg cgatttcaag  1740
ctgctacttt catatatatt ttgtcatgct tcattatgtt tcattatatt gattcagaca  1800
cctgagtaac tatagtcgct aaatttttag aataacttca ttagtctctt aaagaattag  1860
tatgtatttc atgcacttga aaattttact tttattttc tagtctgtta aatactatat  1920
tcctaaacaa tcacaatatt tacttttaaa gatgatagtt actgcaaaac tgaacaacat  1980
gtgttcttat gtcaacttca gaattgtatt tgttaagttt tcacatgcat taccattggc  2040
tataattatt acattgtcat taagtataag caaaccaaaa gcttctgcca aactattgtt  2100
tatgactctg tcaattattt aagtataaat gaagctactg gaaataatat taaatatagc  2160
tcaaatattt caaaataact aaaatttatc attttagctg tgcctgaatt gtagacttaa  2220
tctaaaatcc catttttttaa aattttcatt atgagaggct gtaaattctt gtccaccatg  2280
cagctatgtt tgtcctttct aataaatctt caacattgtg tcacaaaaaa acctatgcca  2340
actccctcaa tgtatgggaa tggtttattt taataaaata ttggagttta aagtagcatt  2400
```

```
gatttacacc tgctctaaat atttaacatt aaaacatatg cattttaaac attatttgca   2460
agttatcttc ctatcttaca gatagcttat ttacagtgga gaaaaattgt tttcctgttt   2520
cagaaagaca cttggaaaaa catgttattt aaccttatat attaataggg aaaatcttga   2580
ttctcccagt agttaacttc aattaattat attttaaata tcagcctatt taatttcagt   2640
gcaacaaaat ttccagctaa aatggtttac ttgtaagtat ttaaagcaac aaaaatattt   2700
tggcagcttt atatgtatct cctcattgac cagccacctg actgacagct gtcaactgtc   2760
catgtgccaa atgtaaccca gtaaagataa aaattacata ttactcatcc ctgttgataa   2820
tacctggtgc cagtaggttt tcaaatagga ataactagac tatagataaa aaacaagtaa   2880
gtggggaatc atttctactg cctaccattc ctcctttgtc attaactcat ttccctttct   2940
ttttcttatt gatccctttt cccttgctgt ccatatctat agagttattt tccttaaagg   3000
aactttcaga atatgttaca agtctgtgtc catgaaaata ctgggcagcc aggtaatgat   3060
gcccacacat ttcttttagt catattttct tttgagctca taaactattt cggagttatg   3120
ggaagaaagc tttaaagctt tcagcttctc attttcaaag aaaatgaaat caaagaacaa   3180
aaatgaaatt taccaaaggt caccaaggtg gtgaccttta tgtagataca gacttgggtc   3240
tgtttcccaa cttaatatcc agggattttt tttctaatta gactttaagc atgttgacta   3300
gtaaactata agtaacaatg atcacatgga aaattaatgt gaattatatt cctttgaaga   3360
acccttttca gtcaccaaat ttaatacctt gttagagaaa tacacatttt tatcacagca   3420
tattaaaatg tagttctaaa aaatacaaag actataaatg tactaaaaca tctatggtac   3480
aaaagttttt tatttgtctt accatttaaa tggatttcca aactggaaat atttatgaat   3540
gtatatgaaa tagcagaaat aaaaaaatta tcaaaggtaa tacatatatt tagaagataa   3600
atgtagaaat caaaaatata agttggaata tagggttttt tttaagattg ggagtaatta   3660
aaaatacaaa atatactaac acataagtat atgtatatat caagtgcata atacattata   3720
tagttcatat aactgactta acaactgact agcttatgtg tgtgtatata taactatctt   3780
atattaattc caaaattatt aattatatta gtaaatatgg tctatttata taatttgttg   3840
ataatatttg tgcaatatat tgatctggtc aaggtcatga aaatattaat attcaagcca   3900
aatatttgtc ttctggatct ccagaaaaga aactgtttag ttgaaatcta ccacattctg   3960
aatttataag aatttatttt agtcctgggc tttggaacag tacttgctta taagaagtat   4020
tagctttaaa acccagacat gtaaattaat aagaaaaaga gatggggtaa agcttaaaat   4080
attgagaaaa aatatggagg gaaattgtgg ctagggttcc cctgcaaggg attgatctaa   4140
aataatcaac atttttatga ctaacaacac catttagcaa ctaaattgta tatctaaatt   4200
tgaaaatata tttgcttatt ccattacatt tagtccaaat caacattagt cattaatcaa   4260
caaaccattt aacaatatgt aataacagta tgcaaatcaa ttgcaagcaa aatagtaaat   4320
agcatccatt tctagcaatt tgaaagatag gcaagtttaa tcattgccct gcatcccaaa   4380
ggggttttag tgaaaataag tgacttgtcc ggtatctgct tttgaaggat catagaggct   4440
tcctcattag agttaaagag tgttcttcaa agagcaccag agcagaagta ggaagatttg   4500
agttagactc tctgtttcac tgcaaagtca ttttgtgact ggaaacaagt cacttaacct   4560
ctgtgaggct aatgaatgga tgggcctttt tggccatttt gtacaaatca taggaaagta   4620
agttttagtt atccaatgaa agatatttcc tctgtttcat gtgaggaagt ctcaaaagga   4680
atctggaata ttattggtgg gttcctgtct gcaatgactg ggccccaccc tatccctatt   4740
```

```
gctataagta gcccaccatg taagcattcc aagtaattaa aactgacaca ctatctagcc   4800
tgtgaagtca gtggggaaaa caaaatcact ttgcaatata ctccagagca gcaggcctta   4860
ttttttccac ttggggaccc tagtaacata atacaaaaag tctcattctc aaaattatgt   4920
tatgacacga agctttgaac ttttcagtat gcactataag gctgaattga caaaaaagta   4980
ctgaatggtc atttaatatt tttaatttta tagaatgaca ggaaaatttt taaacttaga   5040
aagatattct ccacacacaa tgctgtaagc cagcatgata atatatttat ttatgtcagg   5100
aaaatgttgg aacaagaaac agtgttaaaa atatctgaat cctagtacaa tatgtctgct   5160
acatataggt atttaggtta tgtatgatga ataaatggaa tgaaagaatg gataaataca   5220
gctggggagt tcaatatttt taaggaaaac ttgtaaacta aagcaatact tttgcaatag   5280
taataatcat ttattattgc tatttttatg ttcatgagga cagaattaaa acatgattaa   5340
tgtatttttt aaaaaatctt aatacaaaag aggttaaaga cctaagatat ggatcactct   5400
gttgacaagg ttggcaaaga tgtgcaggcc ctttatgact gcttggcaga tggaggtgat   5460
tactgaggtc acaaggaaca tctgcattga ttgaaaatct ctttacagag aagccacatt   5520
cctcaagtga ctatgaccag tgccagtcct attttcctgg agtctaggct cacagcaggt   5580
ggcagtcact gaaggatgaa aatgtttggg agtcacttat caccaatggt agaggtccct   5640
ggatctgaag cccattttac aggttttgca gaggtatcag gacccaatga accgattcca   5700
tccaagaaaa gataatggct atccctcaat taagtaaaga tgaagaattg tacagaaatt   5760
tgagataatt aggtttccat attgcttaac tggttttcta atttcaacag gcagaatatt   5820
tgtggcatgt cttttttttct tgtttacaat tttgaatcaa gattcatctt actatcttga   5880
aaggttctca tgactttaaa agttccacaa aatttgtgaa cattagtgga gagaacagga   5940
gtgaataaca aacggagaga aaaaaaaatt atggcattag agggacctgt ggatcttatg   6000
cttcccctca ccttaagaga gtagcatgca aataagtgct atggaagaac cacctgagga   6060
gcctgttata atgcagattc ctgagattgc agctaagtgg gcctgaggtg gggcccatga   6120
atctggattt taacatgcac ctgggtgatt ctgaggcact ttggttcttt gagctagact   6180
gttaacatcc tcacaaggag ccctcttttg tgaagaggat cagttctcct gctctacagt   6240
aacaggaaaa ctaacattta gtgatcccaa gtcccaaaag atgaaaggga gcatatgcac   6300
acaagtatag actttacctt ttaaaatgta ttgtctgcta taattaaaca ctactgtgtt   6360
gagtagttca tttattttaa ttatcttatg tagactggaa aataagtgtc atcaaatact   6420
agtgaaaagc cagaaaaaaa atcattctta agtttttctt aagtttaaga tgctaaataa   6480
tacagcttga aatgtgataa aacggcttga gcgaactctt caggacagtc attcaaacaa   6540
tacagacagt gcttattatg gaacgtatga gagtgtagag catacacatt caccaagttt   6600
tagaatgctc agttaatcat cactgacctg tggagtttaa gagcttatag cccactgata   6660
atgtgagaga aaccataggc tttattctcc tgtgggtgag tttattttgc ggccgtaggc   6720
tacacagact agaatctcac ggctacgtaa ggatgagatg agactgtgtg gatgcatgaa   6780
cataaatcct tcacaaatac tatataacca acacaagcac agaccttatt cattgtaagt   6840
taatcatcat tgcaatcata gagtaattac agtgattaat aacaaaaaat aatcatagaa   6900
gttattctat gaccatatta tctataacat gcatcatcaa ttgtttagaa ataagctcct   6960
ttagtgaagg tattttattt tgaagtgatt ctgataaatc aaaaaagaat aataccctat   7020
ggttctgaaa cagaaaatgt aattttccaa cgcaaaggaa aaatcctgtt aataaccagt   7080
tgtgcgtgtg tgtgtgtgtg tgtgtgtagc tttactgagt tcacaactga tactaaagaa   7140
```

```
tttacaactt gaaaatgaaa agaggaagca gaaaagatga aggaaggaag gaaagaatga   7200
atgaatgaca gatggaagga agaaaggaag ttaaatggaa tagttgggag gaaatctgtt   7260
ggctagctat ttagcctttg ctaaaggggt caaaaggaat aagaaagttg tagaatgttt   7320
cttactttag tagtgttcaa aatcttttac ttagaatctt atttcttcct tttgaatctt   7380
gagtgatgat ttttaatata aaattgcatt ccatttgata tggatactct ttatttaaag   7440
atttaagact acactaagtt gggaaatatt tgtttatgta ccctgtcttt gcacatagga   7500
agatgcttta tctgtgattt aatagaggag atagaaggca gaatgaaatt tgccctctgt   7560
ccctaaacct ctccccaacc gtttcaaatt ctctctttca tccaacaagt ggtacatatt   7620
ctcttcaaag agttcttaaa ccctgttcaa gacatttctg gataaataat cactaattac   7680
acctctggtg gctttggtgg ggcagaaggg agagcacaca gggtaagtct gagtgacaac   7740
atagtcacta tggtacaagg gacacgcagt ggctgcctgc ctcatattgc aaagagggaa   7800
tagaaaaaga gaccagggga acaggtaatg caatgtacaa ttttttaagt atataaattt   7860
tcaaggagta tcttaatatt ttgctgatag agagttcatc ttccaatccc aacattttca   7920
aaaacaaaat tgcttcctca agtaagggcc aggtttccca tttgcttgca tccaaggctt   7980
agatctgtgt ggacaaatga agtggctgct ggtgggaggg acctgagaca tactgaaagt   8040
gctccctaaa acaccacctg accaacacag cagggtatct gtggaagcat ggatactcct   8100
ttggattatg aattcttttc agaaaacttt tgaagagagg ttcatttaaa gtgattgcac   8160
aatgataccg tgtcatggat taggcggctg tagtggccgg ctcctctgat agaacatagt   8220
tggaaagaat tccgcggaca taaaggggcg gctgagggat gaaaggactt tgtaggtcgc   8280
atcagtggaa ggcccagagg agaaagaagc actcgtgaaa gagctattac tgattgtaaa   8340
aattgctgct gggtgagtgg agcatgccaa agtgaaagca gggcctgctg aaggtgagta   8400
tagggaagag agtgatgtaa agacaaactt tcacaacatc acaactgcgc atatgctaca   8460
cagataagag ccctgtttta agaggagttc actgggatct aataggaagc cactaattca   8520
acatatttat gctcagttcc cttaaattta agattatata atgaataaac aatttagaag   8580
atgtctgagg taactaaaaa ataaaatctt ggagcatcat tctgggcaaa tgggtatgtc   8640
attactttca taagtctgat gaaatccaat aagaataccc caaaaaagtt tatctaaaga   8700
caatattata tagaacactg acaaggataa tatagttagc agtccaacat gtaagacttc   8760
ttgatataat acatattaac tgaataaaca tacgaccata aatgtttata tttactttat   8820
atatcaaata ctttacataa aataactgtt tggaagcatg aaactgacag aaaagaaaac   8880
atcttttaaa atatcattac ataactacaa cattgagatg ttttccagga atatggggta   8940
tttcttgaaa gtgaaatggt atataatagc taacatttat tgagaatttt ctatatgcga   9000
ggcactaagt ggccacagaa gtacaatttc atgtgcttct ctcggcaaaa tcattatcat   9060
gggtagttcc tgccaccttc cccattttac aaaaagggca tttagaaaat taaggtcaaa   9120
acaattattt agtgtctaaa cgtggattct gctccagagt ttcctagtta ccctccgctg   9180
cccattttat actctttgaa aagaacattt cccatgctgt ttatacatga tctataacta   9240
ttaatttagt gaaaatgact tttttaaaaa aataccagac cttttacgag tgttacttgt   9300
caaaactgtc tccttaaagg ttataaaatc atatcaaaaa tactttgaaa ttcctctttt   9360
atatcttcaa ttagtgtcaa tttatgagac aaatatcaaa taatctaatg ctttatactc   9420
aaatcttagt tttcatcctg tttactacat ttggcttgga tttacttttg gaaaaaattc   9480
```

```
atccttaatg ataaggattt gccaacaatc aggccagttt taagactgtg tagcaaatcc   9540
ctgaggagat ttctaaatag acttgagcaa agacaacatt actgaaataa atgaatagtc   9600
ttctaaagtg tctaccttaa agaggatgac atgcctttag atatgtattt ctgaaatatt   9660
ttctggtggg acaaaaatat ctattatatt atcactataa gtgaacaaac gttatgaata   9720
caaggaagca gtatagcatc atagctaagg gtagagtatt ggaaacaaac acattggttt   9780
tatgtcgttt ggcacttagg aactatgtgg ccctgggcag gtcatgtcag cactcacagc   9840
tttagtgtgt aaaatcttaa aatggggaca ataatagtac atgtctaaaa ggttgttctt   9900
tgaataaaag gaaacaaaag tttataaagc aattaataca gagcctgaca aatagtatgt   9960
ggccattaaa tgttaggtac ttcaaatatt catttcaacc cacattctaa taagatagta  10020
ttatttttgc atatatactc cagatatcat tgtattatga ctaagaacat tactgattta  10080
aaagatttaa ctacacattt agtataaatg aataaataag taatagtccg taggaaatct  10140
ggccttttgt ttgagtcttt gactcaatca gtactttggt gaaacaaact ggttttaatc  10200
actcacttaa atttaaaagt tttattgagt tttactttta attctcacca tattacaaaa  10260
taatttagaa actcctccca gtgaaaattc tgtttcttcc taagaaatta gaatattgat  10320
ataattatgt gcctccttgt tccacaattt ctataaaatt acgtattgaa agcatataga  10380
tctatgcatg atcttacctt cttgaaaaca taacattttc tattatattg cttggtttaa  10440
aatttaggat tataaataaa atattttata aataattttg taagatccag ataagtagaa  10500
catagtcatt taaaaaatta cctagaaatg gcttggtaca gtagctcaag cctgtaatcc  10560
cagcactttg ggaggccaaa gtgggcggat tacctcaggt caggagttca agaccaacct  10620
ggccaacatg ttgaaacccc atctctatgg gaggcagagg ttgcagtgag ccaagatcac  10680
accactgcac tccagcctgg gcaacagagc aagactccat aaaaaaaaaa aagaaaagaa  10740
agaaaaagaa aaatacctag aaagatagaa taatgtacat tttgccatgc ggtagctctt  10800
ttccttcttt tctaaactct tctgtcttaa cttggggtct tcacttaata actagtgtta  10860
gcgtgaatat cagatataaa atttttattg acattctcta agtctgtttt tttctgtaat  10920
acatacttaa tcataaaatc agtataaatc ataaacatct caggtgggac tttattagaa  10980
ccaaaaatgc aaaatgacta tgcttctgtt tttcaagaaa tggtacagtc ccctaacaca  11040
gctgtagtgt tgatcatatg tctaacagaa ctacttctag gtcctcttga acagaacgct  11100
ccattaggca ttctgtgggc taccccttcc cagcaggctt ttgcccaacc cagttgccat  11160
agacggccat cagacacttg gaatgacatc aggagacaat ctgagcggac tctgacctaa  11220
agaattcaag ctagggggag actgaagata tcaatgtcat cttggctgac aatagcattc  11280
caaaggtcaa ccagggtgaa aagaggatag actctgagtt ttcagtgcct tttcagcaac  11340
caagtggcta acaagtataa taaagcatcc ccccaaaaaa gaaaaaatat cctagaggca  11400
tgatgtcagt gaaagggaaa taaggcaacc tgtacactta agtcatggta ttttaaaaca  11460
ttttacctct tccaaggtaa atctcatcct gaaccaattc ccacctctcg gatgacctac  11520
ttctttctgc tgtgataacc ccagtatagg tgaataaaga acttaatggt atagaagtgg  11580
aaattctttg cattagatta agaatggcta atttttaccg cagtttgtca cttttccagc  11640
cctgtgcttt atgctgaata gctcatttaa tccttaaaca aagttttgag gatagcacat  11700
tttgttccac attttacaaa tgaggaaact gaggcaaagg gagatttaaa ccatatgcat  11760
aatcaaacag ttaccatgtg atacagccaa ttggctgttg gccacacagc ttcttccaag  11820
tcagaccagc cttctcggtt gtcagccatg gagaaggtga ggccttcttc catgtctaca  11880
```

```
agcacctgaa gaagtgaaac attttctcta aggatactgg attttaggga gaatgggaag  11940
aatgctgaac cacacgcaaa tggtaaatta agaagagcaa taaagacaat aattcaaata  12000
aaaatgtaaa tctacacttt taaaataatt tattgttatt aatttaaaat tatttaatat  12060
tcataagtac tcttatttgg acacttcggg gatccttaac taagtgttaa gttaaaaggt  12120
aactactata aaagagcaga attaatacca acagttcact cctaattaac aataagatat  12180
atagaataca aacatggcat taaaaacaaa acaaacccaa aagacagaac aaaacaaaac  12240
aataaaacta ataagaaagc ttatgctttg tctaaatctt tatgatgtat tctgttgcct  12300
tatatgtttc agatagtgta atttgtaata atgttttgtt tgggccgggt gcagtggttc  12360
acgcctgtaa tcccagtact ttgggtggcc gagacaggca gatcacgagg tcaggagatc  12420
gagaccatcc tggctaacat ggtgaaaccc cgtctctact aaaaatacaa aaaaagaaaa  12480
tattagctgg gcgtggtggt ggacgcctgt agtcccagct actcgggagg ctgaggcagg  12540
agaatggcat gaacccagga ggtggagctt tcagtgagcc gagccaagat cgcaccactg  12600
cactcaagcc tgggcgacag agcgagactg cgtctcaaaa aaaaaaaaaa aaaaaaaagg  12660
ttggttggtt attaacattt ctgagccaat tccatcctag ttatatcata atcaatgtct  12720
ccgatatctt tatcaaattt gagaaagatt atgctttgct aaaaattttc actttaggtg  12780
acacctttcc tccctgacct taagaatgct ttttagctct ttaagaggat aatcccattt  12840
cctcagaatt tttaaagtag aatgaagcac agtgttatcc caattagcct cttagaaaag  12900
gcattatatg aatctatgac actaccaata atacattttt agtttgggag atagtattat  12960
tccccatgct cctcattctt tgttaaatgg aatttcttcc tggaggaata cttagcagta  13020
tttttcttg taaaagggta ctcttgccta aaattttcag tcaagttgac tttctgtaag  13080
atgaatttgc ctagaaagat gtccttgtct ggcacaaagt atactggacc ctgttagggg  13140
accttatctt ctttccaaat ttatgacata actttggggg catcacttaa cttctctggg  13200
cctgatttct cttgcctata aaaaaattag gtgtctgggt gaagtgttcc ccaaggtctc  13260
tttcagcagg aagatactga aagtctgact ttaaagcttc tcacactagt gccaagtaac  13320
agaaactcca agagtgtcct aaaatgtggc tggtatcagt cataaagtaa tttctttctt  13380
tctttctttt tttaaccagc attcattttg aactctatag cagtattctc cagcagaact  13440
ttatgcagtg atggaaacgt ttgacatgtc gctgtccagt aagggagcca ctagccacat  13500
gtggctattg agcacttgaa atatggccag tggaactgag ggacagaatt tatttttatt  13560
ttatcttatt ttaattaatt taaatagcta ccatcttggt agccgctaaa tgtttcaaga  13620
acatgataac ataaacgttt ttacaccttc gatgtaattg agtattccac aatgccagac  13680
aggtcaaaga acagcacaga tatctgcatt tagtgacagc atttttgtaa gacatcccag  13740
aaccgttccc ctgtgttaac aaataaaggg ggtacaaggg gaaaggaagt tttctgtttt  13800
gtctttaaag tgtgtgtttt atcctgaata ccctacttct tgctttactt tgtggctttt  13860
tcctagccaa aactcgcaca cgcgttagct taatagagct atgagttggc ttttgttttt  13920
tgaaatataa ttccttagat gctgagagct cagactataa aatccagttt ggggcccgtg  13980
ttctttccta ttggtctgtc aggtgaaaaa ctccggctgg ccagagtggg acaggggcgg  14040
cggctagacc tgcagagccc ctcttgctct cccaggtttg caaaatggtt ggagcgcttc  14100
gggcagcctg cgtcaccaga cgtggaccgt gtgccagcgc tttgtgcact gttaaagggt  14160
gggttcattt tacttggccc ctggtatttt cgtgggtcgc tctgagccca tcccgagctc  14220
```

-continued

```
ttttggatcg catttctcca gcccaggatc ccaaaaccag accagcagga caactacccc  14280
ggcactgcca ccgcccgttt ccacagtcca cccacagccg ttgcgccctc ctccattccc  14340
cagagcccat cacgcaccct ctttaccaac aaaccaccgg acgcttttcc cccagccgtg  14400
acttccacaa cccccaacta aatacaagtc ggcacacccc cttccttccc cgcgccaaac  14460
cagcgtggcc gcccactcgt cgcacccagg tccagcaggt ccagcaggtc cccaggaggg  14520
cccagagcct gcctcctgct cgcccgtggc gcacgcacgt ggcgcactca ccccctacca  14580
gcagcctccg agctctagaa acactccaag gaaggaaccc ccgccccttc agctccgtcg  14640
gccgggagaa aagggggggg ggaagggggg ggaagcagag acgggcagag agaagagtat  14700
ataggtgatg agagcagtgt tggaggggag gatcggcaat aattggatgg cgttgcagct  14760
gttgcgcctc tgctgaacgc ccagccagag cggattcact tttcacacaa atcaaccgga  14820
gggattgttg ctgcctgcaa tcaataactc agcggagtga gttgctcaaa ctagaggcgt  14880
ccctcgtctg ggtctttgag ggccgtccgg attgagtccc agcgctctgc tttccaaaca  14940
aagaagtggg caccaaaacg caggacgaga tttttaatcc ccacttccac cacaaccccg  15000
ggtaaagatt ttttaaaatg aaaaagcaca cacatagtaa ggtatctaga agaaacagtt  15060
aaaaggggaa gtgtgaaaat ccattccttg aattgaaggt ttctgtgata tttcaagaaa  15120
tgggatagaa tcaatgttct gatgaacaac atttaacaat tttgtaagta aaggtaaagt  15180
cgcattaaat ttattcatgc atgtggttat ttttgaatca gccacacact tgcaagcaaa  15240
ttactgatca agccttattt ggacatactg attacaggaa aagaaagaaa tgtatcataa  15300
tttgtagtgt cgtttaaaaa aaaaaaaaaa accttaccat acctttcaga tgttatttca  15360
tgaagattgc atttctataa ggtgaatagg ccctgggaga tgtgtattat gattctcact  15420
taatagactg taaaatgaag cacaactgga agaaagagaa ctcaccaaat cacttggtag  15480
tgactacaag accaagtttg gactcactca ctgtgggcct aagcctaaaa acctaaactc  15540
aactaacacc cataaagtaa aactggccaa aatttttcat ttctctttga ctctgaagca  15600
acttaaaaat aaacctcaga gatgtcaacc caaatataga ggctttataa atgattcttc  15660
actatgcaaa gtcctcctgc tattacaaat gggaaaagag atattgacca tcctggtctg  15720
atgtgtctca aggctggttc tctttctggg actagcctca gtctgaagcc aaggaaaggt  15780
tcatttgtgt gcacaaagtc atggaaagcc agactaaaac agaaatcaga acacaggagc  15840
atttgtctgt gctcagtata gttaaacact gcttggaaaa ataaggtatt attggtaata  15900
gaatttataa accgtactga atacacatca ctaatcccaa agtattttaa attggccttt  15960
aggcaatgca taaaataagc cctttcagta acctcaactg cattgcaaac atttcccgat  16020
ttgacaaatt gtgttagctt cggatataat ggatttgaca ttcttctgta attctctatc  16080
agatataaaa ctgaaggtac agaaatacag ataaacatag aatccttaga tatgtgtaaa  16140
ccttgtcttg aaataacaaa tcctttgtat attgcaaatt ctcaatcaca gacattccac  16200
atgctgtata ttcttcttgg gttaatgctg cacctagtga atttttgaaa tttagatatt  16260
tggcactatt tatgttaaag attattatca caatgcatga caatttcagt tgtcttatat  16320
tcaaaacact ttggtttaaa atcagaatat tgttacttca gattagaagt tttagaaata  16380
aatctatttg aaagtatttt catatcagca ttaacaaaat actatatact gttttgcact  16440
tccacatttg aaggtgccaa agaagagttg caaactgtga agtaacttct atgaagagat  16500
gaagtaaaga acggaaggca aatgattgtg gcagtaaaga agtgtatgtg gtgagtgctc  16560
acatttgttt ttatcattta ccacagagtt accataaagg taaaactgcc aaactccttg  16620
```

```
gccttaggta tttacagaat agacgtgtat aacaataata aagagttaaa tgaccaccat  16680
acactttata ttataagcaa tgacatatca ttttgcttaa agatcatgtc atctttcagg  16740
gcctactttt gcaagtactg tatcttataa aattaatcta tttcatggga agtcctgtgt  16800
atcatcaata ctataattag acaaagatta aaatatgtaa tgctattgga atttgtgttt  16860
cactgctttt tagatttttc taaaccacca tgttcactta tcatgtttgt gttaaaagta  16920
ttctggctga ggaacaaata ctatacagtt gaataatctt aaggggtaca ttaatctata  16980
gcctttcttc atctcagggt gggttgctgt ggcaaccgcc ccagttcact ttaaaataat  17040
ttttaaagct cacttcaaga gctacaccca gcgtgggcca ggcttaaaag caggcagacc  17100
cagtgcacag ggctttagtg gaccgctgct ttaatgtagg gaagtagtga agagaggagg  17160
ttggagtaag atggtatgca gctctgaaca gaaattgcaa tattagcttt ccctggagtt  17220
aaaatcccga ggagcatgct ctctgtaact tctatgacac tttaattaaa tatattgcta  17280
aacataattc ttttgaggga aaaacaagtg actctatatt tacattaaca ataaagcatt  17340
tacaacttaa tgtaggagaa atatttggtg attagaaaaa aataaaagct ggtacagtag  17400
tacatcaatc ccagacataa ttttctttta aaggaattgt cacctattat ttaactggat  17460
agaccctacc ttccaattgg tttaaagggt agaaacattt tctgttttcc aatgatagaa  17520
ctggaatagg ttacagaact catttaacac ataagcgaac tgaagcctag aaaggacaaa  17580
tcccttagta aggcacaaat tttgaactag atagagaatc caggtctcct gacacctagt  17640
acaagctcct ccctacatga gaaaatagtc tgatcctaac caagtatcat tagatggcaa  17700
ggatcaggat gattttaaag aaaaaacaaa aacagaaaca gaaaccaaaa gtccagaagt  17760
atttaaagaa tacaaagcac actctggatt aactactttg tggattactc atgaataatt  17820
ttaaatctca ggtgattttc taatgtatat ttcttcatat ctcttctgct tcaactgtaa  17880
aggctcatgg gaagaaaact aatggtaata ttaacttagg tcacacataa ttaagaagct  17940
aaatctgctg aggggaaaat cctgtatttt aaaaggccaa ctgtgataca ttccagatcc  18000
aaattatttt caaattatcc agtgtggggt tatacttatt tttgaatgct tgcagtatca  18060
ttaataatta tgggtttgtt ataatgggta ttattaaata attatttaaa atatgaaaag  18120
gtaaaataaa ataatttctt tttgaaagaa catctaaaac tgaagtgtac tgtggtaaac  18180
agaaataccc tctataattc attaaaaaca gcagggctga aattcatgta ttggctatgt  18240
gtttgctcat gtcaaataga ctgttgtaac tcactgcatt aattttaggt attatggcaa  18300
taaacttaga tggtccttca aatgctttgc tttttcagga ccttcgtgaa tcttgaagaa  18360
aattaatttt atttttacca ccatatatag acatatctta gtattcgaaa tatctttgcc  18420
ctttaaattt ttggattttc agagaagttg tactttgaat ggaaacctga tacagatgtt  18480
ctctgccata ttattaaaat gaattcatgg taatggcaaa ctcaacattt gaaaaaccgg  18540
caaacaaaat acattgtaaa tactaatctg caagaaatac tactatttca gatggttttt  18600
gctttgtgac agtttgtgat gcattcctat aataaaaggg agggaatggt cttagttttg  18660
ctgatagtca caatgatgag ctggaacttg aagattgttc agatctagtt gtacttgcct  18720
ataaaataaa ccttcccctt tcaagtgaag ccttgggaca gttgcctaaa tgttgaggcc  18780
actcttctga gagaagctac tcacatcaaa tacctcctac attgaagcag gaggcttttt  18840
gaaccatact gtcctcatat attaaaatag tcatctggag gcatattgct gaacttaaca  18900
ggaaatacaa ctagtcattg ggttaaacgt agtgctaaaa ggaattttct aaagtgagga  18960
```

```
aatctttagt tagctagata tttcaatata ctattgtcta atctcatata ttccatgttc  19020
tattaatttt cccttcttgc tttcacaata ttttttaaaa aatagtttgg tttaaacatt  19080
ttatgtaatc tataattcta ctggcatgca atcttgtctt ttcatgattc tatactagtt  19140
gatgtatttt atctttggct ttattgggca tggtatatat taacagttgg ttagggcggg  19200
aggtgcccaa tctctagtag cctaaatatt aaagcctttt tttttttttt ttgtaaggaa  19260
aagtgtttat catgctttaa ccttaacata agtatcctcc cttatcagtc tctatttctg  19320
cttcctgtgc agctgaaact cttcaggata agtgaagtca tcagctatcg gctagggtag  19380
cctaatgcat ttgggaagtt ggtttggttt acatgttaat gacctggatg aagtccagta  19440
aggtgtggaa aagatagagt ggggggaggg ggggaactcc gaggaagctg cttcctcggt  19500
aaatatttcc aaactgatta gaaagttcat ggccccgcga tgaagtcgag atctcaaata  19560
ctggtaatta ttttattatt tcgtacatta ctaacattag agaaaccttt cggctcgctt  19620
tctagcgctc caacctctca gggtgaaaac cgcgacttct gggcgtgcag gaaaagcacg  19680
ctggaatcga gtgctgcaga catcctggac cgtggttttt acgcgtgagt aacggaggag  19740
cgcaccgacc ggtggaagag agaagtggct aacgcgtgtc caaaaggggg aaaagtcaca  19800
agagcaacta ttagggtcgc gctcctattg gtcagaggaa agatcccgac tttagaagga  19860
ctttcctgct ggctggctcg cagcgtcccc ggagagcaag cgagcgcgcc gcagcgggag  19920
actaggttct ctccgagcgt cctccgcaga ggcgccgcga gaggagcagg gagccgcagc  19980
tcgccgtgtt gtcttcattt cgtgcaataa agaattgtca ttaggtttgc gtatggcatg  20040
tgctattacc ccaccgtaaa actaaaatta gcaaaatgtc aggaatggaa agattgattc  20100
accaagatgc aattatcatt taaaagtgct tgattgaggt actgatgttc agtgatttat  20160
tctgcatacc atatacataa ttaaagtagt gtagtggagt aatttatcaa tctagttgag  20220
actggagggg tgaggaggga gctgctgtat gtttgtttta ttaaaatgct ccgaggtcta  20280
gtcccgcccc ccttttgcaa gagtgaaact gatgatttct ccagctcgcg aggaaagagt  20340
caacggtttg ggattgtggg ggagagagag acggagagaa aaaggcagcg cgaagcaaag  20400
gcaaggacaa aattaaataa agggggaaaa aaggaggcaa aagacatttc atcggacgtg  20460
ctgcttagaa ccccaaccat tcgtgctccg tcttccctac cacccccgcc tcccctccca  20520
gtatccttca atcccccccg cccccaccac ccccagtctt ttttacgcga tgtttcaaac  20580
gctgtgagct gttctccttt tcccattcgt cttctgtcac ttccttcctg gacgcagttt  20640
tctggacgag tctggttact tttaatccga ccggccgctg agagccactt tctcctcctc  20700
ctcctcctcc tccttctctt cctcctcctt cttcctcctc ctcctcctct tccgagcggc  20760
ctcggcgcgc gcgaatgcgc ggccccgcgc cccccccctc gcgcgcgctc ccctcgcgcg  20820
cgcgcacaca cgcacacatc gtctccagct ctctgctcgc tctgctcgca gtcacagaca  20880
cttgagcaca cgcgtacacc cagacatctt cgggctgcta ttggattgac tttgaaggtt  20940
ctgtgtgggt cgccgtggct gcatgtttga atcaggtgga gaagcacttc aacgctggac  21000
gaagtaaaga ttattgttgt tatttttttt ttctctctct ctctctctta agaaaggaaa  21060
atatcccaag gactaatctg atcgggtctt ccttcatgta agtacccctg atatttctcg  21120
aggaaataga aaacccgggt attgtctcta aaatctgcat caatatattc cacggcactg  21180
tgtctatcta tccctgtgcc ttttttgaag gctgaagttg aggctcgttg tgcattcttt  21240
ttcgttagat tccatgattt ccttgtttgt tgctaaaagt aactttttag atagtcgtat  21300
ccgtttgcca tcagctattg aaatcactcc tgactcgttc ctgtcacacc agtgtattta  21360
```

```
aagtttcatg aagttagttc acgtcattag catgtttgat atggtggagc gtgtggagcc  21420
tggtggattt taatatttca cagcatgttc tgtgaccttg aagtagacgc cttaagattt  21480
agcagttagt tcactgtgga aagatgctcc catgagtccc cccaaagaca ctgatttgcc  21540
ctgggttatg cttctgagcc actaattctt gggattagtt tgacctaaag catggctgtc  21600
tgtcagagta tacctttgtg catttccttc cctcaccaaa gtgccggctt gacagagggc  21660
ttcttaattg gtgtggacaa aaagtaatat ccctgccata gtagtctaca catttcacaa  21720
ttcacgttcg atttcagcat atggattgct gttcaggtca agtcaaatac atagctgttt  21780
aaaagcaagc aaggttaagt cacttaaatt gccttctctt tggacttgga atgaaagtta  21840
ccaaactcga tgataaagtt tgtcacaaag gaagtatata tagatgtggc acattgttta  21900
ttttattatt aaatattgtg gaagtattta aatttaatgc taatgttacc ttccttccct  21960
gaacatggct attgcttttt aaaggaaatt ttatatctga atcacttctg actattctaa  22020
gtccagtagt tatcattctt tggggagagc cttttttttgt cacattttag gaatgcgtgt  22080
cttttgtata aaatacttta tatgtaaatg ctgacagtag actaagtaga attgggctct  22140
ctgccagttc cttaaccggt cctcagtgga gaattgcttt gacacaaagt gcgttttact  22200
attgtgaatc tgaaactaac tctaatagta actgtcttat gaaatgcttg ggactgcat   22260
ataatttcta agtgctataa aggaaactcc agccacctca ttataccagt ccaaaaaaaa  22320
aaaaagcgac tagcctactt tcactggcac cttgcaatgg aattgtggtt gcagagtaaa  22380
gatgtttatg tggagtataa taactccaat ccctagagac ttggtaggac atggaaatgt  22440
gaccacctgt gaaccccgtt taacctcgta ttgcatacca attttagctt taaatagatc  22500
aacaatctct aatttgaaac taaaacatct tatttaattt taaaaaatgt cagttttggc  22560
tagtctttaa aaacattcag catgtaccaa tatggtataa gcagtatttt tgtttctcca  22620
tcagtttcaa ctaaagataa tgcagttaaa aagccatatt attgtcttcc agtgtatgca  22680
tgaaattaag ttaaaagaag tagttctaaa gcaagactca gaacttgata ggtaaaatga  22740
gatgtcccta tctaacatcc tatttcaaga ggaaagaaat attttaaatc aaatatctca  22800
ttctatttgt agaaaagtac atttagctat gtattctgct actaactcaa ttctaaaagt  22860
tttcatcaaa acagtcttta aacataacat ttgcttaaaa tttggttctc ccgtcaaaga  22920
gacagtaggt ggctgttacc tttacttcaa attttactaa attttataaa aacctactat  22980
ttttattaat ataattcaca cagcattcga atgtttgact ttttttcaga cttcttagga  23040
aaggcagcat tttacttcat tcattaattg caccatttac gtcctgattg ctgtgcatgt  23100
ggaatatatt gaaagataat attaaagtgt aagttttatt aaatgttaat ttgtttttta  23160
tttcaataac aaatgagcaa tttataataa aaacagtttt ccaccttttc tgagctattc  23220
atattttaaa agtgtgcaat cacagatatt aacttttcaa gagagaagca cattaatact  23280
agataactcc atgaaactta gataacaaga ggcactttgc ctcttttctt ctttgtaaac  23340
atgttcattt tgaaaaattt gggggaaaag atacctgaaa ttttttcctt ggccctaact  23400
taacggaatc aataaattcc ataacactgc aaacgtatct ttctaataaa tactttattt  23460
aaacttcttt tataaagaac agcactgaat aactccttag catatcttaa cattatcttt  23520
taaaactttc ttctgtttat tgtagtatat tttgtggttt tatttctcaa ctctaaagtg  23580
tggtataatt tgagtctatg aaatctcaga aagtgacaaa aatggggaaa tagctgtgca  23640
gcaatacttg tgctacataa caacaaagac atagttatta aacagaattc tggctttggg  23700
```

```
gacatgattc gaagcaacat agaagaattt aatatgcaat taatggtcac aagatgaact  23760
gttaagagat tattaataaa gttacacttt tttttcaaaa gcacatcctc tgagaaaata  23820
ccacacaaat taatatctaa aacttatcaa aatacacgta ttcattctat actaatgtgg  23880
tgattgccta gacacgatga aatgatttaa tcactgttgt tccatcagta tgctgcatgt  23940
ggaaagacag gtaattaaga tccccgtcct tagcactgta ccttaatctt ataggcgcgt  24000
ggactgtctt gcactcagta aagcttgact gttcaccgag atctgtcacc tttaggaaat  24060
caaaccagat tacagaggtg attcacaaaa ccaggaacaa cagagtctat gcacgttaca  24120
aaaggcagat tacatagttc acatgttatt ttgataggtc aaagataaaa gctgattgtt  24180
gaggaatggc aagacactca atttcaaatg attgcttaga taagcatact ttgaccctgt  24240
tgcttcatca ttatgatcca ttcaaacaat ggaaaattca gttttcaaat gacaggcttt  24300
cagtagtgaa gtaagagaaa acatgtcctt ttttatgtat gtcttcattg tgtaaatttt  24360
aagttccatc atttctttat gaacaaacat taaattgtct gcttacatga agcaggtatt  24420
gtaaggctta aatgcattag acattttcag aggcgttata aagagcacaa aacagaattt  24480
gccagaaata aaacatacac tcatgttatt gagtaattca gcagaaaatg cataatagtc  24540
aatatccatt atgttattct gttaccaaat atattctaca taaaaatgtg taattacata  24600
gttatgaatc catatatgtg aaacatatct tcataaaagt tcattggtca aattttatat  24660
atatatataa tatatatatt tcatgaatgt tatataaaga tcattcttta caacagaata  24720
tgatgttttg agagtttatt tcagagaata aagttttggt ttacataata acattttgaa  24780
aatcttaact tcttacacac ccaactttac agtaattttt tgcttcttct aaaattgaag  24840
tcctttttta cccaactgat gcctcctagt gtttcacaca ataaaacact aatgagtcac  24900
ccataaatgt aaacattgca ttttcattgc ctacatcatc tgtgatacat aaaattaata  24960
tttatgtgtt taattttctg tgcactatta taataagata gaaaatttta gtgaatgaga  25020
tgtttcatct gagtggattt gtggcacgca cttgcaggtt ttctttgacc atcacaatat  25080
cttactaagt tttaacaagt ttattacctt cagttgcagt tatatattca ctctttatat  25140
tcactcttat ttcaagtgag aaacataggt aaataacaaa gctttcattt tgtaggcctg  25200
ggaattatac agttgggttc attctgaaat gcctgataaa ttgcacaagg actatccatt  25260
tcatttacac actaaaatat cttaaaagag atataatttt ttttcctgct gtgtctttac  25320
acttgaaaat ttctttgtaa aagtggaata aagaaagact atttagaaaa gataaaatca  25380
aagataaatg caaaatttc tataaatatg gagtatattt attagaaaat aacaacaaaa  25440
gaaaaacttt ccttggaagg aaacatatta ttctacataa agggaagtcg tgttagaaca  25500
caatatccaa tgaccagcag cttgccttaa tgaggtagaa gttagtgggt gccaactttg  25560
gtgtgagttt tctgccatta ggatggtaag cgtagacctg tgatattttt gcatgtttgt  25620
gatttcaaac agctctctga ttctacttcc taagtttcta aatgtttttt atccaatata  25680
cttatgaaag aaaggggtca ttcctgtaat gggtcttaaa ttgaaaggag gccatcaaaa  25740
acttgtaaca ttcatgggcc tcttcctgag gtgtcataca acatacctgt acacaaaaac  25800
attcatgagt ttcttctact aacacaaaca ttctatagca tccaagtgta gacactagat  25860
tgaacttcat tctgtatatg tgtcatttag ttctcctgac tcaaaataca cagtgtatta  25920
acaatatttg actatcactt aagattttct aatttagtca ataatacagt gctattacaa  25980
ttgttggaca catttcaaag aatgtaaggg ggtgtgttcc tttcgttcaa ggaagcaaac  26040
atgtagaaag gggtggacct ttcccacaag agccacattt cttcccttgg agaattgaag  26100
```

```
caaatatgca gtacgtaagt gaatagcagc atgagaaaga aaataatttg caatgatctc  26160
ctatagttag tgagcaaaga aaattgtcag ttttttttaa agtagctctt attgacaacc  26220
tatcttaaac tgaatactga aaaaaagtct atgaaagttt tataatttca gtatgtttta  26280
acattcatgc gtgaaataac tgtaaagtac actgtaataa ttttggtctt gctcaaatca  26340
agaatttttt agtaaccatg ttattttaca gacaatattg aggcataaca aaataaaggg  26400
tgctggaagc attcattcct tacccctctc ttttaagaat acgaagatgg cattgatgtt  26460
cttttgttat ttttgtctgt gaaagaaaaa taattaaaga atgttctatg acaaagaata  26520
ccattgtaaa aataagatta tagaaaaggt tatttaatat actattatct cacatctcct  26580
tgatactatt ttaatgttta ctgcaaaaaa tcatattcct attaaatatg gaaattaggt  26640
gatacatgtt atacaaattt atggtttagt tttaggtgat atgagtaaca tttatttgtc  26700
atcgccataa ttcatttgct gtacattgtc attttattgt acaagttaaa tcttggtata  26760
tatttttaaa atacagccaa tgtaaacaaa gttcaaagta catgaagaga atcttttgag  26820
ggcattgaaa aggaaattga cgacattaca agcaataaaa acagtaaaca tattacaggc  26880
agatttcttc aggaatcatt actcttaaat aatgcagaca ttataaagac tttattaatt  26940
cttaatgctg taaatttgaa atgaatggag caatgttgtt cctcctgcaa gtggttggga  27000
ttcatgtaga atgacagtgc aagtcctcaa gcagtgattt aaattaagta cccaaaactt  27060
gtttttagag gctggaggaa ctaactgatc tttgaatcag tcccttttga gaacctgctt  27120
tttccaaata gcatcatgag cgtggtggtc tggttttcct cttctatctt gttgtcatag  27180
ataagatgca catgaagaat tcatataaat tgctctcaga tactatggat tcctagcata  27240
ttggattaaa aaagaagtgg atatggtcct tcgatagaat gtgaagtgtt tttttaaaaa  27300
tcagccaaga actatgcctg tcttttttc acacctgtga ttctttcagc aagttagaag  27360
gatagcaaga gaatgtgcat ccttccccaa accccgaaga caggcagctt tggcttaaat  27420
atgcttattt attttcaaaa ttagaaaata aacacattaa tgtaaatatg ttgagacaga  27480
caaagaaatt tgtctgctac ttaataaaca cgcgatttat actttttgtc ttctaattaa  27540
ttgtcgaccc tgaataaggt ggtacaacta aggcatatta tggaaaactg gcattattgc  27600
ttaatgtaac atgagggatt ggaatttctt taaagtaatt ttaagatatg attatttagc  27660
agaaatattc actggagcat tttactttta gaaattatcg tcacacaagg aagcctttat  27720
aggaccgact acctaattgc agtcaaagat ctcttgaatg aatgaacaca cacacacaga  27780
agaacacaca ttttaagaat atagtggtcc tatattttta aaaatttttg ccacattttt  27840
tatatctgaa cagaacgtat gtgtctaagc agatgtttta agttatatcc ttcatgtagg  27900
tgagtctgta aatgtaccat ttaacttaaa tggctttgtg ggaaggtagt ttgaggagtt  27960
taaaaaggaa aaaaaaaaaa aaaaaaaact ccagttacta cagtttcagc tctttctttt  28020
taaaaaacag taattacact caggataaag aaagaaaaat aaactctttt aattctttgt  28080
aacatccaca gtttttcagg tagagttctg gtatattttt attcctgaat atgcagggca  28140
ggtactggca gcagagctac aaaatgaaaa cttcctggct gcagaccaga tactgtgcac  28200
agtgccacat cataaacttc ccctcttctg tctcggagtg atttcagccc taactaatgt  28260
cctttatttc cccctacata gggtaaggaa cagagggcct tcttcctggg aaatagggga  28320
aatacctttg ggaaaggaaa agtataatgt ttcccttctt taacttgaaa attctgcctc  28380
ttaaattact aagacattaa ctgcaaagtg gattcagtat gtttcctttt tattcccata  28440
```

```
tagcagttta gaatacataa aacaataggt gtgagataga aaatgagacc tcttccccac  28500
cccctacctc cagcacaccc agacccaatc agatatctgt actttttgtt tcgaaaagaa  28560
aaatataatg gtttcttttc aatgaagctt gtgcattata ttccagatat gttagatcat  28620
tttgtgatgc aaattagcat tgaggttttt tgtacttatc tcgggaaata gcaacgttcc  28680
accacaatgt gtggtgctgc aaaaattttt attgataaac acccacactt taaatgatta  28740
ttaggtcaaa atagagagta cagggggaga aaatgtgagc ttttagtttt cagatttgtt  28800
ttatgctttt catttgaaag gtacagtgta agttctgtgt ataataccat gcaaaataaa  28860
ttgacttcta aatatctgca ctaatattcc ttgtatctga aactatagtc taaaagcttg  28920
tacttctcct taaaaaataa agtaaaactt tgttaagaag caggctttaa ttaccagtta  28980
cattttcaac tgttacccat gtgattttta aaaaatccta ttaaaaaata atttctagct  29040
gccatggctc ctttcaatca gtagaattct catttgtatg aggtgcaatc agattattgc  29100
cagcacacct ttctaaaact agccttcttc tttagaaatg tattaaatgg gagccttcag  29160
gagaaagtgt taccacttaa taaatatttg ttctaatttt atttttaaac taaattattg  29220
atttaacagt atatgaatag tgtataaatg ttagcttagt tgttaaccca ctacactaat  29280
tattaattgc ctatatgaaa tttaccaaat tagaccaaca gttaagtgta atttaatttt  29340
atttctcttg aaacttaaat agataagaat gataatttta attatgttta aatatcaagc  29400
atttattttt ctgtgaatgc aaatgttccc gataaattgt taagaaatta atacaacata  29460
gatcttaaaa aatgtataag gcagcttata agaatatgat aacaatggca tattcctaca  29520
cctggcactt tttcaagacc cattagcaag ggaggaaaaa gatgttaaac tttgttttgt  29580
aaatgctaat atatatatga gtcaatactt tctgacattt atttgttaga aaattacaca  29640
catttaaaaa ttcaaattaa aactatgctt ctatttaggc tattgtaaga gatttcttta  29700
ttttcttgga aattctctgg aacagtaggg tcatttgaat catacccgtt ggtattgtca  29760
gatacattgt aaagtttcaa ctattgaaca tatgtatgga atagaaattt taaaatagaa  29820
aattcgctat cttgccattt aagtatgata aaactatacc cgattaaaac gttgactcta  29880
ttagaggttc gcctagtaag taattctctg gtcaagaatt tgggaaattt taaactctgt  29940
taaccattaa aacaattact tctttaaggt accggatttt catccatatt tgaggagcct  30000
tattaagttg ttgggtggtc tttttgtaaa ggtttatgtg gttaaaaaag tagatctttt  30060
cacccttcta ttacagttaa cattaatatc tttaaaaggt actatataaa tccagaccta  30120
atttattctg gatgattttt cttaactaaa tgaaatctaa caaatttgtc tatttttaag  30180
tgaatctttt ttttatttct agtatttatt ggaagttcac ttagactcta tataggttag  30240
aagttaaagt aaataatttt gactattttt ttctttcatt tcatgtttga atatttcccc  30300
ctttacataa accaaaaaaa aaaaaaaaaa aaaaaaaaaa aaatccgtga cgacattgat  30360
agatttgcag aaggctgagt aagatactca gtacccatta attgtttccc tatgactctt  30420
gggttgaaat gaatcggcaa tatcccttcc aagactgttt gatcttgctt gatttagagt  30480
gagcgttatg tgatttttc cctccgcttc tctcatttta tagcttcaaa aaaatcagag  30540
aattcttgac ttcagtgttt tttccttccg ttttcattgt ttttggattc tctcctgtct  30600
gagcttcctt cttgcttcaa agtatttggt atcgtgaaag caagtgcact tttaacttgt  30660
tttgactaca catgggcgac agaattgttt tagatgctaa cttacctcct tacacttgag  30720
aaactgatgt ggttcatcac agcccaatgc catgtcttga aacaactgcg gacactgatc  30780
ttgaaatagc cagggctata ggatcatgtc tttgtaaaga acaacagcag ctttagagtc  30840
```

```
actggatggt atattcgttg caaacatgaa cagcttcatg aactcccagg aagtggtaca  30900
gttattggac aaggtcaacc acattatgcc ttttaggttg ctctatgaag taagtgttag  30960
accagaactc caacggtgtg agtgtgtgtg tgtgtatgtg tgtacggtgt ggggagcatc  31020
ggtgtgggag agcagagaga gagaaaaagc atgaaaggat gaagatacac tctcgagaga  31080
gaagatcgtt taaacaagca taaagagttt ggagactcca tttccacact taatatcatt  31140
tctttgattc tacatattat gctattagac aaacatgtcc ataaacaata aagaataatg  31200
attaagaaca acgaccaaaa ctgggttcaa aagccagcct cccatttact gattagtggt  31260
tttaggcagg tgttttaatg accagaaagc cccagtacca ggatctgtaa aatgggaatt  31320
ataaaatcac ccacctctta aagtttttta aggatttact aggataatac atataaaacc  31380
gtaatgcaga tacatagtaa atgatcagta aatattaaat tattatcata gcattgtact  31440
atattttagt cattttaagt ttctgctaat ggtgatttag aaatttttgg tgggatggtt  31500
attaaaatta tttttcaata atactttcag tccattaaat ttgggtcaca ttcagagcaa  31560
gtatctaatt cttacacagt cgtgggtcaa ttctaatgat tgctaagttc aatatacttc  31620
tttctccaaa aaaatcaaaa cctttcacag atttgatgtt attaaataaa tatattattt  31680
ttagaaccag aaatggaacc aaagaaacaa aatgatacca tccatgaatt ttaaaagtca  31740
tttactcaaa gttctgaatt gcaggtagat tattccttag tcttaatgaa agttcagttt  31800
ggaggaaatg tttcatgtac agttattaga tgattttaat ggtgaaacca gcctcgccaa  31860
gagttctagg tgtttttctt agtattatcc acttttgtat acattaataa cctttttttt  31920
atttttctta ttagacaact ttgattatat gtagaaatgg aattaattta tgatgaatgt  31980
gtgttctttt agtctttata tttcttcaca agaactcttg catataatag gtactctata  32040
gatatttgtt gaataaatga atgaattgta ttttcccata aagatgaaat gcatttttta  32100
tttgaaaaga aaatataacc agcaaatgct acccttatta tcctattttt ctctagattt  32160
gagggcttat tcattatgac cacagcttat caactttgag atgatgaata agtgaacttg  32220
tcttaatttg ggtattttta tttatgtaag aaaaaaacat aaagtataga aaatgcagaa  32280
ttgtacctga ggattatacc ttctgataac gcaaacaaat ttaggtaaaa tgtagattta  32340
aaaatgtgag tattactggt gtcagggaac cccttttgtt cagcttttct gttcacatgg  32400
tttctcaaaa aaaatcatat tttggatgtc aggtaatatt gatgagacat gcccagttta  32460
tacaacctgg ctagttgcaa ccacttgaaa ttgttatcat gcttttgaat aatgcccctt  32520
tagtgtgcac cttgcatttc agctttcttt tctaactctg ttttaatgcc tggataaaga  32580
gtgctcagca caaggaatac ttgcagagtg gacttcccta tggtaaaaca gcatggacag  32640
ctcccaacac tgcaatcaag gacgcctcta aaagctttaa tttaaaaata ataataataa  32700
taataagtct gcatgaagat gatggagccc tctaaggcac atgggcttag agaattattc  32760
ccatctgcaa ccccctcccc ctacttagta gccctttcca gggttatgat tactggaaaa  32820
tggctgttaa tcaccagaat ttttttgac tgcagctgct tcagtcagac tactaatcta  32880
ttaaacaact tcatcttcag tttaaaattt gcattgtaac tgtatagaat aaattttcat  32940
tgtaatcaga gcatccgaga aaacttcttg atatgattta tagaagcaca tttgtttttta  33000
tgtatggacc tctctaccgc tattgagcca actgtttaaa caatactgtg gttgatcagc  33060
ataaaataaa atattgtagc actcttgagc acaagcaaca tttacaatag tcacatttgc  33120
agaatatttg aattgtggca tctttggcac ttgtcaatac aatacccaca taattcaaaa  33180
```

```
acttacccca gatatttaaa atttgacttg aacccgaaag ggtttttata agtttagtgt  33240
ttttgtacca ggctgtggta gagtggtttg gcctcttttt ctaccctaat gcttattaca  33300
ttgccataat ttgaagaaat aacccaaaac cggagtcaat atttagtgct gagagaggac  33360
aaaacagctc taatttacaa agaactcctt taaaacacat ttttatatgt aaaattgaca  33420
ggctaaaaga ggtggttgga tgatgttcat catgttggaa agaatgtttc aattaaagtt  33480
gaacactttc tcttccaggt cttttttttct ccatttttta tttgctgtgc caaggtatcc  33540
atgtgcgttt ttccactgtc atctggctca ttcccagcag atgcacacaa tctgttctgc  33600
tgtcactaac agggttcggt ttatgaaaag aatgtgtcag aacatgccac tatagtcact  33660
tttacaggtt tttttaaaga gtaactgaga atatatgcat tgccctagtt ttattgtgct  33720
cagcccttaa gagatttcta agaaactttt atattcataa accaaaagct ttcttccaaa  33780
catattttttg accaaatatt tactttccat taaaaataaa attttaaaag ttcacaaaca  33840
tctttaatta tgaaatgtat tatattaaaa tttgagtaaa tttttatagg attgtttaaa  33900
ataaaccaaa gatttttaga taaaattatt aaatttccaa ttatgaaatt tactgcataa  33960
tccttcaata catatcttcc ctcatactaa aagcaaacct accttcctac tcaagtcaaa  34020
gcattgttta aaaaatgtat tgtaatagaa tacttaggat atggccgtaa gtaccagtta  34080
tttgatctga tatatagtac tgatttccct aagtgtttga caccactaag ttaaacccaa  34140
agtagttaaa ctaccaaaac tttcttagcc catatagaga cgcgtgatac accatccttt  34200
cacaaaataa tgtgacattt tatttttgta agcatgcatg ttttaaaagc atactagata  34260
attagttatg aaattaattt ttgttcgtta agatttctct atttctattg actgttctta  34320
ataaaaaatc agtttttgtt gtcttcataa aaaataattt ttctggtact atgtgaatta  34380
aaaaaatttg agcaatggaa gttgcattcg tttctgaatt aataagtgta gtaagttaac  34440
agaatttgaa atgtcaagta tgtgtagtaa gtagggactg catatgcaga tagataatgg  34500
acatatttac atgttgtgta cagttcatgg tatttaaata tctcccagaa ttgaaggctt  34560
taaaaaggta cttaagtgct agttttagca ttttaaaata atttttgact tggagaacaa  34620
tacaacgttc aggaaaatta aactttttta aataagttat agttcacatg cactaaaaat  34680
gcagattaag aaaatatttt aaggaatgac aatttgtaca aatgaagcta tatgtgtata  34740
tatatatata tatgtgtata tatatatata tatgtatata tatatatata tatatatatg  34800
aaaactagtt ttagatttct gcctaggaaa aaattacaaa atacatttaa gacataacgt  34860
gattgtgaaa ctgatatatt gtcacataga caaatccagc aatataaatt aagacctttg  34920
tgaaacaact ttgccattat agcaagataa taatttacag ttagaactca ctggcactgt  34980
tgtcacatca tatagattaa ttgctaaatt atctttctag agttctatca tgtgcttgtt  35040
gtagtaagtt ttcttaattc gtaaagaaaa aggaatcctt gttttatatc aaatattata  35100
atgtatacgt gcctattgta agttgatttt ataatgtttt ttgacgatgt gaacatagca  35160
catagattta agatgaatca taaagaacaa ttctggagtt cactttttac tgccaacatt  35220
ttaatttatc tgtaatctta cacatcagat aactcgactt tttatctaac ctgtaagtaa  35280
tttcattgct ttgttttggg taattcggaa tatttgctct tggcataaaa ggccaagaat  35340
cataggtggt gaactgataa gaatgttcta gttgaatcat gtgggttgtc atagcctctc  35400
tctcttctcc ttaaagtacc ggtggtagag gtgggggaga attgtagtgt gttacaagaa  35460
agtagacagc ctcactaact aactatgcca gtattgggtg gggggtgtca cacggacttg  35520
gagaacaagc agaatcattt attttgctgc aatttgaata tacatgacat cctttcaaga  35580
```

```
caaaactcca gaggcaaact tagttatact tatcctgatt tactaatcct taaaatcttc  35640
tatcactcaa agtgtaaata tcatcccaaa tttcactggg ggaaaagctt acgcctctta  35700
gcagtattca ccgaaactga atatttgcag ttgtgttttg ccttgtgaaa tgcttgtaaa  35760
taccagatct tctaaaaagg taggcttttt tatttagtaa tgcttcataa agaagtaatc  35820
agatattttt cccccagctt tatttttaa agttaaagga agagtagttc cgaaacgtga  35880
aattttcctg gttctccagg atatgcaccg tggggccatt tttatctcaa aaatactttt  35940
taaagttttg ccagttgtct tgatttccaa cacagggggt accaccctcc tttgtggttg  36000
ggaggtaatt ctttctttgc gtttgcttag tcataggtct ttttggagca aagacagatt  36060
atttttgtga cactgtcccc aaaatatata ttattcacag actaagaaat ccatcaaaga  36120
gtctcgctgc acgcgtaatg ataggttgga ctgcagtgac cagaaggctc tccactcagc  36180
tttctttagg gaatttaaag acagttgtat cctttttcca tctgcatcga catatgttga  36240
ccagttggtt ttcaattctt gctggcttgg tggttgaaag taggactgat cttctataaa  36300
tataattgat actttcaagt atgacttagg aattccactt ttactttctt cagcgtcact  36360
actcaaaata tctctaataa ttttaataac ttttatgata tgtgtgtaaa agcttatatt  36420
attaatttga aagaattact aattataata agacaataaa aaccacagct aacatttttt  36480
tgagagcata ccgtatactt gagcactatt ctataggcct gaagttttat atgcattaat  36540
tcatttattc ctcaaaactt aatgaggtag gtgcagttac tatcccgatt atatagatga  36600
ggaaactgag gtaaaaattt acaaagtaac ttgtccaaag ttacccactt aatggcagac  36660
ctagaatctc aaccccagat agtctcaagt ccactctctt cttattaagc caaaatctca  36720
catacatgat cttatctgtt agataagaag aaggaaagag tcaattattg agtcttaatt  36780
ttgcctggca tcttagggaa aaatatttag taaccttgga atgacaatat aactaagttt  36840
gtgtaaacat gtttgtattg tttttaaaaa gaagtgtatt aattcttggc ctgtgatata  36900
tacttccaca ttgttgatgt gaagtgagaa aaacatatat tatcaactgc ttgataaatc  36960
ttttcacaag caatgtctta ctatttgcga aaatatattt ttccagctac gatattagcg  37020
ttaattgaaa tgggaaaatc tcgttttatg tcatcactgt ctagtgacca ctttgctatt  37080
catttcttga gctgttttaa tttttaacct tcatttgcaa gaatcatagt aatttatatg  37140
gttttaattc aaaaatgtga gatgtataac agagcctata aatgaatatt aaatggattt  37200
caggagttat tcagtaaatt taattagtgc agatggatat tctagagaat tcaacttcaa  37260
gaacaccttt aaactttttc tttgtagtta aaaaaggaaa acaacaaaac tttaaaacca  37320
aagttagatg tgaaataact actgatgagt tagaacaagg tcatattata tttgaaaata  37380
agaaatatta tatcaagttt attcatcaag tgcatagctt ttagctttta actgaatttt  37440
tctgggttca gtaaaagacc ttttgaaaaa ggaaaaggat catttttaga atttttacca  37500
tgagaaacaa tatgaacttt ctttattcta ataaacagtt tccttgtttt ttcataaaag  37560
tattgccgta ctgctgacta gaagtgagga cagagaggct ggccagaggt caaatgggac  37620
tcagatattt ctgaattacc agatatacaa gctttggact tcaaaattaa tagctaccat  37680
atctttaatg tcatggattc cttgccaaat ttccacagtt catattagta actacatttg  37740
cttccgcttt gtttcactgt tgaagagaat gaaatgcttg tttggattac catgcaagca  37800
tgcaaataat ctatgctctc tgtatttaaa aattcgtcta tttgaaatgt gacttgggcc  37860
gggcgcggtg gctcactcct gtaatcccag cactttggga ggccaaggcc ggcggatcac  37920
```

```
gaggttagga gattgagacc attctggcta acacggtgaa accccgtctc tactaaaaaa  37980
tacaaaaaat tagccgggcg tggttgcggg cgcctgtagc cccagctact cgggaggctg  38040
aggcaggaga atggcgtgaa cccaggaggc ggagcttgca gtgagccgag atagagtcac  38100
tgcactccag cctgggctac agaccaagac tccatctcaa aagaaaaaaa aaaaaaagaa  38160
aagaaatgtg acttaaagat ttggggattc aatgtgttat ttggaattaa ttgatttcag  38220
tgataaacag ccttcctgtc acttacgatg cccactggcg gggaagtttt gtgtgcttta  38280
tgcaatatta agtcccattg gtaacactca gtgttcattc ttctctttcc agcaaaacca  38340
ctgaggccag ttatatctac ttcctaatgt gattttgact aaagttgttt gaattctgtc  38400
tctttggaat cttctaactg taaagcacgc tctaagactc cataaaacac catatttata  38460
ttaatatcca tttgagttgt aaatatgcag gaaataatta ttcactgtaa aggcctggat  38520
taccctaaga ctgaggagga agttatagct gttggctaat tctataaaag ataattgcat  38580
aaacttatta gtaatattcc ttgaagaaga ttgcgatgta gctaatactg cacttcaaaa  38640
gcctttttaa aaaatttaat catccaaaga ctaaaatcaa ctaagtttct cacaagcaga  38700
attcgttaga aaactatggg ctgtaactga tctttggtat atgccaagtg acaaggtcat  38760
aggtataaaa cattggattt cctttgaaca gttagcttag ataagtggtt ctgaatcctt  38820
ggctgtaagg agaattattt taaaatactg atgttaggtg ggcacagtgg ctcttgcctg  38880
taatcctaac tactcgggac actgaggcta cagaatcact tgaggtcagg agtttgagac  38940
cagcctgggc aacatagtga gatccagtct ccaaattttt tttttaaat ggccaggcat  39000
ggtggctcat gcctgtaacc ccagcacttt cggaggcagg tggatcatct gaggtcagga  39060
gttcgaggcc agcctggcca acctggagaa accccgtctg tactaaaaat acaaaaattt  39120
gctgtgtgtg ctgctgggca cctgtaatcc caactactca ggaggctgag gcagaatcgc  39180
ttgaacccgg gaggcggagg ttgcggtgag tgagccgaga ttgcgccatt gcactccggc  39240
ctaggcgaca gagcgaaact ccatctcaaa aaaaaaaaaa aaaatttgaa aaaacaagcg  39300
tgatggtgtg gcatatgcct gttgtcctaa ctacttggga aactgaggct ggaggatctc  39360
ttgagccagg acttcaaggc tgtgctgagc tatagtagtg ccactgcact ccaatctggt  39420
gacagagtaa ggcctggtct ctaaatatat aaatatacat atatataatt tgtgtattta  39480
tgtatattta taatatgcat atttatattt atgtgtattt ataaatatgt aaatacacat  39540
attacaaata tacaaatata tacacacata caccaatgcc caagttccac tcccagattc  39600
agattaaatt ggcctgccat ccaggtattg cagtttctcc gagctgcctg ggagctctta  39660
atgtaaagct tgggttgaga accactagtt aaaagaagat aaatgtgaat ttttattttt  39720
aaataacata taataactgt atatattgat agggtacatg tgatatttcc acacatgtat  39780
acattatagc atgatcaaat aaggctaatt aacataacta tcacctcaaa tatttatcat  39840
ttctttgtgt ggagaacatt gaatacacag tgaaatacca ttcagcctta aaaaaaaaaa  39900
caaaaaaaaa aacagaaaac atggctgggc atggtggctc aggcctgtaa tcccataatc  39960
ccagcacttc gggaggccaa ggctggaaga tcacctgagg tcaggagttt gaaaccagcc  40020
tggccaacat ggtgaaacct cgtctctact aaaaatacaa aatagagcca agcgtggtgg  40080
cacatccctg taatccctgc cactcaggag gctgaggcag gagaatcact tgaacctggg  40140
aggcagaggt tgcagtgagc cgagatggtg ctattgcact ccaacctgag agacagagcg  40200
aggctctctc tcaaaaaaaa aaaaaaagaa aaagaaattc tgtcatttgc aacatgaatg  40260
aacctaaaag acattacgtt aagtgaaata agtcaggcac agagagacaa atactgtgtg  40320
```

```
atctcatttg tacgtgtagt gttaaaagct gaatttacag aagtagagag tagaaaggca  40380
gtttccagaa atggaggcgg gagtggatgg ggaaagggga gacaagacat aggtcaacag  40440
gtacaaaatt tctgtgagac aggaggagga ataagttctg gtattctgtt gcacagtgtg  40500
ttgactatag ttaataataa tgtattgtat atttcaaaat agtgaatctt gaacttgggc  40560
atacaaatcc atgcattctt acagtttcag aaacaaataa acctataaat tgaaaactac  40620
ctttggctct gccaataaaa tgtctactgc tattgcccaa cacttcttgg acgtcaactg  40680
tataaattta ttaacacatc agtcaacttt tcactaagtg tttcatggga gtgtttcatt  40740
agggatacaa aagtgagaga tggaaactct gttgttgagg aattcagtct gatgagggag  40800
ttgaatatgc aaagtgcaat tataaatgta atgtgataaa cactatactg caggcatgtt  40860
gaaaatgagg taaacgctta attgatagaa tgttcagctc ttttgggaga tgactggtta  40920
ggtcaatctt cagtcaagga tgcctaaggt gagtcttaaa tgatgagtca aatcctggca  40980
gtactccaga aaaaagtttt gggggctagt ctgccctctg gaagcatagc agactttcat  41040
atgtttttcg tatggcctgc catattctca actttgcttt ctcatttaga aaagctgtgc  41100
aggccttgcc cagaacttca gattctgtgg aaattggggg cacctaatga agccgtgaag  41160
atggtatcag aagtaggaag tgccaaccta atcttctttc cattctctgg tatgccatag  41220
aaacctcact gtggcagatc tcaaggtaac tgggaggaca tactcctcct cagcgcccac  41280
tcctgcccta tttcctagac acagctgaaa ggaaggatgg cctgatccgg gtcctcccct  41340
gcaacccact gttttgacaa gggatatggg acaagttatg aataagagaa aagggccaaa  41400
cagggagcta cccaagaata ctttatatag aggagattca acttacatct cttacaaagt  41460
aatttttaaa aaactttaaa ggttatttct cgggtttttt ttttccttct tgttctaaaa  41520
gaataaaact aaagaaagac aagtacttca gggatgtcat accagtagga aaacatcttg  41580
tatattttaa aagaacttcg ggtactctaa tagaagggga taaatctgta aacatagcaa  41640
accatgatct tataagacac gtagaatacg agaaactaag cttgtccctc ctatgttgcc  41700
aaacaaacat acacatgtat ctctgtgtgt gtgtgtgttt gtgtgtatga cagaagtcag  41760
aaaaggcaag acatgacagg aaaataaaaa tactagttcc acaaattcta tagaaaaaga  41820
ttgttttatt atttcgtagg aagccttacc ataaaatgaa ccacataaag ttttatgtaa  41880
agagcaggga ttagataatg atctcagtta tataatggaa caaaattcca agtctgtaaa  41940
ccttttggtc gcagctgcta gataacgtta ccttcacaaa ccaggtactt aatgaaaaaa  42000
gacctgtttc atgtggaggg aggtggaaga actgggttgc actgcttact aataccattt  42060
cccagtgact gaggtagaga aataaattag ttgtgaaaga ctgagaactt tggtctaatg  42120
gattgacttt tttggaagtc acaaaatgta gtgaatttga tctcaaatag ataatacatt  42180
aacatcatac atgcaattag aaaattatca ccttgagtaa attaagtata cagcattgaa  42240
tttaattagc atactattag agatttgcaa gtcagtaaat atcacaaggt gaaatttata  42300
tttttaaata caactgaaaa ccctccaaag agtcaatatg atccagataa aaatgattac  42360
tttgcaagcc cttgaaagtt cctaatactg gttctgcaga aaaggggcat atttatcagg  42420
actgttgtct cagaaaggca aagctttctg tgattttaac ttataaatct attaagtgtc  42480
aggttgtcca tatgaatttt tttttctctc acttcgtgca gtagctgaga aactctctca  42540
ggtgaattag ctcagaactg gatagaccgg taaatttcaa gaacatacca catccaaggg  42600
agataatgca acaacatacc tgtgttgcag tggttatgtt tctaagagtt ttaatatgat  42660
```

```
tcatttcaga tctggcttca cattggaatc tcctggagag tttttaacaa gtaacaatgc  42720
cagggaacct ggtccaacaa tcctgatttc atcagtctgg gatgggtctg ggtatcagtg  42780
tttttaaaaa gtgtttgaag tgattgaaat gtatagtcag cattaagaac tactgttagt  42840
ggaacattca aaatctctac aactttgaaa catctttgaa cactagggtg aagcaaatgc  42900
agaacattgg tgttacttcc attctagctg tagaattgag aagaaaataa attaatttct  42960
taagttatga caggaaaatt ttctatagaa tcctgctttt tttcatctgt gagaccagcc  43020
gcatcattcc agtttctaaa ttatcggcat ttctaaagat gaagtaacag gggaagtgat  43080
gaactttata aatagactcc ctaaaatatt tggcatgagg ggtcaagatg taggcgaagc  43140
tggaaaaaga ctttagtttg ggtattagcc agaggccaac agttgttaaa ttctctaaat  43200
ttccttaaga aaggaaagag aatcccttga agaacatttt ttttttctcc aatgtgtagt  43260
cagtgaaacc cagaggggga aaaatgtacc tttcaagcca gaattaggtc atgccaacca  43320
cagcaaattg gaagctctac ttaaactgta gtcttgcagg attgctatgt atcatcttaa  43380
tgtcatgcat gtggtggggc caacacttcc agatcatagc tgctaggctc tgctgagcgg  43440
ggcagctctg ctgggtgaat ctgaccaccc cattgggctg catttggcac acagacataa  43500
cctaagactg tctgaaaggt aagccctgga atatggcatt ttttaaagtg aaaaaaaaat  43560
tacaatttct aaaaacaaaa tatttcattt tgttttatga ttttagaggg gggaaatgtc  43620
aagggaaata gagaatggac aaatccacca ttatgaccag caggcacagc ttcctggcaa  43680
ttgagacaag gttgccaaaa acctacctta ccataaaaaa aaaaaaaagc atacaaatag  43740
tttcatgcat ttattcacct gtccacatta gaagtagcag gattgccccc ttaccagcct  43800
tacagaagtg gaagaaaatt agaaggtact tcattcattt ctttggcact ttccataatt  43860
attagaatgt ggaacctact gtaaaaatgg aacatattgc cattatgtaa aagaaactgt  43920
tgtcctttcc tacctgtgaa acatagggtt tcacaggcat ttccagtcat tattagaagg  43980
ctgaattggc cataaaaatg taacatattt ccattaccta aaggaaattt atactctttc  44040
ctacttagag aaagcattta ataaaatgat tagacctgta tggtttaaga aactttatca  44100
tgaattgccc tatcgaactt tatgaagctg tttaaagaaa atattagtat ctgctacagt  44160
atccaatgtg tttgttctgt ttaaaaagaa aataaactaa aatatatttt tgttgaacac  44220
ttctgaattg actcccacaa gaaaataaaa cctcaaattt gttgacttgt tcataaatga  44280
gcaaatattt ttgcagactt gtagccatta gctttacatc tgtcatgtct gcaaagagtt  44340
tttgctcgtt gagcgcaact tcccaatgtg tacaattaat tagatcaatc taattttcaa  44400
attattggct tcttttagga tgaggttgta gcagttatat aacattctgt caggtatgaa  44460
ctaaaatagg atactgaaaa cattaatgct ttcctcttgc tatagaacac tgtcatcttc  44520
agttaattaa tacaggaact ttcatatgtg aaacggcatt ctccttgatt ttccttgcat  44580
gctggttcta catttttgat aacacaggaa ataaaaagcc taatctgtgc tacatgagga  44640
ttctggaaat acttcacaaa ggagaaaaca cttgagcggg atcttaacag aagagcttga  44700
atgtgccttg tcactgggtg tcttgctttt gagtaaagac tctaacatac cattatgttc  44760
ccaggaatac cgtcacactg cagcttatga ataatttgca tcccaaaatt ctgttttaaa  44820
gttatgttgg aaaatccaga atttattttt tcatggaaag agttttttaa atgcttgtta  44880
ttttctcaca tgaacccaca aatacctagt gtacactctt aataacaatt ttaaaaatag  44940
taagaagcca tatggatgtt gtaatacaaa taacaattat atagttcaag tttgccataa  45000
ccagtaatgc ttaatcaaag cactctgacg agacaggcag aatttttgtg gaaacaatga  45060
```

aaacaatgtc gagatgtgca aaatgtaatc caccatacat aggcctcaga atggtttgca 45120
gtgctccttc aaaatacacg tctcactact accttcctgg ggagaacttt gaacatgata 45180
tttaaataat tagaatgtga agtttgagga ttactgctta aagattcaag tattcttagt 45240
ttatgttttt tttaaaaata gcgtttttta ttccttaatg cagatgtata ataagcatca 45300
ctctaaatgt ttattagttg tctttagctg acatgcagaa cacatgagaa agagatttct 45360
ccaaggagta actaactgat ccaggattag gaaactgaca aggatgtgtg catgtaagtg 45420
agggccagag aaggtctgca cacaatgagg ataaggacat aggtgggtgg gtcccagaat 45480
ccataccctt atcaaatgca ctttgctccc ttctttgtct tctagttaac tcttactggg 45540
ctgcctcctc ctgacatccc aggtgggctt taagttttgt tgcctatggt caccaactat 45600
aaatgcagcc aaggcccatg attaacttgc taaattaatg agcaaatgaa ttctgtcacc 45660
ccctttattc caatctctat ggagtcttgc ttctttaagg gtcccctgaa atgactggaa 45720
aagtaccttg aatatattgt aggtgaatat tacacatgaa ttcctatatg agagacagga 45780
aaaaagattg gtgaggcttg aatgtagagg ttggtcttga ggtgataggc atatgtagga 45840
gcgtggaggg aagattgagg agatcctgtt tttgcaagga ggaaagatgt atgcattgag 45900
ttgatttgaa gtacatattc acaagttgga tttcattatc aagaaatgcc tcaatttgtc 45960
aaaattaaat taataggaag aaaatacttt gctggatatt cttatgagtc taaaaacaat 46020
actgcatgta tttaattcac agagtttttg ttgttgctgt tttataaatt tcattgtttt 46080
taaaatcatg ctttgagatt tttctctgcg tcctctagac ttggaccata atttaagcac 46140
acattcagct actttacagg aaatctgaag aaaggaagtg tattagtttg ttcttacgct 46200
gctatgaaga aatagccaag actggataat ttataaagaa aagagattta attaactcac 46260
agtttcacat ggctggggag gcctcaggaa acttagaatt gtggcagaag gcaccccttc 46320
acagggtggc aggagaggga ataagttttg agcgaaggag taagcccctt ataaaaacat 46380
cagatctcat gagaactcac tatcaggaga acagtacggg ggaactaccc ccatgattta 46440
attatctcca cttggtctct cccattacaa gtggggatta tgggacctat aattcgagat 46500
aagacttggg tggggacaca gccaaaccat atcatttctc ccctggcccc tcccaaatct 46560
catattctca catttcaaaa tgcaattatg cctttccaac agtcccccaa agtcttagct 46620
cattctaata ttaacccaaa agtcgaaatc caaagtctca tctgagacac ggcaagtccc 46680
ttccacctat caaaagcatg ttagttagtt ccacctatca aaatcaaaag catgttagtt 46740
acttcctaga tacaatggga gtataggcat tgggaaaata cacccattca aactgggaga 46800
aattagccaa aacaaagggg ctacaggccc caagcaagcc caaaatccag taggacagtc 46860
attaagcttt aaatttccaa aatgatcacc tttgactcta tgtctcacat caaggtcatg 46920
ctgatgcaaa aggtgggctc ccatggcctt ggacagctct gcccctgtgg ctttgcaggg 46980
tatagccccc cagcccccca atcctggctg ctttctcagg ctggcattga gtgtctgtgg 47040
ctttttccagg tgcatggtgc aagctgtcag tggatctacc attctgggat ctggaggatg 47100
atggctctct tctcacagct ttgctaggca gtgccccagt ggaaacacag atgtcagggc 47160
tctgaccaca tatttccctt ctgcattgcc ctagcagctc catgagggtt ccacccctga 47220
aacaaacttc tgcctagaca tccaggcatt tctacacatc ctctgaaatc tgggtagaga 47280
ttcccaaacc tcacgtcctg acttctgtgt acccataggc ccaacaccac gtgtaagccg 47340
ccaggcttgg agcttgaacc ctctgaagca acagcctgag ctgttccctc aggctgtttt 47400

```
agccacagct gggacacagg gcaccaagtc ccaagactgc acagagcagc aaggtcttgg 47460
gcctggccca caaaaccttt ttttcctcct aggcctctgg gcctgtgata ggaagggctg 47520
ccatgaaggt ctctgacatg ccctggagac atttttccca ttgtcttggt gattaacatt 47580
tggcttcttg ttactgatgc aaatttctgc agctggcttg aatttctcat caaaaaatgg 47640
gtttttcttt tccatctcat tgtcagactg caaattttct gaacttttat gctgtgtttc 47700
ccttttaaac ataagttccg atttcaaacc acatttttgt gaatgcataa agctcaatga 47760
ttttaagagc acccaagtca cctcttgaac actttgctgc ttagaaactt attccaccaa 47820
ataacctaaa tcatctctct caagttcaaa gttccacaga tctctaggtc aggagcaaaa 47880
tgcctccagt ctctttgcta aaacatggca ggagttacct ttacaccagt tcccaacaag 47940
tttctcatct ccatctgaga ccacctcagc ctggatttca ttgtccatat cactatcagt 48000
attttggtca aaggcattca acaagtctct aggaagtttc agattttccc aaatctgtct 48060
tcttcagagc cctccaaact gttccaacct ctgcctgtta cccagttcca aagttgcttt 48120
cacattttca ggcatcttta cagcagtgtc ccactctctg cagtaccaat ttactttatt 48180
agtctgttct cacaccgcta tgaagaaata cctgagactg ggtaatttat aaagaaaaga 48240
agtttaattg actcacagtt ccacaaggct gtagaagtat caggaaactt acaatcatgg 48300
cagaaggcac ctcttcacag ggcagcagga aagagaatga gtgccaagtg aatggggaag 48360
ccacttataa aaccatcaga tctcatgaga actcacttac tatcaggaga acagtatggg 48420
agaaacctcc cctatgattc agttatctcc acctggtccc tcccatgaca cgtggagatt 48480
atgggaacaa ttcaagatga gatttgggtg gggacacagc caaactgtat cagaaaggga 48540
ataaaaatca tgcaacatga aaagcattat tttattcact ggcttttaaa ttatccaact 48600
aactagttta ttcttttgta tcagaaaaat aatctgtgaa cagttaagga aaaaatatcc 48660
aaaatcgtta aaagaagtat atcatcttat tactgtatgt tgtgctattc aaaaaaatgt 48720
aatgatgctt ttctaaaaat ggaagtaatt tgttttatag ataaaaatat tttcaaatta 48780
tttaagaaaa taaacttgaa tatggatata tatttaaatg cttcctatat attctatata 48840
gcacttagca aaactctttc aaatcccaac atttaaaaac agctgtttaa aaatgaacta 48900
taaagctgag gaaaagttcc aaagcttctt tttaaatttg tgtctcttct tcaggattct 48960
tcagcaagga cagcacgggg tccagcaccc tttctgtgta cctcctgcca tgcttgtctc 49020
ctttattgtg catagaacca ctttgggtag taaaccacac ataagctatt ctagaatggg 49080
tcaagccatt cacataaata ctaaaattag aatgaatctc agttctcgga agcacaagac 49140
cctaaaggct ctactgaggt agttgtgatt cattgcagtc cttttttcat atcacagtag 49200
aaaaatatca acttttgtga cttcagtaaa catgattctc aaggtctgtg tgaaatgata 49260
tgtgcacata gcactgtaaa atggaaataa tgtacaaatg tacattattc tcaacccaag 49320
ttagattgta aactccttga gcttggagac tgcaccttac tcatctttgt tttctctatg 49380
gtctgtatga gtctgttaca cataatagat gttccatctt tgttgaatta atttgaagca 49440
agtgaatgaa gggtaataat tatcctaatt caggtgagag agatctagga aaagtagttg 49500
atgaagtatt tccaccatga ggcttttccc aatggtgtta tctttcccac atctgacttt 49560
cagagaactt tttgagtgtc tcttttatgg tgtttactaa tttctacatt gtactaaagt 49620
taatttttaa agtatctttc caagtttgat aaaatgtagg ctctttggtg tgcagaggtt 49680
aagttttatt cacctttcta ttcaggatat acttcctgat tgatttctaa tctctcaact 49740
aacaaattat tttttgcacc acatctgcta tactacctga ctggctgaag gatgttgatc 49800
```

```
ataactactc tataaaccca tggcaatagt atctatttat tgtatcctaa tacatatttc  49860
acagagaaga aaactgagat ttagaagtct catagattaa agctttggtc tcaccaaaaa  49920
tatggttctt atatagctgc aaaaagctgc tctcaatggt ctttaattca ttttacatgc  49980
aggtaataga taaagaatgc ttccacctct ttcctaaatt ataattttac agttcttcct  50040
cagattttgc ccccatgtaa aaattaggaa tgattgtggt tcttgtttgt gtcacaagtg  50100
aggtcatgaa ataacaataa tgttgtcact gataaaacaa tgttgaaaga cacatttatg  50160
atttattagg agacatagta catcttatta tccttgtttg aagtttaagc tttatccaaa  50220
gcattcatgt aaattgtttt atttgttttg tgatgagcat ctgaccatgt ggatcgctta  50280
ttcctgtaaa tatctgaaga ttcaagtaca ttggaaaggg tttatatctt ttataaattc  50340
attacgtgga catctaataa aagctaaatc atgcctttat attttccatt gctgtttaat  50400
atcagatgat gatgggaata agaaaatcaa aatgatattc aaatcactaa gttttacttt  50460
tcaccagcag tctttatgat atatttgttt taataatatt gttgcctaaa atgattgtca  50520
tttttatttt gcatagattt cacttttgca ggcagtttac aattatctgt gcccatttaa  50580
ttatagtgac tttatactgt ttcaacttac taaatgtcta ggcattatgg agctaacaga  50640
acgtttcttc ttaatggtcc taatggaagc tccctggcta ccctgtgtac acagctgttt  50700
ggtaatcaac tcttgtttaa acgtatacaa gtccagccta gaagatctca ctactcattg  50760
cacactcagc tagaactaca ttctttttct ttactttttt ttaaaaacaa atgaacaaaa  50820
aaatccaaaa cagatggagt ctcaccatcg ctcaggctgg agtacaatgg tgctatccta  50880
gctcactgca gccttgaact tctaggctca agtgatcctc gcacctcagc gtcctgagta  50940
gctgggacta caagcacagg ccaccatgcc caattaattt ttttcagttt tacagagaca  51000
gtgtcttgct atgtttccca ggcttgtctt gaaattgtgg attcaagcaa tcctctaacc  51060
ctggtctccc aaagagctgg gattaccaac atgagcctct gtgtctggct agaactacat  51120
tctttttttt tttttttgag acagagtctt gccctgtccc ccaggctgga gcgcagtggc  51180
gctatttcag ctcactgcaa gcgccacctc tcaggttcca gtgattctcc tgcctcagcc  51240
tcccaagtag ctgggattac aagtgtgcac catcgtgccc agctcatttt tgtattttgt  51300
attttagtat ttgtgttttt agtttctcct aaaaatacaa aaacggtgaa acggggtttc  51360
accatgttgg ccaggctggt ctcaaactcc tgacctcagg ttatctgcca accttggcct  51420
gccaaagtgt tgggattaca ggcgtgagcc accgtgccca gctagaacta cattcttaag  51480
agcagcacat gcaccatttt aattatcgct tggaaaaata aaataattaa aataaaaatc  51540
tttgttaagg aaagttttat tgttgtacag tatacttatt tcaagtgatg gttaatacaa  51600
ccagaatcca gtgttcaaat aaatagagag accactactc tgaatggtct tttttgggca  51660
ctaagtttag agtgcaattc tgactacctt ttctcatcat gttttatgaa ttttcttcat  51720
ctcaactttt accccaccac tggtactttt aggtgtgtgc ttttctaaca ttttttagaa  51780
gaaatagctt taaaattaac tttttaatta tatagaaaag atttaaagta tttagttaaa  51840
ggatgtgttt tttaatatta taaatctttt ctgttactaa ccaatgttga acatacagtt  51900
caacatacag ttctaaaatt cttttaatcg tgttatgatg tctataatga tagcagtaag  51960
ttatttttttg tcactatagt gcttaggaat gtatatgact gccaagtaca attacttttg  52020
gtcattcgag ttttcacttg tcattatgga aatgttgcaa acaaaaatac aaatagtttg  52080
ataaattgct tatattccag atatataaag tacttattga ttgagtctga ttgtattgat  52140
```

```
tgcattataa aggttcaagt aataatcatc ttggtacatt ttagtacaat tagaatactt  52200
taatctcttt gagatgctga aaatacattt tataatttcc agtacttgca ataaatatta  52260
caacctattc acacaaatat aaatgcatga aactatttta attttaaaat ataaaataag  52320
gagtcgtaca tgaccaaata ctgaattttt aaaccttaat taagttagcc gacttatcat  52380
cgagaatgtg aaattattac gaatagtagc gtatagaacc ttagcaagca gaagctaaaa  52440
gctagtagaa aaattagcca gatcctagca gataggctgt ttatattgag tgggtttagt  52500
aagtctgcat ccaatacttg tacaggttga ttgacatcaa aatggaagac aaagtgaagt  52560
catggcatta ttcaaaaatg aagcaaagta gccaagtttt ctactaaaat acaattgacc  52620
cttgaacaat gtggaggtta gggttactga ccccccatgc agttgaagat ttgtatataa  52680
cttttggctc tccaaaagct taactactag tagcctactg ttgactggaa gccctaccaa  52740
taacacaaac agtcaattaa cacatacttt gtgtgttata tgtattatat actgcattct  52800
ttttttttt tttttttgt gagatggagt ggcactctgt caccaggctg gagtgcagtt  52860
gcgcgatctc ggctcactgc aacctccacc tcccgggttc aagtgattct tctgcctcag  52920
cttcctgagt agctgggacc acaggtgcac gccaccacgc ccagctaatt tttctatttt  52980
tagtagagat ggggtttcac cacgttggac aggaatatac tgcattctta caagaaagta  53040
ggctagggaa aagaaaatgt tataaatgtt cttaagaaaa tcatagaaaa gagaaaatat  53100
taagttaaag tggatcatca ttaaggtctt catcctcatc tttacattga gtaggctgat  53160
gaagacgacg aagagagggg ttggtcttgc tgtctcgggt ggtagagatg gaagaaaatt  53220
catgtgtaag tggactctct cagttctaac ctgtgggtgt tgttcaaggg tcaactgtac  53280
atatatattc tttcttaaat aattatatgt atgtgtgtgt gtgcatatat atgtgtgtgt  53340
gtgtatgtgt atatgtgtgt gcgtgtgtgt gtgtcataga gatcaccaaa atcagagtgt  53400
gtacacaaat ctggaggtta caattactgc tccatgttga agtgaagggc attctgggca  53460
tcatagtggc cctgaaggtc ctcttcaact ctgaatcctc cataccctca tctactttgg  53520
cagttcccac tcagatgctg cattcttatg gcaatcaaaa tagccattat ttttcattaa  53580
aatgttggac tctttttagt gtaatagtta aaaagcagat gctggagtca gatcctgtaa  53640
cttcaaaccc tagatctacc tcttaccatg ggcaaaagaa gtcctctttg cctccatttc  53700
atctgtaaaa tgggcataat actacaaagc atatttctgg agattagatg aactaatata  53760
tgtaaaatga atagaatagt gcatgacaca aaacaagaat taacaatcat tatccttttt  53820
aagcttttac agtcaagaaa ttttgctttg aggacaaaaa accaaacact gcatgttctc  53880
actcataggg ggaagttgaa caataaaagc acatgcacac aggaagggga tcatcacaca  53940
ccggggcctg ttatggggtt ggggggcggg gagggatagc cttaggagat atacctaatg  54000
ttaaatgacg agttaatggg tgcagcacac caacatggca catgtataca tatgtaacta  54060
acctgcaagt tgtgcacatg taccctaaaa cttaaagtat aataaacaaa caaaaaaaat  54120
aaattttgct ttgaaggatt tttggttttt gccttttgag aggaaggtct aggaaataga  54180
ttttataatt accacataat cctacattat cctacaagct accctaaagt cattaaatat  54240
gactttactt ttgtcattta tctcttcagt gtttttttaa aaaagtattg gagtgaaatg  54300
ttaatggttt caattcaaat tattaaatta aaaatggatc tagagtatac tggatttgct  54360
aatttctgga agtttctgca tttcgaaata ttgattaacg atagataatt tcttaaggca  54420
gcttgcagat tcatttgcct gaaacagaga aaacaaaact ttaataatgg ccaatcatga  54480
atgtgattga tacaaagtta aacacttaag acacagatta aatagaataa atatgttcaa  54540
```

```
acttttattg tagattttta aattgagtct tagataacat tgcatgttag tcaaatatca  54600
cactcattct ctgtatatat attatgtgca tatgacctta ttatttattt atttttaaca  54660
aataagtttt gcaatctttg caggacaaag aagagatatt tcccatagaa ttcaacagat  54720
tagccaaaat catgtgtgct ggctcttaga tatgtgaatt ttaagggtta agcagttgga  54780
gcatgtggat ttatgaatgc tttttatttt caaattaaat tatttagaaa caagtaaatt  54840
aaaaatactt taaaatattt taaagtattt ggcacaagaa ttttttttt ttttttttt    54900
tgagacaaag tctcactctg ttgcccaatc tggagtgcac tggcgcgatc tcggctcact  54960
gcaacctctg cctcccgggt tcaagcgatt ctcctgcgtc agcctcctga gtagctggga  55020
ttacaggcag gcgccaccat gcccggcgaa tttttgtatt tttagtagag acggggtttc  55080
accatgttgg tcaggctggt ctcgaactcc tgaccttgtg atccacctgc ctcggcatcc  55140
caaagtgctg ggattacatg cgttagccac cacgcctggc tcacaataat attattttaa  55200
gaagtatttt ccaatattga agaatctttg tgtcatccaa gaacacatac tacttacttc  55260
tacatcaccc gttaagaact ctaaatacct tattcattag tatagaaaat cttttaactc  55320
tttcacagag aagaatgaca taggcaaatg gaatttgtat ccccaggagt gtcaattttt  55380
ttaccaaaat ccaaacttaa ttttcatcag tgtgcccatt tttataatgt gcttacccca  55440
gttgcaaatc actagttaac agtgtggagt gagaagttat actactgaag atttcaaaat  55500
gtgcctcagc ttatctacct tattatgact agaataatta taagaattaa ataatatgca  55560
taaagcactt agcatattgc ctattatcat tactatgtag agagatagaa atgtgtgaaa  55620
atgggagttt ttaccttaag gatgtaattt ttcatccgtg taagattacc caatattcta  55680
taaaataaga gatgttacat aactagaaag ttgtagccat tcaaccattt ttctggaact  55740
agctttatta tcctctacta aaatggtttt ggccactata actttggtct ttcaaataca  55800
gatcattatt aagtttttaa atccagcaga ttctctccac aatgtctttc tgctctttac  55860
ctttgaggag ttttttaaa tggcaaatta ttctatatca tctttttaaa agttatgaca   55920
attaaagatt taaaatctca gctaaaatat tatatatgga tttttagtta cattttatgc  55980
ccaatcgcta gttgtaagca tagttgtaag cgtgctgaat gaagtttatt tgcactttgt  56040
gtattcccac tttttagtta tgtactttat aagtggaatt tatttgactc taacttttgt  56100
aatttagata atcattgttt gtgttcaaat tcaaatgtga ggaactttga atgcatttgt  56160
gatccaagtc attaccaaaa attgtgtaaa tataaatgag ataaacaaaa tagaaatggt  56220
ggtctcatat gaaaggtata gattggtgtc tgatgttgta tcctaatttt atgtaccaga  56280
ttcacatgtt aaaattctat ctagaggtcc tgggattatt ctctctccct tttttttaac  56340
atgtgtttta tagtcaagtt actaagtgaa aaaaaagaaa agaaaagtgg taatagagga  56400
agttggcaca gagaattgtc gctgtactca gctcttttta tctttttcta aatatagtct  56460
taaaatattg tccaggtcag ctgatgtaag cagggaagtg cttcttcatg tcttctttct  56520
ttcccagtca tttcaataat gttttggtga attaaagtat gtaagtgaaa caaagaaatc  56580
agtgctgagt tctgatagca aattgaaaat tgaaattgct aaatttccag atattataat  56640
agattgctaa tctcaaaact aggactacat tggtattcta gggctaaagt gataaatttt  56700
taatagagat gtctcctacg agcaagtctt attataacat actagaatat catttattct  56760
ttcagggtgt gatttattct atttaaatat aagtcctgta aagaagatgt gttaatctgt  56820
ttttactcta cataaatatg actgctactc tctagtcagt agatgtattc aaaagccaat  56880
```

```
atgtctacac tctcacattt cttctgtaaa tgatgaataa tgttgataaa tgaaaattac  56940
aaatccgcaa tagagcttaa ctattgaata ctaaatcatt ctgttgctaa ctccatgttc  57000
cagtgacatt tttgatataa aaagacgtca ttcctgcatt taaaaaatat tttgtgcttt  57060
tgcagcaata taagcaaatg tacatttgaa agaaaattca caatgcagcc acaaataatt  57120
ccctttaaga ttcaaggtgc catttcaaaa atggttcaat tttcaaagta gaatatttaa  57180
aacctctttc ctgccagact atatccattc cacgtgtttg gtacaattaa aatagaagag  57240
ttggtggaat gaaactcttc catctatatt ttggaaaaac atattcactc acctcagttt  57300
gtcagtgtac atttagaggc tggtcattat gcagtagaaa aaagaagaag gcagctccaa  57360
ctcatgtgac tgacatactg aatatggcca ttaatacaac ttgacagtga ccttggcggc  57420
attacaggta atctccctgc agggataaac tgtgtttgaa tgatatttct accatgttga  57480
gcacaaagag atttctcctt ggaactttac tgcttaattt tcttttatgc taacaaagac  57540
attacagagt gatttttgta atgattttct ttttcctttt gctctctgaa atgacagttt  57600
actacatggt attgctgctg tcatttttct gtcattatag ggaaatgcca tatatttgta  57660
gcactttcgt aaagtgttga agtaggccag gcatggtggc tcacgcctgt aattccatca  57720
ctttgggagg cagaggtggg tggatcatct gaggtcagga cttcaagacc agcctgatca  57780
acatggtgaa accctatctc taccaaaaat acaaaaatta gcctggcgtg gtggcgggca  57840
cccgtagtcc cagctaccag gaggctaagg caaggagaat cgcatgaacc cgggaggtgg  57900
aggttgcagt gggctgagat tgcgccaccg cactccagcc tgggcaacag agctagaatg  57960
catctcaaaa aaaaaaaaaa agacttgaag tatatattat ttttattata ggagtaaata  58020
tgtaattgaa tgttatacca cttttaacaa agttctaata agctgaaagt acatatcaag  58080
aagatatagg ctgaaaattc aatgttaaga aaaatctttt attatgtatt ttataaaaat  58140
tatcagcacc aaaattagct gggtgttgtg gcgtgcacct gtagtctcag ctacttggga  58200
ggctgaggca ggagaatcac ttgaacccag gaggtggagg ttgcagtgag ctgtactcca  58260
gcctggcgac agagcgagac tccatctcaa aaaacaaaag ttttctgcac cataagttag  58320
tgttattacc atttaaaatt tatttagatt atgtaagata aaaatgtgta tttttatcac  58380
caacttctga gatgttcacc atagaagact catatgcatt attgcttgtt tcctacttta  58440
gataagctta tcacacagga agggaactgt gatgcgtaag attcaggtaa atgaatggaa  58500
aagatcatga caaatagtga aagtgtactc ttcctcaaaa cttctactgc tgttgtaatc  58560
tcagatttag tggtatgtcg atactgaaat gactacaaaa aagaaatttc acataatgaa  58620
agtttggctt attaaaaagc acttaagtag gtcgtaattt cttacttaca gttgcttcta  58680
cgtcatattt caatgcagga aatgaacagt gactataaag gaagagtttt ttccataatg  58740
tggatccatt taaaaacttt tccttcctga attgtttctg gggtcttttg gcaatttgaa  58800
gcagctgttg acaacagcaa ttataggcac cattgacacg ggaggatatg acagttgcag  58860
ttaagcgttc gttatttgta atgttcattc tggcttcaac ttttacatgc agttcaaatt  58920
aattaacatg gaattaaaac aggttcactg gtccttgacg ttttttagta tcctatctat  58980
tgtaaagtat taaaaagttg cttacaatca atgggtaatt ttaaatgcac aaggtgaact  59040
attttcatac acagaactct taagaatcat ttgataagaa aggcatagac atttattaga  59100
taagacatgt tcaataaatt gcagaacacg gcatttctca ccaattcctc tataaattta  59160
acctttagca gcacattttt ccaattcatt gtcaagttaa tctatatagt cagagttcct  59220
aattatgttt acattactga catacaccaa atggaaaatt agagatatct tatccctagt  59280
```

```
tataagttgt aagtaaatac ttgctggtat actataacac tatttaaaat tttaaccatg  59340
aggaaaagag ttgtttttgg aatgacttta aatagaagtg cattaagaaa tataatttga  59400
atcagagaaa aagttagatt tacttagtat ttttggtgta ctgtgttaaa actacaaata  59460
gcagtatatt ttcccagttt tcaaagagtg gtaacaaaaa accaagcaga aacaaaacaa  59520
aaacccttct ctaatctaat aagaaataaa cttcgaggtg tatttttaga taaaagctct  59580
gatcgtggtt gtacttgaat ttgatatatg tatgtcactg tcaactgatt tcggactttg  59640
acatataata ttttaaaaca acatgataaa aatatttcct taggcctttt tgagaacttg  59700
gactctggag tcagcctccc ttatctcaaa acccaatttt gttgcttact tgcagtatag  59760
agttggacaa gttgtgcatt ttttcaatgc cttgatttcc tcaacagaaa tataatatga  59820
agtataatca tgagattacg aatttgcctg agattaaggt ccaattgaaa tatagaaata  59880
acatgcctgg ggcatgctca ttaaatttta ccacttttac taggatgatt taaaattgtt  59940
tcgcaggggt gcgatggctc atgcctgtaa tcccagcact ttgggaagcc caggctggtg  60000
gatcacgagg tcaggagatc aagatcatca tggccaacat ggtgaaaccc cgtctctact  60060
aaaaatacaa aaaaattatc caggcgtggt ggtgcgcacc tgtagtccca gttactcagg  60120
aggctgaggc aggagaatcg cttgaaccca ggaggcagag gttgcggtga gccgagattg  60180
caccactgca ctccagcctg ggtgacagag cagcaagact ccgtctcaaa aaaaaaaaaa  60240
aaaaaagttt cacaggaaca aacaatcaaa cacaaattaa gacgttgttg ccaatttca  60300
aatttatttc ttcagatttt tttcttctgt gtttccaact tgaaatagaa tctgttaaca  60360
tgataatttt ctggattaga gaaagtcata gatatttgtt tcaatagatc atagctaata  60420
aaaattttaa ttagaaatag aagaaacata tatattacat agttaacacc tctcactttg  60480
ttgtggagaa attgagtctt agaaaaaatg aataaggtat aaaacttgaa tttcagacac  60540
atgaaaaatg tagtttaaat gtaattgtgt aacataaatt gtctgcctaa taattggtct  60600
gcctcatttt tgcaatgtct caatagaatt ccaaagatag attgattttt ttagcttaat  60660
ttcaacaatt tgttggttca cctttgaggg ttttttttgg ggggaaccaa atttaaataa  60720
cacacaaaca atattttacg tgatgtaaca tgtctatcca tctcacatgg ataatggagt  60780
aagataccca aatagaaata gaaatgcttt tttttttacc atagaattaa aaaaaaaaaa  60840
aagcaagcaa aatacacata taactagaga gatttttata aagcccttca tccctcccaa  60900
aaatgagata ggaaaaacgt tagggttgac aagataccac cccctaaata tcaggatgtt  60960
ccaaaataac tccgtctttt gtagctccca atcagtagcc actgatgatc tctgtctgtc  61020
ataccctcct tctccttcta gagcaggact gaaggagggg cagtgtgttt ctctggggag  61080
atggttgtgg tcagcatcat cacgtgccct ctccagtcca gacatttcac tgttccagaa  61140
tagaacccac gcttaatttc aaggattctg gaaaagaaaa agttgttttt cttcacaaat  61200
tattgagatc ctaacccaga atgtcatatt tttaaagaag attattatta tttagattct  61260
cataagcaca tgaaaaatgt atctaggaag ttgacatact ggcagacatc tagctacaca  61320
taagaggggt tttctccttt atctcacctt tttcctactg cgaatttttt caacatactt  61380
aatgaaagtt aaaattatga caaggaaact atcacagtat ttcccatttc tttatttact  61440
gtaactttgt ggctgttgaa tgaattctca ggaaattttt tttcactgta taatttctct  61500
ttttttttt ccatattgtt gacgtttgta atggcactgt ttctaatcca ctatctttta  61560
ttatatgtta gagagtcatt gattacttgc tttcatcctc atataataga aatatctaaa  61620
```

-continued

```
tattacagtc acagattcca cagacatgta atatcagaaa acatgaaagt gagttagctt  61680
tcttgtttta ctagattttt tttctttcag taaagctagg aaaatattat taattaatta  61740
gtttagtttt catcaaacct ggtgattggc cggattctta atattgtagc acccaaatac  61800
aggtaggaat taaagatctg aagaagccaa caataggaaa gatgaatttt aatggatcag  61860
atttcaaaga acttgtaaat attacaagat atttcttata aaatatacta tgtagcatag  61920
aggattgcac aaatggtcaa agaacacttc atcagaaatc acaagcctta aaaagaagta  61980
tctggttgac taaagaaaga tctgtatgag gaatggaaat ctgaatgtat tatgagaata  62040
ggagaaattt caaatagtat aaaaataaaa gttctaagaa ataaggctta aagttggata  62100
aggagaatca aaattaaaag atgattttta tgaatttgtt taaccaaaag caacaacaaa  62160
agataaaata aaacgtagcc catttttaat gtgctatcag gagtgtgtac gttccaccag  62220
ggcatgaaat tttgtctgtt ttattccctg acatattaca tagaatagtg ccttgaacat  62280
agtagtgact cagaaaaaaa ttgttgagtg aaggaataaa tgaaatgctt ctttgcttta  62340
tttttcacct ttattatgca gcgaaatgaa cacatgcttg tagccacata catgaaatgt  62400
aatacaagta tgtgtgactt atggaatcca ttgatactaa gaaacaaaac aaatttcatg  62460
gaactcctcc tggaaaggtt tgactaaagc ctaagatcat tttttttct ttgcttcttt  62520
ttttcttctt ttttttttt tttttgagac aaagttttat tccatcatcc aggctgaggt  62580
gcagttgtgc aaccacatct cactgcagcc tgaaactcct gggctcaaac gatcctctga  62640
tctcagcttc ctgagtagct ggtactccag gcatgcgcca ccacacccac ttaattttta  62700
aatttttgt agaggcaggg tctcaccatg ttgcccagac tggtctcgaa ctgggctcaa  62760
gtgatccatc tgcctcagcc tcccaaagtt cagggagtgc aggtgtgagc cacagtgccc  62820
ggccctaaga tcatttcagt agcaggaact attttaacat aatggcatta cggggccata  62880
ggctgttagt cttaagaatt tttgagtaaa gactaggagt taactatcac actgataaca  62940
tttcttaaat gaaggatgac gctgggaacc acaattagta actctcttat ttgcagactt  63000
aaaagtgtac aaggaaatat tgccatgaaa tccatgtgtt atttatcttt aaaagttcag  63060
ggcgtgagta ttaagcaaca tagcatcata taagaactgg tgctatgaga atattttcat  63120
ctttgttaat aaagtgtgaa ggaaaaagga taggtataat ttcaactttc taaggctttt  63180
gattttcttc catatgacat cctcatccat aaattgggaa aatatcatct aaaccacaca  63240
cagattttaa tggtagctaa aggaatagtg aattaaataa tttagtcatt acattttaaa  63300
tgctaacaaa tcctgtataa agagtgcttg aggtctggcc cttgaaagat aggaattcag  63360
cataaccttg gtaaactaga gaagtggtca gaagtcttga agccaaggag aaaaaaaaac  63420
aaactctcta aatacaaaat gtggaagagt tggctagaaa caaatctggc aagggaaaaa  63480
ttacaaaatt gaaataagtg aaaaggtaaa catttacttt aaaattcatg cagagtgtgg  63540
ataaataaaa atatttattt gataagaata tacaacaaaa gcacttttca aggactatgt  63600
atatttttgg actccagaga tctaggcaaa tctgatgtga aatgatgagc tgcaaagatg  63660
gcgaaaaaat aaaaaccagc gtaaggaaag attaaaagaa cagacataaa gcaatacaca  63720
atattgaagt gtatgacatg aggacgtgat caccaaatgt tgttctctgt acaaaggaca  63780
gaacaagagg agtggacata aagtattctg tgagggatta gctataagta agaatttcct  63840
gagagtgaga gttgtgaaac atcaaaatag gatactgagg aaggttatgt tgctcctttt  63900
ccggaaggcc ttaaaaatag gagaggtgga atctttgtga aataatttgg gtacggtatt  63960
atctgaagga gggaaaaatg atatgacctt gcataactct tgccaatatt aatatccggt  64020
```

```
gtttctactc ttaccttaga tgaatggaaa atacaaatat gtatttctaa ccaaaagaaa  64080
agattttttt ctcttttttg acatggcaaa atttatcatt ttcataaaga ttcattttaa  64140
ggcagttgaa atttccaagt ccattctgga attctccata gtaaatttag tgaaacacaa  64200
aatattcata ttaactaatt tatttcaaag ggacttggta gaggttttgt tatgcttatt  64260
gtttttctat ttcatacgat acaaaagaca aatactctta tataattttg aaagttagaa  64320
tcctcaggat tgtgaccaaa taataatttg gtatgtgaac tagttacttg atggaaatgt  64380
ccgctttttt agcatataag agtaatatgc acactctttc cttttcagaa cacttattac  64440
tggacccaca aacatacctg agggacacgg acataaaaat tatcctagag gtgtcttcac  64500
tttgaaaggc agtatttgcc aacagattcg ttcttactga attacaaatc tcagagattt  64560
cctgtttacc agaagtcctc ttggagtgca tgggatatag aagcagccat tttgagcatt  64620
cgctttgcac catcaactgc ctagcatctg aaattgaagt cagtcttaca taggtaggta  64680
ggtagagata gatagataga gagagagaga gagagagaga gagagagaga taatgtggcg  64740
ttgttgcctt atggagtttt tgaatggttc tgacctgttc tcatcaacta ctacaataac  64800
atatataatt atgtaagtga atatagatgt actatatatg tacaaacata ggtacatggt  64860
gttctgccta tgaaagtagg aaaaaagtct gacaaatgct gaatatatat atacacacac  64920
gattacttcc tcatgctgta ggctctgata gagcaaggct acacaataca ttgtgaaaaa  64980
actgtcatgt taacttctat aatgcaccaa aatgtgcagt attttccaac aattataaat  65040
atatcgccaa ttatgtcagc tgttcttata caattagtat attttattag gcgtgtgtct  65100
tataaagttg aaagccgtaa aattccttct aaaataatgt acctaaagag cttgaattgc  65160
acaattaaac tcagagctct aaaacacaaa gtattctgaa gaagtaggta actgtataaa  65220
attttgaagt ggaaacttcc ctgtaaatag aaggatttgt agtagaccat aatttgagga  65280
gataaggaga agaaagagaa agagcataac gagaaggaaa aagaggagtg gcaaggggag  65340
gagggtaagg ataatggcca gggtcatacc agagctggtt aggtgtgttt tagaaaccta  65400
ctcaaggtac tttgaaggaa agcaaaatga ctgcttcaag ctttggggat gagatatctg  65460
tgtaattctc atctgtaatt ctcagatgag aattctgtgt aattcttaac ttcatcataa  65520
gtgaaaatga ctctcctgac ccattatcag gaagacaatt cttttgggtt tctttttccg  65580
ggaattgtga agaatatata ctgatttata cagtatacat ttacctggtt ttccttgtga  65640
acacattcat ttgtagaaag tagaaaaaaa aaaaccaaaa acagctgctg atgatcatcc  65700
agtaaattat aatagtaaag acaaatatct aacttacatt ctattcccct gctggcacag  65760
ggaagtaaac tcatttttgc catcaagaat aagaaaatgt gagatgagtt gaagaacact  65820
cattttaaaa ataatttgta gattccacca actcctgaac atcacatttt ctacatagaa  65880
ttttaagttt taagtactcc cttgaatatt acttagcagc atagagaagt aacagagtat  65940
gtgattcgat tctctgagtg tgagactgga ttgatatatt gatccaatat tggtatattg  66000
atatattgat attgattata gctctaacac tagctgtgtg accttgggta agttacttaa  66060
ccactctgtc ctccagcctt cttttctgta aaatggaaat tgtaatagtg ccttcctcat  66120
aggctgtttt gaggattaga gttaatatat gtaaagcttt taatacctta gtattttcct  66180
agctattatg tatttattaa acttctaaat gtgattagtg gtccaaagtg cataatgaaa  66240
ccttagtctt aactgtttat attgcttgag gctgaggtga acatatcctt caatatttta  66300
aaatatggaa gaaaacaatt ctatttatcc aaacaataac ttgtcaattt attgtttctg  66360
```

```
taggatgata cttttgtgag aatcattcca accctcattt ttgttttgtt ttgttttgtt  66420
ttcctccttt attgaatgca taccatttag gaacttgaaa ggggtcttag agactgaacc  66480
cggctccctt tttatgtctg aggataatga gacttaaaga agttgactgg cccaaagata  66540
tgcagctagc gaacccaact gagagtctga ctccaaatgg agctttcttt ccactgtgca  66600
gtattgcttt gcgcttagtg ctttgcggtt tggaaacaaa ttgcactctt taatggcaaa  66660
ataatttatt aatactttta cttcaagtga acagcaattt tctgcacctg atcttatgtt  66720
tgcacttttt ttataaaact gaaaaaaaaa agttttccat tgttttatca tgtcttcagc  66780
aatactattg tattttcctt gtgccaagca ctgagccaag tattggtctg aagtatttca  66840
gcactgcagt gtattcattg gtcaatggga agaagcttgt tattttcttt aaagctagca  66900
tttccaaggg atatctgaaa tatattggga aatagtccag attatgacat tcagcatgta  66960
gaagaatatg aaaagtccta taacaaataa atcagttttc caaatatatt tgatttgatt  67020
tcctgacttt tttttttttt tttttttttg agaaacagct tgttaaaatc ttaggaacca  67080
gtaatctctg gaatccactt tggggaatgc taatttaggc actttgggat ctctaaggaa  67140
aggaaagtcg tgagcttgcc tccacccgag agtgctttct tttagagtct aggtttgaga  67200
gaatcaggct aaaataggat ccattttagt aacttctgat ctatagtacc tgatcttttt  67260
tacaggggaa gcactgtaat actttccgtt tagtgttatc tgccgaggat gacttgggct  67320
atccttgaaa acagcctggg acagaatgtg tagacatgct gagataagga gcctcctgct  67380
aggccttcgg cctagaaact gtctcagctc actctggccc agggcaacat ccctctgcag  67440
cgtgcctgtc cttgccctgc ctggattgta tggaggaaac attttgctcg tctgagaaca  67500
cctctattcc tagctctttg acagtttcac tttccatatc ccctcagttc caaacatgtg  67560
gaaaaagaga taaagaaagg tgatgaaatg aaaaactgga gtggggaatg ctacaagtag  67620
agaggagaaa ctcatatttc catgtctggt ttgtatgcag tcatgactgg gttttggagg  67680
gtgaagcaaa tgtatcccag aggtcatcct actagataga cagggaggga ggtgagaatg  67740
caatgtgaaa tattggttag cactgagaag aaaatcaaat gcaatttttt gttataaatat  67800
ctataccatg atacatttag aaaagaaaaa tatagttttt atttttaaaa aactttcaga  67860
tttatgtttc ttttgtaggg catttgattg attgtaaatg aaaatcgata agtgttcatt  67920
taggcttcat ggtaaattat ataacttacc ctattttaaa actgataaat tatgttcacc  67980
aaacaggaaa ttagaagaaa tggtttggaa tagagaatca aatctattta taacttcctc  68040
caaaaaagag gagggagaat tgaaaatata taccccctaat tccttaaggc ataggaaatt  68100
ttgacctttc cttaaaatac tatcatttgt cattaggcat ttctgtttca caaccttaaa  68160
aattaaagtg ggagcctgtt gtcctttaat tttctattta ttagaattta taatccttcc  68220
tttttttttt ttttttttaa gatggagttt ctctcttgtt gcccaggctg gagtgcaatg  68280
gtgcaacctc agctcattgc aacctctgct tcccaggtta aagtgattct cctgtctcag  68340
cctcccgagc agctggaatt acaggcaccc accaccacac ctggctaact ttttgtattt  68400
ttagtagaga cgggatttca ccatgtaggc taggctggtc tcgaactcct gaactcaggt  68460
gatccacatg cctcggcctc tcaaagtgct gggattacag gcatgagcca ctgcgccagg  68520
cctgtatttt tttcttaaaa acgctttcat ttaaaatact agataattca atttgtctat  68580
tcattccaag ttggaaatta atctgttggg cttgaggcta cacagcttaa tctataggtg  68640
gggatgtcca aagatacatg aatatttcca atactgtgag acactgggat tttcaaatac  68700
tgctgacatc ttaatcaaag ctctgctgat tacttgggag ttgggtcctt tgagagatga  68760
```

```
aataaatcaa cctagcccac tgacaagtta cattagtacg gttgtaagat tgttttttc  68820
tcaaatttta aaaagtgtga tttttatata attctatatt ttacacttgc agaaattttg  68880
cattgtattt atcagattct tcatggtgtt atccatagtt agcattgtga aatgaaaaga  68940
ggtgtttcaa ccagtggcca ttgccatcat gaaatactca catttcaagg gaagagggat  69000
gcttttggac tcaattgatg tcaatttaga aacattttgc attatgctat attcctagag  69060
cttcaaagta tttacaattt ttataaaatt atataatatc agtgaaggaa gcaagtttac  69120
acaattagtg tatgaaattg agttgtatcc atctgaattt ttacaaatga gtgtggtttt  69180
gtcttttatt tgagcctcac aacctcataa tagaatgtgt atgttgttac tattcccact  69240
ctatagagaa agagactggg gtttagaaaa ctatgacttg gccaggcttg taccaccagt  69300
gacaggcaca gtgacggagt attcatcctc caaataatgt ctgactccat tgtggattag  69360
ggctttcctc aaacgtcatc tcctcaaata acccctccct ataaatcagc ccaatagata  69420
gccacctctg cccttctcca cttcatcacc ccttggtcca ttccactgcg atattttctc  69480
tatagcactt ctgtatttaa aatcatcata ttggtgcact tgtgtgttgc ccttttttccc  69540
cttagaacgt aagcttcatg aagactgaga ccttctgttt tgttttcagt ggtgtccatg  69600
gcacgtagca tcatgcttga caacttcatg tctctgtgac tgattgaatt ttgtcattga  69660
tatctgtgat attaagcatc atgattttgg ctcatggtat accccattac agtgacttag  69720
ccagggtttg attcccatgt actccaacct gaaatctaca atcagaatac accaagtatg  69780
ttacatgtaa ttggtctgct ccaaagctgt ggcaggtagc gtggactgca ttctgttaga  69840
ggacctgaac tccatgtgtg tgccttaatc tcatttctga catttaactg tcaccctgcc  69900
tgcccaccac cctgagagaa gttctgaagt attcgaacag tgtgttacac agccccagca  69960
tgttttacag tgagccaggg cagtcatgga gaggtctctt gttctggagt tttgcacaga  70020
taaagggagg atatagtttt gagaggaatg ctataactac aaagtgcatc ctgaaggcca  70080
tttagctcac aatgaaggtc tgtgttttaa aatagcacta taacaaagta actacagagt  70140
tttggcaagg gcttcaacta tttatagaac taagtaagga atagtaaata gtgccacagt  70200
acccagttct cccttgccat aaccccaaac ttataagaag cactataatt atatttttct  70260
acttaaaaaa aatcgtagta gccattatca gtttaaccat acggaagctc aggctgagat  70320
ttcttttttta aatgcatagt tttgattttc agcagctgca ctgggtcttt aatcatatat  70380
tatctttatg aagccttttt ctaacatatg ttaattggct gttttctgtg acaaattatg  70440
agctcttact ttgatgaggt tcaattgcaa tcatgttgga gtcgagtacg tagagtttcc  70500
acccctgctg gctcctcaaa ccactacaaa catccgcacg tcactacagt gctgagtaat  70560
ggcaggattt gggctggctg atttctctac agattttttt ttccacagga tattttcagc  70620
ttctttgtac taaatctgtt gcagggtttg cccttttttag cagaagcatg ctctaaaatt  70680
aacatcaaat cttattggag attactataa tacatgagaa atatttcata attcaacatc  70740
cagtgtctgt actgctttgc taaaatttta gtacatttat tacacatttt taaaagtcag  70800
tcagttgtaa ggctggtaag tattttctat atcatcagca ttttgtaaca aatattttga  70860
attttcctct tgagagggat acagttatta agtgaataga tgatcaggta tatatttaat  70920
tatcataaag aaaatgcaca taatgttttt cctggcatta ccaaatttat cactatgtta  70980
aaaattccat tgtattttca tttttctttg cagttaacat ctgttggttg agtcataaga  71040
acaattacat gtcccatcaa ggctaatgtc ctataagatg catagcatgt atttcaattc  71100
```

```
tctaacagtt tttaatgtat gattaggatg aacagatatg ttctaatcca tctgctctga  71160
gaactgtgac agcctgcatc aagtaccagc agatgatcag tgatagccat aattagcata  71220
tatatataaa tacagtgtat ttgtttatat tcacaagaaa gtagggtaat tgattaaagc  71280
cttcagaacc tgtgtcagac accagtcata gtgggattaa tttaactgtt tctgctttga  71340
catcaaaata ttctaggtaa actgctgcag ttgttcaaaa tctaaatcta tggatcaaat  71400
cttcatacag gtattagact ttagaatcag atgagccaga tgtgaatagg agctactcct  71460
cctcatgagg ctgtttttaa tcagtcattt ccctggagta gcacacaatc aatgagctct  71520
aaatcctgag gctacctgcg cttgtaggaa ggcctgggaa catcattaca gaacttacaa  71580
ttgggcatat gtgaaaaaat tagagcagaa attaagggta agaaaggtta acttcagaag  71640
tcttactttg gtactgcttt tttagaggga ggtaaagaga taatttcaaa tgttaaaaaa  71700
aaaatagaat attaagccca acttctaaat gcagagaatt tctattaaaa gatcattata  71760
agcaagccaa ataaaagtta ttattgattt atgttagcca gaactgttta aacacgtgta  71820
ttatttcgag aatgtacatg tgggtccatt tcaggatgag taaataaatg taaagattct  71880
ttttcgctag tacctctgca gctgtataga atggcttcag aagtcctatg tgatactttg  71940
gtgtgcagtc aattgacaca ctgtgtctgg agctaatgta cataaggaaa tttagttcca  72000
cttgataaga cacatgctta actggcttta agaaaataaa ccaagaacaa tgtgtgaatg  72060
aaacagagaa cttggcactt gactgtatgg aagcccatga gccatgtggt ttaattgggg  72120
ccagttggga tcatttaatg attgctgtca gaagatcaga tttaattctc cttataagaa  72180
gaccacagtg ggatagagtt aaacaaattg tcatcagagg tttcagatga acaaagcctt  72240
aattaggttg attaggatgc tgtaaaagag atgaagagaa atagaaaaat tgatgaatca  72300
ctgagttcca tgttgagcca catataatag caatatcata tatattttga gagatagtat  72360
tatagcattt tgaacatcac atatttgagc atgtaaagtt tctgtgtaaa ccttctaaat  72420
gtgaaggttt agagataaaa ataaatgaca ttccacttaa ataacagatg atttatctag  72480
cattttctct ttaatgtaca acaaaaacat tggcaggggg acaatggtat ttcttcccat  72540
ttcaaggtca tctttaaatg ttaagtaaat tggaaaataa ataatgaaag aagcaaatta  72600
ttttcaagga cataattttc aatcatttaa cataatattt gaatgcagag taaaataaag  72660
cttttactga gaacgtcctt ttaggcattc acaccacgat cttaataata ttgtgattat  72720
ttactggtga taatactcaa gacaactcag gtgtcttaaa atgtactctt attgttttat  72780
ttacacattt cgacagacta aaatgtgttt ttccatgtgc tgtgcacaca tgtgcacaca  72840
tgcacaaatg tatcagtaag actgaaatat gtgttcaaca cttataggca tatgagaaaa  72900
atatttttag agtatttcca ttttaatcgt gaaatatgat atattaaaga tgaagaatat  72960
aacgaacata atttttttct aacagggtca tgagatgcct gggaatttag atgtttttat  73020
cataatagca tgaaaatcta taatagcaac atctccaact tctagcctag cttgctttac  73080
agactatttt gtttgactga ggttgatgtt gtatagtgct taacttgctt tgttcaataa  73140
cagcaacaaa aatccagctg catgtgctta ctgagaggtt agagctgggg aacagaacac  73200
aatctgatgt taaattgtag ctcttgcttt gtcataagac agtgcaggct ttacctttgt  73260
ggtgagccct accacatcac tcagaggcct ttgaaagaaa acatggtggc tgcactgttg  73320
tgaaaaatta gaaaaacaaa gacatgatag aaccctgaat taattaccta atatgatgtg  73380
gaaagactaa aagctgtggt agggttggat agcacaaggt tcttcacata tttagaccat  73440
ttggagttta ttttggcatg ggaatagaga atgctatttt agctgcagtg tgaaaaaagt  73500
```

```
gtccaagaca aaatagacca tggataacta tgacagggag actgtgcttc cctcacagtt  73560
attaaattgt ttataatgca atacaattgt ataaaggtat gtgtctccta aattctggaa  73620
ctgtgtaaat aaaatgatgt atgtcaggga taatggcagg ttaggcccac ttattaaatt  73680
aattgcaggg gttaagaaaa cgagttcctt tttagcctta ttatatttct gacatacatt  73740
tcatctcttt ttgtccttgg ggaaagatat taaagtagga ctagaagcat taatgtagag  73800
ttttcagcag ccgtggtcat ggggaaaatt gatgtatttc cctagttatt tccacttttg  73860
cagcctgaag ctcttccgta gctgatatgt aagagaaact tcttaatttt tttaacactg  73920
taaatttatt cttcatttgg tgattattgt tacaggataa atgaggcatt atctgtcaga  73980
attgctaatc attagctttg gaaagtgaga tcttcatggt aaatgtaagg actacactat  74040
tcacttgata gcattactat atgataggac tttcacttta tgccttcaaa cggaagcaat  74100
catacgagca gcaggccatg ttcccagtac tactgtgtac ccaggattca catatagtac  74160
cacatgttat gatcataacc atcctacaaa tgaagatttt tttcccagtt atgggtaggg  74220
caaggaaaca acagttccaa gggattaaat aatcagtctg gagtcacaca gcgtccaagt  74280
accaagctag aattctaacc ctgtttttc tgaccccaaa atccatttaa cttccaattc  74340
tcagtatcaa ttattctaat tccacatagg agatgctatg taaatatggc gaagtattaa  74400
gtgaggttat caatctgctt ctgtgtaagc aaaaatagta aaatattttt agtagtagtc  74460
agtaaaagta gaagctgaag aaaagaaaat acgtcagttg agagatacac atcttaactg  74520
attgtcagtc aacgaatagt cattagctct ttctatatgt ttgacactag ggtatatatt  74580
gtggataaaa cggtgaaaca aacaaataaa acagatgttg aggaagacaa gcaaacatac  74640
agtttcaatt gctgcgagtg ctgcaaagga gaaggactca gtgcttagat cttatgagag  74700
ggaaattcga tgtcatcagg agggcgtgga gtacttcctg aggaggtgaa actgaagctg  74760
agacagaagg gaggagaagt caaggaggta caaaaggaaa ggaggaacat ccaggcagaa  74820
agaattgcct agtacacaaa ggcctagtgg caggaaggag catggcagat gtgaggaaat  74880
ggaaaagatg gtcaacatta tttgtatatg tggtactatg ttactgagac ttgaagatgg  74940
tttgaaattc atattgatac taaattggaa taaattagga aaataaattg gcatatggca  75000
tgatggtatt tatctagtgg aaaagaatag ctgttctttt attaccctta gaagagtgag  75060
tcttgggtat gtgatttgga aataaactca gaatgcactc atagctaagg taatggtata  75120
tttataaaat acatggtaag cttagagaga aatggagcaa ctttcaaggc caaagaaatc  75180
ctcctcaact caagacatca cgcagtcgag catcaatagg agtagtaatt tggttatacc  75240
ttttgaagtt cagaatagct cctaatggaa aaaaagtaaa agttctgcct gttcctttta  75300
accaaaatat aattgcatgc ttcatacatt ttatcaaaca aatcacaaaa tagaaaccta  75360
aatgtaacta gatgtaacat attgagcaaa gttttccact taaaaagata atgaatcatt  75420
taattatttg atttagcaat actaggtttg cagcaactgg gcttatgatc atttttgccc  75480
cttacgatgt atccagcttg tatttattta acagtattat ttagtgttgt gtgatagagt  75540
gtgctcagtt ttcagctttg agtttttaca aaacattatt tgaggatact agtgttagtg  75600
aaaatgtaag tcaatcaaaa agatctgcta atatgaatca aagaaaaccg gaattttttt  75660
ttgaaaattg acatcacata tttcaatgtt ttaccattat tcataggctg tttttattta  75720
agtgactgca ttgtacttat tgcagaaaaa tacatgcttt gcaaagataa gtttagcaga  75780
agagaattaa tttcttccca catcttttaa tgtggcatgg cagtttcact ctaagatcaa  75840
```

```
aacacataac tgaaggttat gtttaacttc taaatcaaag tgttgtggga agatgattga  75900
aatctgatga tgactcagat acgcttgata tgtggttttc ttcctacaga aaccttatgt  75960
agaatgccat ttccatgtta gaaagaacct aatagtgagg agattaaata gtttcactat  76020
agatgcagag tttgtgttat tcactttggt tcctagtttg aattttttta aagaacctcg  76080
agaaactcaa taaccataag aatcttttcc ccctcagtat atcttttttt ttttttttaat  76140
gtgggagcaa acaaatgatt agcatatttt accagcatgc attgattttt tttttgccgg  76200
ttttcataat tctttttttt aaccaaaagt tttaatgtat ctattttggt tctttgcttg  76260
catatttttc atttgcctca aagggtaaat tccaattata tgactgcatt aactgtgtac  76320
gatgactttt gtaaggcctg gtaaacaata actgagatat atctgctatt tcaatgaagt  76380
caatgtgttt gttttcttat tttcatttct taaagcaatc ataataaaac actaacctag  76440
agctgacatg aatttttctc aggtgtttta aagatggaaa ttaaaaatca cgctcccggt  76500
ctgaattgtc ctcattgtcc cttatctgaa cctctccaag gcctctgtgt gtggggtgtg  76560
cagcacagca cactcagacg gttctgctca gagaaggaag tggagagttt tggttcccat  76620
tttacacttc tggaacagtt tagggaagga agcaccttta caccttttat tgttcgtggt  76680
tgctgacatc atatccttcc ctgaccagtc tgtgtgcgtg tttcctgcca ttctgtcaaa  76740
attcttctgt gctactggga gagatttgta ggagggaagg agggaggaag agggcaagaa  76800
agagtgaggg agggaggagg gaaatggagg ggggaggtat gtgtcactca agggaacttg  76860
tttgtaaatg agatagccca gtgggagaat gatctttagc atctgtccag aagaaattct  76920
tctcgacttg ggtctcaaac cactttgcct tcatctgcct gcttatgcca aactcaaaat  76980
gagcagaagc ctgccataat gaagttcccc tttttagtaa gcagcctcat tttagttttc  77040
ttttatctgg gttggcattt tttctttaga aaaaaaaaat gcagaagact gtaattctat  77100
agagtgtaac tatagtagag cagttcttca tctttttttt tttaaattag tgattattta  77160
tatgtagctc tgtcattttc taagaatgct tctttcctgt ggaaaaaaag tagtggcaag  77220
gctgttggaa ttattttaag cttatggttg attgtacgta atgaaagttc tcagcataac  77280
ttgaaatttt actacatgta ggctagctgt tatattcctt tttcatatac acacaaaaca  77340
gttttacaga ttactaaagt taaataatct ctttcttcgc ctctctaggc ctcctacaaa  77400
ttgatacttg aaactgacct tttaatatag tttttgcata aaaattaggt tagagaaaat  77460
gttgtgctaa gaaaacaatg cgtgagctat tgttgacctt cctaattctt taaattttta  77520
gtgacagcct tgaaatgtgg tgacccataa tcaaatgttc taaaccacgt ttcatgatag  77580
actttacttc atgaccagtt acttagtgtc atcatcacca catattactc tgcacgtgta  77640
cttcatacta aattttggat tttagaaatg ttctgaaggc aatacctcaa gaaatattta  77700
tacagaaaac aaaagtttag ttctattgaa atttaaactt gcttctctct acattgcttt  77760
gcatatttca aaaaagaaaa tatattcaat ggcattttta tcaaccactt atatatacat  77820
agatacatac acacattctc tttggcaaaa tttttttcca gcatgtttta agaaattttt  77880
ttttaagtcc ttgctctgct ctttttaaaa atggtctcat tcaaagttgt gaaatatggg  77940
gtgatgatat ggaggaactc tcctaagttt ggttcatcag gaactctctc tgtctttctg  78000
agacttttct ccaaggatgt tttgctgctt gtttggttat ttgtattttg aaatcaggat  78060
ctgtagatgt tcttgtctct tctgccttat caccacactc taatctgctc accctgacct  78120
tccaccttga agtgaataag cgcttaggca ggcatagtcc tgtaagccga tagtgccacc  78180
ggcctcagct aaatgaaagg aaaggaaatt gtcctatatg catttgctgt ggattcatgg  78240
```

```
attggctttc tgtgatagag aaagcttgtt tgtatctttg gggtcttaaa cgtgcatggg  78300
aaataccatt ctaacacact gcttgcttct aaggtaagac tataggaaac acaggaaagt  78360
tgccccattg agtgacattt aagacgtttt ctaaaaatag atggacagtg tctagcaaca  78420
tcaaatatat gatgcaatta tgctttgtgg gtttttcata ttttaatgtg atttcaatat  78480
gttataacta tttttatatg tatttgtcaa atgtgtgtta tttctataac tctttagaat  78540
tttgaaccac ctccaacatt taaaattaca gctggagcaa tagtttttga tgagcactgt  78600
gtggtcataa tgttactcaa catacatatt atgagaggca gaactgagct gcagtttagt  78660
agagaggcgt gaggcaaaag agaatggata gtcttagtat ttaagcagca cttaatccac  78720
cagaagtaat tatatcataa tagcttctgc aattaaataa tcaccaaaaa ctaaaaaaaa  78780
aaaaaatacc caaggtgata aagaatttgg aaattaaatt aaagaaatca gaagacagct  78840
aatggtcaga ccgaatgtgt aacagccttc ctgttccaag aactttgaat tggagccaaa  78900
caatctatta aatagccagg acattggctt agcattacat aatacatgtg ggaatttatc  78960
aggtccgttg tcagacacca gctaaaataa acagggaaat tctgagcagt gtgtaaagtt  79020
gttgcattca ttgacctaaa acgaagtaga ataattggag ctgttgcttg aaaaacccat  79080
tgtggaatgc tttcttgtta actttcacat ttcagagcaa ttaacttccg ttgtgttcaa  79140
atattttcag atgtaattta aaaccaagta aagtatgtac ttttaatatt ctgggtttct  79200
tgggcttatc tcatgttatt gatgatcatt tctctaattt taattcctga cccagagatc  79260
tccagtatgt aatgtgaagc ttctgcaatt ttgtatctta ctccacaaag acatgatatg  79320
tctgtttcta aatatttaaa tttaaaggaa ggatggcttg ttataaaaaa tatggttata  79380
aattgaagaa taatcttaat tttgcaccat ttattttgtg tcaatgctta tctttttttga  79440
ttcttgttat ctaagatgta gtttaagggc tttcaaaaag aaaagatctc actgctgata  79500
gatgcttgta atctaagatt aaatattcca tattattttt aaggtgttct cacagcaata  79560
attttttttaa agtaagatta aaggatttag atttaaatta gttgacattt acatatatca  79620
aatagcactt tcataatcgt ccatcctatt tgcataacga gggacgttat cacctctgct  79680
gtcaaaacag gagattgttt tcccttcaga aatgaattag ctgccctact tagcatacac  79740
aggtacataa aggttcatta actctctgat ttaggtaatt tttcataacg ggtgaaattg  79800
tcacctaatt tcattaaaaa gattaggaaa ctttttacaa aaaaaaatac atttcaagtg  79860
ttagtcttta aaaaagcata gtttgcatca tttaaatgac ttgttaaatt acttatgaga  79920
tcattttaat tgttaaaaaa taaaactact tgatctgctc ctgtctgtga tataccatat  79980
atttttaaca aaaaagttat ttttattcat tttattgctt tagctccata tagtttattt  80040
ccttgataaa attagaatat gatagttctt atgaaactga cttgctgtta gagtggtatt  80100
taatttttct tttttgttca gcaggaacga atgcaggaat ttgggaactg agctgtgcaa  80160
gtgctgaaga aggagatttg tttggaggaa acaggaaaga gaaagaaaag gaaggaaaaa  80220
atacataatt tcagggacga gagagagaag aaaaacgggg actatgggga gaaaaaagat  80280
tcagattacg aggattatgg atgaacgtaa cagacaggtg agtggagtaa actttttttg  80340
tatcattatt tattaattat attttctcca catatgttaa gggtacagaa aatatcttga  80400
atctgtaaat atctattaag agaagtttgg gttaattaaa tgtgaccagt taaagtgctg  80460
atagtctctt atatataaag gagaaaaaaa tcactttatc tgtcagaaac atagtttaca  80520
catttgtcat tattcacttt ttacttcaac acaaatttga aatgggaagt gtagttgtgt  80580
```

```
gacatgaata gcttgataat taagagttaa tcagcataac attgctacat tgcacgcatc  80640
atcaaacaaa gatattctta tattcatggg aactagacct tttgtggtca ttcacttaaa  80700
ggtttataat ataggataaa tatcctgtat gaaaatggct ttcattttat tcatagtaaa  80760
tgagattttg aaacacatcc aaacatttta acattgtgct gacaacaaca acaaagaaaa  80820
cacccacaca agatattaat aacttaaaac atataggcaa ggactatcgg ttaattcata  80880
ccattttaaa tctgaatttg ataaacatag aggcagatgg tgttataatt tttttctaga  80940
atgccaatga taatgtctgt gtgatacaat taatctgttg tgaagacttt acacattcaa  81000
atgctcagtt tggcattaaa gacttgtata tcatgaatgc ctgcaatttg actctatttt  81060
tcttcacact aggggagagt ggatttagtt aggctatgta aggacagctg ggtagtttgt  81120
ataacgttaa atatcaaata atggtcctgg gagaaattat agtactgctg ggtcccaacc  81180
atctcatatg gatcatggaa cctgcagaga agacgtttct ggactgtgga agagaagagt  81240
gttttgccta cttttcggtt acactgaaga aggctacaca gtagccctgg ggacaaccac  81300
cagactgtaa tttccccaca aatgtagaca ctcatgtcct ctattgtcct gttttgtctt  81360
cttggacata caaataggac tagaactgat tgattcattt ttttaaatgt aatgttgttt  81420
catgtgtaaa ctataatgaa taggaattaa ttatttcttg catcaaagtc agtacgccat  81480
taaaaagtag agaaactttt aggttttcaa gtttatactc ctctaaatta ttatatattt  81540
tcaggtacac acaacttgaa ctatttttgg ctgcatgttt agctagaggg tgaataatac  81600
taagatttat ggtggattcc tttagtgttt tcatgcacat cgtttcttgc tgtggatcaa  81660
gccaaagagc aatcattgtg tcaatagaaa accgctattt tttaattggc ctatagcttg  81720
aaattgaaat taagactgaa atattgaatg tcatgtaaca ctgtttggac cttgttattt  81780
ggaccagaac ctattttgag tatagtcaaa aacatatgaa ttagcatttg cactttatta  81840
ccaataccag ataattttta ggtttatgat attcattata tcttcttttg cttgcaaagt  81900
tagaagaaaa tttttgcagg ttgaattcat gagcttttat tatgctttat tagaaaaaac  81960
agggatacaa gatttttttaa tttctatttt taattatggg tacataatag ttgtatataa  82020
tatggaatac atgtgatgtt ttgatacagg tatacaatgt gcagtgatca aaatcagggt  82080
aattgaggta tacctacctc aagcatttat catttctttg tattaggaac attccaattc  82140
tactctttta attactttca aatatatgat aaattcttgt taactgtagt caccctatgt  82200
actaccaaat tctagatctt attcatttta cctatttttg tatccattaa acatccccac  82260
tttatcccct ccccactcca tgcccagcta cccttcccag cctatagtaa ccatcagtct  82320
actctctatc tcagtgagtt caatttttaa aaaaaaaaag tttagctccc acacgagtga  82380
gaacatgcaa aatgtgtcct tctgtgcctg gcttatttca cttaacataa tgtcctccag  82440
ttagtttcac tcatgttgta acaaatgaca ggatttctag ggatacaata attttaaagc  82500
cgggagtggt agttcatgct tgtaatccca acactttgag atgcagatca ctggagccca  82560
ggagttcaag accagcctgg gcaacataag gagatgcaat ctcttatttt aaaaagttaa  82620
aaaaaaatta actgggtgtg gtagtggcat gcacctgtgt tcccaaccac ttggggacca  82680
ctaggacccg agatgtcaaa actgcagtga gccgtgatca tgttactact acacttcaac  82740
ctgggcaaca gagtgagacc ctgtctcaaa aaaacaaaaa acaaacaaac aaagaatctt  82800
aatgtcgcac ttttgagcta ataattgaat atcttttctt tttttatata tagttgcagc  82860
tacagtggct gttaccctca tccaggttag aagtcataat aactttagaa gaagaaaact  82920
tatttaaatt cagcttagtt tgacttatca tttttttaaa ttctgaagac agatttcttg  82980
```

```
attttattct ttagaattta gggtatattt attcttttct ccagtcttta gatacagtag  83040
gcctgtaagt tcaatacttt taaacagaat tagtaaactt gaaatccacc atgttttaat  83100
atatatttca gtgattattt tagaggctgt tgacaatttc aaacatctta catataaatg  83160
cttgtcttgt gcacctctca cctactatga gagcagttgt aagagtcatt tgggaaagag  83220
cctaaattat gtaggtcact tctaataaac aaaaccagca aatccgaaac agcatatcat  83280
actgtgtaga ggcacccgta acctgggctt tctttcaact gtgtattcac atgttgcaaa  83340
gaaaaatgct ttgccctctt tgaagctgcc ccactgtaga ctgtccagta gaacctcatg  83400
caatggctca ctgtcatctt ttcttaaaag ttgtcaaaga ctgctctgcc attgcacttg  83460
tttatttagc tatacacaga ataagttatg ttttttccag aaaaagaaat actgacttca  83520
agtgtgaaat gaaatattac agcactgatg ttataagttg tatatcatta agaaataaaa  83580
ctgttgtgaa atagaatggc tgtttaaatt gaattttacc tttactttag ctgtctttca  83640
taatggaagt agggaacagc tcaaattcag aaacatcaat acatgaaata gtttaggtga  83700
gaataaaaat tgacagctca aattcagaaa catcaatacg taaaatagtt taggtgagaa  83760
taaaaattga cagctttttt atttaaaaaa attttttggc atttccaagt ttacaaaaac  83820
tatttctttc ttagtttcaa gcttagacaa catggatttc ttaagcaagt atgtaaaaat  83880
aacattatga attgttaatt tatcttacag aaattttcag acaacctaat aaaagtagtt  83940
accaattatg tgccaagaac tatatatata tatataatta caaataattt ttattaataa  84000
gtcccatttt atggctgaat aattcattta tctgtgaaat caacaaatat tactagactg  84060
cagtgtacct aacaccaagt attcagtggt gaacaagaat ctcatccagc ttatcctctg  84120
ctttaggggt tcagcgagct ttcctgtaaa ggaccacata gcaaatattt ttagccttgt  84180
gagccatata gtttttgtct caactactca gctctgccct agtagtctga aagccgtatg  84240
cagtatgtaa atgaacctgt gtggctgtgc tccaataaag ctttactgac aaaaacaggg  84300
cgtttggatt tcacttgtag gctacagttt atggacccct gattgagtta aacagacatg  84360
aaatataaaa atatataaca aaaatttcac ttatatgtgc tatgaaagaa taataggagg  84420
tactttattt acatcagggt tggagaaagg cctgaggaag tgctaaaaga tgagctaaaa  84480
gatgattcag agttaggcag gtgacagcat tccagaagca gtatttgcaa agttccttaa  84540
gagaggaaag agcttgactg aggagctgaa ggaagatcag tgggacttaa gcctggtgta  84600
tgactgtaga gaaatgagag aaaagattgg atgttagaca ggacccagat atcgcaaagc  84660
tttgaaggtc ctgttaagtt ctaaataact ggctcaagat tgtacagtta aaactgggaa  84720
gtgaccaaga tctgagcccg gatctctcat attcaacacg aaacaaatta tgctttttaa  84780
aattatgtca tgatgcatct agtgtaatat aataactaag agcatggttt tgtgtcatta  84840
cttttcccaa ttatactgca tccagtataa tcaaatggct aagaggcata gtttttagag  84900
acacacaaac ttcgttcttg tcccagttct gccacttact agctatgtga ccctctagca  84960
agttacttag accctctgag cttcagcagt accctcatca ctagagtgag gatgaaaaaa  85020
agttagtacc tttctcatta ggtctttaag acaattaaat gaagcaataa atgtaaagca  85080
cccaccaaat aataagtgct caataaattt acctattagc tattcctatt aagactcagg  85140
ctctttgaac cattagctat tatagttaat gtgatttcta tcaaaacaac tcttgtactg  85200
tgtagcacaa taaagaatgt tacctaaacc ttcatttcat gagggtttta ttttaaaagg  85260
gtattgagga gatggatgga aaagtggaac aggtagagca ggagcacaaa ggagccttca  85320
```

```
gaagccaaca aggggctaga gaatgatacc agagcaggag tgagctgatg cagagaggat  85380
agtttgtgga caagaaggaa agatcacaca ggacgtttgc agaggattta tgacaaggat  85440
ggggagaagt cgtttcctaa atgttatgct tgtgggacct gttttcaaat atatgttact  85500
gaccaaatta tttttaacta ctcctcacca tttttatcac taccagcttc tagcttatgc  85560
taacactaca gtttcagtct ctccgtcggc attttttttt tacccttgaa atacctccat  85620
cagttaggca gtcttaccct ctttcacatg gtaccaattt ttaatcatgc tcctgaaaca  85680
gatttttttc tgtgacactt ttattgtatt ttacagtaac atatatatgc aaaggtttaa  85740
aaagttcaac aacaaactgg tttttatgaa cagatggttt tgggggtgct tgtttcattt  85800
cttttgtgtt taaaattttt taaattaaca aataattgta cgtattcata gggtgcacag  85860
tgatgtttta atatgtataa tgtatagtga tcaaatcagg gtagttagca tatccatcat  85920
ctcaaacatt tatcatttct ttgtcttgga aacctccaat atcctccttc tagctatttc  85980
aaactgtaag atatattaac tgtagtcatc ctttggtggg atagaacact tgaatgcatt  86040
tgtcttattt agctgtaatt ttgggtcctt taacagtttt taaatgaata ttgtccttat  86100
atgactcttt ctacaaacaa tatatttaga aatctgttat attaggaaga aagatatata  86160
aaaattaggc atgcttagcc taaacctatt tacttgtatg tttgtatttg aaaatttcag  86220
ctttcctact ttgaaaggat aggagaggta agcccaaatt tatttgtgca acttgttata  86280
aaaagacatt taaatatttg tcagataaca cagttagggc ttaaaatagt aagttaagaa  86340
agaaatatat ttaaatgcct taagttttct tttctttcat cagatctggc acactaatag  86400
tttttgccag caaacaaaac ttcatgtaat tatcagtgca ataactggag cacaaactaa  86460
agacaatttg caacattctg ttaatagaac aggagaatcc ccttatgact aaaagaattc  86520
agagttcata gctgttacat tttctaactt tccctcttct tatgtcccca tctcagtctc  86580
ttcatatgaa ttataaatta tataagatga actaggaaaa aagctggaaa aatgtgttca  86640
gtgtagatgc agcttctgac agtttctaca tactgatgtg ttttcaaact aaatctggtc  86700
tattcgacac taaactgaaa aataaaaaga gatgtataga ttccctcaag tgactcttta  86760
aaaagaaaaa attttactcc ttactttttc ctggttttca tcaagttaat tacagttcta  86820
aatttgggag ttacatctta ataacctaat agaaaatttg ttgaaagaga gatacattca  86880
ctctttaaat gtgagtaact ggataattga gaaatacaaa ttaattgctt caaaaaaata  86940
atttttcggt gaattccaaa ccataagttg gagaatagat ggaagatgca gtctccactg  87000
ctaaatgcac tttttttggc cacctccaca aacagaattt ccagacttgt gagtttttct  87060
ttaaatactg tagaagaatt atacttgtta atcaagaagt atctggaatc tctttcagac  87120
ctagtgaaaa aaagctcaat cagtgaaaaa ttattgattt tcctatcttt taatccaaaa  87180
taagcctgca aatacctcat aataatgatg atgatgattg ttttttctta gtatcatttc  87240
ttaacagatg cctgcctccc caacacttgt attaaaaatt atactaaact tatttcatat  87300
aaataaaata agggtgtgtc atagtaatat tttaggacat catacccatc agaattgaat  87360
tatagggtct attgccacat attggggatg ccttcttaaa agctcctcat gcatataagt  87420
taaatcattc ttttattaat cttaaaatta ccaagggaaa agtttttatt caaagatttg  87480
gaattgctgg tgattgaaga gttgaaaaag aaaaccagaa gggaaaatga cctaaataat  87540
acttgtaaga gtttccaaat taaaaaaaaa aaaaaaaaaa aaaaaagcag taggcagaat  87600
gctcagatgt atgtttaaca gctgtggcct caggccattc atttccattt tatcccttag  87660
caatttgaaa agaattcaca aataatctcc ccaccatgta gtaggatcac agcaacagtg  87720
```

```
tgccacacat attactattt atcctgttcg gtgcatgata ttttatattt atgtcagcta  87780
gatctactcc tttactgcca gaaagatatt gctccaactc ccgtcaatct cattcattca  87840
ctttcctttg gtaggaaatc tgagagaggc caacattttc ataaggaaaa gaataattgt  87900
cacttctaga attctgtcac tcttctttga acttgagggc ctcaagggtt tttattgttt  87960
ccagttctaa tttgtatatc tcatataatt tctacttaaa actgtaattt aaaaagaatc  88020
tgatgctttt atttattgta tctcattttg tgaagaaagt tgatactgaa tggccccttt  88080
cacctctggg aatgcatgca cacaccactc tgtctgctac aagtcacctt tagctttgca  88140
aatgcacaaa ctgtgtgaca ttgtattact gagaaaccaa cactaaaaat attaacatta  88200
taaatagact acatacaccg agaagtttct tccaaactgt agattaaaag acatgatgct  88260
aattgtttca aaagccatgt cctctgcagt ctgcacttct ttaacattta gttcaaaatg  88320
aaactacttc aaaaattatt agggtatttt taaagtttgc atcccaatgt attcttgttg  88380
aaggtagttt ggaaacttat tttttctgag gataatggct ttggcaaaaa ttttaaaaaa  88440
ttaagtaaat gacatcatta aggaaaaaaa ttaaaaattg ataatatgta atgtgtattt  88500
gtgtttcttt tgaaatatgt tggaccatta ataagaatta gagaaccagt ctaaatgttt  88560
ggaaatttga cttttaattt taaattggaa cagtttaact aaagaaatca ctaacattta  88620
aataacattt caacaaatgt aactgtttgg aaactataag ggagacagcc ttctgtcttg  88680
caaggattga tttggaaggc cctgggggag aaaatattgg agttaggagg taaaacctag  88740
gctattgtgg aaaggaagaa gttacactct tcctgttatg acaggaaaat gtagacaaat  88800
gtgcttcctg agcatttgct cagcagggaa tgaagtatcc tttgaccttt cccttaggta  88860
catttggctt tgttgaacta gtaaacatgt ttttgccccc aaaatattaa tctggtttat  88920
ttgattcttc tcagattcaa attatatctc ttatgtagat gagatacaga gaaacaaagg  88980
tatttatttt atgactgcat ctacagattg gatttagaat gaaaattagc cctttaacaa  89040
accaggcaga cttgagcagc ccatataaaa aatgtgaagc ctgctgtgtt agtcttctct  89100
tttcaaaagg caaaacattc ctaggcctta aaatgggcca cagtaaaatc tcttatatcc  89160
tgatcaagtt aacaattttc ggtcatcctt cttccttttc ctcatgcaga caaatgcatc  89220
agaattcagc tgtcacaaat tttaaaactc aaacttttat gagtttgtta ataaacactc  89280
gtttcattaa tgtgcattcg attatttaat ttagatctaa ctgtgattta ttattttccc  89340
tccaatgcat aagatttgga gttttatttt gggatttggg atgttgactt agggtgaggg  89400
gttggtagag ttctaaattc cacactctaa gccccttatt ttaatccttt tatcatgttc  89460
agaattttag gaactactgc ttgaaaatcc tttggaaata ctactgtatt tcagcgaaac  89520
ggaggctcaa tttgcttgag gctaacgagg acaatagtcc cctttgcggc agaacacact  89580
gctgtctcat cctcgcaagt tatgctggag ggttacaagc acgtggtagc agtctgctta  89640
aaagagtccc tcgctgctct ttaaagagcc tttcatttac gatggcaggc cccgtcattg  89700
tataaaggaa cgcttgtcta gaacacaagt ctgcagaggc actgcttcct cccaccgaga  89760
gtaatcatcg ggcctaaagc tcgcgagcct ttctaatgac agactgaatt aaacaaaata  89820
aaactgaaga agaatacttt agaacatttg tgccattact tactgtcagg aacaagggag  89880
gtggagaaag agcatttagg agggcatttc cctttttccc aattaaagat tgtcgttgca  89940
gactcttgac tccagcccta accctttaaa cacataggaa gacctgtggc tcctggatta  90000
cagagtgtat tgtatctgtg aactgtccat ctgtcactca ttagtcattc tgtttcctca  90060
```

```
actgggagga aactgagaga ttatctaggt ggggggatga ggtggagtag ccgacctgaa  90120
atattttcac ataatgaggg ttatatttat catgactctt atttggaggg aaaaaaaatg  90180
atcaaacctc aaacctttga aaatagaatt agctgggtat acgaatccca aacacatcct  90240
aaaacaaaga aactactatt tatgagttaa agaatggtga aaataaaaaa ataaaaaatt  90300
atccattcat tgagcactgt aaggttcaat taagattagg ctaaaaatat tgtgtttggt  90360
ggaaagaagt atttgggacc catagatcag atttttgttg cttcccttag tgatatgtct  90420
gaggcaattt gcagttgggc ctcaattatt attatagatg tgagtagctg ctgtttctaa  90480
aggtcctttt ctttcagaac tctttcctgc aaggtgcaag aacagttacc acagttaaaa  90540
tggcaggaaa gttcttctga ggtgacttta tgaatggggc tgggcctggg agggtgaggg  90600
agggggcagg cgtgtggagt ggagaaagat tatgaaatgc cctttccatt tcacagtagt  90660
caaactaatt tccctaccct gtaggaaatg atacaggact ccttctctgt ttttagaact  90720
tgttatttac attgcctgtg taaatcagag ggccaccttt ttttattcta gctgtaagca  90780
gacctgtatt tactaccaac caaaattctt cccattttct gaaattaaaa taaacatcca  90840
taaatataga actagtttgt gcccactagt gcatgcatgt ggttctcagt ggctgtagtg  90900
ggaatggccg gagcgtctga gggcagagtt ggctgcagag tctatacaaa agtagctttg  90960
atttactgtc agaacctaga aaccaactgg ctctcaattt agtgttctta gtattatttt  91020
ttgactttaa cctagaaagc agtccttacg ttaattaaaa tgttatgcat tactgtgctt  91080
gcacttatca gaatttctga tggttcttaa tgtaacatta caaatgacag tgcctgcata  91140
ctgctcaata aacagttgac tgggtccata ttgagctgaa cttcagcccc taaaatccat  91200
agttatctaa aagagggaag gaacactaac taacagaaag aaagatgcac tttgtgtgaa  91260
gagggttggt tttctagtcc atccaggaac aagtctgggg accttggata aggctattca  91320
tgtctttgtt tacggtattc atctgaaaaa tagggatgat aaactgtgct aaagaataag  91380
ttcaaagaga tactgtcgaa tgtagggaga taattaatta taaaatcgtt gaacttctta  91440
gaaaaaatta tcaaataagc aacactgtta tctaaaaaat aatataagaa atctgatatg  91500
cttcacttgc accaaccaac ccacacacaa aatttgacca agtccagttt tttctcctga  91560
ttaattttac caaatgtaag tttctactgt aagttaaaat gacaaaaaaa taaaataaaa  91620
caagtatgtg aaatttccct ctctcagtag caaacttctt gttaacatag tctgagcatc  91680
catagaaatt tattttcagc tattcatttt ggattacaaa aaacactata attcctctgt  91740
ccatatatct attcattcta tcaacattta tttatttagc caagtattat tattggttgt  91800
caggttacaa gaatgagcaa aagatggccc aggtactcga gaaaaactag gatatagctg  91860
agagagacac tctaatctag acctaagtaa ataatggtaa cacaagctga caggtcctag  91920
gagaccagtc ttttacagta tgtttcaagg agcgactaag cctggtgcat cagagaagat  91980
actacttgct ttgtaaagtg tttcacagtt aacaagttat ttacactggt attatatccc  92040
ttacttgacc tctcacaaaa ctctatatga tgcctgttat tatctccact ttccaggtga  92100
ggaaactggg gttccggtaa gttaagcaat tttacgcaag ggcacacagc tcataaaagg  92160
cagagctggg acttggtttt caatttttat gtttttcttt ctacattgta ctgccccagt  92220
catgatgcat gtatcctgtt tctttaaaat gtctttaata atgtgaattt gctgttttat  92280
caatctggat aattattttt ctgtgcattt tcagtacatc atttaatgtt gtctactcaa  92340
attctttaca gtcttttgtg tctcgtctag ctacaaaaaa agttatttta tttcttgaaa  92400
tatggaaatt agaggcgata atgtatgggt gggattgagt aactaaaaca taggagattc  92460
```

```
tgtagggtgc atgcttggtg aaccatattg ccatttgctc ttaactcaaa gccctatgat  92520
acttaggcat agattaagaa catctaaaaa ttagaataaa tattttaaag gtctctagtc  92580
caacttcctg cttaattcag gagccccttc tacaccttcc ttgatatgca gctctatgtg  92640
aacatattca gaaatgagct gcttcctgct tggtgggaag ttctcatcac tagattttcc  92700
cttgttttga atctctttct aattttcaac aatgcttact aattttgcct cttcgcatgg  92760
acatatgctt cagaccttag aaaatgttta gcatttcact tttaattcta tttttttctg  92820
agttatacat tccagattct ttcaatggtt cctcatgcca gattgttctc agaccctaca  92880
tcagtctgtt taccatcctg tagatgctct aattttgtca gtgctttctt aaaatgtcac  92940
cctcagaact gaatatgcta ccaaagatgg ttctgacaaa caaaaagatc agtaggataa  93000
ttaattacca ctatagaacg ctaaaacttt agatcctttc ccaaaattcc ttaattatcc  93060
ccaacctgaa cttttgtaat tgttttttaa aaatatgaat gtggacttta aaattacctt  93120
catttgattc atcttgattg tgacccagct ttctaaaggc tgtagaaggc gctatggata  93180
tagactctta tcacctactg ggtttgctca agcacccaga tttacgttgc atgcagatct  93240
gataagcctg ccttcctata tacccatcta aaccaatgac aaaaatgtct cctgggatgg  93300
gaaaagtact gaattctatg gcactttact agagactttt tgataaactt aacattgatc  93360
aattaagtcg gcctcattaa ttatagttca tcagccatat ttaaatcagc taaattacta  93420
ccatccagtc tcaaattgtg catgaggatt tcatcacttt tccaaatgct tattctttga  93480
aaatctgaac tcatcagaaa gttcagtaca tttttgctga acaaactcag tcatcctgaa  93540
cccatggatc ctccccattc tttctgtatc ctgtgattgt aaaattaaat ttttatcttc  93600
agactttttt atctttcatc ttttttatcc aggcaaggga taaaaaagaa aaaaactttt  93660
ctctgaattt tttgaagtat atttttcttg aagtctacag catatttaca tatatatttt  93720
tctccagaca tcatttacct tctttattat aaattccaag atagtgtaat tactttatct  93780
taagatttgt gtcactaata agctaaacat tgtagtaaaa taaaggtata tgtgtccaaa  93840
atctctattt ttgagagatt aaattattta aaaggcaagt aaaaaagcat ctactctaac  93900
ataaaattat accgaaacat tcagacttca aaatggagta tttccattcc ataatccatt  93960
cgttcagcaa aggttcattg agtggccact ggtcagagtc tgtgagaggc ctgagggatg  94020
gtctttgggg aattcaaatc tggcagaagg gaaaactcat atacaaccaa ctttgtaata  94080
ctggagtaag tctcataata aagatttgta aaaagtgctg gaggactaca atgagaaagg  94140
aatgagtttt atctgaatgt gacaaggaaa gcatcaaaga aagaagttgg catttaaact  94200
aacccttaca gcgtgatggg tgcatccagt ggccaggtgg aaaaggagag atgggagtaa  94260
taccacaatc agctttcacc aagtcaagat tagaaataac cagtaaggta gatttcattt  94320
cgtactcatc ttgactgaat ttacatctac tattattttt ctagctcagt ccagagaaaa  94380
agttagtctg aaaaaaaaac tgaattcacc caactctaaa taaaaatacg aattcagatt  94440
attagatatg actgaaaata taactctgtt ggccaagtca tgcattttgt tccaaataaa  94500
gaaaattcct tttaaacgtt atggaattaa atgacttttt tttgtccagc cacaaggaac  94560
tgatatgaac aagggagata ttattttatg taatggaagc cacagtacct agcacaaatg  94620
cctgacatag agaatattca ataaatattg cttagcataa tgtttgacat gcggaaaatg  94680
ctccataaaa cttggccaaa ttatttttat attttttgtg aatagacttt cttaaatttt  94740
tagtaactga tttgtatggt gctatattta atgaatgttt cttttctcaa tttcaacttc  94800
```

```
taatttctgt ttttccttcg cacctaatag gttctagagc cattatcaac ataagatgta  94860
tggtatctgt ccttactcta ggatttaaaa gtcagggcca ctataaaact taacatacca  94920
tcatcacatt tggggctatt taaagattca aaaatataaa ggaaaaacat aaaataaaaa  94980
acatacagag tagttctgct ttctatgcta tatcacacat taagtctctt taatttgata  95040
acatgttgac ttatgtaaat actggaaaag agagactctt tgcctaacta ctgtaaaaac  95100
ctctttctgc ctcacctaag gttccaaaca tgttatttaa aaagaaatat ggacttgtcc  95160
ccattacaaa ctattatcaa gttaagaaaa atgtaaccat cacaaggcat tatttaagta  95220
taaaagcgca gaattgaaat ctttgttatt gagtggcata ttttaaatga agagttatat  95280
tccagatctc tttagaaagc ctaatgctta aaaataattt tatctaacta tgaacaatga  95340
gaaaaagcat tataaaatac attttgagaa tgctatgaag aatatgaaca taatgcagaa  95400
ttaaatttag agcaattaag agtagatttt gaagatattt tcttacgtgc tttaatacag  95460
tcatcatttc agtttgcagt tttaaattgc agaagaagct atatgcactg acttctttga  95520
tgggtattat taaataagta ttcattatcc agcagcctat ttggttacac aaaaattgag  95580
gagcactaaa agtaaacaca aatagtgaca ttaatgatat ttctgtactg aaatgtactt  95640
tgattatgag tgttgtaacg tgcaaaattc tgaggtctga gtacaacaga aaccatactg  95700
tattgagaca ttccacatat agcttgtggt catgaagtct gattaaaagt ggttttagat  95760
atatgaaagt agtctaggtc agtgccttct gtattgaacg tattctgtag cctatttcac  95820
taagtaaaat gccaatatgc aggtacattt tcatatcaaa attggatcta aaagaaatat  95880
taaaagacat ttagtgcagc tctgtgtaat taatgattat gtttctttat tcattccaaa  95940
aagatggttt tcagcccatc cttaatatca attatgactc atctgcataa aacagaataa  96000
aagtttctaa agtagtatga taatcagata tgaaaataaa acactagcta tattttttca  96060
gaagtacttt agaaagacaa tcaataaaga tgaaatagaa ggtgaaaaac actgacaatt  96120
acaagaaaga agaattatcc aagttgaaat gtaaataacg taactgagta aatattgact  96180
agttgatatg ggctagtaaa tatctaaatg ccttattttc caaacgatgg tcactacagc  96240
tttatctttc tatcagtcat aataacatct tcaaatagcc ataactggta gactcttcaa  96300
gtcaccaaga caagtatatt ttgctagttc ttcttttttg gttaagtcaa ctaagaaatt  96360
tgggggaact aatatttatt gagcacctac tctaagcatt atactcaata ctatacacac  96420
attattggat acaatcctca caacagcctt aagagtaggt ataaatctct gttttacaaa  96480
tgtgaaaaat caaactcaaa gaactttatt taaagtgagg cgaggcacgg tggcttatgc  96540
ctgtaatcct agcactttga aaggcttaag cgggaggatc gcttgagctc agaagtttga  96600
gaacagcctg ggtaacatag ggaaacctcg tttctagtaa aaataaatac aaacaaagat  96660
aaagccagaa catgttggtg cacgcctgta gtaccagcta ctccggaggt tgaggcggga  96720
ggatggtttg accctggaaa gtggaggctg cagttagcta ttctagtacc gctacactcc  96780
agcctaggag acggggagac cctgtctcaa aaaacaaaca aacaaaagag aagttgttaa  96840
gtgaatttcg catgactagc aaattcggca ttcaaattca gagttctcta aatacaaacc  96900
ctatgttctt tgctttctac catactacct tcaatgtcat atgataaaat agtgtaatta  96960
ttattaagta aggaatatat gtattgttaa aacattttgc atatgagttg ttaaaaaaat  97020
ttcatgggaa aatttatcac atatatacat acatcaattg tatctttctg aagatttcac  97080
atagtagctt cccctatcaa tttttatacc atggattttt accatgtgcc cacacatgtc  97140
tactggtcta agcactgggg ataaagtagt gagcaaaata aaaacggcat atacccttgt  97200
```

```
ggagcatgcg ctgtagtgga agagaggtta aacagatcac acaggaaaat ataaacagtt  97260
ttgtattttt tattttgcat attttatata caaaatatat tttgcatatt tttgtatata  97320
tttggtatat ttttgtgtat attttgtata tttgaaaata taaaatgtga ttgtaacatg  97380
aaggaaaaat aaaaggtgat aagtaaaaca ataattaaca aaatgtggag gaatgaggag  97440
actgggaggt caggctttct gtctgctagt ccacagtcct tgtcaacata aatctattta  97500
gttgtggggg agggtgggga gtgggagaag gtggcaggcc aggattcaga gttctctctg  97560
aggtttctag tttggatgac tgagtttatg gtgagatggg gattccaaaa ggggctgcag  97620
attctagact gaagataatg aggttgaact ttggaaggtt tgagaatcca ggatgtttag  97680
acaggtgtgg aactggagga catgcattgg gtgtctggag acaaagagaa agatgaaggg  97740
taggaatatg caattaggaa ttacacacaa atctgtgata aaatgagctg gcctctctgc  97800
aaggtgggtt ggatttgaag gtatgaaaaa agtttaaatg attcattctg aaaacagtag  97860
cttaattaag taaattagct tttcccagaa tatgtgcctc aaaaacctag ttctgaagag  97920
tgatagtaag tgctcctcaa aataaataaa tatgcaaaga aacaaacgat atgtcagcaa  97980
taggttcgaa aagcaagtta aacaaagttt aaaaggtttc atagcctttc atataccaat  98040
gtgcctcttt ttccaaacat attaggccac tgaacttttt tcttaaggag tattttatag  98100
gaacagtact ctacagaatg aatacctgtt gggaaacagg tattcattct gtagatggga  98160
aacactggac catataaagg tttataagag actccgtctc caaaaaaaaa aaaaaaaaaa  98220
aaaaaaaaga atgttcacgc cttttcagta gccagactgg agcaacaagc tgaagttcaa  98280
ttaaaagaga gttgaaattg ggaagagtga aatgtatttt tgcatttggt aggattggca  98340
ggtaggaagt tttcaaagcc agggagaggg agctgttgta ggcagctcat caggaaaaag  98400
acagtaggaa gagtgaggct ttgcagtttg agttaaattg aggaaggaat gattccaggc  98460
agggagatca tcgaggacag gaagctgcta ggctgtccaa aattgaagtg ataaggacat  98520
cagtgataga gttgcctggg aaatagtgtg aacctgagaa atattttgag gaaaggaatt  98580
atgggtcttg gtaatagatt agattaaaag aagaaaatgg tggcattaac aatacagttt  98640
ctgacctgag agaagaagaa agatacacag aagaatgaaa ccaaaaccct aagcatatga  98700
tggctaacgg acttcccagt gccctgttgg gtttctagaa aacagaatac aacatcgtct  98760
gagatcacag tcatatccct tcaagtgttt tcaattaaat gacatgagac tagacaattt  98820
taagacttgt ttgaacacag atctaaaatg ctaagttcct aatgtcatgt ccactcttca  98880
aatagtcaaa aacaagctcc aaactaatta ttaattggga aatatgctaa ccatgctgaa  98940
attaattttt ttttaaatct taacttgctc aaagaaacat gaccagttcc ctggtcacct  99000
tcattaaaat accctacatt aaatcttgca tttagagtct cacattcagc agcaagctag  99060
aaatcacaca ttttcaaatg ataagcagaa attaatatta gatttatttg ctttctttct  99120
gaatgtgtta gtgcccaggg ctctgacaac tacacaccat tgttttgtga aggaaaagaa  99180
aaaagaaaag aaaaaaacca cacatgcatg aatatttttt aaaaaatctt ggctgctttc  99240
ttttttctag gtgacattta caaagaggaa atttgggttg atgaagaagg cttatgagct  99300
gagcgtgctg tgtgactgtg agattgcgct gatcatcttc aacagcacca acaagctgtt  99360
ccagtatgcc agcaccgaca tggacaaagt gcttctcaag tacacggagt acaacgagcc  99420
gcatgagagc cggacaaact cagacatcgt ggaggtgaga gagcatgcgt ggtgagcccc  99480
aagcctccgc aagcagggga gtttggacct ccccctgcca cacacacata cacacatcat  99540
```

```
gttctttttc ttaagatgtt catagtccca tagatagacc caggattatt atctatcgca  99600
actcttactc caccttttct ctccccttca aaagttagag tgatgtgatg atagagacca  99660
tgtaagatct ggtctttgct agaaatcaag taccagtgtc aaactatttg cttcatcttt  99720
ggcaagtggt cattgtccac agctgtgtat caggacacca tggttgggaa ctcttgccag  99780
ggaatagctc atccatattt tagacacttc tgatcattta ttttaggtat ataatagttt  99840
cccggcatca tcaaagaaaa aacgtattta aaaatgaact caccccaacc ttacactttc  99900
agtttttcga tttatgtctc ttctttgtaa ctcattattc tgaatgcttt cttgctggaa  99960
gagtaaaggc aattattctc ctagaaatgt tttttcctaa aaattatatc attatatata 100020
tcaatgaaaa ctgttaatat acatggaatc agaaatcaga tgaaaatgaa tttctaaatg 100080
ttagctcagt gtttaatcaa tgtcagattt aaaaaaattgt tttattgtgc ccaaaataaa 100140
taagcatgat gctgaaagtc aaaaatgttt tagatgtgtt agcataagta acataccata 100200
cagttttggc tggaacattt tttttcccat tttattttat tttattttat ttttattata 100260
cattaagttt tagggtacat gtgcacattg tgcaggttag ttacattggc tggaacattt 100320
taaacctttt cagcatcgat cctatttaaa tactttgtag taccccttcat gagcaatgat 100380
taagactaca aaacaaagga agaggtataa taaggatggt tcccatctgc ctattttctt 100440
aatctatttg tctactctgg cttccctaga ttgtgcctgc tttctcagaa tgaaaagaaa 100500
attaataagt gtttcaaaag tatgtactca agagccagtt tgccagagta cacgtcattc 100560
ttgccattgc ttagactggt tccacattgt aaaaaaatgt agtgctaatc ctgatcaaat 100620
gaatatgcct cccacatcca tctccctttt acctgttaca attgtctaag actaattctc 100680
atttctttgt ttttatttga aagtttttca aaagtattga gctgattatt atattttatt 100740
tttgccttaa cgaggccaag gaaataattt cagagaaaca aaagtgaatg ataaatagac 100800
ctagggtgat atgtgcttaa aatactatgc attattttag tttttcattg ataatttgaa 100860
ttgtgtgctt gccttgatct tgaaatttag gatcactgat aaaatttacc tatgcatttc 100920
agatagtttt ttatttgcat ataaatatga aagtacaaaa atatgaaggt gaacactgct 100980
tgtgtgtgtg cactaatact tatgtaaaat aaattcagaa aacaaaacaa ctatttacta 101040
aaaactccat ctcattacta aaaccattat aacaaaagtc agggtaacaa aagaatttga 101100
gttggaattt atcattacac tggaactgct agtccttaat gtcatgtgaa atgctgtaga 101160
tccataatga gccaattgga aaatatgttg acttctaaaa tttgctttct taaaggagtt 101220
taaaacctag aacattcatc ttctgagggt ttttcttagg aatatattat atgacttgaa 101280
ggcaacttaa aacttcatat attggccagg tgtggtggct cacacctata atgccaacac 101340
tttgggaggc ctaggtgggc agattgcctg agctcaggag tttgagagca gcctgggtaa 101400
catggcaaaa ctccgtctct gcaaaaaaaa tacaaaaatt agccaggcat ggtggcacac 101460
atgtgtggtc ccagctacct ggggggctga agggggaaga tggcttgagc ctgagaggtc 101520
aaggcctcag tgagcctaga ttgtgcctct gcactccagc ctgagtgaca gagcaagacc 101580
ctgtctgttt aacaacaaca acaacaaaaa aacccacttc atatattgta tgaaaacttc 101640
atattttttg ataggtggat atttgaaagt cagacttctt taaatgccac aaaaacagca 101700
ctgggttaag agtcattgtt tttcatttga atccttgtct tgcacttttg tgcagtgtgg 101760
tgagttgggt acctctctgg gctgacgttt tctcatctca aaaatgaagg cattggattt 101820
gaaagtgctt ttgcaagatt ataattttta aaaaagcaat acttgtaaaa caggagtaaa 101880
gaaccagttc cattttcttg ttaacatcaa tagattaaat ctctgaatct ctcaaaaaga 101940
```

```
cacttcgagg cttttgggcc aaatctagag attggatggc tcaattattt ggatgaacat 102000
aacatgtaag tctaacacat tgtgggtccg tcctgttcaa ctccctgaat tatgcattct 102060
tcacatattt ggcttttcca cattttagta ataacagaga tcatggaaaa agaagtaaga 102120
tgggaccgct aagcttgata aaatttacat catcttcaca tggaatattt ttcaaagtgc 102180
tgcatcactg aaattaggat acttgagaca cttggtgaag agggaatctg gattggaagt 102240
tgcatttata aaaagttccc caagtaggcc aggcacggtg actcacacct gtaatcccag 102300
tactttggga ggccaaggca ggcgcatcat gaggtcagga gatcaagatc atcggggcta 102360
acatggtgaa accccgtctc tactaaaaat ccaaaaaatt agccgagcgt ggtggagggg 102420
gcctgtagtc ccagttactc gagaggcagg agaatggcct gaacacggga gggagagctt 102480
gcagcaagcc gagatcgcgc cactgcactc tggcgcaggc gacagggtga gactccgtct 102540
caaaaaaaaa aaaaaaagtt cccaagtaat tcttagacac actaaatttg aaaacctctg 102600
cagcactagt acataaattg tgctggaggc aaagacctat gatacatcag ggatttgaat 102660
tcgttcttag aatggatcta ccataaagtc aaaagttaag attgtttact gctcctgggt 102720
aaaattttaa atcctattta ttttaattta atggaataca tttaactgaa taagtttaat 102780
gaggagcata atatgtttca tgaagggtca ttagttttat atttcccatt tggaccatta 102840
cccctcttcc ttaaccctct aaaaacagtt tactcacaag aagaaaaggt atcgggagag 102900
atagaaataa tataatttcc agcctttaca cagaaataca aatttctggg ccataccaga 102960
gtagtgctac agggtcatag gaaattgtgc agtgcgtggg tgttgaaaaa gattccttct 103020
tttagcaaaa aagctctgcg taattatcat gtctttgctt gataattagc actactccaa 103080
caatggcaca aagactcaca aaggcttaac agacagactg agatcagttt ttttatgatt 103140
atattataat gcagcttgaa tatctgttta gatacaatat ataaatatgc cagatttagt 103200
aaatgtgtta aatttttaat ccattggtta aaaaaacaaa aacagttatt gtattaaaag 103260
cacttccttt gaaggaagtc cattttactt aactctgtga caagtatact gggatattta 103320
cccaaaacgc tagcttgtca gactgttgaa attcagttcg gatggcatta aggaactgcc 103380
cccttcactg cttgttcact agctccactc ctcgttctct tagctgtcta agacagcaaa 103440
ccctaccagt ttatgttggg ctctgttcct ggaagaagat gtggttgttg agtacttcag 103500
gatgatctga agatgcagat cccacaggac atgcttacag cccattgctt catttagcaa 103560
tgatttagca agctccactc atgctcagca ctgtggaaga gactctgaaa cagcaggaga 103620
caggcattct tgttaaggat gtaaaacata tatgcaaaaa atcagcttgg gaacaattgg 103680
acggcaaagg aacaataacc tcattaatgc agtataagct gctgaaatga aggtgtaggc 103740
taaacaattc aacagaactc attcagccag gtcatgtgtt tttccagagc attccaagtg 103800
atccttggag tgacaggact cccagacagg ttacctccat atccagcacg ttttgtaacc 103860
acaaaatcct tatgggagta tcacttagca cccagccagg aaggaatctc tcatcccctc 103920
agtgaactca gtgattctaa tgagctactc attcagtctg ggcccacagt ccagtgatta 103980
agtgtggaag gggaataaaa cacaaggccc tttgctgctc tctaggaaat tcagagatgg 104040
atgtaactcc tgcagaagaa acctttgatt cacaactgtc tcagtagagg attattggtt 104100
tttcttttta gaggaagaac atgtgtgtct ctctctctgt gtgtgtgtgt gtgtgtgtgt 104160
gtgtgtgtgt gtgtgtgtgt gagagagaga gagagagaga gaaggaaagg gacataggga 104220
gatggagaga agatgagaga tgagagatta tatttacctg atattttatt attttggaaa 104280
```

```
ttttatttgc tgtcacctga atcctgactt ctgttttgat ttagagacat ctaagaacag 104340
ttgctgcagc aaaatgtttt ctgcacagta ataattaagg cctaaattgg gatgggaaaa 104400
gccttaaaat agtttataac ttgtatagct tcacaatggt gatgaaagtt atcaacgagc 104460
taagtgctct tacatagttt agtgaaaata ctaaatacaa tttttgttga aaagcaaatg 104520
cagcaaatag cgaaattgga cttctttaca aactcagtat cacaaaattt ggaaatggat 104580
gtaaatgtga aaatatgtct actttacttg accattcatt atatctaatt agcttctaat 104640
tttatactta taaaaatata gatgtaaagc cactgtagcc agactgcctc tctagattcc 104700
tcctctctgg gcagagcatc tctgaaagaa aggaagcagc cccagtcagg ggcttataga 104760
taaaactccc atctccctgg gacagagcac ctaggggaag gggcagctgt gggcgcagct 104820
tcagcagact taaatgttct ggcctgctgg ctctaaagag agcagcggat ctcccagcac 104880
agtacttgag ctctgctgag ggacagactg cttcctcaag tgggtccctg accccccgtg 104940
cctcctgact aggagacact tcccagcagg ggtcgacaga cacctcatac gagagagctc 105000
cggctggcaa ctggtgggtg ccactctggg acgaagcttc cagaggaagg aacaggcagc 105060
aatctttgct gttctccagc ctctgctggt gttaacccag gcaaatggtc tgaagtagac 105120
ctccagcaaa ctccagcaga cctgcagcag aggtgcctga ctgttaaaag gaaaactaac 105180
aaacagaaag gaatagcatc aacatcaaca aaaaggatgt ctgcaccaaa accccatcca 105240
aaggtcacca gcatcaaaga ccaaaggtag ataaatccat gaagatgagg aaaaaccagt 105300
gcaaaaaggc tgaaaattcc aaaaaccaga atgcctcttc tcctccaaag gatcacaact 105360
cctctccagc aagggaacat aactggatgg agaatgagtt tgacaaattg acagaaatag 105420
gcttcagaag gtgggtaata acaaactcct ccgagctaaa ggagcatgtt ctaactcaat 105480
gcaaggaagc taagaaactt gaaaaaaggt taagggaatt gctaactaga ataaccagtt 105540
tagagaagaa cataaatgac ctgatagaac tgaaaaacac agcacaagaa ctttgttaag 105600
catacacgag tatcaatacc caaatcgatc aagcggaaga aaggatataa gagattgaaa 105660
atcaaattta atgaaataaa gcatgaagac aagattagag aaaaaagaat gaaaaggaat 105720
gaacaaagcc tccaagaaat atggggctat gtggaaagac aaaacctaca tttgattggt 105780
gtacctaaaa gtgatgggga gaatggaacc aagttggaaa acacttcagg atattatcca 105840
ggagaacttc cccaacctag caagacaggc caacattcaa attcagtaaa tacagagaac 105900
accacaagat actcctcaaa aagagcaacc ccaagacaca atcagattca ccaaggttgg 105960
aatgaaggaa aaaatattaa gggcagccag agagaaaggt cgagctaccc acaaagggaa 106020
gcccatcagt ctaacagcag atctctctac agaaacccta caagccagaa gagaatgggg 106080
gccaatattc aacattctta aagaaaagaa ttttcaaccc agaatttcat atccagccaa 106140
actaagcttc ataagtgaag gagaaataaa atcctttaca gacaagcgaa tactgagaga 106200
ttttgtcacc actaggcctg ccttacaagg gctcctaaag gaagcactaa atatggaaag 106260
gaaaaactgg taacagccac tgcaaaaaca tatcaaattg taaagaccat tgacactatg 106320
aagaaactgc atcaactaac gggcaaaata accagctggc atgataatga caggatcaac 106380
ttcacacata acaatattaa ccttaaatgt aaatgggcta aatgccccaa ttaaaagaca 106440
cagactggca aattggatag agtcaagacc catctgtgtg ctgtattcag gagacccatg 106500
tcgcgtacaa agacacacat aggctcaaaa taaagggatg gatgaatatt taccaagcaa 106560
atggaaagca aaaaaaaaaa aaaaaaaaaa aaaaaaggca agggttgcaa tcctagtctg 106620
tgataaaaca gactttaaac caacaaagat aaaaaaagac tcaagaaggg cattacataa 106680
```

```
tggtaaaggg atcaatgcaa caagaagagc taactatctt aaatatatag gcacccaata 106740
caggagcacc cagattcata aagcaagtcc ttaaagacct aaaaagagac ttagattccc 106800
acacaataat agtcggagac tttaacaccc cactgtcaat attagacaga acagcgagac 106860
agaaaattaa caaggatatt cagggcttga actcagctct ggaccaagct gacttaatag 106920
acatctacag aactctctac cccagatcaa cgttggactt cagcattctt ctcagcacca 106980
tatcacactt atcctaaaac tgacataatt ggaagtaaaa cactcttcag caaatgcaaa 107040
agaatgcaaa tcataacaaa cagtctctca gaccacaatg caatcaaatt agaactcagg 107100
attaaaaaac tcactcaaaa ccacacaact acagggaacc tcaagaacct gctcctgaat 107160
gactactggg taaataatga aattaaggca gaaataagta agttctttga aaccaatgag 107220
aacaaagaca tagtgtacca gaatctcaga gacacaacta aagcagtgtt tagaggaggt 107280
gaatttatag cactgaatgc ctacaggaca aagtgagaaa gatctaaaat tgacacccta 107340
acatcacaat taaaagaact agagaagcaa gaacaaacaa aagctggcag aagacaagaa 107400
ataactaaga gccgaactga aggagataga gacacgaaaa acccttcaaa aaatcagtga 107460
atctaggagc tgattttttg aaaagattaa caaaatagac tgctagccag acttaataaa 107520
aaagaagaga gagaagaatc agatgcagta aaaaatgata aagaagatat taccactgat 107580
cacacagaaa tacaaactac cattaaagaa tactataaac acctctatgc aaataaacta 107640
gaaaatctaa aagaaatgaa taaattcctg gacacacaca ccctcccaag acaaaaccag 107700
gaagaagtca aatactgaat agaccaataa caagtgctga aattgaggca gtaattaata 107760
ggctaccaac caaaagaagt ccaggaccag atggattcat agctgaattc taccagaggt 107820
acaaagagga gctggtacca ttccttctga aactattcca aataataaaa aaagagggac 107880
tcctccctaa cccattttat gaggccagca tcatcctgtt gccaaaacca ggcagagaca 107940
caacaaaaaa agaaaatttc agaccaatat ccctgatgaa catcgatgca aaaatcctca 108000
ataaaatact ggcaaaccga atccagcagc acatcaaaag cttatccacc atgatcaagt 108060
cagcttcatc cctgggatgc aaggctggat caacatgcac caatcaaaaa atgtaatcca 108120
tcacataaac agaaacaatg acaaaaacca caccattatc tcaatagatg cagaaaaggg 108180
cgtcgataaa attcaacact ccttcctgct aaaaactcgc aataaactag gtattgatgg 108240
aatgtatctc aaaataataa gagctattta tgacaaaccc acagccaata tcatactgag 108300
tgggcaaaag ctggaagcat tccctttgaa aactgcacaa gacagggagg ccctctctca 108360
ccactcctat tcaacatagt attggaagtt ctggccaggg caatcaggca agagaaagaa 108420
ataaagggta tttaaatagg aaaagaagaa gtcaacttgc ctctgtttgc aggtgacatg 108480
attgcatatt tagaaaaccc cattgtctca ccccaaaatc tccttaagct gataagcaaa 108540
ttcagcaaag tctcaggata caaaatgaat gtgcaaaaat cacaagcatt cctatacacc 108600
aataacagat aaacagagaa atcatgagtg aactcccatt cataattgct acaaagataa 108660
taaaatacct aggattacaa cttacaagag atgggaagga cctcttcaag gagaactgca 108720
caccactgcc caaagaaata agagaggaca caaacaaacg gaaaaacact ccatgctcac 108780
ggataggaag aatctatatc gtgaaaatgg ccatactgcc caaagtaatt tatagattca 108840
gtgctatccc catcaagcta ccattgactt tcttcataga attagaaaaa aactacttta 108900
aatttcatat ggaaccaaaa aagagcccgt atagccaaga caatgctaag caaaaagacc 108960
aaagctgaag gcatcacgct acctgacttc aaactatacc acaaggctaa agcaaccaaa 109020
```

acagcataat actggtacca aaacagttat acagaccaat ggaacagaac agaggcctca 109080
gaaataatgc cacacatcta caactatctt atctttgaca aacctgacaa aaacaagtaa 109140
tggagaaacg attctctatt taataaatgg tgttgggaaa actggctagc catatgtaaa 109200
aagctgaaac tggacccctt ccttacacct tatacaaaaa aataactgta gatggattaa 109260
agacttaaac gtaaggccta aaaccataaa aaccctggaa gaaaacctag gcaataccat 109320
tcaggccata ggcatgggca aagacttcat gactaaaaca ccaaaagcaa tggcaacaaa 109380
agccaaaatt gacaaatggg acctaattaa actaaagagc ttctgcacag cagaagaaac 109440
gatcatcaga gtgaacaggc aacccaaaga atggaagaaa atttgtgcaa tctatccctc 109500
tgacaaaggg ctaatatcca gaatctataa ggagcttaaa cagatttaca ggaaaaaaac 109560
aaccccatca aaaagtgggc aaaggatatg aacagacacc tctcaaaaga agacgttcat 109620
gcaaccaaca agcatatgaa aaaaagctaa tcatcactgg tcattagaga aatgcaaatc 109680
aaaagcacaa tgagataaca tctcacacca gttagaatgg tgatcattaa aaagtcagga 109740
aacaacagat gctggaaagg gtgtggagaa ataggaacac ttttacactg ttggtgggac 109800
tgtaaactag ttcaaccatt gtggaagaca gtgtggcgat tcctcaggga tctagaacca 109860
gaaataccat ttgacccagc cataccattt ctgggtatat acccaaagga gtataaatca 109920
tgatgctata aagacacatg cacatgtatg tttattgcgg cactattcac aatagcaaag 109980
acttggaacc aacccaaatg tccatcaatg atagactgga taaagaaaat gtggcacata 110040
tacgccatgg aatactatgc agccataaaa aaggatgagt tcatgtcctt tgcagggacc 110100
tgggtgaagc tggaaaccat cattctcagc aaactaacac aggaacagaa aaccaaacac 110160
cacatgtgct cactcataag tgggagttga acaatgagaa cacatggact cagggagggg 110220
aatatcacac agcagggcct gtcgtggggt ggggggctag gggagggata gcattaggag 110280
aaatacctaa tgtagatgac ggttttatgg gcgcagcaaa ccaccatggc acgtgtatac 110340
ttatgtaaca agtctgcatg ttctgcacac gtatcccaga acttaaagta aataaatata 110400
tatgtacaaa attattttta tgtgctatat agatacatat tatacaagga tacttttctt 110460
aagagaaaaa aacagattca cttacctaat catttgcaga ttttccttct ttcagtcatt 110520
gattgaacaa aaatttgttg aattcctgct ctgtgttata tgctatgaaa tgcctggaga 110580
tacagatata accaaggtcc ctcaaggact ctcagtcctt aagttggctc acaaggccat 110640
gcatgatctg atccatgtat ttctcttact cttcagcctc actttttgca atttccctgc 110700
cattaacctg cccttacaac ccccatccta tactcaagcc acatcgtaca tacgtacatt 110760
cctcaacctc tccaagctct gttttgtctt aaaattcctt actggatctc tacttggctg 110820
ttacttatcc ttcactcaag tcaggtccca attacacttt ggaaagtcat ccttgaagcc 110880
cccataactt aggttaggtg cttcccctgt attacagtca tcatgtgttc tatctttccc 110940
atcagagcac tgttgaagtt gttatccaat tgcctgtccc acactagatt ctaaactccc 111000
aaagggcaag ggactgtaca cgttttgctc accatcatat tcccagtgct taacatgagg 111060
tctagagaaa gttacctcct cagaatatat ttatagaata aacaaacagg aaagacagac 111120
atataatcaa gtgattatca tgtggcataa cgttgcacat ttaaagtatg aaaaaatgtt 111180
tttacagttc caatgaaaca attcattaaa ttttgataga gtttatcaaa gcacaattta 111240
aaaacactca agtaatctag gtccatactc tccaatatag tagccaatag gctcatgaga 111300
ctatttacat ttaaatgaat taaaattaaa taaaatgtcc aattcagttc ctcagttgca 111360
ttagtcatgt ttcaagcatt cagtagtcat gtgtggctag tggctactga attaaacagg 111420
gaagatatac aacagaatgc attgatcatc acagaaagct ctatgagaca gcactggtct 111480
agactgaaat atgaagaggg agatatttaa acaaattgtg ttttcaaatt aataccaaaa 111540
ttaattcttc aatataaaat ttgaggagtc acttcggaag tgagtaactg tgtaccttgt 111600
gattttggaa ttcagagcat aaatgttcac ttcgagagac tctgatctgg aactaaacac 111660
tcaccataaa actaaaagca cactttaccc ctaacctata accacagagt caatcagtaa 111720
acttatgatc tggtcagaaa gcacttgcaa gttgtccagg ctgacaggga acattaactg 111780
tgtgagctgg gtgaagtata ctgtattttt ttttaacttg aagcttgtga atggaaagat 111840
gatagttctg tcttattact atttttaatt tacttgaagc aacattggac cagtatttac 111900
ctatataatt agtaaattaa tttctccaga aaagtatttt tcattataaa aaaatttaga 111960
gaaatagtat tcttgagata cattacaaat ccttcttaga tttactataa aacataattg 112020
atatagatct tactgctagt gactaagtaa gtctaccctc ccctctgtta agccaagcat 112080
ataattgctt ttcaatacat ggtattgaaa aattaacaaa gtattagtat tttccataaa 112140
gatttaaacc ttctatgttg tggcttctga gggaaaaggg gaaaaagatt ttgttattta 112200
aaaagttttt tattttcctg aattttaata taattttgtt tatatatctt taaaagactt 112260
ttattagtac ctgtaaataa tatttttact tgttccccaa agtcttaaag aagaaatgag 112320
tctaaaattt tttaaatgta ttcatatttc tcataactat accacaatga tttgtataga 112380
tcaaatttga agagccattt cttttttaaa aataatcttc ttgcttaatt tacatgtttt 112440
ataaacacga agagctgctt cacatctcat ttattaagaa aataatcatt gttgaacaaa 112500
tagtaatgtg aggcaataaa actgagcttc ctctagtctc tgttattaca cagctctaat 112560
agtttgcaag cattagtatg aacacagtga gcagataatt acttaataat agtagaagca 112620
gaaaagacag ggttcaaaat atagactttt atcagtaata taatttcttt atcaatatta 112680
atcattacca ttttgtcatc attattattt tacatgaacc ttcctgaact agagcaaaac 112740
aaagatctca tgtgatctct cttcacctga ctcccaccat acctggaaat gaaaagagaa 112800
aaatatatag cctggatgat aattgtcaat ttttaatgat atttacaaat ttcatggcat 112860
atggaacttg gtggtaagca gcatatttga accaaatgtt acattctagc cattgatatc 112920
atctaagtaa aactaacatt ggctctaaaa ggtgccgaat aagaatcaaa gtgtagaata 112980
ttcttacttc ctcaggaaaa gttactgaat atatagtcat gaaatattca aaagtaaagt 113040
tctaagaatg attctgaggc ttgcctagaa gcagaattct aagatgatgg ctcttttcat 113100
taaggagtgt ttattttaat ttcttcaccc cactgttggt tttgggggt ttgtttttgt 113160
tttgtctaat tacaaatccc tctcctttcc ctgaagggca tgacgaagct ttgttcatct 113220
ctgtacctcc agctgccagc tcaatgccta gcatattgtg gacattcaat atatatcaac 113280
ttactgatga tcattagcat aaataaaatt tttaaatata caattttttc tttggtgaga 113340
tccgatgtgt tctaataata aaagtgagaa tctttcaagt cagctagagt gagtaaatgt 113400
tgttttgcat caaaaataaa taaataatta aattacaagg cacaggaaac caagtaaaag 113460
tattgcttgt ggtgctggtg gaaaggaaag gacttccaga ccaaggtaca gtattttgat 113520
tactggagaa gagagaagaa acctgttagt gctttggcca gtattgggtc aaatgaaatg 113580
cctgtggccc agtgtgaatc accagagtat cttgctaaaa tgctgattct aactcagtgg 113640
gtatagggca gggcccagga tccctttatt tctgaccagg tgatgctgat gctgctggag 113700
tagaaaggat ctagatttcc ttttccaaac atgtatttcc ttcttcatgg aatttgaaag 113760
tgtgtctgta gactatttcc tctttgtaat tttatggagg gttagaatca tgctataaaa 113820
caggttctta caactgaaat tctgtgaaac taattcttga aaggaagtgt cttaggtttt 113880
tctggaagtg tgatacattc ataaaaggca catcactacc cagtgaggtg ggactctggc 113940
acatttcact ccttagtgtg tgcccatcac tttgtactgg ctgcctggag cacacagtta 114000
aggaagatgc tgagtccaag tccagacatt caggaagtgt gatgtgattg gttaggggca 114060
tgtgccttgg gtgcagagag atagtagtac ccataacttt ttcattattt tcttggtcaa 114120
aataatcaat aggacattct gggaaaagac ttaatcaaag tcagtcatta aaaggactgt 114180
aattaggtaa atgctgcata tgtgtacaac agattaagta aatagattat attattggaa 114240
atatacccca ttttatagct atttggcata ttatccagtc atgtctcaat ggtgtttagt 114300
gtattctgca ctactctgaa atttaaccac ctggaagaag ttatgaataa gaaaaaaaat 114360
tctctgtcaa ttatttctaa aggtcataga gttaatgact agctggaagg ttaattagat 114420
tctgaaaacc tcttcatatc aattaaatct cttatcttta tgttttagta aataaactga 114480
ataactattt agagctactg ttctagggta agaaacgttg taaacagtaa aactacacaa 114540
tgggtgtttg ggtttttcc tcacattaaa aaaaaaaata gttatagcag gcatggtggc 114600
tcacacctgt aatcccagca ctttgggagg ctgagacagg aggattactt gagcctagga 114660
gttcaagacc agcctgggca acatacagag actccaactc tacaaaaata aaaataaatt 114720
agctggatgt ggtggtgcat acctgtactc ctagctacgc aggagactga ggtcagagaa 114780
tcacctgagc atgagaggtt gaggctccag tgagctgtga tcatgccact gtaccccagc 114840
ctgagtgaca gagcaagact ctatctcaaa aaaaaaaaaa gtattacaaa aaagtagata 114900
tatgaattaa taatagtaac ttattttaat aatagtaact tattttataa tttctgaatt 114960
actttatttt tcaaaaataa aagtgtgcat attactattt aatcataaac aagttccatc 115020
actatgatgt caaggaggaa accatttcat agaaaaatag accaaagtta ccctatgcat 115080
gagctactac taatctaaag ccaacttcac tctcagttat ttcaatagga cataagttta 115140
ttgattgact ctgtggttag ttccagaaac ccaacccctt tgaaagttac tgtacacatt 115200
tgtaaataaa tggtatattt agcacctata ctatgacaat tataaactca tttgtgtcat 115260
gtaaattttc tttggataat ataaccagac ttcagatgaa aagacataga tctgcattaa 115320
tctgtaaggt agcctagcca catgtggcta tacaaatata aatataattt aaattacata 115380
aaattaaaag ttcagctttt cagtctcact atccacattt caagcaagat gtgactagtg 115440
gctcccaaat ataattgtcc attatgaaag aaaccctctg ttggacagta aatgacgaaa 115500
ctggtgcatc tagtgttctc tttcattcaa ataactggca tgggctggcc gaggtggctc 115560
atgcctgtaa tcccagcact ttgggaggcc gaggcaggcg gatcatttga agtcaggagt 115620
tcaagaccag cctggcctac atggtgaaac ctcatctcta ctaaaaatac aaaaaaaaaa 115680
aaaattagcc aggcgtgatg gcacacgctt gtaatcccag ctactcggga ggatgaagca 115740
ggagaattgc ttgagcccgg gaggcggagg ttgcagtaaa ctgagattgt gccactgcac 115800
tccagcactc cagcctgggt gacagagcga gacacagtct ctaaataaat aaataaataa 115860
ataaataaat aaacaaacaa acaaactggc atgatggtta atagatacag cccaataaag 115920
gatatgtaaa ctggagaggt tgcacctggc tacttcacct tccattcctg cagcaggcat 115980
ttatgacatg cccactgtgc gtcagtcagg acctgagcca gggcagagaa atccaaccag 116040
gaaagttgaa tcactcagtt ggcatttact ccaaggaaca gaatatttgt taaagtctat 116100
gtgattttgt ggagaaagac gagaaaatgg agggatcact gaagctggaa ttgccctgag 116160

```
gaagaagaga aaatggaaaa ggcacaggaa aaatgagtag taagaacgta gaaataagct 116220
aggtcccttg tgaacttttc caacaggaaa gaaaagatca tgcgtgcaca cggtttcttc 116280
tgatttttct taattagtat gtgcggaatt ttatcttcat ccagactcca tgattggttt 116340
tccttaactg tagttgttct gaattaattt catgtggggg aaaaataaag ctacaaagtg 116400
atttttctaa agaatattgt tgaagcattg ttatgagagt tcatctttca aattttactt 116460
ctaggatata ggactttaaa agctccacaa atttgaagga aagatggaga ttaaaaattc 116520
agttccagtt acagcaacat cacacactct cattctctaa cggagggcga gttatgtaac 116580
cttgctgggc tttaggttcc tcatgagtta atgctgtcta ccctgagctc cttacggggc 116640
tgtcatgagg attgcaggtt ataacagctg tcagagccca ttgtcaaccc ttaagtttta 116700
aaaaattagt tttattttca aagtcaagag aaaaagttca gagaagaaaa aatgctaacc 116760
aaaagaaaga caaaaattct taatttacga ctgcatagtt tatgctaata agtgtattat 116820
ttataagtaa atattgaatg attatataaa taactgtagc attttacata aattaagaag 116880
atctaacaaa ggtcaacgaa ttgatttttt ttttcttttc cacaagtatt tattaagtgt 116940
atgtgcaaag tatggtgttc acggccctcc agggccagta gcagtccatg gtggacagaa 117000
tatacacagt atttgttctc tcattcagta gatattgatg gacatgaaga tcatttgcta 117060
agcattctgc cagttactgg tgatgcatct gtgattatga tacccaatta tctgaaccat 117120
aataagatat agacaaagta cagtgggcta acagaggaga aggaaagcag ttacaactgt 117180
gagcacctga aaaatcttac tgtagatttc agatgaaggc atggccttga ataagtagaa 117240
taatttgata tgctaagcca atctgagaac catttttccc atttaaacta aaagtgagac 117300
taataaatgt agtgatatat ggacattaaa tgcatatatg tatatatata cacacatata 117360
tgtagtatgt atatgtagca gcctttattt tttgttttct gttagcactg gatttttaa 117420
tgtatggttt ttctataaac agatggttat aatttctaga gaaattccat agaacacaaa 117480
tgttagaaaa atgcagtgaa tttcattgcc tttaagctta ataaaaggtt caaccttaaa 117540
gttgcatccc acatcgttag tttaacttta cagatgagat ttttttttcc cctctctaaa 117600
ttctaaaaca tgatacatct ggctgagagg ctggaaaatt gttacatgcc tgtgcaacat 117660
tcttacaacc taatcagttc ttcaactttt ctcgcagttt aatcattgga gaatgttctt 117720
tgtttttgta gtcactgttt cacatagtaa cagcttgttg tattttggtc tgtttgccag 117780
agggtaggtt tatttttaaa accctgaact ctgaattttt ctttattttt ccaagattga 117840
aagcagctga aatgcctgga gttacaggtt gaaggctgct tcacaatatg tggaggaagc 117900
ttctttccct cctccctttg tgtgtgtgtg cttttttttt aatttttccc taacaaatgt 117960
cttctaactg gtagttgtct aaaaatagaa aactgcttaa ctaaaaatag cctggctctc 118020
agtcgtgcca aggaaaatgg agaggaatag gcgtggaata gaaggctgag taatccagtt 118080
ctattcattc agagaaacct ttgagaatgc gggcgatgat aaagtgccct caaaaaacca 118140
caggcccgac tctctcttca gacttctagg tgccaataaa cattttagcc ccaggatact 118200
ttttttttt tcctcatagg ttgtaaacat tttctgaaag acaaggcttt gtttcaggga 118260
acctgacaaa ctgccataaa taactaactt tcctaaggtc ttaaaaattc atatttgtaa 118320
gatgtatttt aaaagagaat cttaaatgaa agtattgtaa aataatgtac gtcgtgtaat 118380
aattaacaga ggaaactctg ttataataaa aaccacttac tgcttgcaat taaactcaaa 118440
actttaagga gtttcacagc aagaaaatta ttcctgtgac tcattgtacc ttaagagagc 118500
```

```
agctgactca ttttagttta gctccctgag acatgaaatt ctcttgttca gtctgtatcc 118560
ccttaacatg ccaacattta gtctctttct taaaattatt attttcactc aagcagattt 118620
ttacttttaa tctttaaaat gatgtagaaa ctactttgaa aaatagcatt tctggagtag 118680
gatggctttt agtttcaaca aatggaattc tgagtaagtc ataaaaaaat acgtgtgtgt 118740
gtgtgtgtgt gtgtgtgtgt gtgtgtgtgt gtatgccagt tttgcaatgg gaatgctttt 118800
tttttctatt ttgttttgct taagtaatct gtaaaccagg tcaaacatag caacagggtg 118860
tggaaatgtc agcacagttc atagggttat acgagtctga gcattgttat gttcagttcc 118920
tgtaatgctg ctggtgataa gactcttgag acaaaagacg ataattgatg gaaagaggct 118980
taaatcattg ctagaagaat caaggtcctt gtatctgtgt acatcgactc ttctggtctc 119040
cttccgtctt gtaaagcatt ttgtcgtctt gcatgttggc cccctactgc tctttgtaat 119100
ggatgcagac cacaagtgat tcctttatgc agcatacagg gtgtaattgt gtctgtgtgg 119160
tgtattagta attaccaagc tgaattccca tattgtatct ttactgcagg catggaaaaa 119220
taggacatac aaccctgcga aaccattttc aacctagata gtgagccact tagagctgta 119280
ttccagggac aaagcctttt acatgaatac tttttaaaca aaattttcat tgttgagtca 119340
tttgtaccat gcaggataaa ttcagtttgg gaaattatta cctttgatat tatattattc 119400
atttctgact cttcagcaaa gtctgtaata tggaaaatat tggttctttt taactgctga 119460
aataaaaaat atttttagat gtaatagtga tatgagctat ggtaactatg ctaggctatc 119520
atacagaaag agtactacgt gaattactac atataataga ttctgtaaca tttataaaca 119580
tgaaataata tagttatttt agtagcattt tatcttaaac agttatatgt tatacataat 119640
ttatcaatat tggctcaagc attgttaaac ttcagaaaaa gctgacaaaa aatttgttta 119700
cagtaaacag atataaatta ttaatttctt tgctataaaa tttgcatcca tcctttatgt 119760
attatgtagc tgatattgat ttgactacct ccaaatcatt gtggatttga aatgtctaca 119820
gtattatctg taatagaaag ccaaaataat gcaagcagct tggcttaaac aaaagaaagt 119880
atgcttattc tatgcatcaa atgcttataa tgacagttaa gaaatattaa atagaagtgc 119940
aaagaaatta atacagcaat ttcattatcg attttcaatg cagttagact tatattgcaa 120000
attattcatt aaagcattca agatttttgt tatattttta ccttcatttc tgaaagtggc 120060
cttccagtat gtatatctta aaaatttgct tccactttta tatgtagatt ttgttttatt 120120
caagcaataa ttattaaatt cttaggatat acagaacttt atattgatgc caggagaaat 120180
acaagtttgg aagacattgt ctgtgacctc acaaaactta cagtccaatt aaggtagaaa 120240
atacatgtgg gaatcaactg gacaaaacaa cgtaatgaga actatggggt atttagaggg 120300
aggcaacata gcacagtgtt gaggagcatc agttctggag atagactgcc tgagttctat 120360
atgtccttgg gcaaattact tagactgtct gttttatttt ttattttatt ttattttttt 120420
tgagatggag tttcactctt gttgcccagg ctggagtgca atggcgtgat ctcagctcac 120480
cgcaacctcc acctcccggg ttcaagcaat tcttcctcag cctcccgagt agctaggatt 120540
acaggcatgt gccaccacgc ccagctaaat ttttttgta tttttagtag agacagggtt 120600
tctccatgtt ggtcaggctg gtcttgaact ctcgacttca ggtgatccgc cagcctcggc 120660
ctcccaaagt gctgggatta caggcgtgaa ccactgcacc cggccaactc tctgtttctt 120720
aatcccatcg tctgtaaata gaggttaata atactatctt ctgcttagct gttatgagaa 120780
ttaaatggat aaacatttat aaaatgctta gaacagggtc tgacacttgg taaggtttac 120840
aataatgata acgacgacca tgatggcagt gccgctcctg ataccatgtc atcaagcaat 120900
```

aagtggtaga aagaagttta aaaggtcagg acaggcagcc atgattggta gtccttttta 120960
ggctcaaaca agtcaaattc agaaagatgg atatcaattg atgaaaaacg tgggcaaact 121020
ttcaaaaaac caagtatgca aagagtcaca agaaaaaaga aacaagggca tgaaaagtat 121080
tagcttgata tgaagagaat attcacataa ataaaaagat ataagaaaga tggcaatgaa 121140
aatgggaaga agagacaggg aaatcaagca ctctaaatat ttgatgtgga attaaatgtg 121200
atacaattgg catcagaaag acactccgtg gtctcgagca gtaaattagc ataatgacaa 121260
ttcttgagag aggttccgct ggaaaagaca gaaacagttg tgaaaagtgg aagtgccaaa 121320
atattttacg ttttgtaagt atgtatatgt gtgtgtgcta aaaagcctga aagctttcac 121380
caaacttata tttttatttc ataggacaag ttgcttcaga aatattcata taattttagt 121440
ttgcactaat aaggtgcaca tgcatttctg tgactgagga ctatttatca catacagtgt 121500
attaaaaaag caaattatag aggcctcagg aggtttttg ttgcgtttgt tgttttcgtt 121560
ttgcttgttt ttattttttt tttttttgag atgatttcat gcccattgcc caggcttcaa 121620
tgcagtggca cagccttggc ttactgcaac ctccaactcc tgggctcaag tgattctcct 121680
gcctcagcct cccaagtggc tggaccaca ggcacatacc accacaccca acgaattttt 121740
gtatttttg tagagacagg attttgccat gttgcccagg ctgttcgaat tcctgggctc 121800
aagtgatcct cccacctcag cctctcaagt gcttggatta caggagtgag ccactgtgcc 121860
tggcctagga ggtttatttt aaactatata agcttcttta cagtaaattg aaacataaat 121920
caaaatctta taaatttaga agttcctaat gaagtagtgc actttttaat ttttagacag 121980
agtctcgcta ggttgcctgg gctcttctca aactcctggg atcaaaagat cctccttcct 122040
cagaacatgt gcagtttttt gttttgtttt gttttgtttt tgacagagtc tcactctgtt 122100
gcccaggctg gagtacaatg gcacgatctc ggctcactgc aacctccacc tcctgggctc 122160
aagcaattct cctgcctcag tctcccgagt agctgggact acaggcatgt gccaccacac 122220
ctggctaatt tttgtatttt tagtagatac ggggtttcac catgttggcc aggctgggtc 122280
ttgaactcct gacctcaagt ggtccgcttg cctcggcttc ccaaagtgct gagattacag 122340
gtgtgagcca ccacacccag ccaggacatg tgcactttta atgatcacct aaacaggtca 122400
ggattctgaa tacaatactg ccaaatatga aaactctccc cttacacttt cacatccata 122460
taataaaagc cctgcccttt cataaaaaag acagtgtggt gctggaggag ggacagacac 122520
acattttagc gtcagacaaa cctggtttct gccactttca taaactctgt gatcttgggc 122580
aacattctga atttccacca agcttcagct tctgaagcag taaaaaaggg ataataaaac 122640
tcacttttgg tcttcctgta agaattaact tatgtacata tatagccatt agcacatgat 122700
gctcatacaa ctggtattta ttttcctgct gttccttttt gcatatgtaa atttaggcaa 122760
aaattttaaa ctttcacttg tatatacaca cgcatacttt ggacactgaa atcttcagtg 122820
tatttggtgc ttacatttaa ataaaatgtc acattttata aattatcata taatgtatgt 122880
atatttcttg tgtaataacg tgatgaaatt cttcagaaat aaggtcctca ctacacagat 122940
ttttaaacta gggaaagggt agaaaaagga aaaaaactag gagtcaaaag taattctatt 123000
aagtccagtc aaaatagagt taaaagaaaa aaaaagtgga actctgccaa atagaggggc 123060
ttgcccaagt tctcttagtg aactctggta gatagcatta ggatataatt tatttcctgg 123120
tgtccccttt gaactacttt gtatccaaga agaggagtta gacaatgaga gagaaagtga 123180
aagaacgaga gagatgtagg gagaaagaga agggggtagg ttgattgaga tttcaagaca 123240
atggaagtaa ttagcaagga taacacaagt gtccctatgc tgccagtttc tcttctgaca 123300
caaaaataaa taattgattt cattgaagta ttagtcagtc aacaatgctt agtgtgatga 123360
tattgttaac agtgaaatat atatgttgtg cattgcttct agggtgaaac ttaagtatct 123420
ttgccctggc tcccgcagta ttttcatggc agtgaggata catactcttg gaaatgagcc 123480
aggaacactc taatgtatta cacatgtggc ttaataccag gtgaacaggt attttaaata 123540
ttctaatcac atacccacaa tgtatatcgc tactgggaaa aggatatcat ttttaaccac 123600
tggtgtttgt tctgagccat accttttca cactctgaag attttcaaga cgaactgtga 123660
tttggggagg gatggccatc tcagtcaact ttaactgata ggaggtacaa caaatttata 123720
gttctgaact ctgcacctgg agtctggcta ccgaaatcaa accacttgct gaccagcata 123780
aaaataaata ggaaaatatt tcagtgtttt ccacaattgc gtttgtacaa atacaagaga 123840
ttttatttat attaaagaaa actgtagttt ttcgtttttt ctttttttctt tttctttttt 123900
ttttcgagat ggattctcac tctatcatcc aggctagagt gcaatgatgc aatgtcagct 123960
cactgcaacc tccacctctt aagttcaaac gattctcctg cctcagcctc ccaagtagct 124020
gggattacag gctcctgcca ccatgcccag ctaatttttt tgtattttta gtagagaggg 124080
ggtttcacca tcttggccag gctggtctca aactcctgac ctcaagtgac ccacccgcct 124140
tggcctccca aagtgctggg attataggcg tgagacatga gacactgtgc ctggcctgca 124200
aattcttata ttatgattag gggaagaaat ttgttttcca ttagaaacca ccattaagtt 124260
tgcaagcatt gtaacataaa aaaaaaaaaa acctcacttt gctgaggcct aaatttctat 124320
attgaaatat tactttctgg gggaaaaaga taaaatctac ccaaaagtac atctaacgag 124380
aaataattct gaagattctt tcagatgttc tgcttcatgc tgtacacaca cacacacaca 124440
cacacacaca aacctacaca aacctacata tattcacata tacatgcagt taatgtgaga 124500
ctggcagttt ccagcacaaa atacatagct tccatttcac tgtgcacaag ttcctgtgtc 124560
agatcaacaa aactttcatt gatttctatc tatctgcttg gcttcgacaa taatgtaatg 124620
caatcgggga gggagagttt ctaacttctc ccagccacct gccttaacct catgcttcat 124680
tcatctcggt atagactgga ttcctttgac aattagtcga tagtgtacat tacctcatgg 124740
aagcagactt tgaactatgt tttgcttcct tttaatggta ctgtttcccc tcatctttta 124800
acagtgatct tttaaaaaga agtgtgattc tgttcagaat gatggtgatg gctgtttgag 124860
acattttaaa actattaggt ggttaatatg tggttaatat tatttattca acagaaaatg 124920
gactttaagc gcatgtgaaa agcaaagcat cataattgta aacttctttt aaaagttata 124980
caactttatt tagtttcaat tttccaaaag tccagtttcc catctgagag acatgggtat 125040
tggcccggct gtgggaaacc tccagagaaa acaggggagc tccgctactg cggaagcaga 125100
gtcagtgact gtgggtggca ttttctccgc tgagtcaggt cctgccagcc ctaccccagg 125160
cttctaccaa cagtgcagat tttctggcaa gatgcaaaac ccaagtgttt gtggttcttg 125220
aagctcttct gcagtttctc cttttccttg gtactttggg aaattttcac tttagaagat 125280
cacatcttac tgtgtcttcc ttgtaactgt tgaaaaaatt gggaagttta agtcatttac 125340
tttatttttc ctctcatctg gcctataaag taacttggtg ttatgtgcat gtttttcaac 125400
aaacaggaaa gggaagagat tatataccca tgattttgaa aataattttt atacagcata 125460
caagatttct cgatgatccc tcgctttgcc cagggagaaa caatagtttc tccataaaag 125520
catacatttt tctcttttcc ccaatctatt ccctcaaccc aagagaaaat gtagtcttgt 125580
agttaccagc ctttgcatcc cccatctgct caagcaaatt gaagagaaga ggcaagtggt 125640

```
tggcttctgc atctgaagaa tataggtgcc aaaataataa agtggacctt tttgttagtc 125700
acagagactt gaggttcttg ctagtattac tctaatcatt gtaataaacc tgtgcttcat 125760
tttatgcaga taggtacagt ctgtatatta ttgggaagga cttccttcct aggcttagga 125820
atgttaggag ttgaaacatt tagcagccgg gcgtggtggc tcacgcttgt aatcccagca 125880
ctttgagagg ctgaggcggg tggatcacaa ggtcaagaga tcgagaccat cctggctaac 125940
acggtgaaac cccgtctcta ctaaaaatac aaaaacaaaa ttagccgggc gtggtggcgg 126000
gcatctgtag tcccagctac tcaggaggct gaggtgggag aatggcgtga acctgggagg 126060
cggagcttgc agtgagccaa gattgtgcca cagcactcca gcctgggtga caaagggaga 126120
ctccatctca aaaaaaaaaa aaaaaaaaaa aagaaaagaa aaatttagca ccctttcttt 126180
tccttggggc ttcaacaacc tacacttcat tttaactaga tagatagtac ctacatattg 126240
gtgaagggcc ttcccatcta ttctagatag tacctacata ttggtgaagg gccttcccat 126300
ctattcagtt gatattatag caaaatagta ggaaaaacat tttagataat attttttatc 126360
agaaaatgaa ttccgttaca aacacatccc tttatgaaaa aataagattt gtcagtcatt 126420
tcaccaattt cagctgagag taagtgttca aaggatacac agatacacag gcatggttta 126480
ggcaatcctt attgttaaac aaccttgcag acgcagaata atttgatagc taagagagaa 126540
aattctggag ctcattcatg ggttcataga cttggttcca ccactcacta actttgtaaa 126600
cttcagcaag ttcttgggcc actgtgtgcc tcttttttc atctgtagat tggcagtcat 126660
tgtggaagag tagcttgtga ggattaaaaa aagacccatg caaagccacg ggctcagtcc 126720
ctggcacatg tacatgcttg gtaaatggta ggtgttattg ctgaggaatg gattcaatta 126780
aaatattaag aaaattaata ttttgatagt gatggaagac tggtttaatt tcctcttcat 126840
gccatagaag aggaaatgtt gtttttataa ttacctaatg aagaatctgg aagaaatgat 126900
tttgcaaatg atacccttaa gctcatcact gaactaacaa aataactgag atttcataag 126960
ttatggaaat tgaaatacct aatttaaaaa gtcaagtttg cagtacattt ccatggataa 127020
tgcctgaagt tattgaagcc atcatgacta caaaatcagg cagccaggag gccaggtcta 127080
cagagtctgt tcagagaagg ctgtctgggg ccacaggaca gagtgcgccg tggggctggc 127140
agcatgcact tggccttgtt gagttagaca acaggtgccg agccactgcc aggtgtggat 127200
atcaggatga acaaaattgc tgatggcctg tcataaagct ttatgttaga tcataaagtg 127260
ctgagcccat atgatgagag atgagttcac atagcaaggg atcacttgaa gtgttcactt 127320
gattttcccc tccctgtctt tcacacgatc ttcaaattct ctctttttca ctcattttca 127380
ttccttccct ctctccctcc ctccctttct ttcctctccc ccttccagta tttttctatc 127440
tatttataac ctctgtctct cattcttggt attcttattt ttaaacattt tctaagtaga 127500
atgacggtta ctggaggccg gaaggggttg aggttaccag aggctggaag aggttgatga 127560
gggcgggaat gaggagttgt tgatcaaagg gtacagatag acagagggaa taggttttga 127620
gagctactgc acagcagggt ggctatggtc aataataatg tatttatatt tcaaaataac 127680
taagagaata aatttcaaat gtctcaccat aaaaaaataag agaggtgata gatatgttaa 127740
ttagttagat ttaatcatgc cacattgtat acacataaca aaatggcaca ttataccata 127800
taaatatata caagtattgt ttgtcaattt aaaataatat tactaataat ttttttaatt 127860
atggggaaaa gttcatcata acagttaaca aattgattaa tgaaatttat cttaacaatt 127920
ttatgaacac caaagcatca tcaaaataaa agtagaagag gcatttgatg aaattcagtt 127980
```

tctattaata aaaattctta atggactagg aatagaaatt tccttaagtt tatgaaatat 128040
atcaacaaaa agggttcata gtaagtgtat aatggtgaaa catttggctc attcctttta 128100
aagttataaa tgagataaat atgctcccat ctctgcttta agtcatactg agggcctagt 128160
caatggaaca aaatgagata aaaaaataaa atgtatataa atcacacaca caaaaatact 128220
ctctataccc ttccattttt cagttctcag tgtcactcta gcttttatag catcatgtga 128280
aatccaaggt gacaatgcac acctaagaat attatcatct gcataatata tgcagtcatg 128340
ggaaatgaga ttttgtgaag taataattgg tccatgattc tggactgtcg attcatatat 128400
ggatagcatt cagagaataa ggaaaataaa ttgagatgaa tttgatttta attattaatt 128460
taatttggaa acataaattt tgaaaaaaat taacctgata ataaagtaac ttagtctata 128520
taggccttga ttagcatgca gtatcagtaa tagtacactt tgcaaaatat ttcttatgaa 128580
ttatatttta tttgtaagta tttaacctag aaagaaggat ctatttgcca taatgcaatg 128640
tatgttagga attttcagat tgtatttatt catgactcgt gtcctctccg agcaattaca 128700
ctcaattcat aattgcctac actagtgaaa aaggatcctt cacattaata ccataaaaca 128760
gcaggaactg caatgtgagt ccaggcacag caacccccaa taacaaatga gccaggaaac 128820
tagcaggcaa gtcccagtgg aaagttgagc agaggaccct aactctgaaa tgctactggc 128880
acttttgatg tcggtcctag aaatactctg attatttttc tggtactagc tggaaataat 128940
tatattgtta ggtaagcaaa taaaggccct ctaattagca aacttgaaat ttacattaaa 129000
ttatgaaatt cccagggccc agtactctgc caggtactaa ggataccccg acacaaggca 129060
cagacctgcc ctcaaggagc gcagccttgt gtggaacaga ggcaggcaca cagtggcatt 129120
gcagcatgca gaactacgac aggactgcag gaaagacgag tttaaataaa gaaagccact 129180
ggaatgatgt cagtgtgttt gcagcagaag ccttgagaaa ctgcctcaga attttgaagc 129240
acatttattt ttaagcacct gaagctctta tcaaacagtc ctatcaaact ttctttcatc 129300
agacacctac ccaagtcaac tgaacgtaaa atccaccact tattataaat tcacatatta 129360
ggtgagtggt aatgagataa cagctacaga ggataaatgg attcaattct ctccatctct 129420
acaagtaatc tataatgtga caggagagat aaaaggtaga aacttacttt gggaggccga 129480
ggcgggcaga tcacgaggtc aggagatcga gaccatgctg gctaacacgg tgaaaccccg 129540
tctctactaa aaatacaaaa aattaacctg gcgtggtggc gggcgcctgt agtcccagct 129600
actcgggaag ctgaggcggg agaatggcct gaacctggaa ggcggagctt gcagtgagcc 129660
gagatcgccc cactgcactc cagcctgggc gacagagcga gaaaaaaaaa aaaaagaggt 129720
agaaacttat ttgcagaaaa gaaacaatta tttgcatttt aagtttactg ctgtgagttt 129780
tggagattta gtctgtgaga ctttcttaat gcatgatgta gttgttggta gatagaggtt 129840
tgttctctga ccatttgaca acatcctgaa actctaacaa cttctacctc caggtcaact 129900
gttgaacctg caaggagcct tttccccaga tctctgactt ccagtcggcc tttctgcctc 129960
ttgttcacta gagagtacat cctggtttcc tgtccttatg ctaagtctga tgaaacccca 130020
ggatgtctgt ctgctggctt aactggccct ggatcagcaa ctgtcccctg accagcaacc 130080
atctacccat tatacctttc actgcctctg ttaagcagaa ggtttgccag tatatgaacc 130140
aatacagtga aaacactaat attgcattag ccaagtccca ggagagattt tacatggaaa 130200
gggagaagta atatacaagt aagactagag accaagactg ctcacctttt acagacctgg 130260
caaacctgac taaaacgcga gagaggtttg gttttcaagg gggaacattt ggattcctag 130320
ccactagctt ttgcttagtc tgcctgagcc tctccattgt atatcatcag gctgtcctta 130380
ccattagtcc cctgtaggac acctatccag aaaagttaac caatttgtag caacattcta 130440
ctgtcagata tcctactagt tgccaaggat ggaaagtcgt caggagactt cctgtctgca 130500
agaatcttat aatctagaaa atgatataaa agcagaaaac agatagcaac aatatgaaat 130560
aactgttcat tatatagttc taaggaagaa taaaagagac attaattcta ttaactctct 130620
cttccacgtg attttttcct tttataattt aagtttatgt acgaggatgg gggatggtgg 130680
ggttgagggg cagatgttgc taagggtaga atcagtgtat atgtacagta tgtatacaaa 130740
cctaataagt gccctctatg tgtttttaga tttcattgta attccatttt aaataagaac 130800
ttctgttgct acagccttga attccattat tctttcatcg acaataacaa catttattga 130860
gtgtcatcca tgtgctggga acattcaaga tgctgtggat acagaggtga aaaagacaaa 130920
gattctgctc tcatagaact tcgttctaac acactgaaac tcttctctcc ccaggcagcc 130980
acaggcggct gtgacttacg tattgtgttc ccacaatccc agtgacgctc tgcactcctg 131040
atacttcact tttctctaat cagaacaata tgggtattga gcagtatgtg ttaacagttg 131100
tcaatggcag tctctgggat ggcatatcac aagctcaggc aaaaccctca attagcatct 131160
aagtgtgttt gttcttcaca gggcatatta actggggaga tagactataa gagaccctcc 131220
ctgctcattg ctgtcagatc actatagaat aaccaaaacc aaagtgaaaa ttttcaagag 131280
tgaatgactt atagccactc cttgaagagc aggctggttt attaggaaga gggagaaatc 131340
aattttaaaa agatttgaat gtcacgtatt atgtgggaag aagttgagga taccataaat 131400
gaaatctgtg ttcacaatcc agaattggtc cttgaaaaat ctctctgcct gctatttaag 131460
aaattgaaga atagaaataa cttgcagtat ttttggtgct gtcccaaatt gaaaactgtt 131520
attggtgatg ttggtcctgt gacttaagac atgacaacca caacatagag aatgttcccc 131580
atcaggacaa gggccagccc aggagaaaag tgggccaggg tcaagcccat tagatgtctt 131640
tacctctctt aagcctggct gtcaactgaa cgtaaattcc accactttag gttgggagac 131700
aaggaattaa aggaaacagc tcaatcttta tcttgggagt tcctgactgt ctcagaaatg 131760
aggaatttga tatcttaagt tctcaggtat gattaaaata gtcatgacat aagtcaatca 131820
gttgccaacc tcaagacttt attttgcaat gccttatgga aagttctgtg tatactctgc 131880
ttttctgata agctggtaat aaactggaga tcccaactga cagatattct gtaaagtaca 131940
tcaagggtaa tgccttgttt cggaggggag acgtagaaat agagaagaga atgcacaaag 132000
gtgtctattg cagtaagttt tgttctcaac atgtttgtgt cttcctggca gtaacagagc 132060
agcagcagcc acagatggct tggaagccca tcatgcccca gactctgagc aggtctaaac 132120
acagagaaat cccaccattt gtgaaccagt tacaatagtc tgtgtcacct cctccattcc 132180
ctcagctccc acagggatgt cctgtgccgc aatcttgaag tcattccaga tattgcttta 132240
acctaccaga acttgtactc cttacatttt gaggtaataa tcttattaaa acaaataaat 132300
agtactgtca ctctacaaga ccacccaact catttgaatt agtgtctgtc actgttagaa 132360
agtatgactg tcaagtttgt ttgcttattc atttatccag tgaaccataa ctgagaatct 132420
tggttgagtc cacacatatt acccaagccc tgtgttaggg accagagatg cccatttttc 132480
acagaactca ctacctggtg gtgaagcaga catgttaaaa aataaattac agtataacat 132540
accacatata aaaaagaggt caaggactgt acaggtacag aaaagggagt tcctgagtgc 132600
cttctacaag cgttaggaaa aagcttcacc aagtaagtga gggcattagg taatagggtg 132660
tcctaggaca attaaggttt gtgtaactga gaggaggagt aaataaggat attctaggaa 132720
ggatggaatg gcgtatatca aagcagtgtt tctaaaggat tgagctgact tgccaaatga 132780
catgaaattt ccccttggc caaaacccag cgatatagtt tggctgtatc ctgacccaaa 132840
tctcaccttg aattgttaca gtccccacat gtcatgggag ggacccagtg ggaagtaatt 132900
aaatcttggg gatggatcat tcccatgctg gtctcatgat agtgaataag tcttatgaga 132960
tgtgatggtt ttataaatgg gggttccccc gcacaagctc tcttgcctgc cgccatgtag 133020
gacatgcctt tgcttctcct ctgccttctg ccatgattct gaggcctccc cagccatgtg 133080
aaactgtgaa gccattaaac ctatttttct ttataaatta ctcagtcttg gtatgtcttt 133140
attagcagtg tgagaacaag ctaatacaca cagtaggctg gagaaaagag gaaatgagcc 133200
tagaggcagg tggagggttt tcaaggagaa cagccatcca attagatgtg cattttaatt 133260
agaccctgcc agaagtatga aggaagattg actggaaggt gggagtccaa aaacaaacag 133320
acaaaacaca gaagaccaaa tagaaagaat aacgataggt gagtcaagaa attacggaat 133380
caagggtgat ttctgagttt tcagcttgaa caagtacatt gtgacatttg ctaggaaggg 133440
aaagatggga gagaaatgga tgaaggggta ggctggaatc cagaaaataa atgggaaaag 133500
aaatgatata gtagaagaga tcgtgggaaa tcctgtagaa atgaggaaat gtggtgactc 133560
aaaagatagc tcagaagtga ctggtgaatg caaagatgta ggatataagc tactcgcatt 133620
tcaaatgact aatcacgcat agactcaaat tgaataaaaa ggcatttaca actaggaaat 133680
aaaaataatg atttgactta ttttgatgac ccaggataac atctacatct tttgttaaaa 133740
taagtcatta atggtttatg aaagatgctc caacatgtta tttgtaaagc atcagtgcct 133800
caagatacag ccttttttgtc cctgtaacca acccatttgc aagtaaaatg ccatagtcta 133860
aaatgtttag tatgtgaagt tacaattatt atacatttta tactttcaaa aaacctgttc 133920
tctgatctta tattaattta ctcctttcct ctctcaacct ttgtttaatt tatagttctg 133980
tcttgtcttt tccttcctca tttaagaaat cactaacatt gcccattctt caaaacaacc 134040
tacaacttga ttctttgcat tccagccttt cttttcttaa cttgcattat aaagattatt 134100
aggataggct ggacacagtg gcccatgccc ataatcctag cactttagga ggcttaggtg 134160
ggtggattac atgaggtcaa gagttcaaga ccagcctgga caacattgtg agaccccatc 134220
tctaccaaaa actacaaaaa ttagccagac ttgatggcac acacctgtaa ttccagctac 134280
ttgggagact gaagtgggaa gatcacttga acccaggagg cagaggttgc agtgagctga 134340
gatcatgccg ctgcactcca gcctgggtga cagagcaaga ctctgtctaa caacaacaac 134400
aactatagct atagatatag atatatagga ttaactgcat atcctatcat gcatttcaat 134460
tattatatat taaatgttct ctctttagta tttcacttca catctctgct ggattgagga 134520
tctcagggag tgttttacag ctaacgtgtg ccagacttcc ccatctcagt cccattctag 134580
gccaactcat gatgcatgcc ctgtccgggt tccaatagag gtttggcgga agaatcctta 134640
caaacaccaa atccttgatc tgtcctgagg aagcctgaat catctgattg gccccagaat 134700
caccctgatt ttccatgaat tccctcaggc aaatgttggc ccagaataag accaatgtaa 134760
aagcccagga gaatagtgga gcagtagact agcatccaag aatgggggaa aatgatgaac 134820
tttgcccaag aatttgaaag catgcttaat tcagatttat agtatctgac tcacattcac 134880
aaatttccct gtgctctttc ctacaaaggt tttgtttttc ctttgctaac ctttaccttc 134940
tgcctaaaat atcactccct tttttctctt tccatgctga aaattctgtg ccctctttca 135000
gctacacttt tgatcactga gattatatgc ttatgacttt ctggcattaa aagatttcac 135060
tgactgctca gtttttctga gggtgtctat ttagactagt acccctaaat tttaagcgtt 135120
caataatgta aaatttgtga gttataatgt ttcatacata gtacaaatca cacctacatt 135180
gcactgcttt ctaacttaaa aactgtacat ttcaaaaagt agtaaatttg ggagttatta 135240
agagggaata aaaacattga gttttaacgt agtgtgaaat ggtagtaata aatggaaaaa 135300
aaagagattg cagttgcaaa atactgcact gagactaatc ttcctccctc taacatttga 135360
acattctttt ctgttctgtt catctattca tttcagtttg tcatgaatgc tgcaaatatc 135420
tagtaagttc cgaccacttg ccaggccttg tgctaagttc tggtgatacg agatgacaaa 135480
taaactattc ctaacctcta gtagctcata gtagcaggaa gaaaaacaca tacataaaca 135540
aatcatcttt atcaaatgtc cagaaaaatc atcttagcat ccagaggacc actggcagca 135600
cctgacatat agtagcagtt agtaaatatg tatcaagggg tctggaccct actacagcct 135660
ttgcctccag ccagccagac agccttggtc aagtcaagaa acctccacat acattaacat 135720
tgaagtggaa atgtgtgttc cattcattca tctagcattt attgagcaac tacagtaggt 135780
cagactgctc tctggtgaaa ctccaaagtg aataaagcaa agtgctttgt taaggacctc 135840
tcaatctagc agaggggaaa aagcacataa aggatcaata atgtatgatt aagactatag 135900
tgggaaaatg tgtagaataa aatgagtgcc tgaatgaagg agaaactgat tcagcctgag 135960
cgatcagaaa gtctaaagag aggagacaat gtgtcagctg ctctttgaag gaggaacaga 136020
tattggtggg ctcattcctg aaggagagcc cagcttgaga agggatgcag aaggaaaggc 136080
atgcagcgtt tgcaccatta ttcctcaccc actgtgggca tgaggaaggg ccggatgatg 136140
cttggcggtc tcatccagac tagagtatca ataattagca ccatttgaat gtttatgtca 136200
aataatttgt ggcccttaag acagagttgg tggatgtttc cttgtgttca atacatgaaa 136260
aggctttcaa atctttaatt agtgtgtctt ttatttccat tatttgaaga tgaaaatgat 136320
tcagtcaaaa aaatttcagc tccaatatta agattatctt ttgaggaagc atataaaaat 136380
aaaaacaatg acaatatcca accccatcca ccccttcccc agtagaagtt gatatctggc 136440
tagaatgagc attaataaat aacctagaga aatacagtat tgtacagttt tatattttca 136500
actttttatt aaaattttta ccacaagtga ataatttttg ttaaaatcta actttttgta 136560
ctctgtattg gatatgattt gcttgcctaa ttaaagtcta cctgctgatt atactagatt 136620
taatatatta atgtgtcttc atttctagaa taagaacaaa gaaaagggac tatggtacta 136680
cagggagaga tagtatagac aatgcttaca gttttattaa aacctgtgga gaaatttctt 136740
ggcatctaat cttccctcag cctaaggcaa aaaccataca atgttataag tcaggtcaga 136800
gctttttagt tttaaatttg gctgctttcc taacacataa gcgtacaaaa cagtatctgg 136860
cacatggtag gttttcaata attgtttgcc gaataaattt taaatgaagt aaggcactgg 136920
gcacagtcct caaagcacct ctctgtagat actaaagggt caggaaacag cagcagcgtg 136980
agtaccagca caccaatatg gaaacacttt caggaaatat tcttagaaac tcaatttata 137040
ggcagtattc atttcaactg cacttcctat tcctacatga atttactact ttctaaagat 137100
tattcagctt gttaagagta gatacttatc ttcataaagc tgtgaacgac aagcaaaaaa 137160
atgattcagg atcagaggaa aggaaactac cttttctaag ttgatgcttt tttttcttgg 137220
tttttgtgtg aacatgacat tgatgcaact aatagtaata attcctgcat gtgttcttga 137280
cacatcaacc ctctgaagta aagatcacac tacctatgca acaaagtgtg attacttgga 137340
tttttaacaa aggttaatag gagtaatttg ggggtttctc caggtttctc tgcatgtaga 137400
atgggcaggc acaggaaaag gatgatgatg aaaatataca ttcttgagga ctgagactgc 137460
agacatgtaa agaaattgag tggttgaaag cttttagtct gtgatggtgg ttctctgaaa 137520
aaaagctgaa ttttacttaa atagcattaa tataaaaata cagcttcata taatcgaaaa 137580
aggtcaataa tttacttatt tctttttact aacgagataa tttttgaaag aataaaagga 137640
aaaaattttt taaataacaa aatagtattt aagaagggaa aaatcagttt taatcactgc 137700
ataagaaaag gattttctag ttgataacgt aatgcctaaa acaagaaatg agagctccat 137760
gtagcattct ttttcattta tattcctttc agtaacgaaa tagaatctgt tcccctaatg 137820
aaattctatt tcattagaat ttttgaagca cctgtcacct atcatcatca gtttgtacgt 137880
atttcaagtt tttccgatga gcaaatggaa taatgcaggg tccatatgtc cacatgtctg 137940
ggaggaaaga ttccacgtgg tttttggatt acctgtctgg actctttctc ccatttattg 138000
cttggaatat gtcaccttct gtcaatctaa ttactcctct aggaaacggc tgttctcagc 138060
tcacagtatg acaatcgctg tcttgtgaaa atatcccaga agcctctgta gttgatggat 138120
ctacctcaac agtgtcactc tgacgtggaa agctgacttc agtatacagg cttgctcaag 138180
atttacttga gttctctgag gaaagagttt cttcagatac gtaaggagag aagctggtgg 138240
ttttaggaga tctcttgcct tatcttgaca tacatgaata aatcttttca aaacgtagtc 138300
agtcagctga gagacagtat atacatttag gacttccagc ccctgtaaaa gaatgacaat 138360
tgaagtacct acattacctg accagtgaca cttgtaaaag atcagagaag ctttcaaagg 138420
ccaacagcag agattttgat tttgctagaa aagggcccga aggaataatg cttatttatc 138480
catttagtca gccctttcgt tcatatcgac tattcattac tgtgataaag acagacttgg 138540
ctgaatctaa cagaaattct tttgttatca ttaaacagct gtagattttt aatataataa 138600
agataaaact gctcttatag ttccacattc acactatgat attcaagttt gtgccatcac 138660
ttccattttc agagctttat aattccacca taatcatttg ttcttggcag aaatgtgtta 138720
tacaagcact cagctgagga taatattttt gaacattttt ttcaatgttc tttctggtta 138780
tgtgattatg ggaatttgga actcaatatt aatttgctct tcagctttgt gtttgtatat 138840
ctcaaaatgc tctttttttaa ataacacaat ttaacttgaa tcattactta gattcgggtg 138900
atattcatag caagataatg cagtcagata caagaagaat gtattgggag aaaatgagcc 138960
acatttttcc ttctcatcac tgccatttcc tttgtgactc catgccacct gccttgtttg 139020
tttaatagtt tatataattc ttcaggtaca aagtgagcca ctgacctaat tggttttttt 139080
cattcataaa ctgatgtgtt ttattgacca atatgcattc caactcttga ctaaaatttg 139140
acatctaaga aaatcaatat tttagctcta ttttcatact tgaaattttc cctcagccta 139200
attttttaaa atttctactt cttttttttt tttttttttt ttttgagatg gagtctcact 139260
ctgttgccca ggctgaagtg cagtggtgtg atctcggctc actgcaatct ctggctcccg 139320
ggttcaagtg attttcctgt gtcagcctcc caagtagctg caattacagg cgtgcgccac 139380
catgcctggc ttattttttg tatttttggt agagacaggt ttcaccatgc tggccaggct 139440
tggctcaaac tcctgacctc gtgatcggcc tgcctcggcc tcccaaagtg ctgggattac 139500
aggcgagagc caccacgcct ggacaatttc tacttcattt atttcagcgt ccagtgtcct 139560
aactatagtt acatatgagt gagagagatc tagtctgcac tcatcacttc acacgggtgg 139620
gaaaacgggc aggggaaagt caggccccac actgtctcca ggcaggaggc aaatactcgt 139680
tgactgacct tggaccatca tgcttggcca tatgggtttg agacctggca taggtttacc 139740
taatctcttc atggaagact tgtgagagat aatgggttaa tatttgtgga gatctttcaa 139800
caaagtgtaa ttgatgtttg aatttttata aaccaaacac aatatctacc ccctgaaagc 139860

```
tttgtgagaa tatttagcac acatgtatgt gccagatgga ttgtaatgac agttgatagg 139920
cctctcctca cccttgcatt ctgttgtcag aaatctgcat atcaaaacaa ctataatttt 139980
tacaataaga tttattggtt aaaagatttg ggtgcacact gaaaaatcta ctgcctggat 140040
aagactataa attaacatta tggaaggctt taaattaaag gtttatataa gaaaattatt 140100
ggcagggtgc catggctcat gcctgtaatc ccagcatttt gggaagctga ggcaggagca 140160
tcccttgagt ctaggagttc aagagcagcc tggacaacat aatgagaccc tgattctaca 140220
aaaataattt ttaaccaggt gtggtggcac acacctgtag taccaactgc ccaggaggct 140280
gagttggaag gattgtctgg gcctacaatg tggaggctgc agtaagctat gaccacgcca 140340
cactgcattc cagcctgggc aacagagcaa gactctgact caaaaaaaaa aaaaagaaag 140400
aaagaatatt tttaacatgt cttatagata acttttgaaa aatatcaaat aatatttttct 140460
tgatctgaca tatttttctc tatacaaatg aattctaatg aaaaatatgt ggaatataat 140520
gcaaaaacaa tcagaaagta ttcttaaaag ctcaaagata tgcagagatc aaagcagaaa 140580
cacatcataa tacaatagtt atcagccaga agaatgtttt tgtggttgag ataataagaa 140640
aagagtatga agcacaggaa gttaagttag taaataaaat tattattcta atgtattgtg 140700
atgttcttta tagtattact gtagaaagtc tctaaaagta cttgttatga gtgaaaaatg 140760
atgcctgtag atccaagata aggggacagg tggccccacc aattataaat tccccaagat 140820
tgtaaatgta tattttatca tgctgtgtca aaatattcat tttaatattc aaacatttta 140880
ccacataata agctgtaacc atatgtttat ttgttatatt ataccactat aacattaata 140940
aatatttaca gagccactgt gtatcccaga tatattagaa atcatagctt tcttgatttt 141000
ttattttaag tgaaaatatt cagtgcctca gaaactaatt ttaaataatg ttacatttgt 141060
tacacattga taagagccaa ggagtttaga tttttaagac tgacaccccc ctttttaact 141120
catgttgttt tatttatttt ccccaattgc atgaattaaa gatggggtgt tatctcagct 141180
ttgaattcct tagcttgatg tcacagcttt tgctttattt gtatgtgaat tctgtcttta 141240
ataaagatga gctctgctga actttccatt aatgagagac acttaggtat gcatctcttt 141300
ataacggatc ttggtggtac caggaaaatt cagaaatgtt gctagtctat taataattaa 141360
catgacaaac tatgattaat cagaagtttt atgatctcta aaaacataac attatctctg 141420
taaatcgaat tgtatacaat taagttgaca accgttagta aaaaaaaata ataataataa 141480
agcaggccag gttgtggtgg ctcagcctgt aatcccagca ctttgggagg ctgaggcagg 141540
cagatcacat gaggcaagga atttgagacc aacctggcca acatggagaa acccattccc 141600
tactaaatat acagaaatta gctgggcatg gtgatgtacc cagccactca ggaggctgag 141660
gcaggagaat cacttgaacc cagaaggcag aggttgtagt gagccaagat cactccacta 141720
tactccagcc tgggcgacag agcaaaatcc tgtctcaaat ttaaaaaacc aagtaaaact 141780
caagactcct aacttatact ttttctgtta caatgttaca ttagtattta ttcttctgtg 141840
acagctgaga ctagaccaga cccacatcca ggagacagga ggttcaagat gaggcactga 141900
ctttttactt tcatgtgtca gtctcagggt gattcctact cagctgaaaa actaggagga 141960
acccttgcta gtttggtagt tattgacttg gttacctgtt ttcagtgttc ttcgtcttcc 142020
ttactcagct cagctgtttt cacttttctt tccacctgtg tttaggaaga gaccttctca 142080
gtattataaa ttttgataag attttcacat atatagaacc ctaacaaaca aaagtagttc 142140
tccatataag cacagcgtct gagcattctt caccgatgct tggtggggat attagctgtg 142200
```

```
ttctcttaca ccctttagct gtcaagtaca tcagaagtgg aggctgtggg gacaggacac 142260
cactaatgcc aaccattagt ttaaattcac acttggatct gtttccaaca tttctgcttt 142320
tgtcatcatc acaggttcgg aaatcattgt gtaatgtcct gatttctgat ttttctgtgg 142380
gaagagagtg ttgcaatttg ccaccttaat tgtattctgc tgtaattgtc tctcactaga 142440
tatttgaagc acgtaagaat tctgtatcat gaaacttgag tccttatacc ctctgttcat 142500
tgactgaatt tagttgcaag aggaatcttt cgcttttatt tttttaaact gctgatgagc 142560
actcgattga aatgactcag ctttcatctg tggtttctct tccctaatag aataaagcat 142620
atgtaataac ctgaaatact ggacagcttg aacttcttta atgcccctga atgtctctta 142680
cagcctttgt ctaggtttga actttccaaa ttatgtattt cagacgttga gaaagaaggg 142740
ccttaatggc tgtgacagcc cagaccccga tgcggacgat tccgtaggtc acagccctga 142800
gtctgaggac aagtacagga aaattaacga agatattgat ctaatgatca gcaggcaaag 142860
attgtgtgta agtactcaga acacccttca tttttttac tcttgatatt tctctgaacc 142920
tggcaggcat tgaacaagaa agaaaacaaa ggctgtgaaa gccccgatcc cgactcctct 142980
tatgcactca ccccacgcac tgaagaaaaa tacaaaaaaa ttaatgaaga atttgataat 143040
atgatcaaga gtcataaaat tcctgtaagt accaaaggta gatggctggt ctgctgataa 143100
ctgctgcagt aacatacctt aaccctctca gtgatggctt tctctaagac tcttcggaaa 143160
gtcaaacaga taaatagcca tctcatccca cgggcagctc atttagaaag caaaccctaa 143220
aggatgctga gattatgtaa tctaacagag ttgccatcga aaagttcatt ctgaggtaga 143280
acagttcaca gcaggaagag aaagatttat gagacacacc gtaaatttac acaatctttt 143340
aaacacacag tccatgcaaa tcacaataca tgagtaaaac actggaacct ccttccaagc 143400
aagtttgaga attgctataa aatacataga ttatacattg tttgctaaga gcagatactc 143460
aagtgggtca gcaattcttt catgtaaact gacaatcatc acctaaataa aagctgattt 143520
ctgaataaaa cttcagcccc tctccctata catgaaattc aacaacagca ctgaagggtt 143580
aaagctaatg ctcgctgcag ggaacagact gcatgaaacc taatggtaag atttcaacat 143640
gtttgtgtgc tggggtgatt ttaaagcttt atcagaatat tatccgcttt gccaccaaca 143700
ttttccatgc tttaacattt ggctaatttt tgttttaacc aaatgaaaaa aattctaaca 143760
gtcaatcata tgccttgcca gatatttaag agaaataact gcatgtatta ttttgttgtc 143820
cacatatata ggaggaaagt acatactttt tattagattc tgtcatcaat caaataatgt 143880
taattttgtg gctgaaaggg gtgaaaccca aggctcacat accttctaaa taactaatgt 143940
tagtgtctga accttaattg tatacaagct cctcagtagg caatcagttc cttttgaaaa 144000
aagttcattt tttgtaagtt agcaaaacag cctaaacctg agaaatgaga gagactgaag 144060
tgaaaatatg ttttggtgat tacaagtgca gatatgtggg gacaaagttc gaggccaaat 144120
tcacaactgc actcacaaga taaattaata ctttaccata gtagctgcac actcaaacct 144180
gaattgaatt aaattgaaca ctttaaaact tatttacaaa atgtgtgcat attaaaattt 144240
ctatccttat aaatacctat ctgcttcttt tgttaaatga aatgtcagca gtagaacttt 144300
tgttgaatca gaattattaa tacactgtat catgaaggaa agctaagtgc tataaattct 144360
taagggtttc ataaaactat tatatgcaca cattcatagt gggcacttta tgaaatggag 144420
tatttagtat tatatgtagc catgcatact tgttatgtcc agaattatta aataataaaa 144480
tatccattgg tattttattt tgcctagaag aaaaaaagaa gcggctcatt tgggccaatt 144540
tttattttta tttatctatt tttatttttg agacggagtt tcactcttgt tgcccaggct 144600
```

ggagtgcaat ggcacgatct ccactcaccg caacctctgc ttcccgggtt caagcaattc 144660
tcctgcctca gcctcccgaa tagctaggat tacaagcatg tgccaccact cccggctaat 144720
tttgtatttt tagtagagat ggaatttctc catgttggtc aggctggtct caaactcctg 144780
accttaggtg atccacccgc ctgggcctcc caaggtgctg ggattacagg cgtgagccac 144840
tgcgccacgc catttgggcc aatttttagt tcttatgatc tgagtttatc ttgctatata 144900
atacattggt gtggagcagc tgtgcattaa ggtttgtaag tgtaggatgt taaggcggag 144960
taccttaggt gtgtcagata gtaagaatcc cctgcacagt tggaataaag acagatgtat 145020
gcagtactgc tgatcactca atggaagcga tcatataggt ggagttttaa cccctaaagt 145080
tctggaagaa tgcacattgg atcttgtttc tcatacttta gggagagaga catgtaatac 145140
acacctgtat tccctcacag gatttcagcc tgttacgtaa agagttcaag atcaagatac 145200
gtgatttctt aaggggtgca gtggtgtgtg gtaggggctg aaaaaccaca ttagagttta 145260
cgggcagagc tgtgagaagg agccacccag ctccgagcta tgccacagag tctccatctc 145320
tttagtaagt gcttcagtct tcacgatgaa aagcccagtt tttgcacatc gctctgagtt 145380
gctggaagtc aattttgttg aaagtttcca cagctgctaa aacatttaca gcagggcaag 145440
gacactctgc cctttgtatg tagagagtgt ctccacctct ttaaaaacat tacaagactg 145500
tttttctatt tcgaagaccc agtttgaaga gtttcccttt taaaacagaa aatttaatat 145560
tgcagtcacc tgttagtata ttgtaattta tgcccatatt cctcaattac ataaaataat 145620
tcatgggtga tttggaactg tgtcgagcag catttcctca tgctgggttc gccatggttc 145680
atgctgggct tcacagcaag agaaaacacc tccgtctgag gaaccagcag aagttaggaa 145740
aggggctgaa tgaatgagag gcgggtgcaa gttggttgag agtaaaaggg aagggaggaa 145800
gtggaaagaa acagtatgta ttttcttcaa aataatgggc tgtgaagaga gagaaataat 145860
gttgtatgta ggatcaaggg aggagttaaa atgaaagcgc ttgagattat ttacatgcag 145920
aggagaagtg cttggaggaa ggaaaagatt gaacatacag gtacaatgga gatagaatgg 145980
caaagcctct caaggaaggg aaggaggatg ggacctaaac aagaaggtgt tacagatgga 146040
gccaggtgta gctaaggtgg tagctgggta gaattacgct gagtaggtga ccatataatg 146100
acctctattt tattttattt ttattttta ttttttgaga cggggtctca ccccgtgcct 146160
caggatggag tgcaacggcg tgatcctggc tcccctcaac ctccgcctcc catgttcaag 146220
tgattctcct gccttagcct cccaagtagc tgggactaca ggtgcctgcc accaggtctg 146280
gctagttttt gtatttttag tagagatgga gtttcaccat gttggccagg ctgttctgga 146340
actcctgacc tcaagtgatc cgcccgtctc ggcctcccaa agtgctggta tcacaggtgt 146400
gagcctccat gcctggctat tttgtttttt aatgtattta gtttagcttc tgtagttaat 146460
tagggaaggg ggaagcaggt gattgaaaaa ggaccgagaa gttagacatc atgaggaata 146520
ggagttggag agggaatgaa caagtccatg atagacttgt caggcagcct tgagggaatt 146580
tagataacca gcattggtac tcacaagtca tcagagttgt atgatttttt ttttcctcta 146640
ctacagccca gcagctggta atggttaatc aaaatttaaa ggtgtcatta gtggcaaaaa 146700
aagggtgggg ggaagattca gttcaatcac tcacattaaa taaaagaggg cccattaact 146760
aaaaatattt tactttaact attttatttg atttttttat tggacttttc cttgtggtaa 146820
gtttgggaaa atagtgggtt ttggatgaga gttcagatac ttttctgatt atgactcact 146880
acagtaaccg tgatcacttt gttcagggat agaaactaaa agttttttag ctgtcatgtc 146940

```
tgtgtccttc aaagctggga ccggcttcat gggccctcga cttggccctg ttctcatagg 147000
gctgcacttg gttaaatact ctgctgtcat tgtcttgaag ttcttaatac ttttttaaaa 147060
agggccccca cattttcatt ttgcactggg ccctgcaaat tacatagcca gttctgctga 147120
cagcatttca tttaatcacc ccaaattctc tctttcttcc tatcttgagt gtttgtaaaa 147180
gttggagcct ggccctgaag tctttgcaag tttggtgttt ttaactactt tttggctttc 147240
atttttttaga caaaaaaaaa aaattgttta aatgtagatg ctttcaagtt tcctaatttt 147300
gaaaagtcaa ggagaaaaag aataatgcca atttcttaga aatatttata tgtgattata 147360
gcatttgcat tccctaaaat gtttagagca gcttcatctc ttcatagata caaccatttc 147420
atgccttaga taagaaaatc aaggtcaagg gagattaaat gacctgcctg gttagatggc 147480
aatttattac ataacctgga ctgtaactga gattcctgat agaaaggcta gtgtttattc 147540
tgattctcta aaatatcttc tcagtgtgct catttttaag cttataattt gctttcaaaa 147600
ttattataga tagttccttt aactcagaaa cagaaaatct aataccgtat gttctcactt 147660
agaagtggga gctaaacaat gggtacacat ggacataaag atggaaataa tagacactgg 147720
ggactccaaa agggggaag gtagcagggc ggggtgaagt ttgaaaaatt agctcttagg 147780
tacaatgttc actatttggg taatgggtac actagaaatc cagtccccac cagtatgcaa 147840
tatatccatg taacaaacat gcacatgtat ctaaaataaa attaaatttt aaaaaattat 147900
tataggtagt tcttgataca ggtaaagcaa aagattaata gaatacaaat gatcttggta 147960
tattttatga attttgaaat tttcaactat actctgatac cataattata tttgactgct 148020
tagccaatca caaagtagtt ttataataat cattatcatc cagttgtttc tgatccagaa 148080
ttctagaagc tgaagaatta attcttgggg ataatagtca gaggaaggaa ggagtagaat 148140
gactttcact gacctgcttg tttggatggt tctgaactca ttacataatt attaataatc 148200
ctctttattt tggatgtgca tataatcacc caagggtgag gggatatggg ctttgctctc 148260
taatgagaca caaccaacat tctatagcat attcagggaa gatatagttt tatagcagat 148320
ccttagatac ctattaacag ttaaacattt ataagtagta acagtgaatt caaattaaaa 148380
catttgtagc ccagagatgg ctttaaatac aaactctaag caaatatgga aaaggggagt 148440
ctttaagatt tattttttcc taaaacctga gacactccag tgtagatact cacccacatt 148500
tcatgagaac ccatttagtt tattatttac atggtccaaa gataataaac tgctaatatc 148560
tagcccttat tcacttaaca gaatgatttc tgactacagt attttatttc tatccaaaaa 148620
cttatactgt gttgcatagt gtttggtagc aaaagcaaca gactcagtca ctagttagat 148680
gactttgggt cacttactta acttaccaat ttgaaaagga aagaattata tctatggtca 148740
agggatgttt aaaaggttaa atcatatcat gtatgtcaac tatacagcac agtgcctgct 148800
caataagtaa tatacagtaa atagaagctt tacttttgtg tcagtagagt gtcttcctaa 148860
aaattctcct ttgaagaaaa atattaagtt cgtataataa gaagtagagt aggctctgca 148920
ttgcctcaca gcaaaagggc actatttaac caacatcata aatgatttta taaccaagga 148980
gaaagaagag caggagaaag agatcaggat atgggcaagg ggcaggacaa attgcaggat 149040
taaatagggt ggtcagcgtg ggcttccaag agaaggccag attttgagca gagacttgaa 149100
ggaggtgatg cagttcgtca tggaaatgag gcagggaggc agaaggtgtt aggcgatgag 149160
ataacggagg ttggcaaaag ctagagctta atagggcctg tggacccttg gaagaaaaaa 149220
attctcatct tgagttttta ttctaagatg agagccctca cagggttttg agcagaggag 149280
tgttggcatg acttaagctt ttaaagggtc aatctaattt ctggtttgaa aatataaagg 149340
```

```
atggcaagga ccggagcagg taaatctgtt aggacgtgac tgcagttatc taggcaagag 149400
atggcactgc ttgagccagt gtaatagtca caccctccag tcattttgat acccaaagat 149460
agtccaacag atttccaaaa tgctccctaa ggagacagtc ccacccctgt agagtaccag 149520
tgttctagat ctagagagtt actattatgg cccaaggttg cagcaggaaa cagatggcaa 149580
actctaaagg gtaattgaag acagtttgtt aaaaggactg tttacagatg ggtagagtta 149640
aggaaaacct gagagaataa tgaagtacat tagggcttgc aacctagaag ctgttcctat 149700
ctctagatct gaaagagtaa gtggagggga aaagtaccag atcacagcaa gatctatgtg 149760
tataggagag aacaactcaa aaagagatgg ggtcttcgct agagaaacgc agcctcagcc 149820
agcctgtggc ccagcaagga tgatgccact ataaaaaaat accctgactt tgctcccctc 149880
ctgctctctg tgctgttgct ggtgcctccc ccactgacca gtgggaagcc agagggcagg 149940
agagcctggt tgatgcagtc tggagggtca gctcctgggc acacagtaca gtgaaggggc 150000
tagagggtgg gtctggatgg agcaagtgga gaatatacct agtagaatca ctttactttg 150060
ttttcttggg tatgctagag caatccttat ttggcctttt aatgaagaaa tacaatattt 150120
tattcatgct atagacttcg actttacagc atatgctgat tttttgttgt taaaaggggg 150180
ctggacatgt aaggctaaat tcattatttg atgtcttatc aaacatttat attccattat 150240
gtcatgatgt ctatccaaaa attatttccc ctgtttactg tagataaatc ctaataaaga 150300
ctgaccatat tacttatatc acttgaacat ttttatttcc ctctaaaaca atgacagatt 150360
gggccagatg tggtagctca cacctataat cccagtactt tgggaggccg aggtgggcgg 150420
atcacctgcg ctcaggagtt caagaccagc ctgggcaaca tggcaaaacc ccatctctac 150480
taaaaataca aaaaaatagc tgggcgtggt ggcacatgcc aaccactgct tgggaggcag 150540
aggcagcaga atcacttgaa ccagataggc agaggttgca gtgagcagag atggcaccac 150600
tgcactccag cctaagcaac agagtgagac tgtgtctaaa aataataata taataataaa 150660
agtaaatatg aaataaaata caaatgaaaa atcaaagatg tgtgaaagaa aagagttttg 150720
aatgtaaagc atttgctgtt gtcaagattg acatgtccag aacatggaag aaaagaaaaa 150780
tgggaaatta ataataaggg agcataaaca taaacaaaga aaagtattgt gatcatcacc 150840
aagataaaca gagaaatatt acacagaaag atgtatgatg caggccagcc aaccaaacag 150900
taacagaaag tggatgtcag cactaagggc aaacaatagt aaaaacaaaa tgggaccaaa 150960
aaaaacaacc aactgagcct caagcacata tgcatttaaa tttgcacaat aacttattga 151020
gaacccccaa gggaatgcct taatgccttc tataaatcct attccatata tatgtccatt 151080
ttatattaag aatgccatat gttttgatac catatgagtt ctctggcatt atattcaaag 151140
agtattttta ctcgtaatgc ttaaaaaaaa gtagctacaa ttatgttcct atgttcatct 151200
agttagtaca gcagaaacat aaacatgatt ttgcttaaat tgacaaaata attactcaaa 151260
aatcaatcat tgaaacctgg attaatctaa ttagacatcc acacagcttc agttcactaa 151320
atatttgcca actttcacaa ttgagataca ggtcttgcca tttgtcagtg gcggtacaca 151380
ccaaaatatg aagcatagtg ttttctgaat tgccacttca aaatgtgaat tattgaatga 151440
tacatgctct gttgaatctt gtatgttaaa atgcctatta tctttagagt tacttttaaa 151500
acatagactt taaaaaatga taattaaggt atatgtgcta tgcacatgct tggagatgat 151560
tttctatcat taaacttcta cataaatatg cttcaataag caattaaatc aaaggcttcg 151620
gtttgcattt taatcctttt tctctgtgaa gtcatcacaa tcaggcacct ttgatcttgc 151680
```

agtcatttct ggcaccagat tcagatatca caaatgaaca attactactt aatagaatgg 151740
aatccaaaga caatggagtc taatgaaatg gggctttgtt ttaaacaaaa gtgaaacatt 151800
ttttaatggt tgcaaagaag gagttctaag cacatttaag aaatcaattt atgatctgaa 151860
cgtcttgaga gctcttctta atggtcttct agacacaaag tagtttggaa tgtagaattt 151920
ttcttggaaa aataagggct gtctgtcttg aagagcttct gttattaatt cttttctttt 151980
acctttgttt tgttttctgt tcctgcaggc tgttccacct cccaacttcg agatgccagt 152040
ctccatccca gtgtccagcc acaacagttt ggtgtacagc aaccctgtca gctcactggg 152100
aaaccccaac ctattgccac tggctcaccc ttctctgcag aggaatagta tgtctcctgg 152160
tgtaacacat cgacctccaa gtgcaggtaa cacaggtatg tcctcataag gatgtaatgc 152220
taacaaatag ttggaaggaa ccattttcgg caaagccaac actgctttat ctacgagatg 152280
ttttctggtt ttccacttac tctccttcat ggcttaccat ccacccccga gctaggtctc 152340
ctgcatgata gagcctaaat tctttagtat gtttttcgaa atctttcata atctgccgtt 152400
tatctttttc attctgtcac ctatctcctc ctgtggctat attttaacca catactctca 152460
aacaggatgt cagatatcct ttctccacac ttttacttct gctcgtcctc cctgcctaaa 152520
atgccatttt ccctcttcct cctggccaag ctaccacttc tgtgaaacct tcccctgtgt 152580
tctgtgatag tatttatccc atttagttat ttattatttg ggtcaatttt tttttattta 152640
tacagtaact tatcccacaa aggacttagg cagaaaggaa atatgataag atagcatcat 152700
ttgtaagaca tgtgaaataa aaacaaagct gaatcagaaa tgaagttaat taaacacatg 152760
tacacctgcc acaaatttgt ctctgcactt ttacttgctg ttgttcaatt cacagtgtcc 152820
aagagaaaaa taaattattt ctcagaaaaa gttcatccat tcttagtact tagaacaatc 152880
aaaatacatt atgatgaatt gtatttaata tatgtctatt ttgatactgg atttaaagaa 152940
catttaaggg aagaatgttc tcttgatttg ctaaactaac agtaggaacc aagtcaatgc 153000
gtattgaata taacaaaatt attcctttat gtttccagaa gcagcatcaa aaataattgt 153060
atttctaagt cacatacagc aaaccattat atatttgcat ttcatatttt taaaagtact 153120
ctataggaaa tttttaatgt atcctacata cacatagctg tatgaaaata gtttattcat 153180
ggaggaattt tcctgtagaa tacttatata tctgccttac aattaaaacc aaacatgtat 153240
tactattttt gttacagaag ctttatatag aaaatacagt taaattcatc caaataaaaa 153300
attttaatct tgagtctggg aaatgtatac aaaggacttc attgagccat tctcttgact 153360
tttgaatata tttgaaaatt ttcgtatgaa ttttcagtaa ccacatgtat tcctttcaga 153420
tcatactaga atgcagttca ctttcctatt tgataaactc atgctcattt ttttgaattt 153480
gatacggtat ttccaaaata ttatctgatt ggaaataata aacatttgct taaactgtaa 153540
cgaaggccag atgcagtggg tcacgcctgt aatctcaaca ctttaggagg ctgaggtggg 153600
aggattgctt gagcccagga attcaagacc agcctgggca acatagagaa accccatctc 153660
tacaaacatt ttttttttaa attaactagg tacagtggct tgtgtatgtg gtcccggcta 153720
ctcgagaggc tggggtggga ggaccacttg agcctgggag gttgaggctg cagtgagcca 153780
tattactgcc actatactcc agcctgggca acagagcaag ctctgtctca aaaaaaaaaa 153840
aaaatcgtgt atatatatgt atatatataa acaaacattt tcttttaatt ccaaaacctg 153900
aaccaactaa taattacaga gtatcactta gaggcaatta gaaaatctag atgatattct 153960
cactattatt cttttggctg aatgttgttt ttttcaaaac taaaagtaat tttttttttt 154020
ttgagacgga gtctcgctgt gttgcccagg ctggagtgca gtggcaccat ctcggctcac 154080
tgcaagctct gcctcccagg ttcacgccat tctcctgcct cagcctcccg agtagctggg 154140
accacaggca cccgccacca cgcccggcta attttttgta tttttagtag agacagggtt 154200
tcaccgtgtt agccaggatg gtctctatct cctgacctcg tgatccgccc acctgggcct 154260
cccaaagtgc tgggattaca ggcatgagcc accgcgccag gcccaaaact aaaagtaatt 154320
tttatgttca ataccttatt gaaacatctt gactctcata aataaacatt gccaaatttt 154380
aacatactgt ctaaagttag caatgaataa gcatatgttt cttaatctgt ggccggtgaa 154440
aaatttgtta tattgtgtca gtcaataaga ttttagtagt aaatgtgggt agattcatga 154500
aacgatcaaa tttctggaca attaacattg cacaaaatta atggcataaa acatatttac 154560
aaagaactaa acatcaaatg tgaggtcatc tgagcatata gtagacctta ctctttcttt 154620
cactttctat aaaacatctg cttagggaaa acctagactt agaaataata aaaatgcaga 154680
gaccaaagac tggatttttt taaatgtaac tttcttagaa aaaagattct gcaaaatgtc 154740
agtgattgaa tgtattttta acgtttgagc acagcatggc acaataaaac aaatgtcagc 154800
catctgactt gggttgtact ttacaagttt atgactattg caagaggaca aaatactgag 154860
gttgctgaag gtaaagtgtt ttgttctgtg ggcctttagc ctttctcgtt ttgatcttcc 154920
tctttaatcc ataggtggtc tgatgggtgg agacctcacg tctggtgcag gcaccagtgc 154980
aggtaagccc agactccata ctgcagtatg tatcattgtt ctgagttctt ctactaggtg 155040
atttgcagga caaagtcttt tgaacaaata aagttaagag atctgtgaga ggcatggaaa 155100
aatgacacca agaattttta aagcactttt ctgaagcagg agtggttaaa tagtaactta 155160
gaagaaaact atttattaac tagaaccttc cttaataaag cttcaactgg tcagcagaga 155220
attaagggct ctgatccaat caacttaatc ctggatacca tccttggaca caagagtacc 155280
tttagcaaac catacttttt gtgttctctg ttaatcattt cacattaaat atgaatcatt 155340
ttccagccaa agaagtattg aacttctatg catttctaaa gaagagtaca taaagaaaag 155400
gaggggttaa gattttaatt attcaacaat actgttaata aaataaaatc acattggcat 155460
taaaatgagc tcttagacaa catgaatata atgcatcccc aaaagaccct aaaatatatt 155520
tcagctaaga acttcttaca ctgtgaccaa taattgtctc agtcacattt ctccaggttt 155580
ccgtgttaat ttgtaatatt gagattattg agatatcgat gtcattttca atgcagaggc 155640
aagatagcac aatactttca aatgccaact gcagttcact attggcataa caagtaacca 155700
tggtaatttc tgcagctgga acatgctata catttaaaat agtaggaggc aggcatgaat 155760
gacacaaggt tatgtttgaa atgtcaaaaa aaatcaagtt tattgaaata gacatggata 155820
gcctaattaa aatattttgc cagggtcaag tagaatagcc tgctaattat aagaaagaag 155880
ataaagaaaa ttggtttaca aatacatttt tataaatata tctatttgag ggtagagttt 155940
ctctgttctg atgctggctc ttcactaatt cactgaataa tgaagaaaaa gtattagacc 156000
tacacagtga ttagcaaaca agatgaataa cactagcttc ctattttata tatcttttga 156060
aaattaggtc gagccaaatt agtgtgtaaa ctcacgtagt attttgctgg acatggaaat 156120
gaaatttttt ccctcaaaaa atactttgtg gtttgtagcc tcaaaatgag agaaccagat 156180
caaatccaga ccaatgtttc ttggatccaa gtctctacca aacactatga ttagaaagaa 156240
tggtgaggac tgagaattgg gtggtcacaa agaccaagat ataatataag aaaaatggtt 156300
tagatgttat gatgttttac ccaatatctc actgcaccga tttgcttgcc attatggaaa 156360
cagctagtag tggttctgaa agtcattaaa agtagtaaaa aagggccggg cgcggtggct 156420
cacgcctgta atcccagcac tttgggaggc cgaggcgggc ggatcacgag gtcaggagat 156480
cgagaccatc ccggctaaaa cggtgaaacc ccgtctctac taaaaataca aaaaaattag 156540
ccgggcgtag tggcgggcgc ctgtagtccc agctacttgg gaggctgagg caggagaatg 156600
gcgtgaaccc gggaggcaga gcttgcagtg agccgagatc ccgccactgc actccagcct 156660
gggcgacaga gcgagactcc gtctcaaaaa aaaaaaaaaa aaaaaaaaaa aaaaaaaagt 156720
agtaaaaaaa aaaaaaatgt ggaggaaaac atggcctact cagctttgat ggaagtggct 156780
tgttactgct taatagctag aatgctttgg aatcctatat tgaaaataaa aagtgtttgg 156840
ttgttcaatt attctgtcat tgtcaattcc cagacagttg gctaagttta atgatcctct 156900
agggatagag aagactctca atcctgtagg cataaaagtt tgacacacgt aggatatagt 156960
aacattgaac taacaaaatc ttatgcactt agcaaattca tcctcttacc tcaggacctc 157020
taccataggt atgagaatct tctaattcag aaatagaaga aaaccaaaag aaagatactg 157080
aattactcca ccctggtgat aataaatatt atatcttgat tgcatattat agctacgagc 157140
atgtagtttt cacagtttct atatagctgt gaaagtgtta cccatatttt aaaaatagag 157200
gaagaagccc tttctaactc tggtcccaag gaacacctgt tgcagatgcc acttagtctc 157260
aagcttagct gtcatgtcct actcataaac tcagccatct tccccttctt tctcatgcca 157320
accagtatca tatgtcaggc tgaatatatc cgtgctgatg tcagagaatc acataacacc 157380
agaggaaaac aaggccagcc agaatgttgc tacattttca gagaagaaaa ccaaagcaaa 157440
aaggccaaaa tatagcttcc aaattttgca tattgtcatt gaaattcaag gtttcagata 157500
aagtttgaaa ctcttgaggc caagtggcga gactgcaatt acgttacttt ttagcagctg 157560
cagttttttt ctaaatcaag tcatctcact ttgttaaaaa aaaaaaaaaa gtgagaggga 157620
gggagagtct catgaggcaa ggaagtaaat tgaacattta ttttgtgcct ataaatacta 157680
aaagaccaaa aaggtaagca tgcttttttt cagctcagtt ttatcataaa gtgtagcatc 157740
tttcccatcc agtgcctgag ccatcctttt ctcatcatac catcatccag taagtttcta 157800
gaacatccta attcatctcc ctgctttata ttgcatcctg cttcagtctc cccaggactg 157860
cttgttcttt cttaaaacct taagctaact gtaggtcatc attcacatgc caaaaatcca 157920
gccatggctt ctctttgaaa attaacagtg aatatcttat ccctaggccc attcctactc 157980
tccagcctta accttcttcc cttctgccac tgctatcaag aacccggccc tccagctcta 158040
ctaacagtag acatctaaac tgctcttact gtgcactcta caaaaagcat cattctcata 158100
atagtcgttt aaattaagtg ttcacattat gccctttcta cagattagga aactgaggca 158160
cagggaaatt aagtaattgc acaaggaaga gcccaggtag tcaggtccca tactgtgtgt 158220
ttgtatgtgt gtgttttgag acagtgtctt gctctgtcac ccaggttgga gtgcagtggc 158280
acgatctagg ctcactgcag cctcaatctc ctggtctcaa gcagtccacc tccctcagcc 158340
tactgagtag ctgggaccac aggcatgcac caccatgcct ggctaatttt ttaatttttt 158400
tccttataga gatggggtct tgctatggtt ttcaggctgg tcttgaactc ctggattcaa 158460
gcaatcctct ctccttggct tcccaaagtg ctaggattac aggcgtgagc ctctgcaccc 158520
ggcctcagtg tgtgctctta attgctacac tgtgccgcca cttggcaatg tcacggccgc 158580
ttactcttac ctatgcaatc ctagcatgcc tttccttctt ctgcttcatg ctattgagca 158640
ctctttgtca tcccacagaa ttcagttcag ccatttgaga aaagcctttc ctgactctaa 158700
cagacaagtt atgcacctct ttcctgtgct tacatagtag cctgtaccaa cattacattt 158760
ctcattgcat tatgattgca acatctgggc acatctctct aggacgctca gctctgtgga 158820

```
ggcaaactct ttctcattca gtttgtatgc ccagtttaac acctaagcgt tagcacacag 158880
cagatacttg gtaaatgttt gttagctgag taagggaaaa atagatcttc tagccatgaa 158940
gttttaatag tgttgatgta aaccagaagg aacatttcaa ataaattatg taattttcaa 159000
taaaaaaaga tatacccttg atctgtaact cacaaaaata atgtattctt ctgaaacagt 159060
atacaacgaa tgtttaatta accatttgat taaatggctg agtaccctgg gccaataaag 159120
caaagtttca ttaactcctc taatattctt aacggaaaac ctgaagagct gacatatagt 159180
agtaaatgaa atgtgggttg gtatctcaga ccatcacaaa tcacctctta atacaacttc 159240
ttatcatcac ttaacttgaa atactttcaa agatgaagac aaagggtaat aaagaagtag 159300
caggatggag ttgtactctt ggtataagag aaatatacag caagtcatta taatacatta 159360
gttagtaaca gtgacttttc taaggtttca gttgatggtt attcatccac tacttaattc 159420
tttcctctta acaacctaaa tgaaaagtca ctgcttttaa aataacattt tgtcataact 159480
ctataaaact tttttttttg agacggagtc ttgttctgtc acccaggctg gagtgcagtg 159540
gtgtgatctc aggtcactgc aacctccgcc tcctgggttc aagcaactct cctgcctcag 159600
cctcctgagt agctgggact acaggtgcac gctgccatgc ccagctaata ttctgtattt 159660
tagtagagat ggggtttcac ccgttgtcca ggctggtcac aaactcctga gctcaggcaa 159720
tccgcccacc tcggcctccc aaagtgctgg gattacaggc gtgagccacc atgcctgacc 159780
acattaaagc ttttaacatg ctaatctgag tggttattga tgatggtaag atcaagttcg 159840
gttgtttgta gtcattagat ttaatggaaa taaccattag cagagcaatg ccttgtgttg 159900
gattattcac tatcccgtta gtatcctttg ttttcacttt gataatacga ttgcctttta 159960
ttgagtagaa aggaccagta tgctcaagga gttattgatt catagttgag atcaaaaaaa 160020
gagaaaaaag aaatgaaaaa cctttaggaa ttcctttgaa catttaagat aattttacaa 160080
tctacatagc tatttgacag taaggcaaag gagatttatg tatattggtt aataatttta 160140
attggcattt attgtaaatt agatataatt ttataaaaaa gaaactaaca tctgttttct 160200
tattttgaat gttaattgtt gactatttta tgcatttggt tatcaagcat tgtcacttct 160260
ggaatgctta atttatgtca gctaaataca tggagagttg atggtggcag tgtactgccg 160320
tggataaata ttgagcagtg aataagagat ctggtttcca gactctggaa agactccatc 160380
tagcaagacc ttaggtcatg actcagcacc tttgaactta gtacttactc agattggaga 160440
taagaaacaa atatttttac aatccattta cacgcaatgt tttatgataa tataatcata 160500
aaattttgct tatgttttg taattcatct agcattgaaa aagaaaaaac ttagcatatt 160560
acaaaataga actaagtgga aagaggaaag gtcagacaat gcttaatttt tctgtaccag 160620
caccattgtt ttgcaagtat ttgttttcaa gaatacttat caaaaatttc ttggctgact 160680
ttcttattgg ccagaaagac ttctctgcaa ttcttactta gtgacttaaa atatcagtga 160740
agtggttaaa aatttagttt aaaaagttgg ctttaacaag tttgcatttt ttgttgccca 160800
ggaaaacata acttaagatt gcaatattca agaaagggag aaagatactt aattaccctc 160860
aaataagaaa actaattgtt agtataaaga tataattttt atattatttt taaaatatta 160920
ttaagcagca aatgaaaaaa atctaggtta atagttgggt tctgttttga aagtattgtt 160980
ccattagttt gaattgttct gaattaaaaa ttctgaattc attggcagtt ttaccttggg 161040
agttcaccca aaacataagt aaataactaa cggcattgct ttattattat tatttatgaa 161100
attaagtaac aatgatattt ttaacccaaa ccaagtttat caagattaaa gaaaaaaaaa 161160
```

```
aacctagtcc tcaaattaga tagctacagc atgtggtatg cagctactgc caagaaaatc 161220
agtgttcact ttccatatac aaaaccaagc aaattataga taaaccatta ccttgatacc 161280
attctctagg ggctcatgtt gaagtgggaa aggcaggtca aagacaagac aaatgaaaaa 161340
tgttacaggt taagtcagga tgttgtaaaa tatgccttcg accccttttgg tttgacttca 161400
ttcttaagga gtttgatttc cagaggaaaa aaagaaaatt ttaggttata acttcctaga 161460
gagtgtttta gcagatttta gagccctttg tttatcctga tttctgactt cacaaattgt 161520
atcctttttta ttctctatcc ttctatatct acagtaaagt actgtgaaga ttggtttctt 161580
tactcatatc ccattgattt aacctaatag tgtgaaggat aagaaaacct tggttgtttt 161640
taatattaaa ttcaagccgt taatatttcc ccctgaaata ctagttttat tcagaatttg 161700
tctttttttc tcaaagcagt cttttctctt tatacaccta ttaggttcct cttccctatc 161760
tttggcatca tgataagatt ttatttggag ataacacaga aaggaaagct tttttcataa 161820
tcatcagtga tgtgacattg tgcatcagta gagagcagat gctgaagggg ggatttggtt 161880
aaaaaccccc tcttttggaa atcagttttt tacttaccag ggactttctc actcggtgct 161940
tcaaggctgt cagccaagag tataatctgc tgtttttaga caaacctttg ccaatcactt 162000
aaattttgca gttacactta catagtatgt ttcagttgaa tttcaatcca aagaatattt 162060
agtcatgata cagtatcata tttgaaagat cattagctat gttaaactta agtattatac 162120
caagaacctt ggataaacag tttaaattta taaccaactg atacgtccaa aaggtgctaa 162180
gtgttcactg tgtttattta ttattgctcc atttcaattg ttttaactga actcaaattt 162240
aagtttatct attttactag acattatgcc ttctttttac aatttcttga ccttagagtc 162300
cacccaccac ctccagttat tataaagaac cgattatgtt gtatttaaag tataaggagg 162360
aaaaagccct gctatactaa tatagaacat tataatatag tagtaagaga aaactaaatc 162420
tatggccagt ttacatattc aaacattata acattaattt acataacaat caagaaaact 162480
gaatctttag ttggctctaa tattaagcaa ctcagtgaaa accgtaaaac catggaccaa 162540
aatttttgcc caaggagtag tttgggaaaa gattccagag gcagatattc aaaaaaataa 162600
aacaaccaag gaaagtatgt gatatacaaa ttattttagg gatggcacta ttgcccttga 162660
aaagtctgtt aaactcctct ttttccggat tgttgtaaaa attaaatgag ataactgatg 162720
caaggggtct agcacagttt ctgccccaga gtaagtgctt gttaataaat gtgagctatg 162780
gttataatca tctacattct tgattttcta gcctttctgg ttataatgtt tagcttaatg 162840
cagttccagt agtatttatg aaatgtgtgg tgaagggagc acaccagtag gcttcacaga 162900
gatgtccagc acggggctcc tatcctcaag ggtggaagta aagcggatgt attaataaat 162960
ctgaagcaga atgtgagagc agtacagtac agtgcaacac atttcacttt gaacgttatg 163020
aacttctgat gtgttcgcag cagttgtgta aatgttaaaa ccacaagtaa ttattctttc 163080
tcttctgtca tgctctctct aatttatact gtctcaatat ttttgtttat aaaaatgact 163140
gaaagaatga gcgattgtgt caataatgaa gacaccccct catttttagc aaagagacag 163200
ccccaaaatc tcaagaagtg aacaattaaa tgagtcataa atctatcatt catagttaaa 163260
tggaattttt taaagatagt gtggttcaat agcattttta tggtgcaatt aaaaactatc 163320
ccttcagtaa atcagtaccc aaaggagaat gatatttggg tttttttttt ttttgtactg 163380
gagacatcag attgtcaatt tcttccttat ttgcaaatac aaggatgcat gctaaatctc 163440
agacatctgg cttttgtaat gtagtggtag caacctgcat tttggattca aatcaaagcc 163500
tcttccttgc tgacagggtg atctcagtca agtaacggaa gcttcttaag cctcagtttc 163560
```

ctcatctgtc aaaagctggg atggtgatgc ctaaatccgc atgacagtta ggacaaatga 163620
gaaaatgttc gccaacacaa acctacttga tggactctca atctttggaa aaacaactta 163680
gtaataagta aaatttcttt acctctccct cacaatccag agcttacaca gtatgtgctg 163740
tacgttaaaa gctcattgtc tcattgacag actgttaatt tcacacacac acacacacac 163800
acacacacac acacacacgc aaaatcgctg aacaaaacac agcccaagaa acgtcaagga 163860
caaataggct agatatgaaa ttcctgaagc tctggtccag catcaggtga catggtcaaa 163920
gagaagagac agctctcttt ttagaacgtc tgatgcccct gaactggtat ggccaagaat 163980
agttcttggc tttggtatag tcttggggta tttctctaag aatataccac aaaatgcact 164040
gaggtttcag agaagtttct tcatagttta acattatgca ttattatata atttccctaa 164100 gaaacccccca gaaaaagtgg agcctttatt ttgtgtgtaa gaatccctaa ttaggagtct 164160
ttagcaagat aagaatcaga aatctgattt gccccctttc tacattaagc atattgaaat 164220
tttcatcata cccagatttc tgacccctga atgttttgtg gttgcctttt ctcttagagc 164280
tattcaatgt aaaatatctt tttttctcaa aaaaataaaa ataaaaacaa aactgatttt 164340
gatacacaac agctgaataa ctcacagttc ctagcatatg taacaaggtt tcaggcattc 164400
aggctaggac tgcagtctag aagatcatat ttttccacta attttttttt caactgtcac 164460
ttccagtaga gtaggggatt gtatgagcaa gtttatgata cacaatttaa agtaattttc 164520
tataaaaaga tgtatgttca tttgaggcac aaaacaatat cctgatattg gaaactaact 164580
tttaatctta aaactttaaa aactaaaata taaaattaat tgatgatagt gagcattatt 164640
atgtatgtga catttcctgt ctaacaaccc agtatgctgt aactgttttc aaaattgctt 164700
tatttttttt ttaaagtgag taaaacattt tgttgaagta aaagcagcaa attgatactt 164760
cagaggtcca gctgtgtgtt cagcttaatg ttttcctgtg tcaatttgct tcaaatccct 164820
caaaatcaga tactattaac aaattactaa acaaaattat ttttatacat ttatatatta 164880
gaagttattt cccgggtaac aactaatcgc agatactaaa aaatactgga catttcactg 164940
taacattggg tgtttctgat agaagctggt ctcttaaatt gacagtaagt aagtaagcat 165000
cattaccatt taagtatatt acaggggaga agattattga ctaaaatatt acaaaatcta 165060
cttttaaaag catatttaat catccactca aaatagcaca ctaaaagtta aacagctact 165120
ctggtgttca gtgtagctaa actcagtatt tcctacttgt aaatatttat ttatccagaa 165180
agagaccaga aatatggttt gaacatcacc attctgtgcc tctttatgag aattcagtgt 165240
cttctgaacc agaactacta tttactatgc ccaagttgac cttacaacat gtccctcaaa 165300
cttgcacatc acctctggct taggacaacc ttgactgtcc tgtccctagt tgtgtcctct 165360
cttcatttgt atccccataa tttgcaaatg agactcgaca tagaaaggct ttcactatct 165420
cagagcatga ctggttctga aggagcagtg tagtgttgta cttcagggca tggactctgg 165480
acatactgct tgggttcaaa tcatagcttc accagttgat agctgtttga cattgagcaa 165540
attcctggac ctctcttttc ttcggttttc tcatttctca tttttcatag ggatactatt 165600
agtatcccac agggttgttc ttgtgaagat taaaagtgct ttatatccat gtacaatatc 165660
tagcacttac atagcagtta caagtgcctg gtactcttct gagcagttaa tgtgtatgct 165720
taatgttgtg ttgttggtaa ataatactat acactgtgtt agcgattgct aatattgttg 165780
gatggtaaga ttgtcaatga ctgcctcaga tgagtacctg agagcctctc attcagatta 165840
ctttcatgct tctctcacac tagggaaata cttctattga gaaaactaag gctctgtagg 165900

```
gttgagagaa ctcttaacag aaacattttg agtagaacct agattactct gccttatctt 165960
ttttttgtcc ccaactcctg gatgcctgta aacctttctc tctgcgctgc ctcattcaga 166020
catcatttct catgtattct agagcaaggc gttctaacta gcttctctaa cagcagtcca 166080
accccctttt gtctctcctt tccactgcca tcattgttcc tttcctaaca caaatttaat 166140
aaagctaaca actaagaagc tatcttaggc actcattttc tagagtataa aatttggtaa 166200
aagcttagta taaagcctac agtgtaaagt taacataatc ttagaggttc atgttagcca 166260
agccttcttt ttcaacttcg gaaaactttc tgctcttcaa gatccattgt ttcatcttca 166320
gaggaatgcc cctccttcta aactctgaga tctctctgtc ctgcattcct tctctccgca 166380
aagcctctct ctgaaccatc tgataaattc ctgttcactc ttaatagcca ccctgccacc 166440
attcttttcc ctaggatacc atgcagctta tcttttggtg aaaagttctg tatgagtaaa 166500
ttagtattga gatttacctt gatataacga caacctgtgg caacaaatac tcgtcagtgt 166560
ggaagaaaat atcagagact tcaacttttc attttcatta gggaaaatgt ctgacttgtt 166620
taattctacc acttgcagtt agctaaggta atgtgctgtg aaatgattaa caggtgcaac 166680
aggtagaaaa gacgctttaa ttaactctct ataaacaaat ttagtaggtg ggcacttaca 166740
tgatttcctg gctttcatat atatggtaga taagcagttt gtctcaatag tgtacttggt 166800
catcaatttg caatcattat ctaaaatata aaattttctc aagtagcata aagagaagag 166860
acccttgatg tttcaattta acaagttact cattacattt tcagttctca cctcattgtc 166920
cctcaataac ttacctttta gtgcctttcc tgaataattc ttaatttttc tagcatattc 166980
tatatatcta tttgtgaagc acctgaaaca tataaagaac tagtactctg tgtattatcg 167040
ctgccactaa ttgcagcaga ggggagtgaa ttcagtgtgg gctgaagttg tctgaaaggc 167100
atcatgaaag agttggaact ttagttgatc cttaaaagat aaatttgaat taaacaggag 167160
agccaatact gccagttatt gaactgctag agcaaagatt tgcatatatt ccgaggacca 167220
taaggcaggc tgtgaccatt ggaaattagg tttcatagat agagtgtgtc aactgtagac 167280
agttctgaga gccaggcagg gcactgactc aactgtgtta agcactcatg tatgaaaaag 167340
gaacatgatg gaagtagcag ttcagaaaga cttccttgag tgggttggtt agcatcacac 167400
aaatgcacaa aagtttgcat acagctttaa ggaactcctc tgaaggcctg aaactcctct 167460
taaggcctgg tgaagaaccc ctcaagtaga gaccagaggc ccagatggag agttgctgaa 167520
atattttttt tttttttttt tttttttttt tgagacggag tctcgctctg tcgcccaggt 167580
cggactgcgg actgcagtgg cgcaatctcg gctcactgca agctccgctt cccgggttca 167640
cgccattctc ctgcctcagc ctcccgagta gctgggacta caggcgcccg ccaccgcgcc 167700
cggctaattt tttgtatttt tagtagagac ggggtttcac cttgttagcc aggatggtct 167760
cgatctcctg acctcatgat ccacccgcct cggcctccca aagtgctggg attacaggcg 167820
tgagccaccg cgcccggccg agttgctgaa atatttattc aaatggtgat ggaagccaaa 167880
gctaagatgg tggcagtgga agtagagaca ggcatttctg aagaaaaatg aataagattt 167940
ggtatctcat tggatatgga gatggaagga ggagagggga taatagaaga tgacagtttg 168000
gtagattaaa aaatggttat gccaatggca gaattagcca tggtccatag tgactaattc 168060
tgtttatgct tattagtctt atatgcttgt attcataatt caaagtccta gaaaagaaaa 168120
agaaacaagt gaagaaaact caaaatgcct aaacatccaa ataaaagaaa gtttcagaac 168180
tttgagctca aagagagcta catgttcaag tgagctctgt gagacaaggc aaaatgcctt 168240
cctcataata tcttaagcca ggaatatgtt ctttgaattt acgacttctt aaaataggag 168300
```

```
tcaataaaaa aaatgcagca agtgtttgca agttaactgg ggagaaaaat gtttttctcc 168360
taacaccaca ttcaagttct atgtattgac actaatatga gtatatacaa acttgtaacc 168420
agaagaggta gattctctaa tcctttatgt aagttaactc atatatgctt aaatttgtta 168480
tttttatgta aaacaatatt tttaatcaaa tgaaactata aaacaaactg actctaaagt 168540
tggtctgtac ttcattttct tataatctat aatcaggaaa tccattcact cctgctttat 168600
aatttttgtg cctttaagtg gtcagaggaa tgtgacatct gcatacagtc acgtctaaat 168660
tgataattgt ccaggcagag ggtaatttta aaacatagca tgaaaaaagg ttgaatccat 168720
atattagaag gttgttgaga ggtggtgttt cccacctccc ggacccctga atttaaatgc 168780
gaccattctc tttggtgaat ttatcttaag gtgggacaac aggctcaaca caggccgcag 168840
cattctgagt gaggaggagg ctgcggtttc ccagccggtt taaatgcagg ctcttcttag 168900
cagtaaacca cacgcatgta ttcatcattg attttcaaat cataggtttc tatatcactg 168960
gtttaggatc cacagtcttg cattcctgaa tctatattat gtccaaagaa taacaatttg 169020
gtggctggaa acagaaatgg ttattatacg gctccaaaat gctagctggc acaatatgct 169080
aaaaacagca gaaattcact agcaaaaagc agaatttatt tgttcttaaa aataacttga 169140
tgctctaaaa atatgaattt aagaagtgtc atcatggttc aaaatatttt acatttcagt 169200
atgtaaacac cttaaaatat gtgactaatc ttctaaaatg gcgtaatttc caaataacag 169260
gaaatattcc aagagaaaaa tagaaggctt ttaaaatcaa tttttttagt tttgaggtat 169320
ttactgaatg aaaagctaca atgtatattt actttttttt cccctactgc tgccctgaat 169380
cactgtttaa aatgtgggca aaaagacata ggctttgttg gaatttctca gagagtttac 169440
tgtagaaaat gctaaaaaaa aaaaaaaaaa aaaaaaaaaa aaaaaacaaa cttttctcaa 169500
ggcctccgtg aagcatttcc attttcgcac actggcccag tgcttgtcat atcacaggac 169560
aacacatttc acgaagcggt tttacttcct tttagcaaaa taactcctcc atgcaaacca 169620
gtatcggcat ctaccgagct ggggttttag tttcttctga tctattcaag cttcattgca 169680
ctgcttaaca gactttttc tccccttct tttgaaatta cccagctaat tttccatttg 169740
attgtttata taaaccagat ctcacacagg cttaatagat aagtgacata tgtcttcagt 169800
gtgtccatct gaccttcagc tgacagcaaa gtatagagca gaattgacct tgatgttctt 169860
attctctttt tatcccgtag aatctattaa ttcaaactaa gttcataaca tattcacaat 169920
aatgattcag gatgacatat taaatataaa actcctctaa gcactccatt ttgtcaagct 169980
ttttttttt aagtgaacat actctctttt gtttgttttt ttcttctagt gagaggaagt 170040
aaatgcattg ttttatgtaa cagcttttgc catggaatac tgttcgaatt tactgtaaag 170100
aaaatttggg ggtttgtcat atttatctag ctttagagaa tttggctaat attccagaag 170160
ttttcttata gaagggaatt gatattcaga ttcaaccaac atttcttaag tgagtcctgt 170220
cacttaacac acgttttggg ggtgtccagt ttgctttatt tttgtttttt tgccccagga 170280
actgggataa ttttattcat aatccaattg acagacttaa tcttgtagtt atttgttata 170340
tattcagcct gtttattcat gcataaaatg agacaggtaa atgaatggga tatgaagaac 170400
aaatctgctt tatacagtgt gcctcaaata tattttgctt ctaaagatgt tcccataaat 170460
atctcctgaa atataccttt gctctgcctt cccagttcct catggcctct atctcaggcc 170520
atcaaagtag tctccagact ggtccacact agcaggcctt actaattcct gagtatacca 170580
atgccagtag atctttctga ccacttagag gtctgtgtca tacctctact ctgaaacttt 170640
```

catttccacc atataaaccc aaggactttt agcctggaat ttgagatctc cacagcccaa 170700
cccctgcatc cctccagagc ctctgacacc cctctctttt cacgggtccc cttctaaaca 170760
ggttcctctc agtgcccctt accatgctct ttaaactcct acctcagccc tttcctactg 170820
cccagtcaca agcctaacat atcttcctat ggcctttctt taaggccctc atcaattcct 170880
gcctcttctg tgaatctttt attggatcac ctcttctctc ccgggaactc aataacactt 170940
aatctggatt actctgcagg cacctcaccc tacgctgcct tgtattggtc tttatgtttt 171000
ccatgagtat gtattggatt accacaaaga gatttcagag cttttcaagc ctggggcctt 171060
gtctttgcat cctcactggg tagcacacaa tctcactcat gcaggggtaa tagatacttg 171120
tgttttgtaa tgatggcaat aacaatgagg tttaactgtc tcctttagaa agcttcagaa 171180
aacaactgtc tagtttctag caaggattgt tgaatcaggt agctgagttc tcttattctc 171240
ccttcagagg cagtggagga aatcagcaga tgtctttctg agtccactgt catgccagct 171300
ctgctggcat ttgtaatcaa ctcctcccta gctctcttgg tcatattttg aaatatgaaa 171360
aacgcagacc ttgggatacc cacttttctg ttagtaggat actgaacatc agagacctaa 171420
gaaaaccctt tcagtcttcc agttcaatgg ctattcctgt gccttggtga atcagcactt 171480
tagcggaggc atcatcactt catttcagct ccagggaagg agtcttgctt tctgaagttc 171540
tgtgtgagga ggaaagcaag ggttgtacac tgaacttagt aaggagggca aagcagatgg 171600
aagaaaaacc atagagagaa ttcactcaga gaaaagcgga actgaacagc aaaatgtgta 171660
agcggcttcc cctcctcctg cctgtcctag aaattacagt cttgctggta tgccctttct 171720
tcatttaagg acacacagac acacaaaata aaacccaaac cagtgaactg aaagagtgag 171780
tcacgccagc caggcctccg ccaagctagt caattaaagt gcaagaccag ttctgtgctt 171840
ttcttagacc ctgaactact gtctgacttt cttcctgaat atttttgata ggaaaaaaag 171900
tatatgctga cttctgagca agttgatgta tattggctct cttctcataa aaagttttta 171960
atcttccttc agaggactat tgaatactta attgggttac ttgtcccatg gaggtcaaat 172020
cagtcatcct atggttttgc aatgtacgtc ttaccattaa gcttttgttt ttattctcat 172080
gttgtgtatt cttcggaaac gtatttgacc tagatttctt cctaaatgct ttattgtttt 172140
ttgttaacag ggaacgggta tggcaatccc cgaaactcac caggtctgct ggtctcacct 172200
ggtaacttga acaagaatat gcaagcaaaa tctcctcccc caatgaattt aggaatgaat 172260
aaccgtaaac cagatctccg agttcttatt ccaccaggca gcaagaatac gatgccatca 172320
gtggtaatac aaaactacat tttaaataaa tattgataat gttttgtata tgttttgctg 172380
tttttatatt tgtctaactt gatgaattac ttaacattct cccagaaaat taacataaca 172440
gtgccattga cagagccttg cttgtattta gctattattt ctggtaactg gtttgcattt 172500
ccctttttccg tgtaaaaaaa atatatatat atatctggtg aacttcacta ggctgatgtt 172560
ctaggataag aaaaacattt tcttttaagg ctttcaattt atagttggaa aaaaatcaga 172620
cactaccatc ggtcaatctc tacgtcccat aagcagagta ataataggta atgaggtact 172680
ttataacata gtatttttac aatatttatg tcctcaacac gctgacaatg agaaagtact 172740
ttccacaatt tctaaatgaa ctttctcctg ttaattagca aatcctttct tagatgtatt 172800
gcaatgatta tatctaatac atcgcatgcc tacacactgc ctcaattcat ctttccatac 172860
atttacttca tgaaaatagc tatctctcaa aagcaaatta aaatcctagg cattttagga 172920
acaaaggtta tattttacat caaaaaagaa ttgtagcacc tctaaggaag ataaataaat 172980
aagaaatttt aaatagaggt tatatcccca gaccctgtca tttttctttc ttctgggtct 173040

```
gcatgcctaa gatgaagata atgttatggg accaaattca acaacaaaga gacttacatc 173100
agtgttctac aaattagctt tgcttaagag caagaacgtt taaaaccaag attcggtaga 173160
caaatttaga tcattctgca aacacattta tttctttttt ctttctctgc tctgtggcaa 173220
gcttcagggt aaaacagtcc tgtgagctga ttagtttatt atggcacagt gcagattaat 173280
tttgaatatc aaccaaaaac atcacataat atgcaacatt cccttcagaa aaaaactggg 173340
tctaataaat ataacctcct acagggctac agccaagcag tgtgggccgt gcatggcagg 173400
ccatctctat caacagattt attccaggtc ccttaaaact gatgctgtcc cagggaatct 173460
gtgatgggtc agttaggtcc ctctctggca gccaggtgtg tagctcccct tcctccagca 173520
agtgaggttt caaagcacag tctttttttt tccttcaaaa tgaagtgatg aaataatgaa 173580
cattgagaca ctgacctggg ctgaaaaccg ggtagattgt cttcacattt gagacaaaca 173640
gctcattaag ggaaacaaag aatgtctttg taaggagtta tctttggagt ctgggtttta 173700
aaactgttta aactgttgtg tctatcggaa gatgcttttc cttttgttga aaagattttg 173760
cccaattata aatatttacg gacactaatt aataaaactc cttccgcatg ctctcagtct 173820
gaggatgtcg acctgctttt ggtaagtggt gagagcgctt ccctcaaatg gcatgtgcaa 173880
agctactttt aggtagaggt ggtagctttg ataaaattgg aagatattgg aagttaccac 173940
agtatgtcaa cattgattat gtttaaatac cattaatttc tggcatcact cacaggtgaa 174000
aagaatgtca ggtttttttt tttgtttcaa tatttttttct gttttcaata ttttaggaca 174060
atttatagta aaattcaaac aaaaatattc tttcattaca taaaactaaa atatttcttc 174120
ttctgggaat taaagtctca tgattttaag tttatgtggt ggatctttta tctctttact 174180
gtaatgagtt aaatattcgc attagctgct ttgccatcta gtttgaggga agtttagaag 174240
aatctgaaca aagtggtcac agcaccacct gctggtcaaa atataacatg agcccctact 174300
catttgctct ctgctgtatg tagaactgaa cataaaaact accatggttg attttaattt 174360
ttttttaatt tgcatttgaa tgaaaactga aacaatggaa gtacagtata catatttcat 174420
cagttttcaa catagtctgt ttttacccat aataaagcta tggtacttgt tactagttca 174480
gttgcctagg agatactgat gtaatgggtt actatggcaa cagctggtct cttgaaggat 174540
tgtaaatgat agggttggca gagttcatag agacacatgt taaatgatta atttcatgag 174600
atttgtacca agttatctct ttatgtggaa aactaatact gaaatctaat atttttaact 174660
tttaaaaaaa ttcatcagta atgtcttttt atttatttta aaagaatcaa aggataaata 174720
actcccagtc ggctcagtca ttggctaccc cagtggtttc cgtagcaact cctactttac 174780
caggacaagg aatgggagga tatccatcag ccatttcaac aacatatggt accggtgagt 174840
agctttgtca tgtgcaatta gtacactaaa tactttttat tgaaaatcaa gatgaaaaag 174900
ttatctttta ctctattagg aagctttatt tagggcctgc gccgtccaca gcactgcagc 174960
attacccatt cttcactaag acaaagtgaa tatccacatt tttctttctt aactgactga 175020
aagttttatt tatgcaacct gagttcaaaa tagaaacaca ctttcaagaa aattgagctg 175080
tttctttgat gtaataaaaa gctcactttc tcaggattgt ttaacatttc tacatcatca 175140
aatatgtaca tacctttata ctagattgta gttctaataa actagaattg cggactatgc 175200
tacttcagag cattcgtgga atacttattt ttggtttata gtatattcct tttaaattag 175260
aattatcgct gatgctttat ctcccctccc ctcaaaatta aaaatatcta taataacgat 175320
aatcctaata gaatattttg gaaattgaaa atgtttattc tatttaccat ttgataattt 175380
```

ctaaatttaa tattttccct tgttgtttta ttctttaatc tagagtactc tctgagtagt 175440
gcagacctgt catctctgtc tgggtttaac accgccagcg ctcttcacct tggttcagta 175500
actggctggc aacagcaaca cctacataac atgccaccat ctgccctcag tcagttgggg 175560
taagcaatat tattttttat aatataattt tagaatgtat tttgaaaaac aaatgacagt 175620
ctctaaatat gtgcttcaat atcccattaa cgggtataaa actctacttt attgaaatcc 175680
aagtgtaatt ttcagatcaa tacttttcaa gtagcttaaa tcttatatac ctgtttttta 175740
agaggacagc gagctctgta ataatgaggt aaattctttc cttattgttt taggctacat 175800
ttgtttccac ttctatcagt gatataattt ttatttagtt ttcacacagt tcatttggga 175860
cataagaagg catttatagt ataagcttag atatttgaga atttttcttt tttcacataa 175920
accatatggt ttatgctaat gttaacctaa tacacatagg aacaactagt caattgatac 175980
acaggcttca tgtatttata atgtactcat agtatagttg tatacttata gatattttaa 176040
gaaatatatg tatataatac taactagtac atataatact aattacctaa atttggatat 176100
aaaaataatt tttgttttat gtagtcagag gatgtatctt tctgccccct tgtggtagtt 176160
ttcagatatg tctttatcat agaaatgact cttgtcattt atctatggaa acgttcaaac 176220
ctttaaaaag ctctgaattc acaattcaca ctatttcata taaaacaaat catttttta 176280
aaaaagctta aaacgttaac tgaaagcctg actgtaaatt taataagtcc aaaattgcaa 176340
ttaatcttca aaagaaaata ccaggaggat ataaaatatt taaagataac aagcttttat 176400
attttaaaaa tattctgtct gcctagccca cttttacttt tctgcttagc catttgttat 176460
cgttaatcac ttagctgtat tagttaacta gttatatatc catatgtcta aggagacagt 176520
gagaataaaa cactgattag tataaaagtc actgatttat accacaactt tgtgtctctt 176580
atgtttgctg gtgccctctc tccccccacc cactagcttt cacatgatag tgatttagca 176640
tatattagtg atctgattat gaaatattca cccgtacact gtttgcttat gttcatccta 176700
cccgctaatc actgtcattg aaaatctaac ctttcattta aatagtaaga taaattcacg 176760
tgatactgtt ggtcagcttt cttgaaagat agttaacttt gaagatacat tacatattga 176820
tcagcgcaga gttttatctt tttaggacac ttaaattttc tctggaatgt taactattca 176880
agtagacatt aactgtggga acttcttcag gtaattatca ccaagcacat aattccatcc 176940
aggcaactaa aaaatatgta catgtataca tattttgtac aaagtatcaa ctgctatggc 177000
ttagcaggga atccactgaa catgattctt gtcaaaaata aacataactg cttatttccc 177060
atttttttca caaaattcat ccattatagg gctagatttc cctaaaagtt atcaatgtca 177120
aaagccatat tattttctct gaatgtggct tttttttgtt ttcaatagta cctgataatt 177180
tatattttta catataaaca catatttatt tacatatttt agctgtacta caattttaaa 177240
actcttttct attacaagga agaatctaat tctctgctgc ctctaataga ggtttcagaa 177300
aatgagaaag gagggacagc cttagacaga aaggaactga attacaacag ccaaaggtta 177360
agcattttgt tcagctcccg gttcctttca acacttaatt tcgttgtgct taatttgact 177420
cttagttttc tctgtgagtt ttaattgcac ttaatcactt cccttacccc tcaaatcaat 177480
ggaatgaccc ttccagtcct tccactgttg gcccttctct ctctctgctt cacacacact 177540
cttttctccc tctcacaatc acacacagag tagctttttg aaaggaggtt ccttcacatg 177600
gactacctca tattcacacg attaaatgtt aaactgtttt tttaaaaaat cccaagctgc 177660
aatacttatg taaagtaatt cacatgagca tccttaattc tttacagtgt aaatcaattt 177720
aaaaagaatt gatacatttt ccaggccaaa gttgtcgcag agatttgtgt tgcgggctca 177780
cattcttttg gctagagaca atgttcatag cagagtggaa tatatttcag ctccaccaaa 177840
gtagatattc ccagcagccc aagatggtta ccacaattct ttctcaaaat tgcaaaacca 177900
taaacagagt tcttcatatt ttgtccatgg aaaaaaagtt cattttgtcc tttggagctt 177960
taagtcttca aagctatact tttaaaacct agtatctgat tttatctaac caagctaagt 178020
aagcaacaca aatttatttg ctatagggag agagatggct gacagaggaa cttgccatca 178080
agagttaatg aaagtccttt gaatactaat atttgattta gtgtaacact aagttttagt 178140
gtttttctaa accaccacct ataaaaaggg cagcctgttt tctggaagca tttccatacg 178200
tcaactttgt tgatgtgggt gttcagtaca tactgagaga gataactctg agtagagatg 178260
acttataaaa ggttaggtta aatatagttt gatagtctaa tttccaggcg gaggcagtaa 178320
aaattttgaa taaaactatc cagtcatgtt tgatttctga acaattatgg gaaagggtag 178380
gagttttccc aattcaaaag catctgtaat agatgaaaat ttgcatagag gacttgatat 178440
gggtaacttg catatctggc ttctatctcc ccacccacct ctttatcacc cacccacaca 178500
tatgcagtat ttcacaatta tcagggtcta taattattcg tgtctatatt ttgttctcaa 178560
gtagaccaac atgcttatat ctgaacctag catatatgca gttaagttat tttaatgcta 178620 ctttttctt ttcaagaaaa tacttctttg ttaacagaga ctagccattc tattttatat 178680
cctatgtcac agtataatga agctgaatct aagatatcac ttgcatttta ctactgtgga 178740
tttagtcccc agaactactc aaaatgcttc atgtatgttt tcagtgtcaa atgaaattcc 178800
accaaaagat aaatttaagc tagtctgttt gtaggaaggg ataaccaata attgttacat 178860
ctttcatggg gaagatacac agctaaacct atacaggcca gttaacatag gaagatgatg 178920
caaagaggtg aataatgcag cttccaaaaa ctgtattaaa gaaacagaat tttggttata 178980
ttatttttcc cttaccttgt ctagattaac tgcttagact gtccaactca ccaatttttt 179040
cttctaattt tctatgtcac cctccctgtg aagacataat ctgtatgtca aagagcaagc 179100
aaaagtattt attgacatat cactttttat tttcagactc ctaattcata ttcattatta 179160
aatagttgtg tgattcatag cagaagcatt taattaaatt ttagtgaaat ggtctttctt 179220
agagccagga aaattcttta ttccagaaat caaaagacga tttcctcaaa catcagaatg 179280
aatcactaag taactttgaa ccaagataaa atagtctacc attatgaatc cttttgaaat 179340
acaggtgttc cctctcccca ttttaacaag gcttatttaa ttaaaacttt tggaaaatta 179400
gtaaactgat agactataaa ttaataagct acaaataaat agctccaaat ataaacaggt 179460
gtttgaaaat tatatacagt cagtgtagtt tcttgatata aatgctaaca ctgctttgat 179520
tatataagat cataaaagct agagaaagag acgcttatta aggaaacaaa taattctcct 179580
ttatattatt ctctacatta gctcatctat ttattaatag gagaaggaaa gtaattcttt 179640
gccagtaggt ggtgcttttg tacaaaacat cactcaaaga taaactcgtt tctgactaat 179700
tttatatcac tatacatctt gagtttgtat tgcatctccc aaaaagccag ccccaagtta 179760
cttcactttt tttctgaaat atatactttt tctctcagtg gtcataatga cattgttagt 179820
gccaactaat tctctccact ggaaagcagc ataattacat acattagtaa gtaggcttgc 179880
tttcctttgt ttaaaatggg tgtgtctgta tggataattc ttcacttgga ttcttcctca 179940
gtaaaagaga gtaccatgct cttttgacaa tatagtcaag taatcctgac tctagctctg 180000
gaagtcagtg taattagtgt aagaagagta aaagcatctt aaaattgatg cgagcaatgc 180060
cactatggtt tatcctgatc aaagtcattg tgattgctaa tctacactta agggcttaat 180120

```
actttttcc tctagaattc caagtttcta aattttccca gattttggaa aaaggaaaaa 180180
ttattctctc tgggaatata tgaggattaa ggattataaa cacagtaaaa tcacactaca 180240
tccttcttgg caacaagctt tccttaggca acaccagatt catcaactaa tgccaatgat 180300
aaataagagg agtggtagcc taagaaccgc acgcatcagg gagtgactaa cattaataaa 180360
attgaggtca ttgtggaaca caaagtattt tcatctcatg taactgcaaa aggatgaaga 180420
aagtcaaatt atcagtttta atggagtaga aagtcttaag tgtttgaaaa ccaacgttta 180480
aactttctgc agataatttt caatttccct ccccctttcc attttttcca cctccaaagc 180540
tttttaccag atacagttat tgtgcagcat ttgagttcta gtcatttaaa atttaactcc 180600
cttcactttc tctgaagact atgtgattcc atctgtatgt gcttattaat tggaggcaaa 180660
tatttatatt gataataagc ttttaaaaat aatattcaaa cacaagcatt agtaaatcaa 180720
ggaagtctaa ttccagagct aaacactgta tctaaatgct tagaaattta atttttagaa 180780
ctagtctagg gatagagtcc atgaacacag aaaatgcttt ttccattgtg tcttaaacct 180840
ttctgaaatg gtaacctata tgtttaggga gcctctcgga gactagagat ataattcatg 180900
aggcctggac cagttaaatg ctgtaattac taccgggcaa atcaacaaag gcatcctaaa 180960
tcgccctgag aaggcgatgc ccttatgtgc ttccaagcac gttttcttca ctctgggcat 181020
gctctggtgt ctatgcgagt ctttaagctg atgtttgatt taattgtgag ttcctggggc 181080
ctccaggcct ccttcatctg taactgggtt tcctttcctc ctacagagct tgcactagca 181140
ctcatttatc tcagagttca aatctctccc tgccttctac tcaaagcctc aacatcaagt 181200
cagaacctgt ttctcctcct agagaccgta ccaccacccc ttcgagatac ccacaacaca 181260
cgcgccacga ggcggggaga tctcctgttg acagcttgag cagctgtagc agttcgtacg 181320
acgggagcga ccgagaggat caccggaacg aattccactc cccattggga ctcaccagac 181380
cttcgccgga cgaaagggaa agtccctcag tcaagcgcat gcgactttct gaaggatggg 181440
caacatgatc agattattac ttactagttt tttttttttt cttgcagtgt gtgtgtgtgc 181500
tataccttaa tggggaaggg gggtcgatat gcattatatg tgccgtgtgt ggaaaaaaaa 181560
aaagtcaggt actctgtttt gtaaaagtac ttttaaattg cctcagtgat acagtataaa 181620
gataaacaga aatgctgaga taagcttagc acttgagttg tacaacagaa cacttgtaca 181680
aaatagattt taaggctaac ttcttttcac tgttgtgctc ctttgcaaaa tgtatgttac 181740
aatagatagt gtcatgttgc aggttcaacg ttatttacat gtaaatagac aaaaggaaac 181800
atttgccaaa agcggcagat ctttactgaa agagagagca gctgttatgc aacatataga 181860
aaaatgtata gatgcttgga cagacccggt aatgggtggc cattggtaaa tgttaggaac 181920
acaccaggtc acctgacatc ccaagaatgc tcacaaacct gcaggcatat cattggcgta 181980
tggcactcat taaaaaggat cagagaccat taaaagagga ccatacctat taaaaaaaaa 182040
tgtggagttg gagggctaac atatttaatt aaataaataa ataaatctgg gtctgcatct 182100
cttattaaat aaaaatataa aaatatgtac attacatttt gcttattttc atataaaagg 182160
taagacagag tttgcaaagc atttgtggct ttttgtagtt tacttaagcc aaaatgtgtt 182220
tttttcccct tgatagcttc gctaatattt taaacagtcc tgtaaaaaac caaaaaggac 182280
tttttgtata gaaagcacta ccctaagcca tgaagaactc catgctttgc taaccaagat 182340
aactgttttc tctttgtaga agttttgttt ttgaaatgtg tatttctaat tatataaaat 182400
attaagaatc ttttaaaaaa atctgtgaaa ttaacatgct tgtgtatagc tttctaatat 182460
atataatatt atggtaatag cagaagtttt gttatcttaa tagcgggagg ggggtatatt 182520
```

tgtgcagttg cacatttgag taactatttt ctttctgttt tcttttactc tgcttacatt 182580
ttataagttt aaggtcagct gtcaaaagga taacctgtgg ggttagaaca tatcacattg 182640
caacacccta aattgttttt aatacattag caatctattg ggtcaactga catccattgt 182700
atatactagt ttctttcatg ctatttttat tttgtttttt gcatttttat caaatgcagg 182760
gcccctttct gatctcacca tttcaccatg catcttggaa ttcagtaagt gcatatccta 182820
acttgcccat attctaaatc atctggttgg ttttcagcct agaatttgat acgcttttta 182880
gaaatatgcc cagaatagaa aagctatgtt ggggcacatg tcctgcaaat atggccctag 182940
aaacaagtga tatggaattt acttggtgaa taagttataa attcccacag aagaaaaatg 183000
tgaaagactg ggtgctagac aagaaggaag caggtaaagg gatagttgct ttgtcatccg 183060
tttttaatta ttttaactga cccttgacaa tcttgtcagc aatataggac tgttgaacaa 183120
tcccggtgtg tcaggacccc caaatgtcac ttctgcataa agcatgtatg tcatctattt 183180
tttcttcaat aaagagattt aatagccatt tcaagaaatc ccataaagaa cctctctatg 183240
tcccttttt taatttaaaa aaaatgactc ttgtctaata ttcgtctata agggattaat 183300
tttcagaccc tttaataagt gagtgccata agaaagtcaa tatatattgt ttaaaagata 183360
tttcagtcta ggaaagattt tccttctctt ggaatgtgaa gatctgtcga ttcatctcca 183420
atcatatgca ttgacataca cagcaaagaa gatataggca gtaatatcaa cactgctata 183480
tcatgtgtag gacatttctt atccattttt tctcttttac ttgcatagtt gctatgtgtt 183540
tctcattgta aaaggctgcc gctgggtggc agaagccaag agaccttatt aactaggcta 183600
tatttttctt aacttgatct gaaatccaca attagaccac aatgcacctt tggttgtatc 183660
cataaaggat gctagcctgc cttgtactaa tgttttatat attaaaaaaa aaaaatctat 183720
caaccatttc atatatatcc cactactcaa ggtatccatg gaacatgaaa gaataacatt 183780
tatgcagagg aaaaacaaaa acatccctga aaatatacac actcatacac acacacgcac 183840
aggggaataa aataagaaaa tcattttcct caccatagac ttgatcccat ccttacaacc 183900
catccttcta acttgatgtg tataaaatat gcaaacattt cacaaatgtt ctttgtcatt 183960
tcaaaatact ttagtatatc aatatcagta gataccagtg ggtgggaaag ggtcattaca 184020
tgaaaatatg aagaaatagc catattagtt ttttaacctg caatttgcct cagcaacaaa 184080
gaaaaagtga atttttaatg ctgaagataa agtaagctaa agtaccagca gaagccttgg 184140
ctatttatag cagttctgac aatagtttta taagaacatg aagagaacag aatcacttga 184200
aaatggatgc cagtcatctc ttgttcccac tactgaattc ttataaagtg gtggcaagat 184260
agggaaggga taatctgaga atttttaaaa gatgatttaa tgagaagaag cacaattttg 184320
attttgatga gtcactttct gtaaacaatc ttggtctatc tttacccta taccttatct 184380
gtaatttacc atttattgta tttgcaaagc tagtatggtt tttaatcaca gtaaatcctt 184440
tgtattccag actttagggc agagccctga gggagtatta ttttacataa cccgtcctag 184500
agtaacattt taggcaacat tcttcattgc aagtaaaaga tccataagtg gcattttaca 184560
cggctgcgag tattgttata tctaatccta ttttaaaaga tttttggtaa tatgaagctt 184620
gaatactggt aacagtgatg caatatacgc aagctgcaca acctgtatat tgtatgcatt 184680
gctgcgtgga ggctgtttat ttcaaccttt ttaaaaattg tgttttttag taaaatggct 184740
tattttttcc caaaggtgga atttagcatt ttgtaatgat gaatataaaa atacctgtca 184800
tccccagatc atttaaaagt taactaaagt gagaatgaaa aaacaaaatt ccaagacact 184860

```
ttttaaaaga atgtctgccc tcacacactt ttatggattt gtttttctta catacccatc 184920
ttttaactta gagatagcat tttttgccct ctttattttg ttgtttgttt ctccagagag 184980
taaacgcttt gtagttcttt ctttaaaaaa catttttttt aaagaagaag aagccacttg 185040
aaccctcaat aaaggctgtt gcctaagcat ggcatacttc atctgttctc atttgtgcca 185100
tctgccgtga tgtcgtcact tttatggcgt taatttcctg ccactacaga tcttttgaag 185160
attgctggaa tactggtgtc tgttagaatg cttcagacta cagatgtaat taaaggcttt 185220
tcttaatatg ttttaaccaa agatgtggag caatccaagc cacatatctt ctacatcaaa 185280
tttttccatt ttggttattt tcataatctg gtattgcatt ttgccttccc tgttcatacc 185340
tcaaattgat tcatacctca gtttaattca gagaggtcag ttaagtgacg gattctgttg 185400
tggtttgaat gcagtaccag tgttctcttc gagcaaagta gacctgggtc actgtaggca 185460
taggacttgg attgcttcag atggtttgct gtatcatttt tcttcttttt cttttcctgg 185520
ggacttgttt ccattaaatg agagtaatta aaatcgcttg taaatgaggg catacaagca 185580
tttgcaacaa atattcaaat agaggctcac agcggcataa gctggacttt gtcgccacta 185640
gatgacaaga tgttataact aagttaaacc acatctgtgt atctcaaggg acttaattca 185700
gctgtctgta gtgaataaaa gtgggaaatt ttcaaaagtt tctcctgctg gaaataaggt 185760
ataatttgta ttttgcagac aattcagtaa agttactggc tttcttagtg at         185812
```

<210> SEQ ID NO 25
<211> LENGTH: 26269
<212> TYPE: DNA
<213> ORGANISM: Homo sapiens

<400> SEQUENCE: 25

```
gagagactcc tgcggcccag gtaagaggag gtttggggtg ggatgccctg cagcccgtcc     60
acagagcccc caccgtgagg gacctccttc accaggagtg ggtgcaggt  cagttggagg    120
cctaagggct ctattaaaac tgcctatctc caggcccagg gaagttcccc ctgacacaag    180
gaggttccac aggaaaccca gaaacctctt ttctccttct ctgactctcc atttctttct    240
ctgcatcatt ctgagtctcc tacatgttgt ctccatcttt ccatcttcct tcctcctttg    300
gatggcttcc ttcccttgat cctggtttta tcttgcctct tggtcttcat cgacacttgt    360
cacaatcatg cttctttgtc tctctccctt gtccttcctt cttggcacgt gttctcacct    420
ccctgcctct ctgcttctaa ccctgtttcc acaccccgtc cctcgcactc atattgactc    480
ggtgcccttt cttttctgcc tctgcgtctt tccctttctg actccctggt ctgtcctgcc    540
tgtctgcgct ctggggctgc ctccatcccc gggtggcctg cctctgttgt tcttcactct    600
cctcatctgt tcttctctct gcccggctct acctctgttg ttccttgctc cacccacggt    660
ccagattctt caggattctc cgtgaaggga taaccaggtg agaactgccc ccattttctc    720
tgcagagact ggggcatgct tctcctggga gccggattgc tggaccaggg gtctgctgtc    780
ccaagcactc agcgccaacc cttagcatac tccagccaat gccaccccag ggaaacccct    840
tacagagatt gtccttcagc atcacctcag agggcaggag aagcagagcc ctgagtaggg    900
gagggtgcaa cagcaggtgc ctctcccagg gtggaggaga ggagcggggg tagggagggg    960
ggctgcagag gacaaagcca ctcgctggag cctgggctcc ctcaggagta acatagccct   1020
cctgtctctg acccagggga agcaccaaga tgaccgatgc ccagatggct gactttgggg   1080
cagcggccca gtacctccgc aagtcagaga aggagcgtct agaggcccag acccggccct   1140
ttgacattcg cactgagtgc ttcgtgcccg atgacaagga agagtttgtc aaagccaaga   1200
```

```
ttttgtcccg ggagggaggc aaggtcattg ctgaaaccga gaatgggaag gtgagtaggg   1260
catggcgccg gggcagaagg gaaggaggtc tgggaaagaa gatgcagagg tggagccact   1320
tgcaggggga gctgagaggg ctggagaaaa gccaaggcca gtggggatgc caggacatgc   1380
tcctttgagg agcccagaat ctgatccctc tcaaattgac ctgagctggt gcaacaggtg   1440
ccacccaggg ccatgttccc cctgccagag aggatgctga ggaagaagaa cctcagtgtt   1500
cgcctaagag gggtcttgta gataaagagg gcacagacac agcattaaat gatgcccccct  1560
tcttgcactt gtatccctct tccctgtgcc tcagtttcct ccatgagtcc actttctcaa   1620
attccgttca cccaaatcaa gagtaattct tagacccaga tgaacacaaa gatcagaaac   1680
ttttgagctg agcactctcc ttgactggca ctcagaagct ctggtccctg gtttgctcac   1740
accagccaag agaatcaccc ctggttacca gctgcggctc agggctgtgt gcctcatgaa   1800
ctcgttgact gaatgttaca acccattgaa gtgtagaata acaggccaca atcccctggg   1860
gcttttgact ctgatcccag ctctgccacc cgctagtcac tgtgcaggca aatcatttag   1920
tcatttagag ccacggattt ctccactata aaaaacactg gaatacctac tggcaggatc   1980
taatgacatc agggcatggc aaactgactg ctgccaatca aaccacacca acagtgatgg   2040
atggggagtg tggagtagat gggtgaacta cttttccagc aggggtgaag gtttgccctg   2100
agcaacagat accctaaagc gctgcccgcg ggagacagcc tcggggtcag cataaggtgt   2160
gcacagatct gagagctgcc aatctccagg tctgccccaa gacccttgga acatagggac   2220
tgaagagtga tggtcatggg cacagggtgt ccccaggatg gtctggggat ctggcaagag   2280
aaaggtaccc taggacagtc tctaggatgg gagatacaat gggaagggaa attacctggg   2340
gaaagtgtcc caggggacat cggggtaggg gccggggcac tggtcagagc aaggggagca   2400
aggccaagtc cctgtgtcct gggaggaggt cagtgggcag tgctggcaag ggtcccggag   2460
ggattgtggt cactcatcct cctgcttatg cgccccctcc agacggtgac tgtgaaggag   2520
gaccaggtgt tgcagcagaa cccacccaag ttcgacaaga ttgaggacat ggccatgctg   2580
accttcctgc acgagcccgc ggtgcttttc aacctcaagg agcgctacgc ggcctggatg   2640
atatatgtga gtggctcctg cacactgcag aggcttcctg tgctgcgtgg aggcctaaat   2700
aagccagggg ggctctccca agaagagggg gagagactcc caagggaccc aagtcccctt   2760
ccccctcca cccctagtca gctgcaggag gagtagagcc agctggagtg aacagggaca   2820
tgcctggctg ccaccactgc ctgtcccagg ctctccccac caacctcatg cccagccttg   2880
tctcctgctc cagacctact cgggcctctt ctgtgtcact gtcaacccct acaagtggct   2940
gccggtgtac aatgccgagg tggtggccgc ctaccggggc aagaagagga gtgaggcccc   3000
gccccacatc ttctccatct ccgacaacgc ctatcagtac atgctgacag gtgagcctgg   3060
tggcccctgg tctctgctcc tcctcccaga cacccaccca gatcctcagc cctgacccca   3120
ttgcttctcc tcttttttct tccagatcgg gagaaccagt ccatcctcat cacgtgagcg   3180
agtgccatcc tcccacagaa gggactgggc tgggggcata cacgctgatg cctagggtgt   3240
agttgggagg agaggtttaa ggctgggatt gcagggagca tggggcactg agctctcatt   3300
agaggggtgc cagagcaatg aaccatgtca ggcaaatcct gctgggtgct gggctctgat   3360
ggccaggctg ggaaggggag catgtgatgc tgagccctgt atggagaaca gtaggaatcc   3420
tgagttttga ttggtctctg tggcccccag gggagaatcc ggggcgggga agactgtgaa   3480
caccaagcgt gtcatccagt actttgccag cattgcagcc ataggtgacc gtggcaagaa   3540
```

```
ggacaatgcc aatgcgaaca aggtgccatg ggggacacag gctcggcaga acaggggttg   3600
gggggcaggc tgacccgagt taccccctaac cctcccctcc ctgtgacgtg gtggggacag   3660
ccacactgag ctgggctccc gatggtcagc ccagtatgga agaccttcct gacaggagac   3720
actcaccctg aggtctgggt aggatcctgt ggagtcgcag acccactagc ggttcaccca   3780
gccccgcacc cccattcctc agggccaggg cagcctccct gccctctcac cactgcctgg   3840
aggtggatgg aggatgaacc catgcagttc tgctcctttc atagggcacc ctggaggacc   3900
agatcatcca ggccaacccc gctctggagg ccttcggcaa tgccaagact gtccggaacg   3960
acaactcctc ccgctttgtg agtgcctttg accactccca gtggcctcat ccagccttga   4020
caagaaaaag gggtgctgt tttgccacac ccagttgatt gtactgtatc tggctttggg   4080
atatcaacat gcacacgttg gtgggaagag agcataggct ttggagccaa aggtctgact   4140
ttccacttgc tcagcaagtc cttacacctc tctgagccct agttccttca cctgtgaaac   4200
agggggacta atatccaccc tgcagattac tgggaggatt aggtgagatc atatgagagg   4260
tatgagcagg aggcattctg tatgtgttcc cctctgggcc gaggttccac taggaggtcc   4320
ctgcacagtg tgtgagggtg gcatcctctg cccggcttca cttatactca actgagacac   4380
caaagaggtc gtttacattt ccagaaccat ccagggcttc tgggctgaac agagggccag   4440
gatttcactc tgtccttccc gccagttccc tcactctgtc ccattcgtcc ccaggggaaa   4500
ttcattagga tccactttgg ggccactgga aagctggctt ctgcagacat agagacctgt   4560
gagtaccagc agggaggctg ccaccctcta ggtcccctc tgccttctct ccctgcctgg   4620
cggccagtct catcattcct gccatctcct gttttgtctg catttgcctc tgggctttag   4680
gatccttttt atttaagcca catcttctcg cctggccctc ttcatcaagc tgtgggtgcc   4740
ccctgccctc tgcccccatg gccacctttt tctggctcta ctctctttcc ttcctcacct   4800
gccttcctcc cctccgccca cctcagacct gctggagaag tcccgggtga tcttccagct   4860
gaaagctgag agaaactacc acatcttcta ccagattctg tccaacaaga agccggagtt   4920
gctgggtgaa cctgcctgcc accccccacc cactgctgtc cctgctgcac accccaacga   4980
ctcctgcatg cagggcaggg ccctcctgct ccccactgtg ccccaccttg ctgctcactt   5040
cccttctccc tccactcact ccgccagctc cctctcgctt ccctcccaag accacctgcg   5100
tctcctctcg cctccctgtg cagtcacaca cctcactcct tctccaccct tctctccact   5160
cctccctcgg cttgtctttg ccttctcctc tttatttgcc tccccatctc ccatgtgtca   5220
ctcccctgcc accctccctc ctccttgtta ctggagcccc tgccagggcc cctcttctac   5280
cctttcactt cctctgggtt cactccttgg tccttgctga cttctcttct ctccctgctc   5340
cctgtcctcc cttcctccat tcaccccgtc ccttacccct ccctgcccct ccctcccttt   5400
cccaactcta cctgcccctt ccctgccctc cgcctgcccc cttgcccctg cctcacccct   5460
tgcctggtgc agacatgctg ctggtcacca acaatcccta cgactacgcc ttcgtgtctc   5520
agggagaggt gtccgtggcc tccattgatg actccgagga gctcatggcc accgatgtga   5580
gtgagggggc tgctgcggcc gttcgaggga ccccaggagc tcctggggcc accgctccaa   5640
ccccccctctt tgtctctcgc tctgtcccag agtgcctttg acgtgctggg cttcacttca   5700
gaggagaaag ctggcgtcta caagctgacg ggagccatca tgcactacgg gaacatgaag   5760
ttcaagcaga agcagcggga ggagcaggcg gagccagacg gcaccgaagg tgggaggggc   5820
aggcaggcag ccctgggaag gcctgaggtg ctgaccaggc tctctgcggg actcagatcc   5880
cagagactct gaggcttgtg gggcagtggg gtgtgttgtg ggatggtgag ggacagggac   5940
```

```
gtgggagacg tgggcagaca gagagtccac cacaatccca actcctcaac cccagctgca   6000
ctcaccagaa ctgaggtggg gaattttcct cctgtgccca agactccccc agccccagga   6060
agcacagccc ctgagctctg cacatcacca tcactaatgc agggcctttg cctgcccagc   6120
ccttgggtaa gcccctcgtg ggctcatacc atgttgtttg ggaggcagtg ggccaggggt   6180
caggacatag cccagggcat tggtgtgtca gtttcctcct cagtgaaatg gatcaacaat   6240
ctttcctcac tcctctggtg gctactgtga ggtcctttga gaaaatgtga aggtgcaaac   6300
agtgctagac aggtgcccaa gaacattcct ccctaccttc agggaccctt ctccaagtct   6360
gcccagatca aagtgtcaag ctggggttca tgataacaca ccaacagtta ttacaacatt   6420
cttgaaatta caccaaataa ctcctcctct aaacagagaa atacccatgt tgggtggcac   6480
atttggatgg ctgggggtag gagcgtggta ctgtctgata tactctcagc cagtcagatt   6540
gggtaacatg tggatggaga agacagcatg gccagtccag ggctagacac tggggtagag   6600
aacgaaggag acagggagca gaggacatct agcccctcag ccacaccctt gccctggaga   6660
ggcgagggat atggtgaagg tggggatatg cccacagcag tgcttgtgaa agacctgacc   6720
cagagatgcc acagatgtag agacagagct gagaagagcc agttgtggca agaggccatg   6780
ggccggataa gggggctgtg ctccagcctg actcaggcac acgttggttg agtaaccaag   6840
gcaagccctg tgctcttcca ggccttgatt tcttcctctt taaggaaaag aaattggacc   6900
tgatgcttcc taaagtcttg gccccaggac agggaaggag gctcactccc tgaaagtgtt   6960
cactcaggcc aggtgcagtg gctcatgcct gtaatcccag cactttggga ggccaaggca   7020
ggtggatcac ttgaggtaag gagtttgaga ccagcctggg caacatggtg aaaccctgtc   7080
tctactacag atacaaaaat tagcctggca tggtggctca tgtctgtagt cccagctact   7140
tgggaggctg aggcaggaaa atcacttgaa cccaggaggt ggaggctgta gtgagccaag   7200
atcgtgccac tgcactcaag cctgggtgac agagcaagcc tctatcttaa aaaaaaaaaa   7260
aggaagtgct cacttatcct ttccctctca accagatgct gacaagtcgg cctacctcat   7320
ggggctgaac tcagctgacc tgctcaaggg gctgtgccac cctcgggtga aagtgggcaa   7380
cgagtatgtc accaaggggc agagcgtgca gcaggtgtac tactccatcg gggctctggc   7440
caaggcagtg tatgagaaga tgttcaactg gatggtgacg cgcatcaacg ccaccctgga   7500
gaccaagcag ccacgccagt acttcatagg agtcctggac atcgctggct tcgagatctt   7560
cgacgtgagt tgggacccct gggagtggga gaacaatcac tcgcttgctc ctacattcaa   7620
cagccatttg ctgagagcca gctgtggacc agacatggga aggcagtggg gactgtgtgg   7680
tgacagaggc agtcattgtc cctgtcttca ggggaagccc tcctccactg ccctgacatg   7740
gaggggacag ccataccctg ctgggctcgg cacagtgcac gggcacagcc ccaatggcca   7800
ctcacaccca ctttctgact gctcccaccc ctcatgcccc ctgcagttca acagctttga   7860
gcagctctgc atcaacttca ccaacgagaa gctgcagcag ttcttcaacc accacatgtt   7920
cgtgctggag caggaggagt acaagaagga gggcattgag tggacattca ttgactttgg   7980
catggacctg caggcctgca ttgacctcat cgagaaggtg cctccttggc ctcaccacct   8040
atgccccctc ctctgccatc cagacaaagt ggtggctgag tcccttctac acccaagaaa   8100
ctagagtccc aagaatccca ggcctttctc caggcccagc ttctccccac tgtgaagtca   8160
tgggcatgaa caggatgatc cccccactct tcctttccca ggaccttgca ctttatgccc   8220
ctttgtggtg gtcccctcag tgtcttaaga gtgagatgta gtgaaggaga ggcccctggc   8280
```

-continued

```
ccctctgacc gcccatgaga agcgtcattc atggaaagat cctaggctga aattagagat   8340
gtttggcctc ccaccacctt cctgttggtt gagaaataag ccagtctcca gccctcttgc   8400
ttatgggcat tcctcagaag agacaaggcc gcaggcggga ggccccatag gccggggctg   8460
acttgctctc agtgaacctc tgctctttgt cagcataggc cagagcccgg attgtctgac   8520
ccacacccag cccagccacg gccttcatga aatgggagct tccccacatg ctttgggtca   8580
ttatccagat tcttaaccag agttctcatg tttcagagcc ctcagaatgc cataaaactg   8640
tgtgtggaaa aaagcatgtg tacattcata catacatgtg tgtgcttgtg catgtgtgtg   8700
tgtgtgcgtg tgtgtgtgta catgcgtttt tctggagaga cagtctttag cttcaacaaa   8760
ttcttaaaag gattcctgcc ccaagaaaaa tcaagaacca ccaggttttt ggaagtgcag   8820
agtgtggtaa agaacctgga tccttctatc taacccttga agaattgcta ctggtgtcat   8880
acagacagag cctggcccgg tgcctctgac acacatctgt ccctgccctc ctgcccctgg   8940
ggcagtgagc catcagagag aaggggctgt gctgtgaggc actgtgggcc ttgtgggggg   9000
tgattaggag tgcatgactc tttgttggac ccactgggca gaaaggagga ggaaggggct   9060
ttttaaattc caggaatatt ggcttcctgt tttagggtaa gaggtaccag cacagcgccc   9120
cttcagcagg ccagcgctac tggctccaga ttcctttttcc tgtcagggta tgggactgtg   9180
gaagcctggg agtgtgctca gtgattctct ctttgcctct tcaccctgcc ctcagcccat   9240
gggcatcatg tccatcctgg aggaggagtg catgttcccc aaggccactg acatgacctt   9300
caaggccaag ctgtacgaca accacctggg caagtccaac aatttccaga agccacgcaa   9360
catcaagggg aagcaggaag cccacttctc cctgatccac tacgccggca ctgtggacta   9420
caacatcctg ggctggctgg aaaaaaacaa ggatcctctc aacgagactg ttgtggccct   9480
gtaccagaag tcctccctca agctcatggc cactctcttc tcctcctacg caactgccga   9540
tactggtaag caggcagccc ctgcactggg ccaggggact tctgaagaca caaagggcca   9600
gggtcctgct gcttcaaagc acatgactcc ataggcaggc acaggggagc ccatgagtca   9660
agccacctcc tggctcacct caccacagtc cagctgggct tctgtagcac ctgccgttct   9720
ccactttgtg ttatgagtgt tgatatagct gtctcatgtt tcctcaagat ggggagtaac   9780
tggaggtcag tgagggtggc acatgcatcc ctgtaccatg cccagcaggg aacgatgcat   9840
gtgggagttc tcaacaaatg ttgagaggac actgaacaaa agagcctcca gttcagaaaa   9900
ggaagagaaa ggatgtggct tgaaatgaag aggataaagt gtaagaagaa aagtagaggt   9960
tgggcacggt ggctcacgcc tgtaatccca gcactttggg aggccgaggc gggtggatca  10020
caaggtcagg agttcgagac cagtctggtc aacatggtga aaccccgtct ctactaaaaa  10080
tacaaaaatt agcctggcgt ggtggcacct gcctgtagtc ccagccactt gggaggctga  10140
ggcaggaaag ttgcttgaat ccgggcgacg gaggttgcag tgagccaaga ttgcaccact  10200
gcactccagc atgggtgaca gagtgagatt ccatctcaaa aatagaagga agaagaagaa  10260
gaagaagaag aagaagaaga agaagaagaa gaagaagaag aagaagaaga agaagaagag  10320
gaggaggagg aggaggagga ggaggagaac tagaatgtgg aaagatataa gaaggaaggg  10380
caagtagagg gagagctaag ggcactgatg tatgtcagtg cctactatgg gcaagcacca  10440
gtgagctgcc ctacaggcgt ggtcttatct aatcctcttt acaactttgg gaagttgtta  10500
ctgtcatcct catggtaaac tgaatcttgg agaattcctt gcccaaagtc tcagagctac  10560
caagcgagca gcagagctct gcctctgccc aagggctcct ttattttcca gctcctgttg  10620
attatttctc ctctcgctgt ttaggggaca gtggtaaaag caaaggaggc aagaaaaagg  10680
```

```
gctcatcctt ccagacggtg tcggctctcc accgggtaag aagggcccag gggtgccagg  10740
acacctggtg gaatggccca gcccagagac ttctggctgc accacctatt ctgatgcttg  10800
agtttgatga ggaaagaagc tagggctacg tagtcgtttt ttagtgtgta gattccacaa  10860
aagcctgaac tcacgtcaca aattatgtgg cagcccctgt ccctttgatg attctggtgg  10920
agagtgtctg gggaccaggg tttaagggcc taagggatgg tccttgtggc tcctaactcc  10980
ccaccttcat ctgcctccag gaaaatctca acaagctaat gaccaacctg aggaccaccc  11040
atcctcactt tgtgcgttgc atcatcccca atgagcggaa ggctccaggt gagccaggag  11100
aagaccttag tctggggagg acagctggca tccactttac cctaaggctg accctttccc  11160
cttccctcct gacacagggg tgatggacaa ccccctggtc atgcaccagc tgcgctgcaa  11220
tggcgtgctg gagggcatcc gcatctgcag gaagggcttc cccaaccgca tcctctacgg  11280
ggacttccgg cagaggtggg tatgagggtg ccccagagct catagaacag gggggagccag  11340
gctgccctga tgggaatggg atctgcaggt gaccctggaa ttctgtgggc agagcagatc  11400
actgcagagc atgggtgact ctggacactt ccctcctcag gtatcgcatc ctgaacccag  11460
tggccatccc tgagggacag ttcattgata gcaggaaggg gacagagaag ctgctcagct  11520
ctctggacat tgatcacaac cagtacaagt ttggccacac caaggtgagt ctagagcccc  11580
attgggtggt tgcagggcag gtggccatgt tgagtggagc agagaggagt ttaggaggca  11640
gaagcctaat tctggcttcc ttatcaacct tatcaagggc tgaaacccag gcttcattcc  11700
ggtcttgttt gtcaaatttt tactcttact tctagaaggc atggggtgat gggtcacctg  11760
ggagctcatc cagggtcttc caccctggat actcccctct gaggctgcgg cctgttgcat  11820
ctaccccttg cctgcaggtg ttcttcaagg cagggctgct tgggctgctg gaggagatgc  11880
gggatgagag gctgagccgc atcatcacgc gcatgcaggc ccaagcccgg ggccagctca  11940
tgcgcattga gttcaagaag atagtggaac gcaggtgaga caggaggaaa agggaggcat  12000
gcactagaga tgtagaggca gatccgcaat gtcaactagt gtgggtcaga agacctgggt  12060
tcagacctac cagctggcct gggcaagtta ctttaccact tcgaatctca ttgcaaattc  12120
ttcttcttct tcttcttctt cttttttttt ttttaaagaa acttctctat aggaaaatgc  12180
aaattaagac accaatgaaa taccatttta aaacactaga ctttgcttgc tcagatggtc  12240
tacaaatttt aaaaaatgaa agaaacaagt agataaaaat aaaatgaaag gaaaaataat  12300
ttttaaaagt tttaaaaatc actagactga caaaaattaa gaagcctgac ccactgctta  12360
cagatgtgta aattagtgca acttcctagg aaaacagttt atcactatct tttaaagttg  12420
aacagctgca ggccaggcgc ggtggctcat gcctgaaatc ccagcacttt gggaggccga  12480
ggcgggtgga tcacgaggtc aggagatcaa aaccatcctg gctaacatgg tgaaacccca  12540
tctctactaa aaaaatacaa aaaattagcc gggtgtggtg gcagatgcct gtagtcccag  12600
ctactctgga ggctgaggca ggagaatggc atgagcccgg gaggcagagc ttgcagtgag  12660
ccgagatcga gccactgcac tctagcctgg gcgacagagc gagactccat ctcaaaaaaa  12720
aaaaagttga acagctgcat acttctccat tccactcctg agtacattcc tacagagaaa  12780
ctcttataca tgtacaccat gacatgaaaa ataatctttt agcagcattg gtcataatag  12840
caaagatctt aaaacaactt gaatttccat ccacagggga atgggtaaat agtattacag  12900
tcattcagtg gaatattata aaacagtgaa aagatgtgaa ctccaactac atgatacaat  12960
atgtttgaac attaaagcat attgttagta aacaaaggca aatcttggaa ggatacatac  13020
```

```
agtatgatgc aatttttata aagctcataa ataatcaaaa ccagccattc attgtttaaa  13080
gatacataca tatggctggg cacagtggct tatgcctgta accccagcac tttgggaggc  13140
taaggcaggc ggatcacctg aggtcaggag atggagacca gcctggccaa catggtgaaa  13200
ccccgtctct actaaaacta caaaaattag ctgggcatgg tggcaggcac ctgtaattcc  13260
agctactcag gagctgaggc aggagaatcg cttgaatccg ggtggcagag gttgcagtga  13320
gccgagattg tgccattgca ctccagcctg ggcaacaaga gtgaaactcc atctcaaaat  13380
aaataaagta aaataaaaat aaagatacat tcatatgtgg ttaaagtaat ttttgaaaaa  13440
gcaaggaaag gaaaaataag attcagagtg gcggctgctc ctggcggggt gacaggggtg  13500
taggaaggaa cgcacaggta gatcaatggc tggtaacatt tcagctcctg tttcagtggt  13560
aggttcatgg atagtcattt tgctttcatg ctgcataact tacatactta ttatagacat  13620
tcttatatgt aaacccctac ataattttta acatatttga agttcttatg agaatagaaa  13680
aaccaaacag agtagacatt ctataagtgg tagtttccat taccactaat atcccagctg  13740
ggaggatata aactgccctt tcatcaaatt gattaataaa tatttatcaa gcaactccat  13800
gttcagtgta gtgatgttgg aggtgggtgt gcacaagaag gaagtctacg tgcctacgaa  13860
cttgcttagt agggcccatg attgggaagc tctcttttat agtgccccac cctgcctcca  13920
cgtttccttg ccagggatgc cctgctggta atccagtgga acattcgggc cttcatgggg  13980
gtcaagaatt ggccctggat gaagctctac ttcaagatca agccgctgct gaagagcgca  14040
gagacggaga aggagatggc caccatgaag gaagagttcg ggcgcatcaa agagacgctg  14100
gagaagtccg aggctcgccg caaggagctg gaggagaaga tggtgtccct gctgcaggag  14160
aagaatgacc tgcagctcca agtgcaggcg gtgaggccac gtgattatct cttcagccct  14220
ctcctcccct cccctagatt atagcccatc tcacaaccag ggactgggag tctaggagtg  14280
ccagctcttt ttaagaccct aggtctcctc tctttaacca tcagcttcct ccctgttctc  14340
ttctcccagg aacaagacaa cctcaatgat gctgaggagc gctgcgacca gctgatcaaa  14400
aacaagattc agctggaggc caaagtaaag gagatgaatg agaggctgga ggatgaggag  14460
gagatgaacg cggagctcac tgccaagaag cgcaagctgg aagacgagtg ctcagagctc  14520
aagaaggaca ttgatgacct ggagctgaca ctggccaagg tggagaagga gaagcatgca  14580
acagagaaca aggtgagggc agctccctct ggcttcagcc caggtctcct caagactccc  14640
agactagagt gttgtcctgg tccttggcat ggaggtcccc atagatgtct ccaggctggt  14700
gatctttgac cctaaagggg atgggttttt ggtcggcagg tgaagaacct aacagaggag  14760
atggctgggc tggatgaaat catcgctaag ctgaccaagg agaagaaagc tctacaagag  14820
gcccatcagc aggccctgga tgaccttcag gttgaggaag acaaggtcaa cagcctgtcc  14880
aagtctaagg tcaagctgga gcagcaggtg gatgatgtga gtagtaagaa ccatgctcct  14940
gctctcagag caagattttg caggcaacac caatggccca gaaagtcctg atccctagaa  15000
ttaacttcta tggcccctga agcttttttg ctctctgtag ttcctcacta cagtaggtct  15060
ctgaatcctt tgtgcttgca ggatttctct gttggtttga cttccaatcc cactggactt  15120
caagtttaga aggaggcaaa agagcataca ctatggattt catgttttcc acactttgct  15180
tattttcttc cctccaacag ctggagggat ccctagagca agagaagaag gtgcgcatgg  15240
acctggagcg agcaaagcgg aaactggagg gcgacctgaa gctgacccag gagagcatca  15300
tggacctgga aaatgataaa ctgcagctgg aagaaaagct taagaagtag gagactgtgg  15360
tggccaggag gggctaatgg aggtgtctgg cctggtagat agagtgcagg gtgctgcgcc  15420
```

```
tccactggcc acagttgcct tgggtatgct gggaataagg tcaatcacag ccctcttccg  15480
ccactttctg ggctggcgag gggaggggga ggtgccgatt ctggcatact aaggccaaga  15540
agagaatgag ccccagagga aggaaggcta cctgtcactc ccccaccccc acccttctcc  15600
tgcaggaagg agtttgacat taatcagcag aacagtaaga ttgaggatga gcaggtgctg  15660
gcccttcaac tacagaagaa actgaaggaa aaccaggtga cttttttttcc cagtgcatga  15720
aagtgggagc tcaatagccc tgaggtaact gaggctgcag cagctgctta gggttctaca  15780
caatatctgg aactccaggc agcctcatag acccaaccat ccctgactta caggcgctca  15840
ggaacactag ccttccccca tagagcaaga atacattacg ttagcaaaac tgtttgagaa  15900
gggggactca tacctactaa agggcttctc cttctgagat ctgctctgcc tcagggactt  15960
tctactctaa gacaaatgat agagctctat tctcctctaa cccttcctct ggtagttcag  16020
ccctctgaac gcagggtgaa aaaaaaaaaa ggcttcaagg agcaccttcc tgtgagctgc  16080
tctgttcata ttcttcccgg tactaacccc agccactaac ccaggctgag tccccatagg  16140
gcactcatga taagagccaa ttccaacaac tgtgagcaag tcacttaccc tccctgatcc  16200
tcagattctc ttctcacctg taaaatgaga ctgacaatac ctaccacaca ggaccagagg  16260
ggataatgta tttgaaacca ttttgtcaac taggaaattc tatacaagta tcatattaat  16320
atagcccaat ttagagaagt cagccagcca ctagcctaag aaggtattgt tttgtcttct  16380
caatggcctt ctcattcctc tgcagctcaa gatttagtga acagccatag tctcccttag  16440
ctttaatgaa cctcaaaccc taatgtgctt ttagtatcgg gtttgtcaga agagacctgg  16500
aagtccactg ccatccccat tatagagcta cagaagctac atggccaggt ctggacatag  16560
tgaccccaag ggcaacagga actcggctac tggggcggga ccttgtcctc tcactttggg  16620
gcagactgtg gctggtagaa agaggtagtc tcccctctgc acttgaggcc catggcccag  16680
gctgcaagta atgtatgaac acaattccac tcctctgggg ctgcacaggg actggcccgc  16740
cttcattagt aatttgccct cccatcttct tggatgcccc ttctgggttt tagctagaat  16800
atcgggccat cctcaggttc ttctacccta ggtctgggca acttgtttgg cctcttggac  16860
acagaataac agtcctgtta gtctcatcag ctctcggcaa taggctatgg ctcctccttc  16920
atccccaaga tcttgctcag aagtcccacc ttctccatcc tgggagcaga ggcatggtgg  16980
tcctctctgc tgcttgtagg acccatccat gaacagtcca ttaaagctgt ccataacccg  17040
aggtgaaggg atttccactg aacccccgtt ttgctcctgg ctagccagac aacagatcaa  17100
aatggtagat acgatattct cccaatttag tcaagaccaa ggctaaggcc caaaaaatga  17160
ggtaagggca cttaaagagg ataaggagat gaggtgaaga ggagagtagc ctgctagcac  17220
tttcctggcc tggaagggag caatcatgtt gaaacccagc cctgggcata aacacagcaa  17280
gcctgggaga gcaaggaata tggttgattg gactttgtgg ttaacttgga gaattgcaaa  17340
ggtatctgat tgtttcgagg catgttgtca caaatatttg taaaatacaa gcactcattt  17400
tcccgtctta tgaatagcgc aacagagcct agtgaatctg gggactctga acttcttgat  17460
ctcacaggat accaggatcc cccttcaacc acaggttctc aggatttggg gctgcagatg  17520
ctcacactgg gtctgagatg cccttgggag cttcagccaa attcctattg atggcctatg  17580
cattatagga tgtttagtag catccctggc ccctaccctc tagatgccag tagcaagccc  17640
caccaagaca tgacaatcag acattgccaa ctgttccctg gggcacaaaa ttgcccctag  17700
ttgagaacca ctgcttgaga ggaacctaag ttcctggtag cttttcagag ccggggggat  17760
```

```
tccagtggag gggtccaggc ggtgggtctg agccctttgt gtctgaccca ggcacgcatc  17820
gaggagctgg aggaggagct ggaggccgag cgcaccgcca gggctaaggt ggagaagctg  17880
cgctcagacc tgtctcggga gctggaggag atcagcgagc ggctggaaga ggccggcggg  17940
gccacgtccg tgcagatcga gatgaacaag aagcgcgagg ccgagttcca gaagatgcgg  18000
cgggacctgg aggaggccac gctgcagcac gaggccactg ccgcggccct gcgcaagaag  18060
cacgccgaca gcgtggccga gctgggcgag cagatcgaca acctgcagcg ggtgaagcag  18120
aagctggaga aggagaagag cgagttcaag ctggagctgg atgacgtcac ctccaacatg  18180
gagcagatca tcaaggccaa ggcaggctct gctcggcctc ccctcgccct ctcccctgca  18240
cagcggagcc tcccccatgc cttctctctc tgtctgccat ctcccttgtc attctcattc  18300
tcttcatcac cctttggtct ctcttcctgt ctcccctgcc cctctctggc tctcctcacc  18360
ctctctatct cttcatgttc ctcctttctt taattcaagt ctctcttcag actgcgccct  18420
cccacacctt ctgtgtcccc ctcctgccct ctggcattcc ccatctctga ccctctcttc  18480
cttcctctgg tcgactcagc ccctcccaca ctcacccttc ctgtcttgct tcctgaaggc  18540
aaacctggag aaagtgtctc ggacgctgga ggaccaggcc aatgagtacc gcgtgaagct  18600
agaagaggcc caacgctccc tcaatgattt caccacccag cgagccaagc tgcagaccga  18660
gaatggtggg tgcccctaac caaccccctg cctagggcag gacatgactt gtgaaatggc  18720
ccacaagccc ctcatttcac ctccaggaga gttggcccgg cagctagagg aaaaggaggc  18780
gctaatctcg cagctgaccc gggggaagct ctcttatacc cagcaaatgg aggacctcaa  18840
aaggcagctg gaggaggagg gcaaggtgag gcccagtggg gagggtgggc aggcttgatg  18900
gcagccctgg ggcaattcat ctcagtgcca gaaatggagc ctggagctgg aaagagtcct  18960
ctgcaaggga aagaccctcc agtctaggtt ctgccctgca gctaagcgtc atttaatgcc  19020
tcttttctta ttcgtaaggg gatggggtga gcagactggg aaactcctca aacagtgagg  19080
tgccacatca gcccacatgg tgaataaggc tgggcttggt tgaagtacta cataagaaga  19140
gaatctagag aatggggcac agggagtccc tcccacctcc tggtgccccc cccctcccc   19200
aggcgaagaa cgccctggcc catgcactgc agtcggcccg gcatgactgc gacctgctgc  19260
gggagcagta cgaggaggag acagaggcca aggccgagct gcagcgcgtc ctgtccaagg  19320
ccaactcgga ggtggcccag tggaggacca agtatgagac ggacgccatt cagcggactg  19380
aggagctcga agaggccaag tgagctccag atacccccttt aacctgactc tcagagagga  19440
aggggcgaga ggacctgggg tggggacagg caaagtggtc atgagacgga agtggaagag  19500
acaggaggaa ctcggagggc aacagaagtg cttggaagaa agcctgaact ctttgctctg  19560
tgaactctgg ctggccctga cccacttcct gtgacgggcg agcttttggc ccgggttata  19620
cctgatgctc acgtataaga cgagcaaaaa gcttgttggt cagaggagct accgtcgatc  19680
agcctgtgtg gggggtgagg gcagggggca ctgacaccca gatgccactg caggtaggga  19740
ggacgcctgg gcagcccgtg ctggcggact ctgttccagg catgagcagg ctcagctcct  19800
gctaggctgg acttacggtg tctcaaggag atatagggag ggggtggaag gaggtccacc  19860
caaggctcca gtgttgccca gtagagtcac acacacaccc tccaccctca cctgggcaga  19920
aagaagctgg cccagcggct gcaggatgcc gaggaggccg tggaggctgt taatgccaag  19980
tgctcctcac tggagaagac caagcaccgg ctacagaatg agatagagga cttgatggtg  20040
gacgtagagc gctccaatgc tgctgctgca gccctggaca agaagcagag aaactttgac  20100
aaggtggacc atgggcgggg gccgcagcca gcatgcaggg caagggggca tgaggggttc  20160
```

```
agtgagaggc caaaggcaac ctccttggag gtggaggagg agggctaagc ccaggctcgg  20220
gaccagggac agatcttgga catgcggctg aggctggggg ctggggcact gggaagcagg  20280
agggctgggg agctaaggct ggggggctga agagtgagcc ttgtccccgg gcagatcctg  20340
gccgagtgga agcagaagta tgaggagtcg cagtctgagc tggagtcctc acagaaggag  20400
gctcgctccc tcagcacaga gctcttcaag ctcaagaacg cctacgagga gtccctggag  20460
cacctagaga ccttcaagcg ggagaacaag aaccttcagg gtgtgctggg ggtccaagag  20520
gccagagatg agttggtggg agggagggcc atgcaggggc agggggaaca caggctttga  20580
gctttctggc cctctggtcc ccagaggaaa tctcggacct tactgagcag ctaggagaag  20640
gaggaaagaa tgtgcatgag ctggagaagg tccgcaaaca gctggaggtg gagaagctgg  20700
agctgcagtc agccctggag gaggcagagg tgagggccga gaactccctg caccccatcc  20760
ctgttctgcc gctgtctccc acttctccct cacctggggg tgaccctgac cccaggacaa  20820
aatctattca ttccatattc tttgttcaac attatctacc cactattcac tacccatgac  20880
tgcctccaaa gccaaggtct gcacaaagga aaatgtcagt ctgattagag gccaaaggtt  20940
ttgtttccca ccaggtttta aaagttggaa tctggccata ataataacca cttagacagt  21000
gggtaggagt gtggggttcc agagtcaaac aggcctgagt tggaacacag cttgaggact  21060
ttcactgcgg cgttgggcaa aatctttaat ctctctctgc ctcagttttc tcatctgtaa  21120
aatggaatta actgtacata cctcatatga ttttacacat gattattata aagattaaat  21180
gaggtaacac atttaagcac ttaatatata ttagctattg ttactcttca tttctaagca  21240
cctgggaata gccctgagtt ttctgggctt ctaacttttc tcaggaaagg gtgagggacc  21300
tggaaaacaa gataaaattt tgtatttgtg gttataaaaa ttcctccatt ttctataata  21360
ctttagacag gtcaggaatt tatgcagtgt tagtgctgga gggtctggca attgtgaggt  21420
ccaaaccctt ttcttgacag gggaagccca gagagtccag cactttctcc ccaatagcac  21480
cgtggtgggc atggggtgca gatcccacct ccccatctct tctcagctct tcttctctgg  21540
gcgatagtcc tggctgacac cgtgtatctt ctcatcctcc ctctcaaccc tgccctgtgc  21600
cctgtctgcc cgccctcgcc ccaccccttc ccaggcctcc ctggagcacg aggagggcaa  21660
gatcctccgg gcccagctag agttcaacca gatcaaggca gagatcgagc ggaagctggc  21720
agagaaggac gaggagatgg aacaggccaa gcgcaaccac cagcgggtgg tggactcgct  21780
gcagacctcc ctggatgcag agacacgcag ccgcaacgag gtcctgaggg tgaagaagaa  21840
gatggaagga gacctcaatg agatggagat ccagctcagc cacgccaacc gcatggctgc  21900
cgaggcccag aagcaagtca agagcctcca gagcttgctg aaggtacatg gggcgggag  21960
gtcccctcag gggactggcc tccatgtggc ctggagaagc agtggtgtct ggatacaggc  22020
accagattcc tcctgcccct gggttactgc agggacctct gacaggtgcc ctcagtgaag  22080
ggcaccgagg ctggcttctg ctcacaccca ctctcctgat gctcaggaca cccagatcca  22140
gctggacgat gcggtccgtg ccaacgacga cctgaaggag aacatcgcca tcgtggagcg  22200
gcgcaacaac ctgctgcagg ctgagctgga ggagctgcgt gccgtggtgg agcagacaga  22260
gcggtcccgg aagctggcgg agcaggagct gattgagacc agcgagcggg tgcagctgct  22320
gcattcccag gtgagggggt caggagccac cttgtggaaa cctactgagt gcagagccca  22380
ggacatctag aaaagccaga tgttctaagt gagcacatct agccagggtc acaaatcatt  22440
tcctctctta ggccaactct catctgtggt ggctgcagaa ccattatatt aagaaagcgg  22500
```

```
tctctactta gaagctaaga gggtcatgat tgattgctga tacctgccaa agccacaaat  22560
ctgggagtag tggaatgtat cctgttattt gatattcttg atctgaaaga cagcctccgg  22620
cttgctctgt aaagatgaga gtttgggagt ttaaagaagc ataactgcat ctcttgcaaa  22680
ccaagctggc tagaacacca ttttctgcaa tcccacccac actgttttca gttatactct  22740
gcaatgagac tttgtgctca ccttttgcag tgccctgtgg agttttgttc tttaatctag  22800
tatgtgtgag aatgacatca tccacttacc tcatcccctc ttccttaccc cactacattc  22860
ttggtatagc tataaacatc tctggaatat tgtcctggta aaaagttgtt tccatcttcc  22920
ttggaatatt gtcatgctcc tacgtaaaca tgttgctaaa gagctccagg gtaatactgc  22980
agaccttttg ctatttgaag tctttttca gagtttagta atcttagata caatgtctag  23040
aatgtatgca ctttcatagg aaaagggaaa gcaggtacaa aacgatcaat agtctaaaag  23100
tgggcttgtt gttttaaaaa aaaaatgacc acctttaatt ctttctggag aaagggtatg  23160
aaatcaggta acaaagtgta gtatatattt gatcattttt ctctctccat gtctagaaca  23220
ccagcctcat caaccagaag aagaagatgg agtcggatct gacccagctc cagtcggaag  23280
tggaggaggc agtgcaggag tgcagaaacg ccgaggagaa ggccaagaag gccatcacgg  23340
atgtaagtga ccgcccacct tccgcctccc ctaaagacag aaacaaggcc ttgggtccag  23400
gccaggccac tgtgctgtaa caccaagcca actctgcagt tctgtggatt tgagggcctg  23460
atgggagaaa ggagatcctt gggggcaaa aggccccggc ccctggccca tgttccttgc  23520
cacctctctc ctgcacacag gccgccatga tggcagagga gctgaagaag gagcaggaca  23580
ccagcgccca cctggagcgc atgaagaaga acatggagca gaccattaag gacctgcagc  23640
accggctgga cgaggccgag cagatcgccc tcaagggagg caagaagcag ctgcagaagc  23700
tggaagcgcg ggtgcgggag ctggagggtg agctggaggc cgagcagaag cgcaacgcag  23760
agtcggtgaa gggcatgagg aagagcgagc ggcgcatcaa ggagctcacc taccaggtgc  23820
ggcggacgcc agacaccagg agtagatgtg gaagtttctt ctctggcccc actgccccgc  23880
cctcacaggg ctcctctcac ctcctccttg agatgctgtt ggtagattta acgttcttct  23940
cacgctctgc agtcagtttg acttgagtct atgagttttt ccagcaaatg aagaatctac  24000
ttctacttcc tgaaaactct tctaactagt ctttccccag gtttctttct ttcttttttt  24060
tttttttaa taactctaag tgctaccatg aagacttcag aacagttcaa agaatccttc  24120
caccttcgac tgtggggata agagtcaggg gaggggaaaa gacccggaaa tcttccatag  24180
aacttctggc acacaaagag aaggccacag agaaagagga ccctagaatg ctctaaaacc  24240
tccacttgca tagctgagag ctgtgccctt ggcccgttat tttcagtgta cctgggaaga  24300
aaaggccaag gagacgaggg tgtcagtcca tttgatagat ggataccaga ggcacaagaa  24360
agaggttaca gatacagaac cacagagtga tttgtggaca gaagtagaaa tggcatcctg  24420
gcacatacaa tgataaagag ataggaatga tcgagtgacg ttggagccag tgatcccgat  24480
gcctgaattc tggcccagta caatatatta gaatgtagaa taatctggat tatgataata  24540
ccccccttctt tctgcattct ttttctggtc aagaactact ggccaagaga acctatgtaa  24600
gtccaggttg gagctttatc caccatactg gagctggaac agacctggtg cttttatatt  24660
accacattag ggaattccat taggttctga gcccctcccc ctacttctag ctttatgact  24720
tcagccttca ttgctctgtg gatccctgac tgacaacctt gcattgcccc tttgacctac  24780
gatagagtca gagaatcttc cccaccacct ctttgacctg gatcattgca gggaggggca  24840
gcaaaggcaa ggggagaaga gtaaaatgat ggaggaggga aaggtgattg catttgctcc  24900
```

```
ccctccaaac cagcttctcc caccctccca cccccagaca gaggaagaca aaaagaacct  24960

gctgcggcta caggacctgg tggacaagct gcaactgaag gtcaaggcct acaagcgcca  25020

ggccgaggag gcggtgagtt cagagctttc ttccctttct catcaacaca cctactattt  25080

gtgagaacca atgaatatct cctacagagg ggcctggaca aagagtttgc tataaacttt  25140

aactctcaaa catttgtttg acacatctgg tatgctcaga gctgtcaggt gttctgaatt  25200

aacaaaggca ccacctacaa gctgcttaca attcagatac cataacccaa cagaaggcag  25260

tgtagatgct agtgcaggac gtggggcagc cgaagctgaa ggcaggaagg tggcggtgga  25320

attgggccta gaaggggacc cagctagcca cagggcagtg gggaagacat ctgggtggat  25380

gtgagttgct gattagcatg cctgcacagg aagctggggt ccgggacagg tgcagcaaaa  25440

caggattctg aaggggccca gatcgggcag catgggattt gtctggggca gtggatggcc  25500

gtgaaggact ctgagtgctg gacatgtttg agaagagtgc aaggcagttg caggataccc  25560

ttgggaaggc tgttgcagga atatgcatga ggcatgggtg cctcagggac agggagctgg  25620

aacctcaggt tgagaggctg agaatcccat agcccatctc cagctcattc acccatcccc  25680

actgtcccac cacaggagga gcaagccaac accaacctgt ccaagttccg caaggtgcag  25740

catgagctgg atgaggcaga ggagcgggcg gacatcgctg agtcccaggt caacaagctt  25800

cgagccaaga gccgtgacat tggtgccaag gtgggtccct cccctgggct tcactagtca  25860

cttccacatt agcatgcccc ctgatatggg tgcccttcag agtgggcact gcttgcccta  25920

tatgtaggca gttctgaggg tcccatagct tacataacct gagaatccac tctcctgctc  25980

aaaacagccc cccactgact ggaacttctg cagagatccc cagttccatc cccctaaacc  26040

acaagtgcct ctaacgtggg accacaggat ccctggggcc ctgcctctcc ctccaagggc  26100

atctccctta ggcctctgaa agccccaggg atttgtcccc acacacttct ccctcttgcc  26160

agctgccccc tcacacctct tattcttttt gcagcaaaaa atgcacgatg aggagtgaca  26220

ctgcctcggg aacctcactc ttgccaacct gtaataaata tgagtgcca             26269
```

<210> SEQ ID NO 26
<211> LENGTH: 3209
<212> TYPE: DNA
<213> ORGANISM: Homo sapiens

<400> SEQUENCE: 26

```
cgctcctgtc atcgaggccc ctggcccaat ggcaggctga gtccccctcc tctggcctgg     60

tcccgcctct cctgcccctt gtgctcagcg ctacctgctg cccggacaca tccagagctg    120

gccgacgggt gcgcgggcgg gcggcggcac catgcaggga agctgccagg ggccgtgggc    180

agcgccgctt tctgccgccc acctggcgct gtgagactgg cgctgccacc atgttcccca    240

gccctgctct cacgcccacg cccttctcag tcaaagacat cctaaacctg gaacagcagc    300

agcgcagcct ggctgccgcc ggagagctct ctgcccgcct ggaggcgacc ctggcgccct    360

cctcctgcat gctggccgcc ttcaagccag aggcctacgc tgggcccgag gcggctgcgc    420

cgggcctccc agagctgcgc gcagagctgg gccgcgcgcc ttcaccggcc aagtgtgcgt    480

ctgcctttcc cgccgccccc gccttctatc cacgtgccta cagcgacccc gacccagcca    540

aggaccctag agccgaaaag aaaggtgagg aggaaacaca ggcccccttc tcccctcctg    600

ggtcgctttc gtccccaaga aactcagggc caggaggagg agacacgcgc ccttgggccg    660

agggctgggc tgcggcgggg ggttcagaat gtaagatgcc tggtgttgtc gccaggctcc    720
```

```
cgcgccccgc gtccaatcgg aggttcagag gaaatgccgg attgaaagga tcagaagcaa    780
gagaccaaaa aacgtttccc cccggcctaa caaagccccg ggcggcttcg gctctgctcc    840
tgggtctggt aggaagttga gaaatcggtt tatggtagac agaacagaga gacaagcaga    900
taatctctgt ttttaaatct cctttggatt tacgaatctt tttaaagatc tgatgagaac    960
cgctaaacag aaattgaaat gttgctcacc agacagcttt tgcgtacaat cggaggaggg   1020
tcctggacct tctttctgca gcccacccac gacccgggtt tctggtgcct ttctttcttt   1080
gcgccaggaa agtggagtct gggatcgagg gccttgattt taaaatggga tactgcggac   1140
cctcaggaat ctgacttcac tttatttttt cagcacaact tgccggcgcg gccagggcgg   1200
agaggttccc tcgtggaaaa gttaggaaat gctgcgctac cgcgggcaca agggagtgga   1260
cgagatgagt gcgggatcat cccgcaggcc atcccaggat cggggaggga ggccggcccc   1320
gctgcagaaa ggggccttct gggagacccc ccagcccaag gcaggagccc gggcgattcc   1380
cgggaggccg caggcgctgg gcgaagcgct gggcgaaggg ccgctgccag ccgggagaga   1440
attcataggt ttgttgagga gcagaggcct gggaacaaat tcgggcgggc acggcggcta   1500
gaactgatcg ctaccaattc gaggaagcca gcaaggcagg ttccgaggcc gcctgcccac   1560
ccgcagcttc ttggacactg cgcaaaccct gctgcggcca ggctggagcc tccgatcacc   1620
aaaccaacac tccctggcct tctgtttctt gattccttaa ttttgagata agaccgtccc   1680
tagcagtgag gcctcggcct ctgttcattt aacttctcaa accaaactag ccctaattca   1740
gttcacccca gagcatcacc tggttttatt tttatttttt tattttttta tttatttttt   1800
ttttttttgc agcctgaaat tttaagtcac cgtctgtctc cctcaccagg gtgtgaactg   1860
ccccgagggc agagacctcc cgttttgttc tccagcgcct tgagccagcc tgactttcta   1920
caaatgctga gtgagacgtg tcggtggctc ccagtgcact tggcagagtg agccgcagcc   1980
agctgggcgc tccaggcagg acacagtggc ctccacgagg atcccttacc attactgtgc   2040
ggccgcgctc cgtaggtcaa gccgctctta ccaagcgtct ctctgcctct ctgttccccc   2100
tcagagctgt gcgcgctgca gaaggcggtg gagctggaga agacagaggc ggacaacgcg   2160
gagcggcccc gggcgcgacg gcggaggaag ccgcgcgtgc tcttctcgca ggcgcaggtc   2220
tatgagctgg agcggcgctt caagcagcag cggtacctgt cggcccccga acgcgaccag   2280
ctggccagcg tgctgaaact cacgtccacg caggtcaaga tctggttcca gaaccggcgc   2340
tacaagtgca agcggcagcg gcaggaccag actctggagc tggtggggct gcccccgccg   2400
ccgccgccgc ctgcccgcag gatcgcggtg ccagtgctgg tgcgcgatgg caagccatgc   2460
ctaggggact cggcgcccta cgcgcctgcc tacggcgtgg gcctcaatcc ctacggttat   2520
aacgcctacc ccgcctatcc gggttacggc ggcgcggcct gcagccctgg ctacagctgc   2580
actgccgctt accccgccgg gccttcccca gcgcagccgg ccactgccgc cgccaacaac   2640
aacttcgtga acttcggcgt cggggacttg aatgcggttc agagccccgg gattccgcag   2700
agcaactcgg gagtgtccac gctgcatggt atccgagcct ggtagggaag ggacccgcgt   2760
ggcgcgaccc tgaccgatcc cacctcaaca gctccctgac tctcgggggg agaaggggct   2820
cccaacatga ccctgagtcc cctggatttt gcattcactc ctgcggagac ctaggaactt   2880
tttctgtccc acgcgcgttt gttcttgcgc acgggagagt ttgtggcggc gattatgcag   2940
cgtgcaatga gtgatcctgc agcctggtgt cttagctgtc cccccaggag tgccctccga   3000
gagtccatgg gcacccccgg ttggaactgg gactgagctc gggcacgcag ggcctgagat   3060
ctggccgccc attccgcgag ccagggccgg gcgcccgggc ctttgctatc tcgccgtcgc   3120
```

ccgcccacgc acccacccgt atttatgttt ttacctattg ctgtaagaaa tgacgatccc 3180
cttcccatta aagagagtgc gttgacccc 3209

<210> SEQ ID NO 27
<211> LENGTH: 5966
<212> TYPE: DNA
<213> ORGANISM: Homo sapiens

<400> SEQUENCE: 27
cagtgtcctc ggggagtctc aagcagcccg gaggagactg acggtccctg ggaccctgaa 60
ggtcacccgg gcggcccccct cactgaccct ccaaacgccc ctgtcctcgc cctgcctcct 120
gccattcccg gcctgagtct cagcatggcg gatgggtgag tgatgcccca aggcagtggg 180
agttgggggc gacctcccgg gttcccaaga ggggtcgcag ctgagaggct ggacccttgg 240
cctgcgaggt aggcgtaggg actcttgggt gaagagagga agtgggtttg cgagtcagac 300
tcctggaacc caaggaaggg gaagcgcggt cccccgacct cttgttcaga ggggactcca 360
ggggtccctt aggagacagg acacagccca ccactaaccc ccctccttgg tttctctcct 420
tccaggagca gcgatgcggt gagagcagcg ggctaaggcg tggctgggac ccccagggcc 480
agggtgggcg ctgcagtgag gggtctgggg cgggaggctg cagccctagc agagggtgcg 540
gtacggtaag ggctgggtgg ggtcttggtg gtgatggggt ccccactcct cctaacccag 600
gctagggaac ctcgccctgc accagcccca atcagacgcc gctcctccaa ctaccgcgct 660
tatgccacgg agccgcacgc caaggtggga cggggcttcc tgggggcaga gtacaggcgc 720
cggagggatc caagaccctg ggagtggggg gaggagccag ggctgcgaag gggcgggga 780 ctacgcggag gggcttcagg ggcggagttt tgcagagggt catgctcgga ttggtgacag 840
cagcctgcgg gcggaactcc gttgccctcg gacttgctta gggatagatg ggaagtgcct 900
atccaaagga agagacccag attggtggat gggaatgagg ggcgtggcct cccgtagact 960
cagggctcaa gttggacgtg ggcccaaatc tggaccggct gggtttgctg ggggtgtctt 1020
gaggtcccct ccaccgtcgt ctccgaatcc ccctccatga tccttccttg ctccatctca 1080
ccctggcaga aaaaatctaa gatctccgcc tcgagaaaat tgcagctgaa ggtgaggacg 1140
ggcgggactg ggaaagagca ggcaggtgct caggggggcgg agcttgagaa tgggtggggc 1200
tttcggggta ggtgggcgga agtgggcggg gtttggccgc tcggggcgtg gctttagcgg 1260
ggagtactgc tcggggtggg acggggcctt ggaacagtgg agaccaaact ggagggttta 1320
gaagggcaga ggcggttccc cacgcctggt ctttatcctg aagccccggg tgggctgcgc 1380
ttccctccca cccctctgca gactctgctg ctgcagattg caaagcaaga gctggagcga 1440
gaggcggagg agcggcgcgg agagaagggg cgcgctctga gcacccgctg ccagccgctg 1500
gagttggccg ggctgggctt cgcggagctg caggtaccgg ctcccaagga tgcgaggttt 1560
ctagtcccgg aattcagcag tacagcctct atcccctctt ctgctcggga cccaggcgtc 1620
caatatggct gtccttaccc aattatatat ggttcgtggg actcctggcc cctaacaccc 1680
tttgtgtgca ggtctgtgga gtcttggctc caacctactc cttcaggacc atgtggccct 1740
cctatcccag acagaagccc aagccccagc ccctcctccc tcagaccctg gagtccaggc 1800
cccagcccct cctccctcag acccaggagt ccagtcccca gcccctcctc cctgagaccc 1860
tgaagtccag gccccagccc ctcctccctc agaccctgga gtccaggccc cagcccctcc 1920
tccctcagac cctggagtcc aggccccagc ccctcctccc tcagaccctg gagtccaggc 1980

```
ccccagcccc tcctccctca gaccctggag tccaggcccc agcccctcct ccctcagacc   2040
caggagtcca gtccccagcc cctcctccct cagaccctgg aatcgaggcc ctcagcccct   2100
cctccctcag accctgaagt ccaggcccca gcccctcctc cctcagaccc tgaagtccag   2160
gccccagccc ctcctccctc agaccctgaa gtccaggccc cagcccctcc tccctcagac   2220
ccaggagtcc agtccccagc ccctcctccc tcagaccctg gagtccaggc cccagcccct   2280
cctccctcag accctggagt ccaggcccca gcctctcctc cctgagaccc tggagtccag   2340
gccccagcct ctcctccctc agaccctgga gtccaggccc cagcccctcc tccctcagac   2400
cctggagtcc aggccccagc tcctcctccc tcagaccctg gagtccaggc cccagcccct   2460
cctccctcag accctggagt ccaggcccca gcccctcctc cctcagaccc aggagtccag   2520
tccccagccc ctcctccctc agaccctgaa gtccaggccc cagcccctcc tccctcagac   2580
ccaggagtcc agtccccagc ccctcctccc tcagacccag gagtccagtc cccagcccct   2640
cctccctcag accctggaat cgaggccctc agcccctcct ccctcagacc caggagtcca   2700
ggcccccagc cccttctcct ccctcaaacc caggagtcca ggcccccaac tcctccctca   2760
gacccaggag tccaggcccc cagccccttc tcctccctca gacccaggag tccaggcccc   2820
gagccccttc tccctcagac ccaggagtcc aggtctccct gtttttggtt cccccaacaa   2880
cacacaccac gttcctcctc caggacttgt gccgacagct ccacgcccgt gtggacaagg   2940
tggatgaaga gagatacgac atagaggcaa aagtcaccaa gaacatcacg gaggtgggac   3000
gcatgggcag ctcgggtacc ttcggggtag ggtgagatgg ctgggacttg gtctctgcct   3060
gacccettgc agctgctttt ggctgcacat cccaggagac ccaggacaac tgtgagcctg   3120
gcagggctgg ggcagaagga tgagtacaat atagtcaagg aaagctgttc taggcagagg   3180
gaacagcaca tgcaaggcca tgggttggga aacagaaaat aagttagtga acatgctcag   3240
ggcatcacat gttggtaaat tagctcaggc actggccagg gaattgtgat ttgcatgtag   3300
ctggaccagg ttatgccagt ggttttgaga ggtgaggctg gagcatatga ggagggggat   3360
tcagttccag gattagaagc ctagactggg agcctaagcc gggaagagac tggtaaggcc   3420
tcggtactgg aagacgagat aaggagaata aaaaaggagt gtaggatgga ggagttgggt   3480
gtgcgggaaa tggaaggaga agtacccacc ccctcgtttg cccccagatt gcagatctga   3540
ctcagaagat ctttgacctt cgaggcaagt ttaagcggcc caccctgcgg agagtgagga   3600
tctctgcaga tgccatgatg caggcgctgc tgggggcccg ggctaaggag tccctggacc   3660
tgcgggccca cctcaagcag gtgaagaagg aggacaccga gaaggtgagt gtgggctaag   3720
gccaggaaag aggatgctga ggggaagggc tgtgggtgcc aacaacccta ggcctgaggg   3780
cagatggtgc ttggagttgg aggtagaagc agctagtaag ggtcctcag aaatgcaaga    3840
ggaagacagg aagtagaagg ggaagacagg aagtgcatta gggctacagg aagtccatgt   3900
aagagcaaag aggtacatga aggtccaggt gcagtggctt atgcctgtaa tctttgaggt   3960
ttaaaaaaaa ttttttttta atttcctttt tttttttttt ttgcgatgga gtctctgctg   4020
cccaggctgg agtgcaatga caccatctcg gttgctggag tgcagtgaca ccatctcggc   4080
tcactgcaac ctctgcctcc caggatcaag tgattctcat gcctcagcct cccgagtagc   4140
tgggactaca ggtgcacacc accatgttgt tgttttaatt tctacaaatt tcttttttaa   4200
attagccagt cacggtggtg gcatgcagct tctcaggagg ctgaggcagg aaaatcgctt   4260
gagcccatga gatcgagggt gcagtgagct atgactgcac cactgcactc cagcctgggc   4320
aatacagtga gaccctatct taaagaagaa gacaggaaag ataggagtgg atgcctgaaa   4380
```

```
ccatggattg tactgaaccc tatatgtaat tttttttcct atacacacat acatacctat   4440

gataaagttt catttctaaa ttagacacag taagagatta acaataaata acaacaaaag   4500

aaggttgggc gtggtggctc atgcctgtaa tctcaacact ttgggatgct aaggcaggca   4560

gattgcttga gctctggagt tcgagaccag cctgggcaac atggcgagac catgtctcta   4620

taaaaaatac caaagttacc gggtgtggtg gctcgtgcct gtaatcccag cgctttggga   4680

ggccaaggcg ggcggatcat gaggtcagga gtttgagacc agcctggcca acacagtgaa   4740

accccacctg tagtaaaaat acaaacattt gctgggcgtg gtcgtgggtg cctgtaatcc   4800

cagctacttg tgaagctgag gcaggagaat tgcttgaacc cgggaggcag aggttgcagt   4860

gagccgagat ctcaccactg cactccagcc caggcaacac tgggagactc catctcaaaa   4920

caaaacaaaa cagaacaaaa gttagctggg catggtggca cacacctgtg gtcccagctc   4980

ctcaggagtc tgaggtgaga ggatggcttg agcccaggaa gttgaggctg cagtgagccg   5040

agattgcacg actgcactcc agcttggatg aggcagccag accctgtctc aaataataat   5100

aataataaaa tagaacaatt ataacagatt gtaataaaac tcatgaatgt ggtctctttc   5160

tcaaaatatc ttatagcact gtaatcaccc ttcttttcct tgtgatgtaa aatgacagtg   5220

cctatgtgct gagatgaggt gaggtggatg acataggcat tatgacctgg cgttaggcta   5280

ctattgacct gagaatccat caaacttatg aattgtttat ttctggaatt ttccatttaa   5340

tatttttggg ccatggttta cctcaggtaa ctgaaaccac acaaagtaaa attgcagaaa   5400

aggagggact actataataa gaagagaagg aaggagacag gaagggcata aggcagacag   5460

gaagtggagg ggaaagatag gaagtgcagg aaggagacag gaagtggagg ggaaagacag   5520

gaagtgcatg agggagacag gaagtggatg gggaaagaca gaaagtacat gagggagaca   5580

ggaagtgctg ggaaagaca ggaagtgcat gagggggaca ggaagtgcat gagggagaca   5640

ggaagtgcat ggggaaaatt ggcagggatt atcttgaaaa gacaggaagt gctccagaac   5700

tagatactta ggcatccagg gtagagtggc cccacaggct ggagggaaga cagggattct   5760

tgagagactg gagaccaaga agagacccta acctctgact catcgccatc ctccaggaaa   5820

accgggaggt gggagactgg cgcaagaaca tcgatgcact gagtggaatg gagggccgca   5880

agaaaaagtt tgagagctga gccttcctgc ctactgcccc tgccctgagg agggccctga   5940

ggaataaagc ttctctctga gctgaa                                         5966
```

<210> SEQ ID NO 28
<211> LENGTH: 55793
<212> TYPE: DNA
<213> ORGANISM: Homo sapiens

<400> SEQUENCE: 28

```
cttggaggcg gccggcgcag gggccgcgag aggcttcgtc gccgctgcag ctccgggggc     60

tcccagggga gcgtgcgcgg aacctccagg cccagcaggt agggcttttt tcttcccttt    120

ctttgctcct tcccgcggtc ccccaaactc ggagcttctc cgcctttgct tgtctggagg    180

tagagaggta gctagtggga ggaaaagaga cgtgcgctac tcacttcacc gaaattgccc    240

aacccctgct ctgcttttga ctttgcctta gcaacttctt taagtcaaag taagacttgg    300

gggcaaaaca gagaaatatt ggaagcgcct ttggattctt tccgtgtgaa cttgaacgct    360

ttcaatccct gtccccgtgt gcacattctc caacccttgt ttgcatatcg caggccgggg    420

cctgggtggt gatggtggcc gcgtgaagtt accgggactg acgggcccgg gacaggctgc    480
```

-continued

```
acggcagctc gcacatggag ggaagtagac ggaggcttgt cgcccaccag cgactccggg    540
gacgcagggt ggcagtgcca ggcagctccg ctgggcctca ggggccccg ggagccgctc    600
tgaggtgcgg agaggctgct gagtggcgga actattcatg ccctttctgg ccggcctcct    660
cgccctcggg gctggggtcc agggactgaa tgctcctctg gaagctcacc accccacctg    720
cccgcgctgc ttctacctga aactggccaa gggcccgagc ccggaccgga gccgtgactt    780
ccctccgccg gccacggggc tgcccggatc cgccgggtta tgtcgcttgg ctttgggctc    840
aggggtcacc gtgggcagag gggggtgccg gggtcgcgga ctgccaccag gttgaggaaa    900
ggaggggcct tttggctggg gaaagagcgt ggtgggggac ccgcggccga tggaatccct    960
ggggcagcgc ggcccgcacc gtggaggttg gggaagcgcc tcggggaagt gtttcctgtg   1020
ttcccagaaa aggaagacaa ccgagagcag gtttcaggct tttaaagaaa gcctggggtg   1080
tggaggtgat gctccgcaca cgtctgtgtc tcctcccctg ctgcggccgg cttggttgtg   1140
ccggctagcg tgcgaccgtc ctcctcgctg caggccgaga gcggaggcgt aaacccaggc   1200
cagcgaggag tgtcctataa agggacgggg acttttcggc gcttgcaatt ctcccattct   1260
gaaaaataga tcggaagagg gctattggtt gattcttgaa aggggagcgc atttcctgtt   1320
ggcctgcgaa tttggggtga actgggacaa gtgatcagaa ggagagcaaa aactccccga   1380
ttttggcagc ctcgggagct gctgggcttt ctccgccaac tgcaggatcc aggctcaatt   1440
tcaacaacca gccagaggcg ttttccaaga gcagctaatt ccttgttttt ccagaaagtt   1500
atagaggagt attttctcca ccttctgttg ttctagtaat ccaactcagg cactatatca   1560
gccatttgaa aaggcagaga atgtgataaa gacaaatatt agattgatga catttttttgc   1620
atttaccttt taaagtctgc aagttactac ctgtgtgtat actggaagtt ggattataaa   1680
attctaaatc tcctttcttt tccaaagtta tgaaagaaaa aaaattacat tatcttgaag   1740
aactgcagga gttgagtatt ccagaaaatg caatgaaata ggtcagctac ttgattttaa   1800
aagtcaaata ctggatcttt tattaaggta aacccataat tctttaactt tattttcaaa   1860
gggaaaagtt ggtgacctca ggtcaatttt taaaaaaatc tattctctaa ccaaacttgc   1920
tggaatgaac tatttgccaa accaataagt tattgcatat tttgaaagca aataagcttt   1980
taggagttac catgtgacta tataatacaa tacagtacta ttccattatt attactagtg   2040
atgttgcaaa aaatggtgaa aagcattatg tagtgtgtat taaagattcc atttccagat   2100
ttttacagta ataaagatga tcatttatta tagtatatac atttgaggta ctttcttgta   2160
ttatactaga aatctgtagt aatagtcaac tgttatttag aactttcttt ttgcctgtta   2220
ggacagtttt ataaaaatct gttataagtg ttttacaaat attaatttat aatcctcact   2280
cctaagcttc acgatgactc tacaaaataa gtacctttaa tatctgcatt ttgcagatga   2340
ggaaactaag gcacagagag gctaagtaat ttgtctaaag gtgtttattc cgtaagtctc   2400
agagcctgga ttcatatata gttaacattc ttgtaaatct actattgaaa taaaaaagaa   2460
aactttgtcg ggagtagttg cctcttctta aagagagaaa tggagtgtgg tggacagctt   2520
caagcccctg gagccctact gatcccattc ccttccccca ccccttctga ttgtactttg   2580
atcttagaca agtttcaaaa ctttccagtg ctccagttcc ctcttgtaaa atgaggagag   2640
acacctgtac ttagtagagt tgtagagaaa aggacctgga ggtaattcag acagcaggta   2700
attcaaaaag tggagctctt attttatcag aaaaattgcc tgataataac aaaacgcagg   2760
atgctgggaa gtatataatc aagttccaca aactgctctt tccccaagca cccaccttgg   2820
tgttatgatt ctgcttatgg gtggatttat tattctatat gaagaaccca ttcagtgaat   2880
```

```
tagaatggtc cagtgggtta ttctgtagag cggcattgta cattcttctc acttttctgg   2940
ttctgatata caatttgcaa aacgtctaaa ttgtaactat ttgcaagaaa cctgtaactt   3000
gtccgatttg acgtccacat ggttagtgta tggatgaggg tttcagaacc ctcttcagga   3060
ggcttagcag acaccgttgt tcacttataa acatttggac tctacttctg gttttttttt   3120
tttttaatta caaacaaaac tttgttaggt tgttgttttg tgtaaagttt gtccttgtcc   3180
ccccaaggac aatctaaagt tctttctagg ccagtctccc catctttctt ggggagagat   3240
ggggaacaga ggagatgaga gatttcttgg gtcccaggca ctctgcatta acgccaaact   3300
tttggactta caaaaatatg cttgcagaat aaggtaacat taaagtcctt cctgacaagc   3360
aatacaaaaa tcattgacca agatcacaac caataactgc acaccaaaga cccgggaagc   3420
ccctggtccc tggggcgcct ctccccaggc ttgcctgggc cgcctgaccc aacgcctgga   3480
caaaacaaag gcccctgctt cccggcaccg cgcggcctcc ggagctgcac ccccaaatcc   3540
ccgtggcgac ttcatttgaa gcgtggaaga agcaaccacg caagtggaga gtgggttctg   3600
aaagctctgg gatgaaccac cctctctctt tctgtcgttc ctcttttagg accccggctg   3660
cggcgaggag gaaggagcca gcctagcagc ttctgcgcct gtggccgcgg gtgtcctgga   3720
ggcctctcgg tgtgacgagt gggggacccg aaggctcgtg cgccacctcc aggcctggac   3780
gctgccctcc gtcttctgcc cccaataggt gcgccggacc ttcaggccct ggggtgaatt   3840
cagctgctcc tacatcagct tccggaacca ccaaaaattc aaattgggat tttccggagt   3900
aaacaagagc ctagagccct ttgctcaatg ctggatttaa tacgtatata tttttaagcg   3960
agttggtttt ttcccctttg atttttgatc ttcgcgacag ttcctcccac gcatattatc   4020
gttgttgccg tcgttttctc tccccgcgtg gctccttgac ctgcgaggga gagagaggac   4080
accgaagccg ggagctcgca gggaccatgt atcagagctt ggccatggcc gccaaccacg   4140
ggccgccccc cggtgcctac gaggcgggcg gccccggcgc cttcatgcac ggcgcgggcg   4200
ccgcgtcctc gccagtctac gtgcccacac cgcgggtgcc ctcctccgtg ctgggcctgt   4260
cctacctcca gggcggaggc gcgggctctg cgtccggagg cgcctcgggc ggcagctccg   4320
gtggggccgc gtctggtgcg gggcccggga cccagcaggg cagcccggga tggagccagg   4380
cgggagccga cggagccgct tacacccgc cgccggtgtc gccgcgcttc tccttcccgg   4440
ggaccaccgg gtccctggcg gccgccgccg ccgctgccgc ggcccgggaa gctgcggcct   4500
acagcagtgg cggcggagcg gcgggtgcgg gcctggcggg ccgcgagcag tacgggcgcg   4560
ccggcttcgc gggctcctac tccagcccct acccggctta catggccgac gtgggcgcgt   4620
cctgggccgc agccgccgcc gcctccgccg gccccttcga cagcccggtc ctgcacagcc   4680
tgcccggccg ggccaacccg gccgcccgac accccaatct cggtgagtag gagcgcgagg   4740
gctggggcgc gtgagggccg gggcaggggc cgtcttgagc cctgtcgagg gcctcttgtt   4800
tttccaccaa cgccttcgtt gggctgggga tggtgcttca ctacctcgag tttctaggga   4860
aggcagaagc cagtgcgggg ctggcgacat cacagcccca gaagaccggc ttctgtggaa   4920
ggggccgggc ctgcccgccg gggcctcttc tgagatggtg tcagggtcgg agtgcggcct   4980
ccccgccatc ccagacatcg accgtggccg cgctgcgctg tgggtgacgc gggaggacag   5040
cgggctccct ggagagccgg gggcagcggc ctgggatttc ctcgtggaag gtgctggaga   5100
ttgctgagtt tctgcgcccc tttcctcccc gcccgccctc gggcctccgc agggaactga   5160
ttacaatggt ttggaccgca gaccttctgg gccatttggc ggcccagctg gaggatccct   5220
```

```
cggggtagct gatgatttc ccgtcggggg tctcacaccg agaacaaagg agggatggac   5280
aaaggagacg ccggggagat gcgcggaaca ggagccggca ctgtgcgggt gccacccggc   5340
cgagcgcgtg ggcgcatcat gcgggcagcg gggggggggg cgcacacgcc cggtcagtgt   5400
ccgggaacat agggacctca aacgcgcttg ttcatgacac ccgagttaaa tggagacttt   5460
gcagtcgctt gcacgcgtgg agcctcctct tctcgcgtgg gccagggttg gaaataaccg   5520
ttgtggtagg ttccatgcag tgtttccatc ggatgtcaga cggggaggga cggcaaacct   5580
gtctcaacct ccactgattc acaaataaac gcagcgggat ctgagaaggg gcctgagtac   5640
acgggccggg ggagaaaggg aagtggcaac ccctagttca aaatgcaaac gacctctgga   5700
atttcgggaa gagacggagg agtgagtttg gattgagccc accctgtggg ggaggggaag   5760
cccaggcttg agaagcaaag ctcgcgttta ttgaccacct actaagtgct aaatccttct   5820
gcatttgttc tcactttgaa gagtaaaggc taccccctgcc aggtttccag tcttgggctg   5880
gctccgagaa gggcctaggc tttgaagcgc ttttaaattg tcctctggcc ctgggtggcc   5940
agggaaggtt cccgggggtg cagccaaata cacatcgccg gcaaactgat taaccctgaa   6000
agtggcgccg aggcccggtc tgtggctctt ggtgttcccc tccccctcac ccctcttggg   6060
ggagccagac ggccaccccc aggggaggag gggcccggcc gagcctcgcc gcgacttttg   6120
cgagatagcg cggcgacatg gccacacaat ggagcccgca ggcgggagtg cggggcgggg   6180
cgcggcgccc tggccttgcg cgcttacggg gtcctctcca gggccctctg gggcctctga   6240
cttaaaatag ggaggactgg gccaggagat cgagaccatc ctggccaacc tgttgaaacc   6300
ccgcctctac taaaatacaa aaaaaaaaaa aaaaattagc ggtcgtggtg gcgcgcgcct   6360
gtagtctcag ctactgggga agctgaggca ggagaatcgc ttgaacccgg gaggcagaag   6420
ttgcagtgag ccgagatcgc gccactgcac tccagcctgg taacagaaca agactacgtc   6480
tcaaaaaaaa aaaaaaaaaa aaaaaaaagg actggtccag ggagagtttg ctttgtaacc   6540
ccgacaatcc tggagggaat ttggtgtttg gttaaggaaa agagagaagt taaaagtcat   6600
gagttacatc cagcagtgta aaaacgaaat acccgccggg cgcggtgtct cacgcctgta   6660
atcccagcac tttgggaggc cgaggcaggc ggatcacaag gtcaggagtt cctggccaac   6720
atggtgaaac cccatctcta ctaaaaatac aaaaattagc tgggtttggt ggtgtgtgct   6780
tatagtccca gttacttggg aggctgaggc aggagaatcg gttgaacccg ggaggcggag   6840
gttgagtgag attgctccac tgcactccag gcctggcgac agagggagta tgtctcaaaa   6900
caaacaaaca aaaaaccgaa ataccatgtg aatgcacaca gtattcagat tttgaaatgt   6960
cagccatgcc atgtagaggt tgctgatgaa gtgatgtttc ccaaattccc atgtcagcaa   7020
atggcaagct gacctccctg tgcgtctctc tgccaagaac tgccacctgc cttctctggg   7080
ctcttcccgg atagcttatg aagtccacag cctttgaatc tggcctagag ggtggttttt   7140
ctcttctgca cccagccaag tgttttagga gaggtgcggc tctctgtgag ggaacacagg   7200
gcatgttgaa cttgttggca ttcatagctt cagcgtgtta tgcaggtggc acttacataa   7260
aagcaactga aattaaaagc agtgcatgtg gccaggcgca gaggctcatg cctgtaatcc   7320
cagcactttg ggaggctgag gcaggaggat catttgaggc caggagttcg aggtcagcct   7380
gggcaacata gtgagacccc atccctacaa atcattttaa aaaattagcc aggcttgggg   7440
tggcatgcct gtagtcccag ctttggaagc tgaggtagga ggctcacatg agcccgaggc   7500
cactgcactc cagcctgggt gacagagtga gaccctctct caaaaaaaaa aaaaaaaaaa   7560
aaaaaaccag tgcatgtgaa tgtgcttttt atatgttctt cccattactt gggctctcct   7620
```

```
acctgcctgg cagctttagt gaggaccagc atcacatagt agctgaccct gagtcatgga   7680
gggaagatga gaactgaccc cagctttctg aggagttgcc actgagccct aagatggcca   7740
gacagtgtgg tgggaggagc acagggtttt aaagttgggc aaacctagat tcagttccag   7800
gagcctcgtg tcatcttggg caagttactt acctctctcg gtctcacctc tttttctgta   7860
aaatgggatc atcataacaa tttttagtgt tgccttaaat tagaaaagta aggtaatact   7920
tttgaagaat ttggctttag cccttcataa atgatggtta ttttattgaa tagccactca   7980
ctgtcatgta gagttaccaa ttttgctggt gtgcccagga ctgagggttt tcccagaatg   8040
tgggattgtt cgtggtaaac ctgggacagt ccccagtgaa cgcagattgt tggacactca   8100
atgtgaaaat gggtgcatta cccatcgttg tggtttggta atgagctgag aacaaagaag   8160
aaacagcaga ggagaagcag ctgagagcaa aggagaagca gcatcattct tccctctgct   8220
gagattctgg aagtagtcat ttaagtgctg ccagcttcat ttggtcttga agggtgagta   8280
ggagtttgtc aggaaaagaa ccagcaattt ttttaaaaaaa gaaatattga ccattttata   8340
ggaaaaaaaa gaaagacaaa gaaaaagagg ccaggtgcag tggctcacac ctgtaatccc   8400
accctttggg aggctgaggt gggaggattg cttgagctcg ggagtttgag accaacctgg   8460
acaacatagt gagaccacat ctctaaaaaa aaaaaaaaaa aaaaattaac tgggcatggt   8520
aatgcatgcc tataactcca gcaactcagg aggctgaggt gggaggatcg cttgagtcag   8580
ggaggttgag gctgcagtga gccgtgattg caccactgta ctcctacctg gagaacagag   8640
caaagaccct gtctcaaaaa aagaaaaaga aaaagaaagg atatactctg ctttactaat   8700
atgttgtgta gtaccatgaa ataatacaat gcaacctggc ctttgattta aataatatat   8760
ttgtcacaat aggtaaaact atacagacta attaacctta actcagaaac tgtttttaat   8820
ttcaatgagg agaaacaaga gaacactttt ttttttctat gtaactgctg tagttttaac   8880
aatatcttgc catagttctt atgttggtta tgtgaatagg gcaaaaatca aaacaataat   8940
aaataataaa agttaacagg ggcctctgta aagccctgaa cttaggttgg aagaaataag   9000
tgtggcctga ctgcaatgta tgtgaacttt aattcactcc aagttccata tgagctacga   9060
ccctaagaca aatgttaaaa tcattaatta ggctgcatga atggaattat gtgaccttac   9120
tgagggcagg tacagagtct tactcatttt taagtgcctg gcacatgttg ggcacttagc   9180
aaatatttgc gtagggatct tggtggtaat tgccccagga ctctgccctg cctgggtcca   9240
accacacaga atggctgcgt gagtccttta agaagcaaac tggagagccc taggggaacg   9300
gtgggcagga tggaagaggg ttctggaaac ttcagggaac cactggagga aagcagggct   9360
tttaggctgg agaagtcact gagtggatga aagcaagatg gagtatgact gtgtccaaat   9420
ttctgaaaag caaaaaaaaa aaagaaaaaa aagaccatga ccttttaact ctgtgttagt   9480
gaaggtgagc agatattaga tgtgagaaga acactcctag acaattgtgg ttgtgtggaa   9540
atgcagtata gaatatggct tgtcttcatc ataaactcct gggcgctgga agcacttgtg   9600
gtggagctct gcggatagtt cttgccttgc agggctagga taggatctgc atgtgcctgt   9660
gaaacggacg tagccggaga acgtagctgt ttccttttaa agaacccagt cacggtggtt   9720
acacgtgtat ctccatatgg caaaattgtg gagctgtgct cttaaaatgg gagtctttta   9780
ttgcatgtac attacacctc agtgaagctg atttttatac cagttaatgc ttgtgagtac   9840
ttaaggctga aaaggagacc gaaatggaaa tagattgtaa atatgccttg acggatatat   9900
ggtggtaggt gttactggaa aggctaggaa aatatattta agtatggaat aacaattatt   9960
```

```
ttgtgtaatg gagacataag caattatgat attctccaag gatttcaaaa agtttgaatc  10020
atttttagag tcgataaaaa taacaacaca atgaaataca tgtacagtat atcactgtgt  10080
tattcaaaca atttatttaa aagaagtttt gccccattag ggatggagtg ggggcattca  10140
aggtgttctc agagtttttt tatggtgcag gtcagtgaaa aaccccgaag tgttttctgg  10200
atcttttggg acctgcttat caagtacgct agtggctttc aaagccggtt catttgtgca  10260
gggaactttg tgagactgga gaatgatttg tcgatcttca ggaaaaccaa agttgtttaa  10320
ctttccggtt accaccctga gcaggtcagt cagagttggg gttggtctgt ggtgctaagc  10380
tgagaacgaa ttaaataaga aaggtgtgtt ggggtggcca ggggtgtgtc actacctcta  10440
gtgagccctg tcacttgccc agttgtgtcc catcaaaagg tcaggccaca tttgctaggc  10500
actttctaag cactcaggtg gaatgatgcc cgggagacag ttctagataa cgctttattc  10560
tgtatccctc cccatttctt ttctaactta aatgcactaa gaaaacaaac acactgaggt  10620
gtggggaaac aggaactctg atacctgtgg gtgggagtgt aaatcgctct gacctttatg  10680
gagagtctta ggtgtagtag ccataaaatt gcaaagtaga cagcctggac tccggaattt  10740
tcacttctag ggatttgttc cacaagcaca ccggcacata ttaatttcag cattgctcgt  10800
aataacaaaa ttggaaataa tctaaatgtg catccttagg ggaatgtttt tatgcacgtg  10860
gcacatacaa accataagct atgtaggcaa gaaataatga agttcattat ctaatgtatg  10920
gaatcctcac aaagacattt ataaatgcag gaagtgtata tagcacttta ctgtttgtgt  10980
taaaaaaaag aaagaaaaag attatattca cttgaaaata caaaatctca caaaaaattt  11040
gtaacacaga tttgcctgtg gggaggaaag cgggtaggtg agggataatg gtagaaaagg  11100
gactttcact atgcatgcct tggaactttt tgaatttttt aaccacctta atcattttta  11160
tactcatttc tgtgccttat taatccattt aataacaaga aaatacattt aacatacagg  11220
gaagttaaag ttaagtttaa tgtaaaaatt tcaaatcatc ggctgggtgc agtggctcac  11280
acctgtaatc ctagcacttt gggaggctga ggcgggcgga tcgtgagatc aggagaccag  11340
cctggccaat gtggtgaaac cctgtctcta ctaaaaatac aaaaattagc tgggcatggt  11400
ggcacgtgcc tgtaatccca gctattcagg aggctgaggc aggagaattg cttgaacccg  11460
ggagttggag gttgcagtga gccgagatca caccactgca ttccagcctg ggcgacagag  11520
caagactcca tctcagaaaa aaaaaacaac tcaaatcatc ttagccactt ttaagtatac  11580
agttcagtag tgttaaatac ctttgcattg ctgtgtatca gatctttaga acttaaactc  11640
tgcccattaa aataccactc ccattcctct ccacaccagc ccctggtaac ccccattcta  11700
ttttcttttt cttatgaatt tgaccactct agggacctca cacaagtaga atcgtacagt  11760
gtttgtcgtt ttgtttctgg ctaatttcat ttaacataat gtcttcatga ttcatccatg  11820
ttgtagcatg tgccagaatt tccttccttt ttaaagctga ataatgttcc attgtatgtg  11880
tagaccacgt tttgtttatc cattcatcca tggatggaca cctgagttgc ttctccgtct  11940
tggctactgt gaataatgct gctatgaaca tgggtatgca aatgaaacct tttgaatttg  12000
gagaatgtga ctatattacc taattttaaa aacatattaa actaattaag ttttaaaaaa  12060
cagatacatg atattcatga atcaacctga aagtagcatc tttttctttt ttttttaaag  12120
aagattctct atttagtgtt tatggatgca caggaaaact gctttaaggc ataagttgtt  12180
ttttattaaa tttgtctttt acctattctt ttacaatttt gggggttttc ctttatgctc  12240
aagcttcctc aagattcttc aaggcagatc aaaaccatcc tcagtggcaa tcctgtattt  12300
ggcttttgat tttgcttatt tcacaggagg ttgctttact gagaggggga aatctctact  12360
```

```
cctggtctca gtgctggtag tggatctaaa tcagcaatgg gcggacaccc cagccccaca  12420
ctactgtggc ttccccactt gtgggcacaa acagtcacgt actaggcaat ggtgacctct  12480
ccaggtaggc agttttccct caggttatat tggagttaga acctgcctga aaaccactaa  12540
ccggctgcag cggtgggatt gtgtgaagaa caagttacct tcctccaggg caaggtgatt  12600
cttttaaaca aattttaaga caatttagtt gtactgaatt tagagctgaa gccagttgca  12660
aatgtagctg cttgtgtctg cataagaaag aggaagtatg ctagttttcc tttccttgtt  12720
ccagaagagg gcagttcttg ccaacgcgag ctgctgcttt aagaacttga agcaactttt  12780
ctgacatctg aaactatttg tcttttggga acttatttgt cctagcctgc ctgcagaacc  12840
agctgttaag gctctgttgg gaaggagtat cgctctgcta tattgacctc tggtagacca  12900
tgacatggcc ccatatgcca tacaacataa actggttact aagagtaatt taatggctat  12960
ctctagagct actcttttgt taccttctaa agaaggcagg gaagaaaata taaatggggt  13020
tataatagga ataatcttga atctgtttta atttatacaa aatacattta taagttttgg  13080
cacattcacg tttggatact ggctaacaac tttttagcga gagtagcctg tatcttgcat  13140
gtcattccat tgaacagtaa ggtggatccc tgtcaatgaa gaaatcatct gatgccaggg  13200
actttgaagt ctttctccaa gaggtagata cgatgatctc tgttttgctg gaaagaaagc  13260
tgatacccag aaagagcctg taatctcagg tccccgtggg tagtaaacag ccctggtttg  13320
gaacccaggt aagtccaacc tgcaggattg tactttcccc ctttccccac actttgtatt  13380
tgccaaatct gatatgaggg cacttggctc ttcagaacca gaagctatgt gtgattgaag  13440
ggctctatta aaccttagga ttttccatga cttgtcgctc ccatccgctt cctctcccca  13500
gggtagcttc ttgtctgagt ttccgtttgc ttcccaccaa tcactgtctc tctaggagca  13560
atgtcgtcct acggaatctt ccgtatcatt cctcaactgt aagctctgca gttcaggaat  13620
gcaatgttag gaatcccagt gttgcacaaa cttcctttct agccgttgga ttctggtgtg  13680
cagagaacta aagagacttc ccaggattca gacccttcca atgggaggat tctcctaact  13740
ctaggggaac tgttggctgc ttaagagcaa aaccatatgg ctcactcaaa aatccctttc  13800
ctaagagaaa tctataactg accctctgtg ttccctttc tctgaagatt tcaaatatat  13860
ttgtggtaaa agcagagaaa gaagaggaga aaatcataat aaaagcacaa taatgatgat  13920
tttagtaaag ataagaatgg ggcatggatc aagacaatga ctaaaacccc aggcaggaaa  13980
agccccgtgg aattggtctg aactgaatgt agcagcccat cagtggaagt tttcttgttt  14040
ctggcaggtg gcctatgctt ttatctatta ctgctctgta atcagaattg agccacgata  14100
ttcaagtttc ttatctgaat gatgggaatt tggttttctg gccttctgca ttttgcagga  14160
gcccaagaat tgacctgatg ttttaaaata tattttccct ccaaaggagg agtaaaatcc  14220
agacaggtgg gccattctgt gtgtttaaag tcattgaaaa gcctctgcaa gtaaaatttg  14280
aggctgtctg taacccacat tgaatagtta cagatatatt ttattttgga ggataaaaaa  14340
tcaagaagtt actaccacaa tttggtggga attttgaatt ttggagtttt cctttgtact  14400
caagcttcct cacgattctt ccaggcagat caaagccatg ggttttggga tcccctaatc  14460
gcaaatccag ttttgcttct taaaatctaa tcagtcctta agttattttt taaatcttcc  14520
tttctactcc ccagttgaaa tctccatttc tacttctaga aatccagtca aaccttatcg  14580
cctccattta gaactgatcg atagcaactg gtgagcaggt taattataat cgcagaataa  14640
acgctgaagt ctcaaagttc accacttttg caatgtttcc aaacccctcg ggaccatgcc  14700
```

```
aggaggcgct cattgaccca ttccgagcag gtgtgggagt ttgaaccagg ggcagacaat  14760
cagatctgat tcaaacaact caatttggtt gcttatctag aggttttcct atcttatgat  14820
atctgtcatt ttagataaaa aagagttcat caattgagct gggaaatggc aaagttacat  14880
tttattctga taaaagtttg ctagttgttg ttttatcagc ttgggttgaa attgtgtctc  14940
cgtcaaggtc tgcaatgacc ttttcagata ttttatcagg tattaggtgg gggagtcctt  15000
ttttttttt tccttctttg acctagaaaa gaatgacctg acttccaaga tcataaatca  15060
aaccaggtaa agacaggcaa taatacaggt tgcccctcaa aattgagtag gcggggaaaa  15120
caaacaacaa ataaaacctt tccctagcat ttggggagaa cttaacttga cccgaaataa  15180
agaatgtagt tcccacggag tgcacagatg taggaaaata ctgcttattt taaaaaagaa  15240
aatgctttcc aggcaaaaat ggcttcagag aaacacgtag taattttttt tcaagtagta  15300
taagggaaac ttctttattt tatgaaactc aatgtatatt tattatagaa aaatggaaaa  15360
ctcacataaa ccaatgtaaa aataattggt aatcttacca tccaaagata accactgtta  15420
ggcattaatc cttgacttcc agttatccta catacacagg tatgtgtata actacattat  15480
taagtagtcg tgcaagttac tgtttaaagt catttcagca ctgatggcaa tttctgtaaa  15540
attagtgacc cagattggat ccttaaacac tgatgccatt tttaaataaa gcagaaatga  15600
gaaattgacc agcactgtca ataacagctg aatggaagag ttgggtgtaa aaacatattt  15660
tttaatctta tggtatataa tttatagcca ctttaaaact aaagcatatt tgtaagtttt  15720
aaattagggt ccttgaagcg aggtgccccc aggacgtgtg atttactagg cctcactggg  15780
gaatgggagt tgcagcgctg aaatctgcta tttgaaaagg ggtgacccaa gatcccagca  15840
gccgcaggga ggtgaaagca cattggtctg gcgcggagaa accctgggct cctctcccag  15900
acccttctct tcctgcggtg tgactcactg cctctctctg cttgtgtggc catttgtaag  15960
gtgaagaatt caggtcaggt acagcaatgg tgagaaggac tgctctaccg ccctttggag  16020
atgtttaaaa tcgagtgtct tccggcatgc cccgtgatag tcattcaggc tgactttgtc  16080
tttcccggta ccacagaggc cacattaaca ttaagccttc ctgtgcctgc gtggacatca  16140
aactcgaatt catgcttgcc tgtgtcaggt aggtttccac ggctgcctgc cttgttttaa  16200
gcaactctgt gaaatcttgg gtttgatgga ctcatctttt ctttttacct tttattttag  16260
atttgggggt gcatgtgaag gtttgttaca taggtaaact cgtgtcacgg ggatttgttt  16320
tacagattat ttcatcaccc aggtattaag ccccagtacc caatgcttat cttttctact  16380
cgtctccctc ctcccacct ccactctcaa ttagatacca gcatctgctg tttccttctt  16440
tgtgttcata agttctcatc attcagctcc cacttatatg tgagaacatg cggttagttt  16500
cctttcctgc attattttgc taaggataat agcctacagc tccatgtatg ttccctcaag  16560
agacctgatc tggttttttt tttatacggc tgcattgttt ttcttatgca aagtgacctc  16620
aggtgctctg agtttcctgc tgcttgggct ttgcttttca gttaataaac ccactgagtg  16680
ttgtctgcag gtctaggcag tggtggagat ttcatagaag ttcagctccc ttcacacccc  16740
agctccacat gcgtgatttg tttcatccat ccaccagcca ataaatactt ctccccattc  16800
cctgtgagcc tggcgctggt caggctgtaa agatacaaaa tgaacagaag tgtctccgaa  16860
tcccagcaac ttagagcttg ctaggggagg gaacacgtgg atgtgcactc ttaggggcag  16920
gggatctgaa gcgcaagggg gcgaaagtgg gttctacgga gcccttagga taccgaaact  16980
ggcctgggcg cctgaagtca aggccaggct tcctgggcaa ggcagacttg tggcatccta  17040
aaggatgagt aggcgtttgc tgcctatagg aaggccattc tgagcccagg acttagcttg  17100
```

```
aatcaggctg ttctgcagtc ccgagtggag ggcgcgaggc aggaatgcaa gcagaagcac  17160
ggcgttgagg gatgttagaa tgctggaaag gtgagcagga ttcgagcagc acttcagata  17220
tagcgctttg gttatggtat aagaaggcgc aagctcctgg ctgttggttt tgttttgcac  17280
ccaagcaggg tgatgagcgc ctcccgctga gtcacccatt tcccatcgga gaaggaactc  17340
tggttaaaat gaagccgcac gctacaggcc agttttggag gatttatgtg gtgtgcttcg  17400
gcagcagggc acggcggctg tgtggtttga gttcaaattg agggccaaga ggggacaaaa  17460
ctcaagccaa ttttagtccc caaatctgga gccctgccct gggaaggaag aggagtgttc  17520
gtctgaccca gaaggtcaag catcttgtaa ttctgccctc ttcttgtact ttctctaaag  17580
gtggtgggat gacataggat tacaatatag ataattacag gggacaatac tatgatgcaa  17640
ggatggattg ccagaccctg tagggtggat tcacctacct cccaggaggt gtagaggtga  17700
agaggaaggg ctcagatcaa ccgatctttc tttctcattt gaacctctct cactttgatc  17760
catcaccctt cctttaattt taagttcaat ttctaccttt taaataggtt aaaaaacatt  17820
tttttgagac agactctcac tttgttgccc acactggtct ctaactcctg ggcttaagcg  17880
atcctcctgc ctcagcctcc caaagtgcca ggattactgg tgtgaaccac cacaccccac  17940
ctaaataagt tttttaatgt gaaaaatttc aaacataata aaaatagaga gtagaatatt  18000
catccctcag ctttgacaaa tatcatttca tgaccagctg tttaatctat acattactca  18060
ctttccccca cacagtgtta ttttgaagca tattccaaac agcatgtcat tttacccaca  18120
aatacttttg tatatatgtc tgaaaagtac gaggactctt ttattttaaa aaatacagcc  18180
ccactgccat gttatcaccc tgaaacaaat tgtcactctt taatatcatt caatatccag  18240
tcactgttca atttcccagt ttgtctaatt gtctttaatg ccttgttcca atcaggatct  18300
aaatgaggtc taagcattgc ctgtgttatg cctgttaagt ttcttttaat ctatgggttt  18360
ctctttcatc tccttttctt ctccttgcat tctgtttgct aaagaaatga ggcttttccc  18420
agaggacttc tgcagactgg attttgttga ctgccttctc ttcatgacat tgaacatatt  18480
cctctgtccc ctgttgctca tgtaagtctg tgatgggaaa aataggcaca ctcagattca  18540
agtttgtgat ggcagcagcc ctggatgctc attgcctaga ccctttactt tgttaggcat  18600
tgctaatggt aatattctac tgccaccatt ccttcttcat ttgttagctg gaattcttct  18660
atagcaacaa gcacattttt agcttattga atatttggtt acttggaggt acagtttgtc  18720
taggaaaggc aggatacatg cctgctacag tcgctttact tttcattgtt caaaagaaca  18780
aattagttct ctagcatcct tcaacaatta ccaatgaaat gaaattgttt tcagcatgat  18840
taagaactca tggacttcag ctgagtatag aggctcatgc ttgtaatccc agcactttgg  18900
gaggctgagg ctggaggatc atttgaacct aggagtttga agccagcatg agcaacatag  18960
tgagagcctg tctctacaaa ataaataaat aaataaataa attaggcagg ggtggtggca  19020
tgtgcctgta gtcccagata cttgggaggc tgaagtggga ggattgcttg acctgggagt  19080
tcgaggctgc agtgactcat ggtccaacca ctgcaatcag caagaccctg tgttaaaaaa  19140
aaaaaacaaa aaaacctcat gggtttaaac aagcatgatg tgtttctatc catatatcct  19200
gattgatgtt cagattgtcc tatctttgct agagggaact tgcttaaact gagctctttt  19260
gacaaaatct tagtttaata gtttcttgct ttccatccta taaaatgtcc taatctcttt  19320
ttatgagttt tctcttgcca ggcctggatt tggccatttg ccccaagaaa cctggctcct  19380
gttagtgagg aatggcgttt ggagatcaat ctcagagcta gctctgccag ctgggcttat  19440
```

```
tgctattggg ttagtcattc aacatgcaga gtcaggaaat acgtacccct cctaccccaa  19500
agataagata aaatacagca tgtcttcata ctgatgcttt caattcaaat ttagggctaa  19560
aaggctttta cttgcttcat tcatcttttt aaaaaaatta tcttaaacta tacataagat  19620
aaaatgtacc gttttagcca ttattaagtg tacagttggg tggcattaag tacatccaca  19680
gtattgtaca accatcaccc ccagcagtct ccggaactct tgcatcttcc caagtgaaac  19740
tctgtaccca ttaaataacg tctccgtatc cccttccctc cagcctcagg cagccccccat  19800
tgtgctttct gtctctctga atgtaactac tttagttaca tggaaggaca cagtattctc  19860
ttgtgacggg ctcgtttcct ttggcatagt gtcttcaagg tttctccatt ttgtagcatg  19920
tcagaatgca gcatgtcttt ttttttaag gctgaataat attccattgt atggatcgat  19980
actgtatttt gtttatccat tcatccctcc atagacaatt gggttgcgtc tgcccattga  20040
ccattgtgaa taatgccgcc atttttacat gggtgaacaa atatctattc acctccctgc  20100
ttttacttct ttatggtata tgcccaaaag cggcattgct ggatcctagg gtaatgctat  20160
gtggttttta gggaccatca tcccatttc cagagactgc accattttat atccttcatg  20220
gcatctttac atctgtcagt ctttccaaaa atcccattct caacatctcc aacgtaattc  20280
ttcattttct gtatgtcata acatcctcat ctctgagtaa caataggaac acttcaccag  20340
cagtacgagt cctgaaaccc gccctgtgtt gcttgccttg tcttgccttt tgacattggg  20400
ctcacctcca gtgtttctag ctgttggctg tgggctcctc atcaccttcg tgagctggtg  20460
gcacatgggc aggcatgaat aaataagtgc cttagggaca catgcacaaa gaagtgtgtg  20520
tgtgtgtatc aaatgcattg cccacatgga ggctgaaggc agagtcttga gagaggaggc  20580
gatcagaggc ctaacccagc cttgggagtg agtgggtgat gacagaggac atggagggaa  20640
ggaaagtcac aggccaaata gggaaggaag gccatggggg agccagtggc catcgtcttt  20700
ctcttgagct cctgtagcca cagtgtgaag ggaagagctg tatgtgtaag acgccttcca  20760
tgtgcccctc atgcccgcag tgtacacggg ctgggggtgg gtcatcctga cgttgcccgc  20820
tcaggggtgg ccttcacgtt tgcttcaccg cctttcattc tctgctgtcc ttctgtgttg  20880
tcatggaagg agtcacgctc tgtccttgga gcctcgtgcg cagcccatgc agtccctgtg  20940
gggctggggt agagatgagg gaggagggat accctgtagc aaatgggatc cggtcatgtg  21000
gcccaggcca atgtcatcat cctccccagc agggacttag atccatgttt tcccaatagc  21060
tttatttgct gggtggagaa agtctggagg aacttttgaa tagggagttg agtacatttt  21120
gagtaggttg tgaaagttag gaaagactgt ctcaccccca gtcctgttga agccccgtgc  21180
atcacgcaag ggctggggaa tctgattccg tactggcccc caccttcaga agcctccggc  21240
tccgggcaca cgctgggaag tggatgccac tgccagggag ggaacttgca gaaccgaagg  21300
cctctttttg cctggtttcc tgttgggaga agagcaagtt ctacagtatt tctggagagt  21360
gcttgggttt tactgcgcag gctggggtga gtcttggtct tagtggggat ggccaaggtt  21420
cgtgaaactc ctgcccctcg ctcttcactc tggaggtcag acttgctgct gcctgcctgt  21480
cgtggcaggg aagagcgtgg acccagcagc cttggctcac agcgagtgct gaccctaagc  21540
cattattact cggcaccttg gcaatccatc tggtactgat ggcctcaaag agggaagcag  21600
aaggtgcatc ttgcaagtgc atgaaagcca gtggcgggaa aggggcctgg gcccgggggg  21660
tggggtggct tctggcctct gcatctctgt gtggcttgtc tctgcatgca gcttttgact  21720
catctccagc cacaattcct gagcgtcagc ctgtggcctc tgttctcatt ctaccttctg  21780
gtgctgtcct tttatttgga ttatagttcc actagcctgg aagtattttc agggcaagaa  21840
```

```
ttatgccaca tttccttctg gggtccggaa taccatcacc tggtacatac aggacacatg  21900
cacgtattcc ttcacagaaa agatgcagcc cggaatccat cctgaagcat ttggcagctt  21960
tggctcacat attcagacct ctgtgaaagg ctctgctgag acatcttcgg cgggagcgga  22020
gccatccttg taaaaggaac ctgagaaaca gaagcccagg gatgagccca tgtggatccc  22080
tggccagttt tacagggaga aggaccctga gagacgccag ggagactgag gtagcaaagg  22140
cgcccaaaac ctagaaggcc aggaagcgag agaagagcgc agaaagttct aacattatgt  22200
tctcaaaggt agtaacacgg gaacagggca gtgaggtgtg gccaacaccg gggacctctt  22260
gggtctgagg cagggagaaa ggtgcaggtg gagatgtccc agggacaggg ggacaggtgg  22320
cagtggctgg actctgaggg ctaagggctg gtgcacatgt gggatactcc agtctctgtt  22380
tgaacccttg agagcaggag agagccccca ggggagtggg ggcggtgcag aggggtggag  22440
gaggagctct gcagagctgc cttctgatgc agttggaggc cttgggaggc ccagagccag  22500
gcaagggaga tgaggaagtg gataggcgtg tgcccccgtg tttgcctgta gacacccctt  22560
gcatcctcac ttgatccctt gatgctctgc tgggccctga tggtgccctc ctggcttcca  22620
aaggccccct gccatcttta cattccatca gtgttctgga cctggagcag atgactcaca  22680
atctttccct gccagcttgc agagacttcc ggagttttca ctcatctagt ttgtcctttc  22740
ccatcttggg tgcctcagcc cactgttttt ccctccaact cactttgtgt agattctcca  22800
tgatccttcc tggagagccc cttgaggcac caggagagct gtgcgtgcca gccatgcctc  22860
tcagcctcat cataacaaac gtcacaggga aacaagctcc cttcagaccc tgtttaaagg  22920
cgtttaaagg cggtaagtgc ctgtcagtct tggaggatag tgactcactg cctgaaaacc  22980
ttcacagaag tgacaagaca cttttcttcg gggaatgttg atattgagtt tcctcccctg  23040
tgtaaacaca tctccaggag tggcattaat aatggggacc ctttccccag gacaaagcag  23100
aggatggggg gagaaggaag aggagaatgg acccgcctgc tgggaagggg ggagagctgg  23160
ccatataagc agctgttcct ggtgaagggg gagcccatta gccagaccct tttttcattt  23220
gttttcaggg attttgctta taatctttat ggggaccgcc aactttttat ttgacagttg  23280
ataaggagag gcactagagt ctagtaagtg gttaaagaag ctggagtcag gcacctgatt  23340
taaaattcct gctagcctgg gtgcggtggc tcacacctgt aatcccagcg ctttgggagg  23400
ctgaggcagg cagatcgctt gagctcagga gttcgagacc agactgggca acatgatgaa  23460
accctgtctc tactaaaaat acaaaaaatt cgcccagtat ggtagtgtct gtctgtggcc  23520
ccagctaggg aggctgcggt gggacgatca cttgagcctg ggaggtggag actgcggtga  23580
gccgtgatct agcctgggtg acagagtgag actctgtctc aaaaaaaaaa agtaaaaaaa  23640
atccagcttt accccgtata atgtcaccca gttttcatgc ccataaaatt ggaatggaaa  23700
ctactccata gaggctaaga aatattattc ataaagcata gtactcggca tgtagtaagt  23760
gtctataaat gttagtctgc atttacttat ttatttattt agagatggag tttcacgctt  23820
gttgcccagg ctggagtgca gtggtgcaat ctcagctcac tgcaacctct acctcccagg  23880
ttcaagcgat tctcctgcct cagcctcccg agcagctggg attacaggcg cctaccacca  23940
caccagctaa tcttgtattt tcagtagaga tggggtttca tcatgttggc caagctggtc  24000
tcaaattcct tatgtcaggt gatccaccgc ccttgacctc ccaaagtgtt gggattacag  24060
gcgtgagcct ctgcacccag ccaaatatta gtcattaagc caaccattaa taaatgctat  24120
tatcattaaa ggaaatattg aaaatagtat ctttttgtt ttatttttgg ttttgttttt  24180
```

```
gaaacagggt tttgctctga tgctcaggct ggagtgcggt gctgtgatca tagctcactg  24240
cagccttgaa cttctgggct caagcactcc gccttcctca gccttctaag tagctgggac  24300
tacaggtgtg caccaccata cccagctttt tttttttaa ttatcatttt actttctgta  24360
ggggcagggt cttgctctgt tgcccaggct ggagtacagt ggcatggtca tggctcactg  24420
tagccttcaa ctcttgggct caagcaatcc tccttcctca gcctccaaaa atggtgagat  24480
tatgggtttg agccactgtg cccagccctg gattcaatac cataaagggt tagattgcac  24540
aggaggctgc caagttgaat taagtggggt tttatattag tgagaatttg ccttccttct  24600
cagtattaat ctacatttag gtcatagacc ccatatccaa cttactgtct ataatttctc  24660
ttacataggg gggcacattt agataagcac agactaattg gggttatagt catagcttta  24720
gaatagttta aagacctagc tgacggccag gcgtggtggc tcacgcctgt aatcccagta  24780
cttcgggagg tcgaggtggg aggatcactt gaggtcagga attcgagacc agccgggcca  24840
acatggtgaa accccttctc tactaaaaat agaaaaatta gccatgtgtg gtgacaggtg  24900
cctataatcc caactactca ggaggctgaa gcaggagaat cacttgaacc tggttgcagt  24960
gagccatgat cgtgccactg cactccagcc tgggtgacag agcaagaaaa aaaagatcta  25020
gctgagggag ttgggaccag atgattttct ccagtgatgt ttgaacaaaa agaaaaaatg  25080
cagctgggcg cggtggctca tgcctgtaat cccagcactt tgggaggcca gggtgaacgg  25140
atcacgaggt caggagttca agactagcct ggccaacata gtgaaacccc atctctatta  25200
aaaatacaaa aaattagcca ggcgtggtgg catgcaccta taatcccagc tacttgggag  25260
gctgaggcag gagaatcatt tgaacccagg acacagaggt tgctgtgcca ctgcactcca  25320
gcctgggcaa cagtgcgaga ctgtgtctca aaaaaaaaaa aaatgcagaa gctacttagg  25380
ttgaacacag aaaggaagaa ggactgtgta gttcagtagt gtgtgttctg agaaagccct  25440
cacagcgttg gtctctagta atctctggaa ataagtgaat cattccagct tgaattatca  25500
tgatgcaaaa ttgtgttcgc tgaaaagcag gggttaagtc cgctgccttg tgaatttccg  25560
cctggaaatg catctgaccc atggtggttg ctcaattctg agtgagtttg gagaaggaag  25620
gaaaatgagg agttacttat tagttagtcg ttatacattt ttggttttta aacccaatat  25680
ataattcctg gatattccta ccacttacta tttgttgtcg ttgtttctat tgtttttgag  25740
agaaggtctt gctccattgc ccaggctgga gtgcagtggc gtgatcatgg ctcactgcag  25800
tctttacctc cagggttcaa ggaatcctca cacctcagcc tcctgagtag ctggaattac  25860
taccatgccc agctaacgtc tatatttttt ggaggtaggg ttttgccatg ttgcccaggc  25920
tggtcttgaa ctcatgagct caagtgatac tcctgcctca gcctcccaat gtgctgggat  25980
tacaggcata agccatcgtg cctggcctca gtgagtggtt ttgtgggctg gagtaaggat  26040
ccagctgtct tcgctgcagg agtgacaggg acgtggtgtc catctcagag gagccaagtg  26100
ggcttgccta ggctttcgat tcttgtgaag atgagtgaac tgaaaccaga cacctcttag  26160
atctatgggc ccttctacct ctgatgatct gtgagattca gtgaaggtga acagtcactg  26220
tcggggatgt tttaatgatt ttactaaaaa tcggaataga atgtgaaaca gggggatctg  26280
aagagtgatt atttgtactg ttctggtcag gagctgggag ctttgtctgg cctccacgta  26340
ggggcctgag gacaagaact aggcagaggt gcagacagcg aagaggagga tggctcctgg  26400
gtgttcaggc catggccagc ctggtcagca gagcagctgt gggaaaaggg atgatatttg  26460
gtggtagcac tgaggcccag ccaacactga gcgcttagga tgtttcctgc tgccctggca  26520
ttgttttgtt atttattcca gcgactgtcc tgtgggcagg aactgtaatg tccatgggca  26580
```

```
ggagaagaaa cccaggtcac agggacctgc ccaaggccac agaaggcccg aggctggcgg  26640
gacctaggtc agcctgactt ccccggccag tgccctctct gtttgtctcg tgtcatctgc  26700
cttgggagct cacatttcag ggcatgtggc ccagtgccca ctgaggtgca gcccgcgtgc  26760
ctggacggct ctgtcagggc gagcttctcg ggcagtcttc cttccctctc catttgttgc  26820
tgcaggattc tcctttggtc ctgacttttc tggtttttca tttccttacc tgtaatctgt  26880
tcactcttgg tcagcaagag aataatattg cagctaccac tgcctctgag tttcctcctg  26940
gaagactgag tcttatgaag acccggtttt gaggagtttc ctggctggat cagcaaaacc  27000
acagtgatcc acatttgatt gatgtatttt gagtttacat ttattcccaa tgtttatttt  27060
cttgtaaaaa tgagcgcatt attgattaaa agagagagac acaatatcca aaaggtggaa  27120
gtagcctagg tgtccatccg tggatgaatg aatgaacaaa tgtggtctgt gtgctcagtg  27180
gagtattact cagccttaaa aaggaagtct tgcactgcta caacagatga atcctgaaga  27240
cattacgcta agtgaaacaa gccagtcacc aaaggacaaa cactctatga tcccacttct  27300
gtggggcccc cagagccgtc aaattcatga cgacagaaag cagaagaggg gttgccaggt  27360
ggtggggcca ggatcggggt gcgggaggat ggggagttag agtttaatgg gtgcagagtt  27420
tcagttttgc acgatgaaaa cagttgtaga gattagtttc acaacagtgt gaacacattt  27480
actatcactg aactgtacac ttaaaaatgg ttaagatggc taattttata tgtattttat  27540
cacaatttaa agaagagaaa aatggagagg cagtgtacaa gcttagtaag tagaaagtaa  27600
attgtgaaaa ccttttttcct aacacttcat tctatttgct tctttggcca aaggtgtaag  27660
tagcattgat ggacgattag gtagaactag ccatccagaa ttggttctac aagattgcct  27720
ttctggctct tcagtgtttc tctttgccca agcctcagtg ttatcctgct atcacagcag  27780
ggctgatcac taaggagaag gttatccttg gtgaggaggt ggaaaatggt gatttttaaa  27840
tgttgtacta caagcaaccg agttttgatc tgcaaatcta tcatatttat aatctgcatt  27900
aaaattttaa gtcacattca taaaatatag gagtggatgc acttttaaaa tttctttgga  27960
atgcaaatca gattggatta aagctattaa ccatgtgtaa taaaagactg tagattttgt  28020
agcagcttca tgctctacct aagatgtctg ccaagtaagt gaaatgtatt tgtaaaaagg  28080
cagatggaac tactagacgt attgtcatcg aactattctc caggggcact gatttcagtg  28140
caggtgcttt agatgggagg aaggctgaga gcagggtctg tggggcccct attgcagaga  28200
agctccgttt catctacttt atatttgatt tgtaaatgtt tgatttgctt ggctaaagaa  28260
ttctgaggct agagcaacaa aacaaaacag aaggagagag gttgggaaga aaacgtgaag  28320
taacaccaaa aaactaactg ctattgcaaa acaaggataa aatagataat tcaagataga  28380
tgtgattgat tgccataaag attcatgaac acgtcaggtg aacccgagtc tggaggctag  28440
aggaagagga gccgacggaa tttgaggagg atgtgtgtct ggtctgaaga ggaggtagag  28500
acttcctgcg aaggctagca gagtaaaggt ttgctttctc cctttcctcc ccgaagacca  28560
gcacatcaga tgaaaagaac cccccaaatc aagtaaaact tttatctgca gtgaaattaa  28620
gagataactc atatccccaa ctatagaaaa ctgccgaata taatataaat ccagaccaca  28680
tggagggaaa gacttcgaga gctggtccat acctctcagc tctcctgcct gttcgcctcc  28740
caaatgccca acctccaaat accatcacat gtgggttagg gttgccagga gtaaatttcc  28800
ttgttaataa aatgaatgag ataggaaaga aagcggcaat gttttcatta tttgcagata  28860
aaatactggt caacttcact aaacaaatgt aaattccctg tggagggagc tataaagctt  28920
```

```
tactgaaggg cataaaagaa gacatgaata aatggagaaa gatactagat ccttggattg  28980
gaaaagttgg cagcattctt tattccaaac tccctcaaac aaatctataa atttaacaca  29040
gtctcaggaa acatcccagc aagatttctt aaatacaacg tgtccagctg attataaaat  29100
ttatatgaaa gagttattgt acaagaatag ccaagataat tttttaaaag gagacttaag  29160
aaaggggaac ttgccttatc agaaatcaaa acaaactaga gacacactgg cacggaagct  29220
aaagcagtga tgttcattgc agccctgttg tgtgtagcag tgaaaaatta cttgctgaaa  29280
tgcagccaag gtattaggaa tggggaggct gtggcataaa aagattggca ttagcattga  29340
atcctttcaa atatcatgta cagctaaaca gctgtgagaa ttatggagta gaatgtaagt  29400
gttatgtgcc ttaacaatgc caaactaata aatcctcttc gaagagagaa gtagatctgt  29460
gctgatatgg aaaaatgtct aaacagatat gcgtccctgc agaaacagct gcagaggagt  29520
atccatggta tgatcccacg tgtgttcagc acactgctct gttctttcct gtactgaggg  29580
agcccatttc tggtgaggat tatttccacc accccgatga cacaggcttg gctatgagac  29640
ttgctttgat caagaatatg tgactcgaag tcactatgca acttccacac agaggcatta  29700
agagccatta cgtggttctg tcattacttt ttgccccctg ccacgaggct ggcatgaacc  29760
acatagaggt tttgccttcg gcctgcatgt ccaattgaag catacatata gaatttcggc  29820
caacttgcag ctgacatgta atgtgaacag caaacaaata actatttgtt tgttacagca  29880
taacagctta aacagcacca aaccaagcat aagtgtttta tacatataca tttgaacatg  29940
gctaaaatat atctcctata tcctagatac acttttctca tgtgtataaa cagacatgta  30000
caaggatgcc tgatgaagca ttgctattac agcaaaaaac tgaaaacaat ctgaatatat  30060
atcagtaagt gtcttagcca gtttaggttg ctgtaacaga ataccataga atgtgtggct  30120
ttaacaacgc ttatttctca aagttctgga agccaggaag cccaagatca cggcactggc  30180
agattggtgt ctggtgagag acccaagcct gctttgcaga agaccatcat ctcactgcat  30240
ccactcatgg ggtgggtgta gggagatatc tattctgtct tttcttttct ttttttttgag  30300
gcagagtttt gctcttgttg cccaggctgg aatgcaatgg cgcaacctcg gctcactgca  30360
acctccgcct cctgggttca ggcaattctc ctgcctcagc ctcctgagtt gctgggatta  30420
caggcatgca ccaccatgct cggctaattt ttgtatcttt agtagagatg gggggggtttc  30480
accatgttgg tcagtctggt ctcgaactct tgacctcagg tgatccccct gcctcggcct  30540
ccgaaagggc tgggattaca agagtgagcc accgtgccca gcctctgtct cttcttataa  30600
gggtactaat cccattcatg agggctccgt ccgatggcct gttcacctcc caaatgccca  30660
acctccaaat accatcacat gtgggttagg attgcaagat ctaaatttgg gttattcaca  30720
gacgtttagt ccataaccat aaagaaatga acaagtaaaa tgtgatttat taatataatg  30780
gaaaactgta aatcaactca aataaagcag atccacatgt ataattaaaa ctgggaaaca  30840
taataggcaa aaaagagact ggaattgtgg gttacacaga ggcatctact gtatctgcaa  30900
tgttgtattt ctttaaaaac atctgaagga aatatggtaa aacaaagatt tgaaaaagct  30960
ggtggtgggt ttaagagtgt ttgctatata tttttttctc agtgactgaa atatttcata  31020
ttttttaaag aaagcattca tgtaaatctt taaaattgca aagcaatgct tatgttcttc  31080
agaggaacat ttatccctgt gtgtagaagt atatagatta attggaagga tatacactaa  31140
attcaatata gtgattggat agcagatggt gggggaataa acagaattgt tacagtgtcc  31200
tttgtgtttt tatgtaattt taaaatttct aaaaataaaa atgttaatta atgcagtgga  31260
agatatctgg aaaaacagga aaattgttag ccacctctgc ccctggagat gggatcatgg  31320
```

```
tgatggtgga gactttttgt ttgtttgttt gtttctttct ttctttcttt tttgagacgg  31380
agttttgctc ttattgccca ggctggagtg caatggtgca atctcggctc actgcaacct  31440
cctccttccg ggttcaagcg attcttctgc ttcagcctcc ccagtagctg ggattacagg  31500
catgtgccac cacgctggct aattttgtat ttttagtaga gatggggttt ctccatgttg  31560
gtcaggctgg tctcgaactc ccgacctaag gtcatccgcc cgcctcggcc tcccaaaatg  31620
ctgggattac aggcgtgagc caccgcgcct agctgagacc ttttgtttct acgtgacatt  31680
cttctgtacc gtttgcctgt ttgaaaaaaa aaattttttt ttgagatagg gttttgcttt  31740
gtcacccagg ttggagtgtg gtggtgcgat cataactcgc ttgcaggcct gaagtcccag  31800
gctcaagtga tcctcctacc tcagcctctg gagtagctga gactacaggc gagggccacc  31860
aagcccagct aattattatt ttatttaaga gatgtggtgt tactatgttg cccaggctgg  31920
tattgaactc ctgagctcaa gccatactcc gacctcacaa agggctggga ttacaggcca  31980
gagccaccat gcctggcctg tttgaatttt tgtagcaatt aaaaattgcg taatttaaac  32040
acaaattgaa ggggacaggg actaaaaaca taaatgagag ttagaatgca gtgccacgtt  32100
gaatgctttc acaggtagga gcctagaaat catctgttcc aactactgca cttttgagtt  32160
gtggagacca gaccaagaga ggtgaaatga ctgttggcta aggcgtccac ctctacttgc  32220
gtctggaatt gcccctgcct ctgcctttaa gtctggtctg cgtggcttct gatagcgaag  32280
ccaggggcgg accccgttca ctgcatcagg agagccctga gcagcgcttg gcaggaactc  32340
tgcagcccag ggcgccctct agaggctgga ggaccttcgt caagaccccg gggggtgtgg  32400
atgtggacct ggaggagtgg tgggcagaag gcggagccac cctttcaccc agtcaattgc  32460
attcctctgt ctttaatgtt gggcttcctc agattagatt ttctttgaag aaagagttct  32520
gcagcttaaa aaaaaagtga cagaagaatc actggtgcag agtaaggtat agcgttagca  32580
tttgatctga tattatctag attcttttca cactaggaag cacctaagtc atctggtcta  32640
acaccttcct tttacaaaga agatctgagg cctatatagg caaaatgtgt gctgcccagg  32700
tccacgactg cagggcattg tctcctggcc ctggtaatgt ggtcttcatt cttatttttt  32760
gttttgtttt gtgttaactg aacttagaac taaacagatc ccttgcaact tggcttagac  32820
tccatatttc atgcaaaaag ctttcagggt agcagggtga ctcggtggat tagcaggaga  32880
agaagatgta aagtgatggc gattggagct taacctcggt ttgattaagt aatcccccag  32940
acacccccga gaggggaaaa cagtccccac gtataaattt ctacaccctt gctcgcctcc  33000
tcttctgaaa ggcgtaaatc tcccctgaaa tgcctcccta gcattcaggg caataaagag  33060
gtcacattat atctccataa atctcccagc tggctgctgc tgctgccatt ccagaggcga  33120
aggggaagtt gtttcctcct gacggcaggc catgggcctg gaaggaaaag cctctccctg  33180
cagacccatt gtctcggtcc ctgagggagc tgccctggca atttattcaa tattcccttt  33240
ccgtcctgcc agctcctaac tggggttgca gagtcaaatg gcccagacta gcccagctta  33300
agtctcctct ggccaaagct ccattgcaat cttcctaata aataaaagaa accaggacca  33360
tatcacagca ttagaagcca ggccagggtt ccctggggct gaggctgggg ctcgctggga  33420
caggagctag ggtgctgtga aagatgacag cgggtcaaca gcttcaggag tgcagcaaag  33480
ctgaggaccc acttgggaaa tgggttccat ttcccatta gggaattaag atgcttttgt  33540
aggaaaggaa ggtgggagaa aagatgcttt tatggaaaaa tctgaaaatg gaacctgccc  33600
agctttaaat taaaaatgtt actgcatgaa agagtgatga tgctagcccc tgacatattt  33660
```

```
atgtatttta tttaacatgc aaaataatca taggacagct atggtggcgc acgcctgtaa  33720
tcccagtgct ttgggagccc gagcctggcg gatcacctag gctcaggagt tcaagaccac  33780
cctgaccaac atggtgaaac cctgtctctg ctaaaaatac aaaaattagc caggcgtgat  33840
ggtatatacc tgtaatccca gcttttgggg aggctgaggc aggagaattg cttgagcctg  33900
ggaggtggag gttgcagtga gccaagatca tgccattgca ctctagcctg ggtgacagag  33960
caagactctg tctcaaaaaa aaaaaaaaaa aatcactatc acaaataaga aatacattaa  34020
cataaacata gttgagtatt taaaaggtac acaacagcaa acaatgagaa gtccttccgt  34080
gagccaccaa gacacctccc tggaaacaac cagcatgatc agtttcttgt ctgtcctcct  34140
aaaaatgttc attctgtata taaacaaatc catgtataga ttcttctccc cttctttttg  34200
taagagaata tcaatgtaat gtccatgcct tctaatattt catagcatat actgcaagaa  34260
ttccatatca gtacatcaag atcattgttt atggctacat agtgtgcctt aattgaatta  34320
accagtccgg tattgatgaa cgtaagagtt gtttttccag tcctctgcta tggaaggaca  34380
tgccatagtg aatatccttg tatataaacc attttacaca gaagtacatc tggaggataa  34440
attcctggaa gtggagtttc tggatcaagt gacacatgca tttatacttt tgataagata  34500
ttgccaaatt gctttcccca ctggctgcgg ggctgtagca tgtcacactt cccatcaatg  34560
cccagggtgt ctgctttccc acatccccca accccagggc acagtactat gactgaggca  34620
agctgggagg agcctggaga ggggcatcat cacaacacag tgacttggag gatccaggac  34680
cagtgccaga ctttgtccac agcgtgactg gaaagctctt catgtacatt ctaccctggc  34740
tgggactgta ccccgaaggg agggcctctc cctttctttc tgtagagtgg gaggaacagt  34800
tggtgccaca gcgatgcctg agcccagatg gggatgccac tgtggtggga ggcagctggg  34860
accgaggtgg aaaaagtact ttgtactttt tctttccggc caggaggatc ccaggaaatt  34920
gaagaaaata aacatctcca atcctgcagt gcctaggcag agatgcttgc ttaattaact  34980
gcatatttaa ctaatttaaa ccatgttaca ggaagagaaa atctgaagaa catagtctat  35040
ccaattgtca tgtaataaac caactccaat ttccgtatgg ctttggtgaa actttgtttt  35100
tgtactcatt cctctaccat tgggcgtttt ggttgtttcc agtatttggc aggaatacct  35160
gaaaaataga tattttccct ttaaaaaagt ttattccagt gaattattag agcagtttta  35220
ttgctagcaa gagtgggctg gcttttagtg caacgtggtg tgattttcca tatacatcca  35280
tcatatatga ttttatatac acacatgtat gtgtacacac acacacacgg aaacttctgg  35340
ccctgcatag ataattctca cagctgaatt atattgtgtg tccaggaaca tggcatctca  35400
gtggccgggc agcccagctg gccggaagcc gagccctggg agtgacgctg tcccatcgtc  35460
atttcggccg cctcatggga ctctctaggc actgggtttg ttgaaactcg atggctctgt  35520
gtgcagagct tctgtcgtgt gcggagcttc tgtcgtgtgc ggaggagttt ctgtcgtgtg  35580
cggaaggcga ggactgggag ctcagatgag gcacttgccc ggcctgctct gcaccttggt  35640
tttctcttat ggatattcac gaaatagccc agacccagct tgcaggtttt aagactgtac  35700
cactgtgcca cctgcccctt gctcctggac cctcgcagcc tctcccacag aaggactggg  35760
gatgtgcaga gagagccgac tcaacaaggc agtggacagg gaagcagcgg cgggggcacc  35820
cttcgcatgc agtccccaga ggccaggaag gagcaaatat tttcaagtgc tgatccccag  35880
ccagggctcc cctggttgta tctgagcctg aagccggaag ccccaggagc tgcaggaccc  35940
agtgcccaat gcgttgtcct ggcctctttc ctggcatgct gcgtgtggct tttctggaag  36000
ggggcaagtc agccgtacta cctgtcagcc gggacactag ggagacacag agaggaggga  36060
```

```
tcagcatgtc acggatgcag gtctcacagt gaggtctgca gagggtggcc acacaccctg  36120
gtgtgaagac tgtgctttca gaataattag taatatgccc cctcccctca gaagtgtccc  36180
attttgtatg gtaggtcaca gggctcccat attaatccgg ggaggcggac ggcacaaaga  36240
ggagaacctt gtcccaggtt tcggggtggg gactgctggg cagggtccct gcaaacacag  36300
cagctgggag gcccaggccc ctccactctg ggactgatcg tagcttccca catggaggcc  36360
cccatgaaaa ctccatagtt ctttcacctg agggtgacag ctggcaagac agtctttgta  36420
aaaaatgtat tggtataggg gcaaaatgct gccattcggg agagttttca aatagaaatg  36480
tagagctcac tgcagtcttt cagtattgcc ttcttttctt tgttcctttt ccgttttttt  36540
ttttggagac acggtctcac tctgtcgccc agactgtagt acagtggcat gatcacggct  36600
cactgcaacc tctgcctcct gggttcgagc aattctcctg cctcagcctc ccgagtagct  36660
ggaattacag gcgtgcacca acatgcccac ctacttttta tatttttagt agagacaggc  36720
tttcaccatg ttggccaggc tggccttgaa ctcctgacct caagtgttcc atccgcttcg  36780
gcctcccaaa gtgctgcgat tacaggcatg agccaccaca cctgaccctt tgcctgtttt  36840
taaaatggta tcccagcctg cggttctctg gtgggaaggg gccatggtga ccattttctg  36900
ggagtctgca tgtttagtgt cgagatgcag caaatgaagt cttattcacc accatacttt  36960
tgtttcactt gtttcaagaa agtgcttgtg gccagaagtg gtggctcatg cctgtaatac  37020
caatactttg ggaggctgag gcgggaggat tgcttgaact caggagttca agatcagcct  37080
gggcaacata gtgagacccc atctctacaa aatgctagaa aaattagctg agcgtggtgg  37140
tgtgcaactg tagtcccagc tactcaggag gttcaggcag gaggatcgcc tggggccgcg  37200
aagtcaaggc tgcaattagc tatgactgag ctgctggact ccagcctggg tgacagagca  37260
agaccccatt gaaaaaaaca aacaaacaaa aaaagtccct gtgagagcaa tgcaacagtc  37320
cacaagttcg cggacttagc tctatggcat tgtgattgca gaggctcaga tttgaattca  37380
gaagcatcct acatttctcc tggagccagc aactgatcct gcattttatg gggaaatctt  37440
tatgctgtaa ttataggccc acatggaggg gttctcgaag gtctcaaaat ctaatcttga  37500
caatgatgaa ggccaggaag cgtttcccaa gtgggtgagc tgagaagcat tgagacagag  37560
atgttgggaa gtttctgaga tcagacaaga tgggaaaaca gcatgcttgc gctctgaact  37620
cctgcagccc ttgctgctct caggccaaat tgagactgat tttccatctg ctgccagctt  37680
ttgccgctgg ggaaggggtc agggatggcc aaggcatctg tgggcagcgc tggtgggacg  37740
ctggcctgcg gttaagagac tgactgccca gcctgggttc gatcccactt tgctgttgat  37800
tagctctgtg gccctgggca ggatctgttc tctaaagctc atgaactttc ctccattgcc  37860
atcctctcct ggaccagcct cccacgctca ccctactatg agcacagacc aggcaggtgt  37920
ggaggtgctg ggagttctta gacctccagg gaggagccgc tggggcccag ggtgtcaggg  37980
gcttgagtct ttccacagtt cctccagtga caggtgtggt tgcctgttac agccttcacg  38040
ctcatctttc tctttgtcat ttgtaaaacc tctttgcata tgagcgggtg tattttcccc  38100
tatcatttgt tcttcaacct cttcctcctc tatctctcta cgttcccccc tccctccgtt  38160
cttgtttttg gtgttttgtt tttttttttt cctttccctt tccctttcac aatgtccttg  38220
cctgtttgtg atttaggaaa aacaaaacaa aacaaaactg agtcacattc tgtcactcca  38280
gccagctgac gtcctgggtt cttgtccttt ataagggtca gaagcagagg ccttggactc  38340
tgtggggtga ctgcaaggtg ggcggtaact ggtaaccgcc tctgttcagc agctgcagga  38400
```

```
gcttccaaaa taggtgattt catccccggc cggagcgccg ctggagctgt gtgggcctcc  38460
ccgtgacagc ctcctgtcac aggcatctgc cgagcctgac gaagcccaga agacccaggg  38520
ctcaagagct gccaggaaaa cctcaggctt tgtttgggcc tcgtgcccca cacccaggcg  38580
ccagccgcag ggacagatcc gggcctgtcg ggaaatccag gctccatctc tggtgaactc  38640
tggatgggac atgggcctgg ggttcagcaa gggacatttg ggtggggctg agactttgct  38700
ctgaagcccc tttggttccc agggaacggt ttctgggcag gtccctcccc tcctgcccag  38760
tctgggctgg ggtctggcct tttccaagaa agccttctgt gttgtatctc cttggccccc  38820
tctggcccct cttgtgtagc actgcccagc tgccccgggc acgggccctt tccactgttg  38880
acgtgtctct ccctgaacgt ccaggatgct gaagatctga agctggaggt ggtgggctgg  38940
gcaccactgt gaggcccagg cccactgccg tttgtcatca caaaggtagt gattattttt  39000
gagttgtgca tccccagcta gaccaaaaca actttgggca aggagttagc atggattttg  39060
ccaacatgtt cgttacgtct agcacttgga caggggcgcg tatacagacg catggcagat  39120
atttgagttt caggcattgc tgtgaagggg ctgagaccca tcaactctgc ctccaggcat  39180
gagggtgagg gtcttccaac acaggctggg gctcaacacc agctctcccc agcaggtgga  39240
agtctgaggg gagcatctgc aggagagcag accaggctct gtggcgccga tggggcggca  39300
gcagtggcct gagctgtctc cccagcggcc agcagtgccc aggggaggga gtggagagcg  39360
gaaccgtgac cctggcctct gattcctctc cctttcttcc tcccgtgcct tccctctccc  39420
cgccctgact ggcctcccct tgttggggtg ggtgggttcc ccaagatgga tggagcaggt  39480
cagaggagag gagaggtcgg tgtctttgcc tctggctgcg tcagttcttt gtagggaagt  39540
caggggtggg atgtttcaac ctcctggcct gcattcttct ttcaggcact agggtgggag  39600
cagcttgttt aattgatagg aatatccata ctgcaccggc tcgctgagaa atcagactat  39660
cagactttgt ttcctcttta aaaaaaactt tttttagcaa ggtatgggag gaagtgaaga  39720
gtgagatccc catccttgga gttaggacaa aatttatttt gtgcttttca ttgctaaact  39780
aatcattaat taatacttcc catgagaagc aacttggaga ctgagtacaa gtgaacgcgg  39840
tcagccttgc tgtcagttgg ttcctggctt gcagtctcaa acctgaccgc tgagagcaca  39900
gacaattctg agtatagccc cagtggttta agaaaggtca gattccccag tctcctagct  39960
cttttatctg tcctcccctc ctccaataac cagcgccaaa gtttgtcctg gtctttccca  40020
ctccctcctg acccctccaa cttcagcctc ctaacaataa tccatcattg ttatctcatt  40080
tgatgtttgc aaagcacttt acagccattg ttgtaagttt ttcctctcat ttgcaaagta  40140
ctttacaact attattacaa gtctttcctc caaacgtggg tgatgccttc caagtggctg  40200
gaggagttcc cgggatgcca gcactgggtg ggaggggctg catccgaggc cacagctgtg  40260
ccccctggct tcggaatcac tcttgccccc agggaagttc ctctcagtgc ctttcgtagg  40320
aaggaatgag aagtggtgct taccgaggtt cataccagat gtcagtgcta gtttgggact  40380
tagttagtgc tgtgtttgtg atttaacatt gtagggccaa cgttttcctc tatggttacc  40440
ttgttttggt aataattgtt taaaaatatg tgtaacattt catggagcag gttggatggc  40500
aggattttgt ggttggaaat atggaaactt ctgccgattt ggaggtgtag gaggttgact  40560
attggatgtc tttaggaagc atagccttta ctttggctgt tttggtaacc cctgaccctt  40620
ctatcgcaat gggacttcta tgctggtggg aattccacac tttctgccct agacaattag  40680
ggtctgccat gagtccccca ctctgctgag ggtgtgttct aaaaatgaac taatattatt  40740
agtcattatt gatattcaaa tccaatttgt ccaaatagat cattagcact ctgagacctg  40800
```

ggttccctcc tagctcctgt gacatctatc agagtgatta aatagcagat gctcagtaaa 40860
tatttgttgg tggcaaatac atacttggca acctccagtg actttacctg gacagtaaaa 40920
taattgcttg aatgcataac ccaactttga ggtgagcctg caggagctgc tgaggcacac 40980
ctgtgtgttg ggctctcaag gcagccagag gtgagtcggc agctgagatc acgctccagg 41040
gattcctgcg tcctttaata agattctggg gtgggcacag ttctggggtg gacatggtgg 41100
ctcacgccca taatcccaga actttggaag gctgaggtgg gaggatcgct tgagcttagg 41160
agttcaagac cagtctgtac aacacagtga gagcttgtct ctaccaaaaa aaaaaaaaaa 41220
aaaaaaaaaa ttagcaaggc atggcagcat gcacctgtag tcccagatac ttgggaggct 41280
gaggtgggag gattgcttga gcctaggagg ttgaggctgc agtgagccga gatcgcagca 41340
ctgtactcca gcctggggga cagagtgaga ccctgtctca caaaaagttt ttctttacat 41400
cagtgtagtg tgggaaaaag aaaaaaaaga ctccattcct gcatataaaa caataattgt 41460
gaggagaaaa gagaatctcc cctccgaaca agaggaacac attatgagat gtttttcact 41520
taaatgaacc agaatgtagg agagaggcca gtttgcttat ttttaggagt gtgactctat 41580
ctgttagagg aacatactga gatatttatg aataaaataa tagaagtctg ggattttctt 41640
cagtaacaca atgtggggga aagtgaatgg aggtacaggt aagacaagat tgaccacaaa 41700
tgattggaag ctggatgata gttaagagtt cgttttcata ttctgtcccc ttctgaatat 41760
gtttaaattt tttcataata aagaaaaata gggctgggtg cagtggctta tgcctgtaat 41820
cccagcattt tgggaggccg aggcaggagg atcacttgaa cccaggaatt tgagaccagc 41880
ctgggcaaca cagtgaaacc ttgtctctac aaaaattagc tggggatggt agcgtgtgcc 41940
tgtggtccca ggttctaagg aagctagagg ttgcaatgcc cactgcactg cagcctgggt 42000
gacagagtga gactctgtct caaaaaaaaa aggaaaaaaa aagatagaaa aagtaaaata 42060
gactgaggca ggagtatctc ttgaggccag gagttggtgg ctgcagtgag ctgtgattgc 42120
accactacac tccggcttgg gtgagagtga acccggtctc taaagagcaa aataaaaataa 42180
aaaaggaaac cagaatggga gggttgcact aggtttggaa tggaaaggtg atcttacaag 42240
gcctctatgt ccaagtgcga ttcaggctag accgcgtgtc ttggttcaat tttgagatgg 42300
tagcgccacc cagtgtttat tgcgaacacc caacaaaacg acgacgttgc ccgcgcccgc 42360
ctcttgctgt ggagtgggct tggtctaatg tccttctgta aattcctggc ctctttaatc 42420
ccctcatggg caggcctgga tgaaagaagc ggggctgaca gcccataggc acggactgta 42480
gaggtggcaa cagtagtgtt gattgtggtg gtccagctgg gagcaagcta tgggcgggag 42540
tggccgcatc tcatgggcgg ctctgagggc aggcgacctt ggtggaggct gtcagtgtga 42600
cccaggtgta aaaatagcct ctgctgtgac gcctgtgctc cgctccctgg cctgagcaaa 42660
tagcccctta cacctgcaca ctgtttactt ggtgtggaca cacagctacc tgtttgcagg 42720
tgcaaatgac tgtttgtgta cccagagttg tggggagggc cccccaccat cctcttctct 42780
ggcccacatt cccctagagc aagtagctgg gccacataac tagcaaaatg cgcaacctca 42840
acccactccc gagctgggtc ctgttggaaa gagagctctt taccacctgt cctcccaact 42900
caataaaagc acccctcttc actagagaaa aatctgccct tgcctctggc agcagcatag 42960
gaagaatctg gagaccaagg tagatgtgtt ttgggacagc aaattaggat aacatgaagt 43020
cagagagact tctggagatg gtgagccagg ctttatagag actacgggga gcaagaaaac 43080
tggcccagcc tgtctcacga gggtgaggag aatggacaca ggtggaatct gtcaattgta 43140
acattctgta gacatggatg ataaaggtga tggcggggag gggtgagcga gtgaagggag 43200
cggcagaccc cggcagcctt gtggtagctg ggagatgct acgcttatgt gagcagctct 43260
aaagtgccat tgcttataat atgcaccttt attttatata ccaataagca agaaaaatgt 43320
ccaactatga tatggcagcc catacaggta tattaaaaca gaaaaaatga atgaatgaag 43380
cttttttgc aggacagtta gcaaattcca agaactgaaa aagaaattta gtgcctttga 43440
ctcagaaatt ctacttctca gagagtatct taaggaataa ctagaaatgc acagacttaa 43500
gtaaggagca gtgtttatga aacaagaatc caaaactgga tgaagattaa tagctgaatg 43560
atactagtta aatgatggca cctttatatg atggaacaat ggtatatgag tgtataaaga 43620
attttataaa atgagtttat aaagaatttg tcattgggaa aatgttttgg tattaagcaa 43680
acgacccaca cagactcaga attatatagc ttggcaaaaa tatggatcaa catatgaaag 43740
tctcacaagg ccgggtgtgg tgtactcacc cagtactttg ggaggctgag gcgggtggac 43800
catttgaggt caggagtttg agaccagcct gatgaaaccc cgtctctact aaaagcacaa 43860
aattagccgt gtgtggtggc gcatgcctgt aatcctagct acttcggagg ctgaggcagg 43920
agaatcgcgt gaacgtggga ggcagaggtt gcagtgagct gagatcgcac cattgcactc 43980
tagcctgggc aacaagagtg aaactccgtc tcaaaaagag aaaagaagtc tcacaaaggg 44040
ctgggcacag tggctcatgc atgtagtctc agcactttgg gaggctgagg ctggagtatc 44100
gcttgagccc aggggttcaa ggctggactg agttatgact gcaccactgt actccagcct 44160
gggtgacaga gtgaccctgt ctctaataaa aagaataaaa taaatacagt cttacaaagg 44220
atacaataga accaaatgct caaaacatta gtgacaatct ggattttctt tatatatttt 44280
ggcactaatt ttcctaaggt aaatatttat tatatcttta tgcaaaagga aaagtaatct 44340
tactaacttt gaaagggaaa aagagagagc aaggtttgcg tggacctcag tgtgaggtga 44400
gaggcctagg gctggaggct ctgaatgtga tacctgcact gaaatccagg tgtcccgcct 44460
cccagcccag gacgtgggtg atcactgcaa ctttttcctc ttctcgtgct caggggaact 44520
ctcagtgtct gggattaggg agcaggggct gaagtcagag tgaggaagag caagagcagc 44580
ccgaggtggt cttctctttc caaggaaagg gcattgtttc tgtgcgctct agattctcag 44640
atgtgagagc tgggcataaa caaagaatta atcctctgtg tcttttcttg tctgttcccc 44700
ccaactcagt agatatgttt gacgacttct cagaaggcag agagtgtgtc aactgtgggg 44760
ctatgtccac cccgctctgg aggcgagatg ggacgggtca ctatctgtgc aacgcctgcg 44820
gcctctacca caagatgaac ggcatcaacc ggccgctcat caagcctcag cgccggctgg 44880
taagcacgtg cctcgcagcc tcctctgggc acctggctgc ggagctctcg ccttggtggg 44940
acatcctctg gttttgaatt ttggaacttg agggtgtgca tcggggatta cgtgggtgag 45000
agccccataa taattctcac aactttagag ttagctggag ccaccagaat gatccaggct 45060
gtctagttca acctcttcgg cacacagaaa ctgaaagtga ggctcagaaa agctagtggc 45120
cttgcccaca gccactcagg tactgagtct cccatctaga actctggaac cagaatccag 45180
gtttcctggt tcccagtcca gtgttgactg gagtgtctcc tccacccaca ccaaccctgc 45240
aaggaaggtc acctcagagg ctggtctcta ccctgacctc agttgatcag ttgataaatc 45300
ccaaagccca gaagtgcaag cagcttgtgt tgggccccgt ggctagggaa gagtttgggc 45360
ctggggcttg gctcctggct tcctgctcct ttttaatata atttgattct ggtcaacacc 45420
aaccagcttg cactatatta aggagggaag aacagagggg ataaacctgg tgcctccctt 45480
tcttgaggtc ccagggccat tcagactttg ataccatttg gacaccgtga ttcctcactc 45540

```
tctgcctgcc cccggcacct gcagccccgg tcagttctcc tctcaggaga agctttcctg  45600
ccggcagtgc ccggcgctca ctggttattc gcctgacggt gaatgatggt taggactgga  45660
aaccaggtct cgatgcccac gttcgctctc ctcgggcagc agaaaccttg ttctgattta  45720
ttcctcgcag tggcgcaggt gacaggagag ttaggtgccg tcacaggtca gagatctcat  45780
gcagggtcgt tagggcccag ccctgcctcc cgttagggag gcccagctcc gcagccacac  45840
gcgaggtgga agggcagtgc acacctttta cttggacatg aagcatttgt ttcctgtctt  45900
gcagtccgcc tcccgccgag tgggcctctc ctgtgccaac tgccagacca ccaccaccac  45960
gctgtggcgc cgcaatgcgg agggcgagcc tgtgtgcaat gcctgcggcc tctacatgaa  46020
gctccacggg gtacgtgggt cctgcgccca tgcggcatcc ttgccttctg atgcccatct  46080
ctcagtcctc ccttgtcttc ttcctttgta ctagcattca tttttccttc ttaacaaaga  46140
gacttagatt tggaaggggc tttcaactac tttgctggcc tcttccgtcc tttacattgt  46200
ataagtgaat tttccgtttt acagatgagc aggctacatt tatatgtagc agtttgatgt  46260
gtaacaaagg tgacgtttcg attcagtgga taagaagctt aaggatagtt gtattgacaa  46320
aattggctgt tcatttggaa aacagaagga aagcatgacc tctacctcct accttaaaca  46380
aaaataaact tgggtgaatt aaggatatta catgtaaaac atctttgaaa taaactaaaa  46440
gtaaggccag gcatcatgac tcatgcctgt aattgcagca ctttgggagg ctgaggcaga  46500
aggattgcat gagctcagga tttcaaaacc aacctggaca acatggtgaa actttgtctc  46560
tactaaaaaa aaaaaaaaaa aaaaaaaaaa tctagctggg catggtggtg catgcctcta  46620
gtcccagcta ctcaggagtc tgaggtagga ggatggcttg agctcaggag tttgaggctg  46680
cagtgagctc tgattgtccc actgcactcc agcctgagtg acaaagtgag accctgtctc  46740
caaaaaaata aaaatattag ataataaaat actgcaaaga aaatcagaca ataaaaacac  46800
tggaagaaaa tgtaagggaa agtatttata taactttggg gatgggagaa cttcttaaac  46860
aagattttaa aactttttag ccatataaga atagttagat atatttgatt ttgtaaatat  46920
ttactgtttg tgcctggaaa tgatacctag ggaaagtaaa gaccaataca cacagtatca  46980
gaaaaagggt taatatttcc agaattacaa ggagcttcta caaagctctt taatttttat  47040
tggaacattc tccattatac aatattaaca aaaaggcaag gtgcccaaca ctacctacta  47100
tggcactatt tttataaata tgaggaagaa tataatttat aggtggttgc ttccacatat  47160
acagaacacc tctggtagga tatgtagaga ttggtcacat ggtcacatgt atgcatatat  47220
acgtacatgg ggtgcctcca ggagaaaaac tggggtcctg gggagaaggg attggaagga  47280
cactcttttt gctgtgtacc cccttggtac cttagacggg acatatgcaa gtcttaattg  47340
ttcaaataca agttaaatta aaaccaaacc aaaccagaaa cagataggtc ttgtagccta  47400
ataagaaaag aacaattgat ctttccccac ttcccccaaa tgggcaaaag atatggactg  47460
acatctcaca gaagctgccc agatagccat gaaacatgtg cacatatgct gaatctcact  47520
aaaaatcaga gaaatgtacc tgaaaatgac catgaaagtc cctagtttgc ccatatactt  47580
ggcaaaaatt aaagtgtttg ctgctatgga tttggggaat tagatactct catatattat  47640
tgatctgtat ttgaattact gcatctatta acttagtggt attttttaag gttgaaacca  47700
tgaacaccat tatatctggc aggtctactg ttgggaaact agcctataaa aaataaccag  47760
tacatgatga cctttgaacc atttattgct gcattgtttg tggtggcaaa aactagaaac  47820
aaccttaaaa ccccataaag gaatggttga aaaaattctg ctatatccca aaatgtggaa  47880
```

-continued

```
tattgagaag aaacttaaaa ataataatct agggccatgt atcttgatct agaaaatgaa  47940
aaagcacatt gcaaagaaat atatgtagca tgaccccata ctatgagtgt cgaaggtgca  48000
ttaaacagac atacatatgg atgggtggac agaccagtgg atgggtgaac acacacacac  48060
aaatatacac gtataggtgt attagtctgt tttcacactg ctgataaaga catacccaaa  48120
attaaaaagt ggcttaatgg actcacagtt ccacatcgct ggggaggcct cacaatcatg  48180
gcggaaggtg aaaggcacgt cttacatggc agcaggcaag agagaatgag agccaagcaa  48240
aaggggtttc cccttataaa accatcagct ctcatgagac ttactcacta tagtgagaac  48300
agtatgggag aaaccgcccc tgtgactcag ttatctccca tcaggtcggt cccacaacat  48360
gtgggaatta tgggagctac aattcaagat gagattttgg tggggacaca gccaaaccaa  48420
gtcaatagat atatatgtgt acagatgttt gagaattttt ttaaatgtaa gaatatataa  48480
caggctgtta aatccatttg cctcactggg ataggattga cggtagtaga gtgagagggc  48540
tgttgttaac ttagtctcat gtatcttttc atgatttctt gttataatga acaagcaaat  48600
ggctaaagtt atgaacattc ataagaaaat atttctacaa agcatgtata caaggatgtt  48660
tgttaatcac tgtaatagca aaaatggagg aaagaaaacc tttggaagga aaatggttaa  48720
actattgttc ttcaatatgg gaatggtaca agaaacttat tgggaaatat tatataggta  48780
ttaaaaagat tatattctca gaaaataaaa aaatagaatt accacatgat ccagcgtacc  48840
atttctggat atatacccaa aataattaaa ggcagggcct caaagagcta tttgtacact  48900
gctgtttata gcagcatgat tcacaattgc agaaagatgt aaacaaccca agtgtccacg  48960
gagaaatgaa cggataaaca cagtgtgata tacatacacg taggatatta ctcagccttt  49020
aaaaggaagg gaattctggc ccctgacacc acatgtcaaa tccatagaga cagaaagtag  49080
aatggaggct gtcgggggct agggaaaggg ggaatgagga gtgatgttta atgggtatgg  49140
agtttgagtt ttgcaagacg agaagagttc tggggatggt ggtcaggctt gcagaacggt  49200
gtgaatgcgc ttaacactac agagcaatat acttcagaat ggttcagatg gtaaatttta  49260
agttaggtgt gtttcatttt actgcaactg aaaaaaaaaa agcataccta agtgaatgga  49320
gattaacgtg agggggagat tcttctgagg ccagaatggg tttgaacatt tgaggcatag  49380
ctagggggat ggggtggggg aggacaccct tccacaaggt gggaaatagg ggtctgggtg  49440
tagagtcaca gagagatgtg cagatggtgg ggtcgggggg tgcaagtgcc accccatcta  49500
cccacagtta aataggaggc cagttcaagt tcacatatgc tggtgcattt ctcgcttaac  49560
cattgcgtgt tcatgtctct gaagcagtaa ttgcttttct ttctgtattt gcaggtgtgg  49620
cctttatcaa tcccacatgg tagacaagca cagcatagaa aaggggctaa aagatttggc  49680
tcagcctaag agaaaccaga tgtggggaag gcaccctgca gtcctgctcc ccaggactgg  49740
cttaggcatc tgtgaatggc tctggggcct gcctcccaac agaactgtgg tcaaagtgtt  49800
gtccagggac attttatctc agaacctggt cacagggcag tctctagcat agtctcttac  49860
tgctccccac cattcacaga agcaccaatg gctccagcca gacccaatgc agtacagagc  49920
tgcaataagt agagtgatgt tacatctcaa ctcactggga ctgttgctgt tgaggccaat  49980
tttcccagca caataattga tagcaccgct gcaccctcac accttttgaa gatagggcct  50040
tgctccacca cccaggctgg agtgcagtgg cacgatcacg gcttgctgga gcctcgactt  50100
cctgggttca agggatcctc ctatctcagc cttctgagta gctgggacta caggcatgca  50160
gcaccgtgcc cagctaattt taaaactttt ttgtagagat ggggtctcac tatgttgcca  50220
aggatggtct cgaactcctg ggctcaagca gtcctcccac ctcggccacc caaagtgctg  50280
```

```
ggattacagg catgagccac tgtgcctggc ctagcaccca ctttttgttt tcagggtcct  50340
tgtgtggatg ataaaggctt ttgaacagtc tgtctctgct gcctgaaatg cctgcctctg  50400
tctactcaaa accttttaca aactcaggtg tcacctccac actgaagcct tccttgatat  50460
cctcacgtgc ccctccttcc cactcctcac cccaggacag agtttagtgt ttctctgtct  50520
ttttacatca ccgaccagag tctggttatt tctccttgtc tgtgaatttc tgagggtagg  50580
agctgtgtgt ctttagttcc ctattctcca ggctctagta aagtagccat cacatcacac  50640
aggtgctcga taagtttttt aaaaatggaa ttgatttctt tctcgctgag ttccaggggc  50700
ctgtgcagcc cgtctgggcc ccaggctttg tggagagatt gcttaggtgt tgccttctcg  50760
cagcaggtgt gtgtctttca atgctgtagc agactacgca gaaatggaaa accctatata  50820
tttacttgtg accctccagg tccccaggcc tcttgcaatg cggaaagagg ggatccaaac  50880
cagaaaacgg aagcccaaga acctgaataa atctaagaca ccagcaggtg aggaaaagat  50940
ctgtgagtga ttatatgagt acatcaggag ccctcagagt gcctaagaat catatcttcc  51000
gggttaggca ggccagcccg ggccgccagg gggtggtgac agcatcggac atccctggcc  51060
tttcaggaca ggatgaagag cccagcaaaa aagtaacaat tgccatggaa cgtgttggga  51120
gctttcgaag caggctcaac tcaagctggg gcctgatcat tgccgactgc aaagacccag  51180
tgctcaggct ggaccagccg aggtcctgca ggaaagagga actttactcg gtcctttcat  51240
ctttggcgct gcagccaccc aaaagctcag ttcctttcaa ttctctttgg gctaacgggg  51300
atccaggagg gcagggtcca attaatcatg tccctaacag attgatctct aagccaatgt  51360
ataattaaca tcatgcagtg ctttgtgctt tagaaagccc cttcagaaat attatctcca  51420
tgaaagtaag actccatgag aaccagttta tgaccccatt ttactaacaa gcaaactgag  51480
gctcatagag gacaatgatt taacgagggt catacagctg ttaatgggta gagaattaaa  51540
acccaagttt ttctgcttct gggtcaatgt tctcttcaat ataccactct gccttcttaa  51600
tttctagatt aagaataagg gctgctcaaa agtttgaggc tgcagtgacc tatgatcgtg  51660
ccactgcact tcagcctgga gagcagagca agaccctgtc tttaaaaaaa aaaaaaagaa  51720
atacatttaa aaagaacgag ggctgttctt ttttaaattt atttttaata aatatattaa  51780
ctatttatta aatttaaatt agatttattt ataaaattat atataaattt ctgacagaac  51840
aacggctgtt ctttaatacg tttatgttcc ctaccaaaac attcctcact cagtactgct  51900
acccagttaa agatttgact ggtcggtgct gcagtcacag agaaaatgaa ttggctgatc  51960
tgacgaaaaa tttatcttct aacctaaggc atgacagagt cagataaatg ggccctttcc  52020
actaccaaga acatgatcaa agttctgctt ttgtacattc aaccatggct tatcccttct  52080
ggcaggcata tttcctactg gaattttcag tgtctcacac ctgtggtctt ccacctctcc  52140
tcctgcttcc ctactgctga cgagtcccct atgtcccctg ggtaacctta tttcctctca  52200
cgtagcaatc acagatagag aagacatacg gttcaggcgc acgattccca gtccaaaatt  52260
ccaaatccag gaagcaagat tcggcagcaa aacctatttt gaacagacac taggctgttg  52320
atagtctctg tttactccat tcagtatgat attcacgtgt tttgctgtgg ggatattatt  52380
gtatttcatt atagagtatt atctcaggcc ctgctggagg tattctgtaa taatacacag  52440
tatttggatt tttaaaaatg tgaatcttca agttgaatga ggaagaatct ttttttaaaa  52500
agttttgaag cctgaaacac acgtggcctc aagggtttga gatgagatag ggggaagaag  52560
ccatccctgt gagaactgta gccctccgca gataaggacc tctgctgctg tccccggcaa  52620
```

```
atgtagataa agccattagc ttgcacccat cccggctgtc tcgcaggctg ccggctgttc  52680
gtttgtccct gccgctgatt tgggtgtgct gactctgctt cattccagct ccttcaggca  52740
gtgagagcct tcctcccgcc agcggtgctt ccagcaactc cagcaacgcc accaccagca  52800
gcagcgagga gatgcgtccc atcaagacgg agcctggcct gtcatctcac tacgggcaca  52860
gcagctccgt gtcccaggta cgcgccatgg ctggggcgcc agggctgttt gtggggaggc  52920
cgactgcaga gtcccagagg ccagcctagt actgggtggg acttgcagcc aggcctcaca  52980
ggtgcaagca gtgagctacc ctctgcgcta ggaagaccca gccattgagc tgtgtggtgc  53040
cctcagggcc gcacgaggct aggggcatct gcatcgggct gtatttcagg acatcttatc  53100
aagatggtga tgtggacatg actgtgactc acaatttttt aacagctcct ctatgccatc  53160
atctttggaa acaaagagag gggagtccag ggctggcata cagcatgggt ggcaggggcg  53220
gaaaacaaca cagaagtaca acctgaatga gactgcgtgc tggggcgagg ggaggcgtgg  53280
ttgcgctgtc ggaggccgag cggaggttct ctaggcaagt ctgcctccta cgtgcaggga  53340
ggttagactt caacagggag ggtggggaag gaggaggaag ctggcatggg gaaaggcctg  53400
gatcctgcag agggcaggca gggcaggctg gtggggaggt cacaggcagg atgccacttt  53460
catgagaccc agctctgcac gtgtgtcagg ggacgccctg gggcagccca tgttccctct  53520
ggcggaggac gatggcgtct cggcctccct gcctcctccc ctctgcagtt ccctctcttg  53580
ggaccaggat gcaccaagct tgatcacggt ctcctttgac cagccctggc tgttatctcg  53640
tctctgctct taactgaagg aggccgtgtc ttagtgagct tcttattgtc tgggagaacc  53700
tgatcccaca gaaccagggg caccaggagc cccttctggg ccgggtggat ggcttctttg  53760
ttggaaagtg gatgtggtgg tgataggatg gtagaaagtg tctcctgtaa ccatcagagc  53820
cttctgggca accacagtat ccacagggcc accgggtcat agccctggtt gtatactgtg  53880
ctcagaagca gctgatgcat cacccagacc cttcatgcct agatcaccgg gatcaggaga  53940
aacagagaga agtgctcctt ggtcccttcc tgagggctga agccatcctg ggacatctg  54000
catagcaggg caccctcccc agcctagacc tcccaagccc tcaggagcgt ctccatgggc  54060
ctcatcgtgt gctttctgct tttcagacgt tctcagtcag tgcgatgtct ggccatgggc  54120
cctccatcca ccctgtcctc tcggccctga agctctcccc acaaggctat gcgtctcccg  54180
tcagccagtc tccacagacc agctccaagc aggactcttg gaacagcctg gtcttggccg  54240
acagtcacgg ggacataatc actgcgtaat cttccctctt ccctcctcaa attcctgcac  54300
ggacctggga cttggaggat agcaaagaag gaggccctgg gctcccaggg gccggcctcc  54360
tctgcctggt aatgactcca gaacaacaac tgggaagaaa cttgaagtcg acaatctggt  54420
taggggaagc gggtgttgga ttttctcaga tgcctttaca cgctgatggg actggaggga  54480
gcccaccctt cagcacgagc acactgcatc tctcctgtga gttggagact tctttcccaa  54540
gatgtccttg tcccctgcgt tccccactgt ggcctagacc gtgggttttg cattgtgttt  54600
ctagcaccga ggatctgaga acaagcggag ggccgggccc tgggacccct gctccagccc  54660
gaatgacggc atctgtttgc catgtacctg gatgcgacgg gcccctgggg acaggccctt  54720
gccccatcca tccgcttgag gcatggcacc gccctgcatc cctaatacca aatctgactc  54780
caaaattgtg gggtgtgaca tacaagtgac tgaacacttc ctggggagct acaggggcac  54840
ttaacccacc acagcacagc ctcatcaaaa tgcagctggc aacttctccc ccaggtgcct  54900
tcccccctgct gccggccttt gctccttcac ttccaacatc tctcaaaata aaaatccctc  54960
ttcccgctct gagcgattca gctctgcccg cagcttgtac atgtctctcc cctggcaaaa  55020
```

```
caagagctgg gtagtttagc caaacggcac cccctcgagt tcactgcaga cccttcgttc  55080

accgtgtcac acatagaggg gttctgagta agaacaaaac gttctgctgc tcaagccagt  55140

ctggcaagca ctcagcccag cctcgaggtc cttctgggga gagtgtaagt ggacagagtc  55200

ctggtcaggg ggcaggagtg tcccaagggc tggcccacct gctgtctgtc tgctcctcct  55260

agcccttggt cagatggcag ccagagtccc tcaggacctg cagcctcgcc ccggcagaag  55320

tcttttgtcc aggaggcaaa aagccagaga ttctgcaaca cgaattcgaa gcaaacaaac  55380

acaacacaac agaattcctg gaaagaagac gactgctaag acacggcagg ggggcctgga  55440

gggagcctcc gactctgagc tgctccggga tctgccgcgt tctcctctgc acattgctgt  55500

ttctgcccct gatgctggag ctcaaggaga ctccttcctc tttctcagca gagctgtagc  55560

tgactgtggc attactacgc ctccccacac gcccagaccc ctcactccaa aatcctactg  55620

gctgtagcag agaatacctt tgaaccaaga ttctgtttta atcatcattt acattgtttt  55680

cttccaaagg ccccctcgta taccctccct aacccacaaa cctgttaaca ttgtcttaag  55740

gtgaaatggc tggaaaatca gtatttaact aataaattta tctgtattcc tct         55793
```

<210> SEQ ID NO 29
<211> LENGTH: 79
<212> TYPE: DNA
<213> ORGANISM: Homo sapiens

<400> SEQUENCE: 29

```
gggugggcag cuguuaagac uugcagugau guuuagcucc ucugcaugug aacaucacag     60

caagucugug cugcugccu                                                  79
```

<210> SEQ ID NO 30
<211> LENGTH: 21
<212> TYPE: DNA
<213> ORGANISM: Homo sapiens

<400> SEQUENCE: 30

```
uuaagacuug cagugauguu u                                               21
```

<210> SEQ ID NO 31
<211> LENGTH: 2133
<212> TYPE: DNA
<213> ORGANISM: Homo sapiens

<400> SEQUENCE: 31

```
gaggtctgag gtggactccc acctcccttc gtgaagagtt ccctcctctc ccccttccta     60

agaaagtcga tcttggctct atttgtgtct tatgttcatc accctcattc ctccggagaa    120

agccgggttg gtttatgtct ttatttattc ccggggccaa gacgtccgga acctgtggct    180

gcgcagaccc ggcactgata ggcgaagacg gagagaaatt tacctcccgc cgctgccccc    240

cagccaaacg tgacagcgcg cgggccggtt gcgtgactcg tgacgtctcc aagtcctata    300

ggtgcagcgg ctggtgagat agtcgctatc gcctggttgc ctctttattt tactggggta    360

tgcctggtaa taaacagtaa tatttaattt gtcggagacc acaaaccaac cttgagctgg    420

gaggtacgtg ctcttcttga cagacgttgg aagaagacct ggcctaaaga ggtctctttt    480

ggtggtcctt ttcaaagtct tcacctgagc cctgctctcc agcgaggcgc actcctggct    540

tttgcgctcc aaagaagagg tgggatagtt ggagggcatg gagggaatca aagtgtttct    600

ccatgaaaga gaactgtggc taaaattcca cgaagtgggc acggaaatga tcataaccaa    660
```

-continued

```
ggctggaagg cggatgtttc ccagttacaa agtgaaggtg acgggcctta atcccaaaac    720
gaagtacatt cttctcatgg acattgtacc tgccgacgat cacagataca aattcgcaga    780
taataaatgg tctgtgacgg gcaaagctga gcccgccatg cctggccgcc tgtacgtgca    840
cccagactcc cccgccaccg gggcgcattg gatgaggcag ctcgtctcct tccagaaact    900
caagctcacc aacaaccacc tggacccatt tgggcatatt attctaaatt ccatgcacaa    960
ataccagcct agattacaca tcgtgaaagc ggatgaaaat aatggatttg gctcaaaaaa   1020
tacagcgttc tgcactcacg tctttcctga gactgcgttt atagcagtga cttcctacca   1080
gaaccacaag atcacgcaat taaagattga gaataatccc tttgccaaag gatttcgggg   1140
cagtgatgac atggagctgc acagaatgtc aagaatgcaa agtaaagaat atcccgtggt   1200
ccccaggagc accgtgaggc aaaaagtggc ctccaaccac agtcctttca gcagcgagtc   1260
tcgagctctc tccacctcat ccaatttggg gtcccaatac cagtgtgaga atggtgtttc   1320
cggcccctcc caggacctcc tgcctccacc caacccatac ccactgcccc aggagcatag   1380
ccaaatttac cattgtacca agaggaaaga ggaagaatgt tccaccacag accatcccta   1440
taagaagccc tacatggaga catcacccag tgaagaagat tccttctacc gctctagcta   1500
tccacgcagc agggcctggg tgcctcctac aggacagagt cggcacagcg gcaagcttgc   1560
atgtatgcca gctctgcgcc ccccagcgag cctgtgccca gcctagagga catcagctgc   1620
aacacgtggc caagcatgcc ttcctacagc agctgcaccg tcaccaccgt gcagcccatg   1680
gacaggctac cctaccagca cttctccgct cacttcacct cggggcccct ggtccctcgg   1740
ctggctggca tggccaacca tggctcccca cagctgggag agggaatgtt ccagcaccag   1800
acctccgtgg cccaccagcc tgtggtcagg cagtgtgggc ctcagactgg cctgcagtcc   1860
cctggcaccc ttcagccccc tgagttcctc tactctcatg gcgtgccaag gactctatcc   1920
cctcatcagt accactctgt gcacggagtt ggcatggtgc cagagtggag cgacaatagc   1980
taaagtgagg cctgcttcac aacagacatt tcctagagaa agagagagag agaggagaaa   2040
gagagagaag gagagagaca gtagccaaga gaaccccacg gacaagattt ttcatttcac   2100
ccaatgttca catctgcact caaggtcgct gga                                2133

99
```

DIRECT REPROGRAMMING OF CELLS TO CARDIAC MYOCYTE FATE

RELATED APPLICATIONS

This application is a national stage application, filed under 35 U.S.C. § 371, of International Application No. PCT/US2011/043438, filed Jul. 8, 2011, which claims the benefit of U.S. Provisional Application No. 61/399,178, filed Jul. 8, 2010, the contents of which are incorporated herein by reference in their entireties.

STATEMENT AS TO FEDERALLY SPONSORED RESEARCH

This invention was made with Government support under National Institutes of Health awards HL073219 and HL081744. The Government has certain rights in the invention.

INCORPORATION-BY-REFERENCE

The contents of the text file named "35327-509001WO_ST25.txt," which was created on Jul. 8, 2011 and is 381 KB in size, are hereby incorporated by reference in their entirety.

FIELD OF THE INVENTION

This invention relates generally to the field of cardiology.

BACKGROUND OF THE INVENTION

Heart disease is the number one killer of men and women worldwide. Generally, heart tissue has a limited capacity for regeneration or self-renewal. After a patient recovers from a myocardial infarction, the organ still bears a scar, and heart function is diminished. The ability to regenerate damaged organs such as the heart remains elusive. As such, there is a pressing need in the art to develop new strategies for the regeneration of damaged organs.

SUMMARY OF THE INVENTION

The invention provides a solution to the clinical problem of non-functional scar tissue in an organ such as the heart after injury or disease. Accordingly, a method for promoting conversion of cardiac fibrotic tissue into cardiomyocytic tissue is carried out by contacting fibrotic tissue (e.g., scar tissue) with a micro-ribonucleic acid (microRNA/miRNA) oligonucleotide, a combination of microRNA oligonucleotides, or a combination of microRNAs and small molecules. The methods lead to direct reprogramming of differentiated cells such as fibroblasts to cardiomyocytes or cardiomyocyte progenitors.

The methods described herein are useful in directly reprogramming cardiac fibroblasts, other differentiated cell types such as adipocytes, or hematopoietic cells such as $CD34^+$ cord blood cells, to cardiomyocytes or cardiomyocyte progenitor cells. The reprogramming is carried out in vivo (e.g., in situ at the site of fibrotic or scar tissue) or ex vivo. In the latter case, the reprogrammed cells are administered to the subject after the cells have been cultured and reprogrammed by incubating them with oligonucleotides or lentiviral constructs and optionally other factors ex vivo. The subject is preferably a mammal in need of such treatment, e.g., a subject that has been diagnosed with scar tissue (e.g., cardiac fibrotic tissue) or a predisposition thereto. The mammal can be, e.g., any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

The microRNA oligonucleotides lead to transient overexpression of the desired microRNA in the target cell or tissue. Thus, the oligonucleotide increases the level of an endogenous microRNA sequence. Similarly, administration of microRNA delivery constructs such as lentiviruses lead to expression of microRNAs (stem loop sequence or mature sequence) in the cells. Preferred mir oligonucleotides (or corresponding miR-expressing delivery constructs) are selected from the group consisting of mir1, mir133 (or mir133a), mir138, mir206, mir208, mir499, and mir126 as well as the following combinations: mir1; mir1, mir133a, mir208; mir1, mir133a, mir206; mir1, mir133a, mir208, mir499-5p, mir1, mir133a, mir206, mir499-5p; mir1, mir133; mir1, mir138; mir1, mir206; mir1, mir208; mir133, mir138; mir133, mir206; mir133, mir208; mir138, mir206; mir138, mir208; mir206, mir208; mir1, mir138, mir208; mir1, mir206, mir208; mir138, mir206, mir208; mir1, mir133, mir206; mir1, mir133, mir208; mir1, mir138, mir206; mir133, mir138, mir208; and mir133, mir138, mir206. Preferred oligonucleotide compositions include the combination of 1, 133a, and 206; the combination of 1, 133a, and 208; the combination of 1, 206, and 208; the combination of 1, 133a, 208, and 499-5p; the combination of 1, 133a, 206, and 499-5p; 1; 206; as well as the combination of mir1, mir138, and mir208. The compositions are introduced into a cell by any method known to preserve the viability of the cell, e.g., transfection or transduction. Transfection is the process of introducing nucleic acids into cells by non-viral methods, and transduction is the process whereby foreign DNA is introduced into another cell via a viral vector.

Nucleotide sequences of these preferred oligonucleotide constructs or combinations of constructs (and their corresponding mature forms) are listed below. Exemplary oligomeric compounds (stem-loop precursors) range in size from 50-90 nucleotides in length (or any length within that range, with an average length of approximately 70 nucleotides), and exemplary mature oligonucleotide compounds are 17 to 25 subunits in length, e.g., oligomeric compounds are 17, 18, 19, 20, 21, 22, 23, 24 or 25 subunits in length. For example, a stem-loop precursor is approximately 70 nucleotides and the mature nucleotide product is approximately 22 nucleotides in length. The uncapitalized "mir-" refers to the pre-miRNA, while a capitalized "miR-" refers to the mature form. A pre-microRNA comprises a stem-loop secondary structure.

```
Mmu-miR-1
STEM-LOOP
                                              (SEQ ID NO: 1)
GCUUGGGACACAUACUUCUUUAUAUGCCCAUAUGAACCUGCUAAGCUAUG

GAAUGUAAAGAAGUAUGUAUUUCAGGC

MATURE
                                              (SEQ ID NO: 2)
UGGAAUGUAAAGAAGUAUGUAU

Mmu-miR-133a
STEM-LOOP
                                              (SEQ ID NO: 3)
GCUAAAGCUGGUAAAAUGGAACCAAAUCGCCUCUUCAAUGGAUUUGGUCC

CCUUCAACCAGCUGUAGC
```

-continued

MATURE (SEQ ID NO: 4)

UUUGGUCCCCUUCAACCAGCUG

Mmu-miR-206
STEM-LOOP (SEQ ID NO: 5)

CCAGGCCACAUGCUUCUUUAUAUCCUCAUAGAUAUCUCAGCACUAUGGAA

UGUAAGGAAGUGUGUGGUUUUGG

MATURE (SEQ ID NO: 6)

UGGAAUGUAAGGAAGUGUGUGG

Mmu-miR-208a
STEM-LOOP (SEQ ID NO: 7)

UUCCUUUGACGGGUGAGCUUUUGGCCCGGGUUAUACCUGACACUCACGUA

UAAGACGAGCAAAAAGCUUGUUGGUCAGAGGAG

MATURE (SEQ ID NO: 8)

AUAAGACGAGCAAAAAGCUUGU

Human miR-1-1
STEM-LOOP (SEQ ID NO: 9)

UGGGAAACAUACUUCUUUAUAUGCCCAUAUGGACCUGCUAAGCUAUGGAA

UGUAAAGAAGUAUGUAUCUCA

Human miR-1-2
STEM-LOOP (SEQ ID NO: 10)

ACCUACUCAGAGUACAUACUUCUUUAUGUACCCAUAUGAACAUACAAUGC

UAUGGAAUGUAAAGAAGUAUGUAUUUUUGGUAGGC

MATURE SEQUENCE FOR BOTH miR1 STEM-LOOPS:

(SEQ ID NO: 11)

UGGAAUGUAAAGAAGUAUGUAU

Human miR-133a
Human miR-133a-1
STEM-LOOP (SEQ ID NO: 12)

ACAAUGCUUUGCUAGAGCUGGUAAAAUGGAACCAAAUCGCCUCUUCAAUG

GAUUUGGUCCCCUUCAACCAGCUGUAGCUAUGCAUUGA

Human miR-133a-2
STEM-LOOP (SEQ ID NO: 13)

GGGAGCCAAAUGCUUUGCUAGAGCUGGUAAAAUGGAACCAAAUCGACUGU

CCAAUGGAUUUGGUCCCCUUCAACCAGCUGUAGCUGUGCAUUGAUGGCGC

CG

MATURE SEQUENCE FOR BOTH miR133a STEM LOOPS (SEQ ID NO: 14)

UUUGGUCCCCUUCAACCAGCUG

Human miR-206
STEM-LOOP (SEQ ID NO: 15)

UGCUUCCCGAGGCCACAUGCUUCUUUAUAUCCCCAUAUGGAUUACUUUGC

UAUGGAAUGUAAGGAAGUGUGUGGUUUCGGCAAGUG

MATURE SEQUENCE FOR miR-206

(SEQ ID NO: 16)

UGGAAUGUAAGGAAGUGUGUGG

-continued

Human miR-208a
STEM-LOOP (SEQ ID NO: 17)

UGACGGGCGAGCUUUUGGCCCGGGUUAUACCUGAUGCUCACGUAUAAGAC

GAGCAAAAAGCUUGUUGGUCA

MATURE SEQUENCE FOR miR-208

(SEQ ID NO:18)

AUAAGACGAGCAAAAAGCUUGU

Human miR-138-1
STEM-LOOP (SEQ ID NO: 19)

CCCUGGCAUGGUGUGGUGGGGCAGCUGGUGUUGUGAAUCAGGCCGUUGCC

AAUCAGAGAACGGCUACUUCACAACACCAGGGCCACACCACACUACAGG

Human miR-138-2
STEM-LOOP (SEQ ID NO: 20)

CGUUGCUGCAGCUGGUGUUGUGAAUCAGGCCGACGAGCAGCGCAUCCUCU

UACCCGGCUAUUUCACGACACCAGGGUUGCAUCA

MATURE SEQUENCE FOR BOTH miR-138-1 and miR-138-2

(SEQ ID NO: 21)

AGCUGGUGUUGUGAAUCAGGCCG

Human miR-499-5p
STEM-LOOP (MMu-miR-499)

(SEQ ID NO: 29)

GGGUGGGCAGCUGUUAAGACUUGCAGUGAUGUUUAGCUCCUCUGCAUGUG

AACAUCACAGCAAGUCUGUGCUGCUGCCU

MATURE (Mmu-miR-499/Hsa-miR-499-5p;
sequence is conserved)

(SEQ ID NO: 30)

UUAAGACUUGCAGUGAUGUUU

Optionally, the microRNA or combination of microRNAs is administered with another compound such as a small molecule or recombinant protein to increase reprogramming efficiencies. Such molecules suitable for increasing the efficiency of conversion to cardiac myocytes include bone morphogenetic protein 4 (BMP4), Janus protein tyrosine kinase (JAK)-1 inhibitor [e.g., 2-(1,1-Dimethylethyl)-9-fluoro-3,6-dihydro-7H-benz[h]-imidaz[4,5-f]isoquinolin-7-one, Pyridone 6, P6, DBI (420099 JAK Inhibitor I)], RG108, R(+)Bay K 8644, PS48, A83-01, and histone deacetylase inhibitors (HDIs) such as valproic acid.

The methods lead to fibrotic tissue or other tissue types or cells being directly reprogrammed into cardiomyocytic tissue without a stem cell intermediary state. The treated tissue is characterized by an increased expression of a cardiomyocyte marker protein after having been contacted with the compositions (single oligonucleotides or combinations thereof) compared to the level of the cardiomyocyte marker protein before the contacting step. For example, the increase is 10%, 25%, 50%, 2-fold, 5-fold, 10-fold or more compared to the level of expression before treatment. Exemplary marker proteins include cardiac troponin, sarcomeric actinin, L-type calcium channel, brachyury, Flk1, Islet1, Mesp1, Gata4, Mef2c, Hand2, and TroponinT2.

The fibrotic tissue to be treated is present in a heart diagnosed as comprising cardiac myocardial infarction or other forms of cardiac disease such as ischemic heart disease, hypertrophic cardiomyopathies, valvular heart disease, and/or congenital cardiomyopathies. For example, the tissue is contacted with microRNA oligonucleotide compositions or viral (e.g., lentiviral) constructs expressing microRNAs after fibrosis has developed as a result of myocardial infarction or other cardiac disease process, e.g., days (1, 2, 3, 4, 5, 6 days after), weeks (1, 2, 4, 6, 8), months (2, 4, 6, 8, 10, 12), or even a year or more after the primary tissue insult. The fibrotic tissue is contacted ex vivo or in situ. In the case in which the organ is treated in a subject, e.g., a human patient, the compositions are delivered locally or systemically, e.g., using intravenous administration or direct injection into cardiac tissue. Other delivery schemes include oral, nasal, intradermal, transdermal, subcutaneous, intramuscular, intraperitoneal, suppository, and sublingual administration. For example, the compositions are administered by direct injection into cardiac tissue. Other delivery modes are characterized by sustained release, controlled release, or delayed release. Administration of the compositions may be via any common route so long as the target tissue is available via that route. The compositions are administered as pharmaceutically acceptable compositions, e.g., formulated with a pharmaceutically acceptable carrier or excipient. In general, dosage is from 0.01 μg to 100 g per kg of body weight, from 0.1 μg to 10 g per kg of body weight, from 1.0 μg to 1 g per kg of body weight, from 10.0 μg to 100 mg per kg of body weight, from 100 μg to 10 mg per kg of body weight, or from 1 mg to 5 mg per kg of body weight, and may be given once or more daily, weekly, monthly or yearly. Examples of dosages based on small animal studies are in the range of 80 mg/kg for single or multiple dosages. However, it is expected with appropriate modification dosages 1-25 mg/kg for single to three repeated dosages will confer clinical benefit in human subjects.

In contrast to other methods that may inhibit fibrosis, the compositions and methods described herein reverse fibrosis that has occurred. Fibrotic tissue or fibroblasts are directly reprogrammed using microRNAs into a cardiomyocyte lineage without going through a stem cell phenotype.

An alternative method of restoring tissue specific function to fibrotic tissue in an organ is therefore carried out by providing patient-derived fibroblasts and transfecting the fibroblasts with a microRNA or combination of microRNAs described above. Preferably the fibroblasts are dermal fibroblasts obtained from the skin of the patient to be treated. Alternatively, the fibroblasts are cardiac fibroblasts or epidermal keratinocytes. In one example, the transfection occurs ex vivo. Cells directly reprogrammed in this manner are useful for cell replacement therapy, in which the reprogrammed cells are infused or injected into an anatomical site that requires repair or regeneration of tissue. The cells are also for direct screening assays or pharmacogenomics analysis, because large quantities of cells are reprogrammed using the methods and compositions described herein. Alternatively, the transfection occurs in situ.

The invention therefore includes a purified population of primary fibroblasts comprising an exogenous microRNA oligonucleotide construct or combination of constructs listed above as well as a purified population of cardiomyocytes or cardiomyocyte progenitors that were produced using the primary fibroblasts comprising the reprogramming oligonucleotides. Each population is substantially free of stem cells, e.g., the population is at least 85%, 90%, 95%, 99%, or 100% transfected fibroblasts or at least 85%, 90%, 95%, 99%, or 100% reprogrammed myoblasts, cardiomyocytes, or cardiomyocyte progenitors. Cells are purified by virtue of selection based on cell surface markers as well as other cell selection techniques well known in the art.

As was discussed above, the cells are useful for therapeutic applications such as direct administration to a subject or as a component of another therapeutic intervention or device. For example, the invention encompasses a stent or catheter comprising primary fibroblasts comprising the reprogramming transgene sequence or comprising reprogrammed functional cells (e.g., characterized as expressing an increased level of a desired mIR).

The composition and methods of the invention include several advantages over previous methods of reprogramming cells. For example, unlike methods that employ reprogramming to a stem cell phenotype and subsequent differentiation of this cell population, the direct reprogramming methods of the invention do not involve an intermediate stage of a stem cell phenotype. The use of miRNAs for direct reprogramming rather than transcription factors can regulate in parallel multiple genes or pathways that are responsible for the reprogramming effects. In addition, additional advantages of the use of small oligonucleotides rather than gene provides include ease of the production and development for biologic therapy.

The invention represents the first demonstration of direct reprogramming of fibroblasts to cardiomyocytes, i.e., it is the first evidence that miRs have the ability to modulate direct reprogramming. The compositions and methods described herein offer an approach to treating cardiac disease long after the initial symptoms have occurred by directly replacing fibrotic tissue with viable functional cardiomyocytes. In addition to clinical applications, the compositions and methods are useful for testing drugs and molecules for target discovery All polynucleotides (i.e., microRNAs) and polypeptides of the invention are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Purified also defines a degree of sterility that is safe for administration to a human subject, e.g., lacking infectious or toxic agents.

Similarly, by "substantially pure" is meant a nucleotides (i.e., microRNAs) and polypeptides that have been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

By the terms "effective amount" and "therapeutically effective amount" of a formulation or formulation component is meant a sufficient amount of the formulation or component to provide the desired effect. For example, by "an effective amount" is meant an amount of a microRNA to directly reprogram cardiac fibroblasts to myoblasts in a subject. Ultimately, the attending physician or veterinarian decides the appropriate amount and dosage regimen.

As described herein, small molecules include, but are not limited to, peptides, peptidomimetics (e.g., peptoids), amino acids, amino acid analogs, polynucleotides, polynucleotide analogs, nucleotides, nucleotide analogs, organic and inorganic compounds (including heterorganic and organomettallic compounds) having a molecular weight less than about 5,000 grams per mole, organic or inorganic compounds having a molecular weight less than about 2,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. A small molecule inhibitor is a compound that is less than 2000 daltons in mass. The molecular mass of the inhibitory compounds is preferably less than 1000 daltons, more preferably less than 600 daltons, e.g., the compound is less than 500 daltons, 400 daltons, 300 daltons, 200 daltons, or 100 daltons.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

DETAILED DESCRIPTION

Figure 1A:
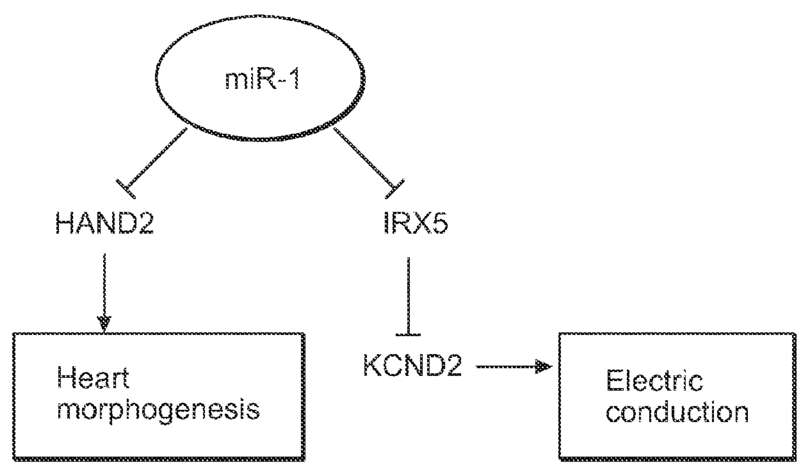
FIG. 1 is a diagram showing mIR involvement in cardiac myocyte function.
Figure 1B:
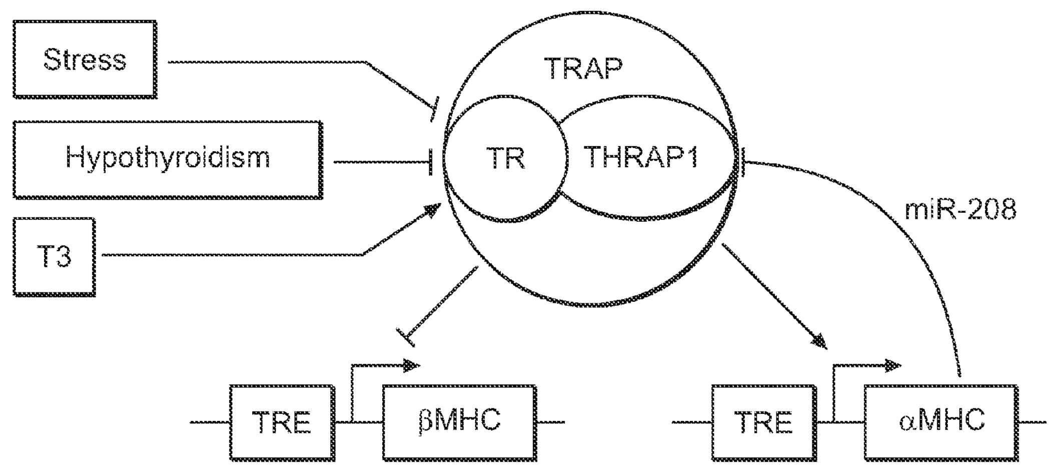
Figure 2A:
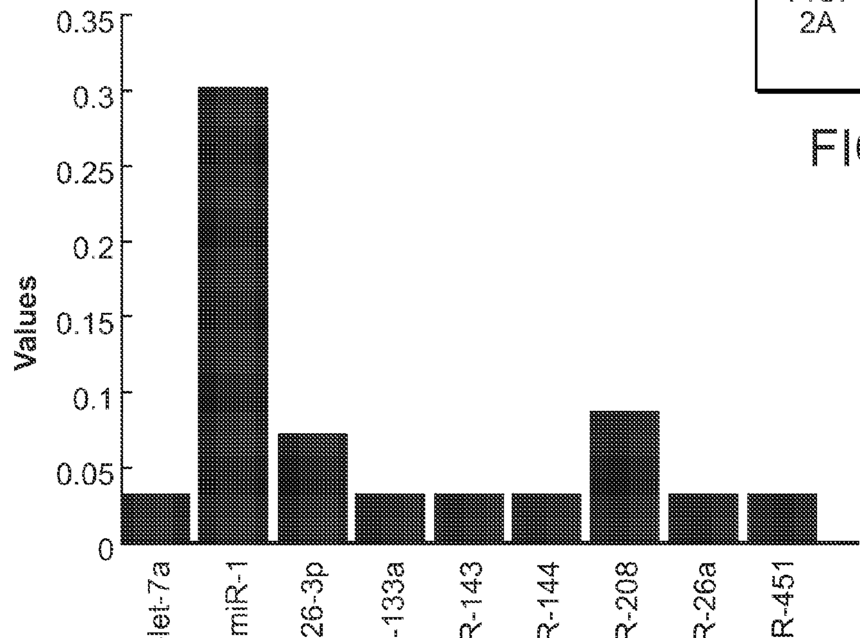
FIG. 2 is a heat map and bar graphs showing the results of miRNA profiling studies.
Figure 2A:
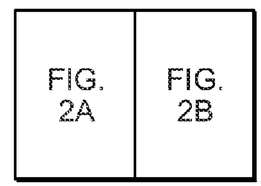
Figure 2:
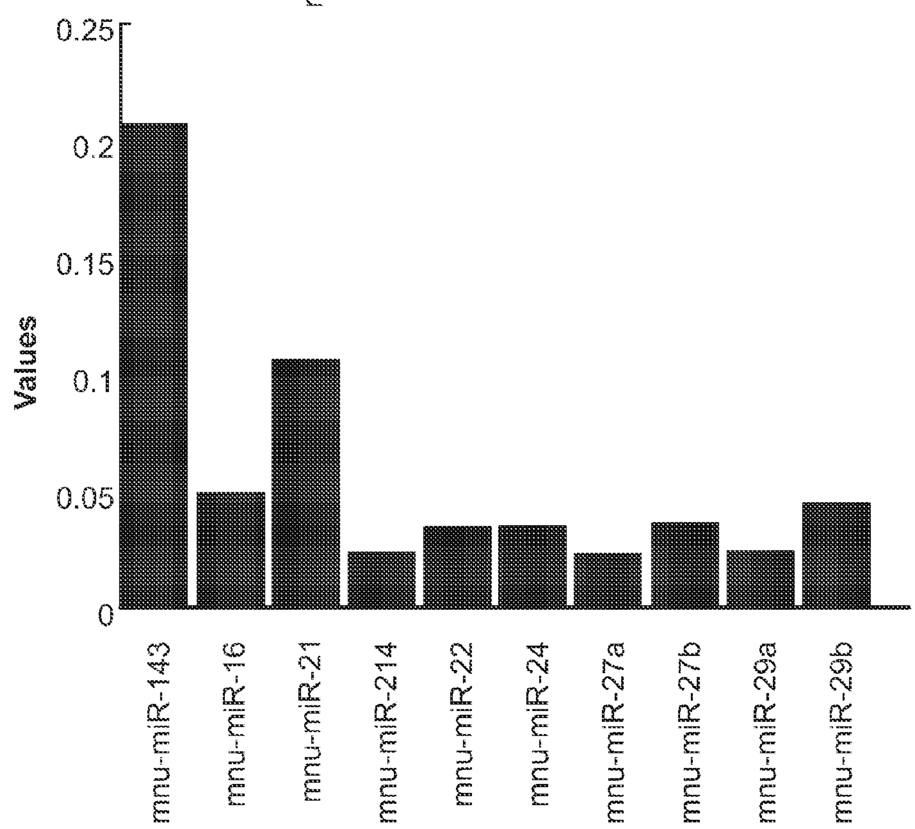
Figure 2B:
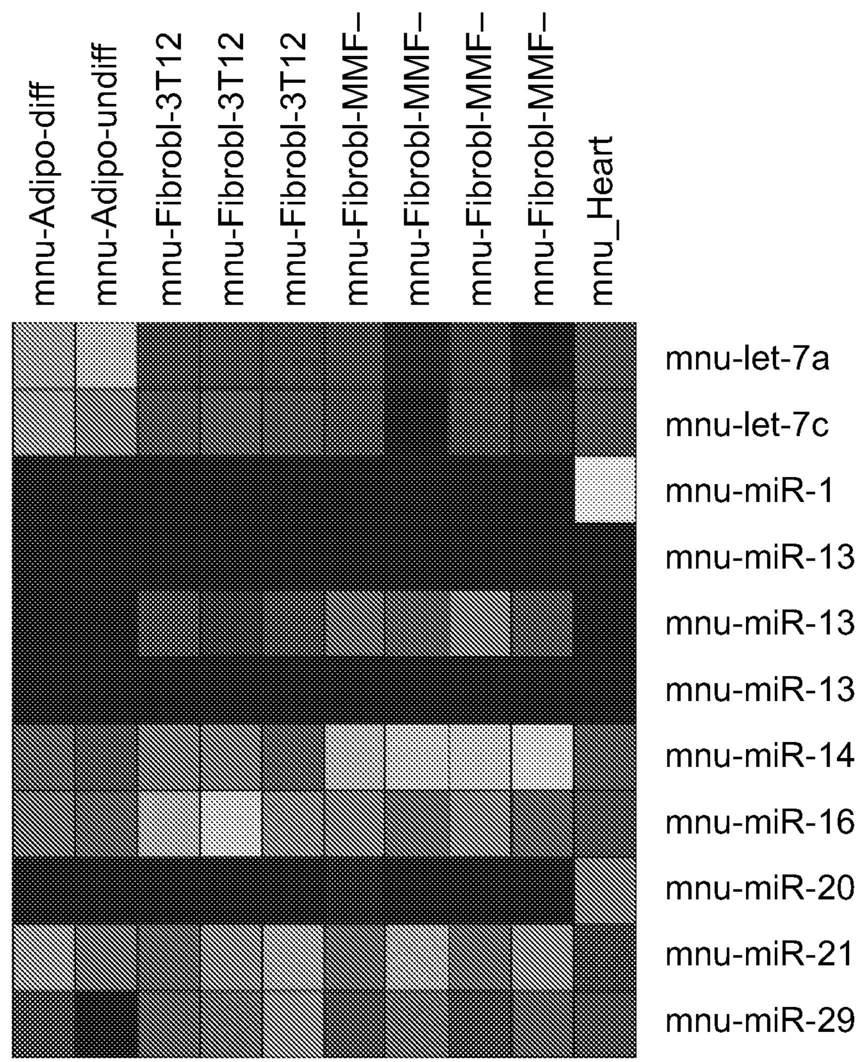
Figure 3:
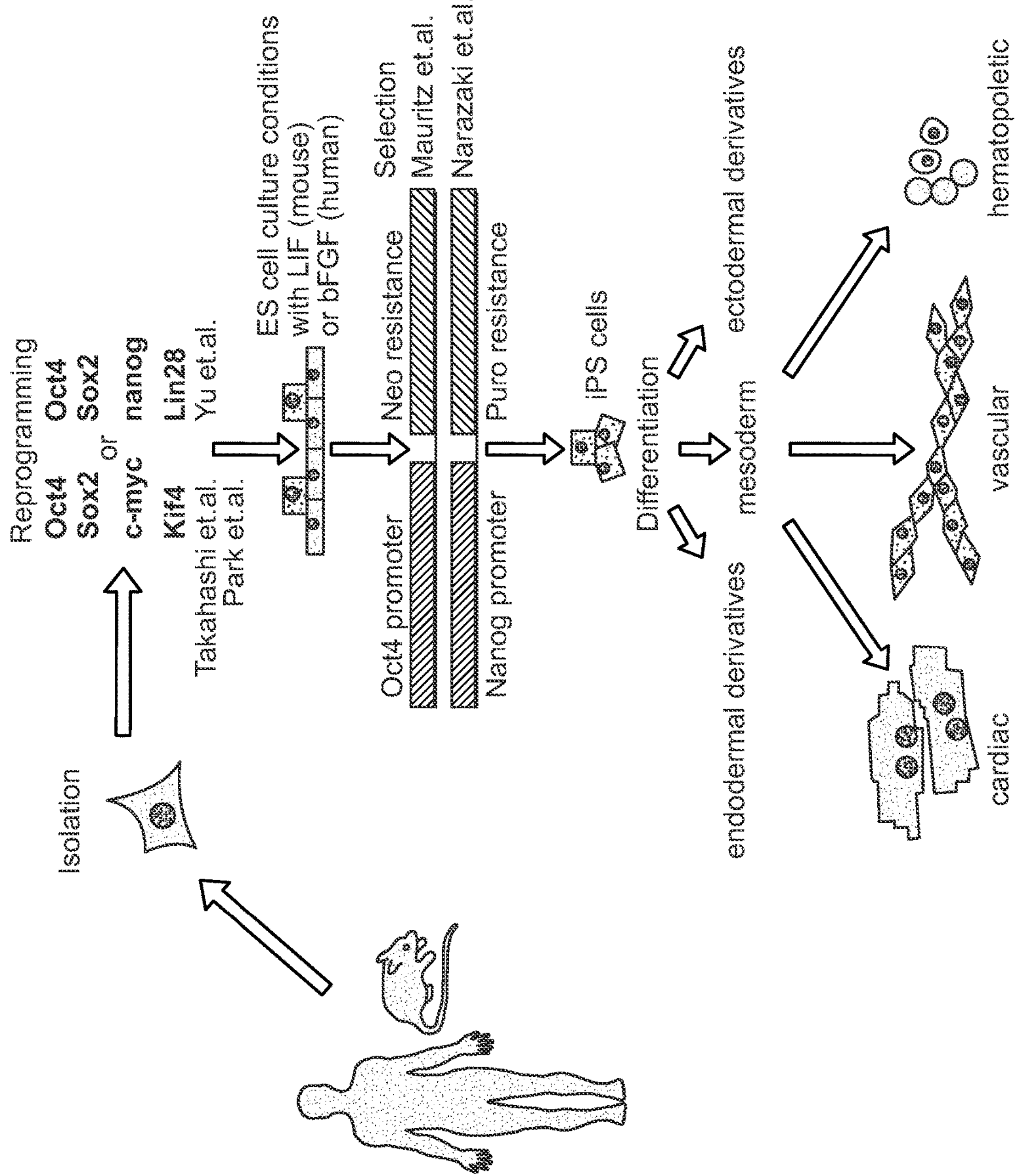
FIG. 3 is a diagram showing iPS differentiation to cardiac cells.
Figure 4:
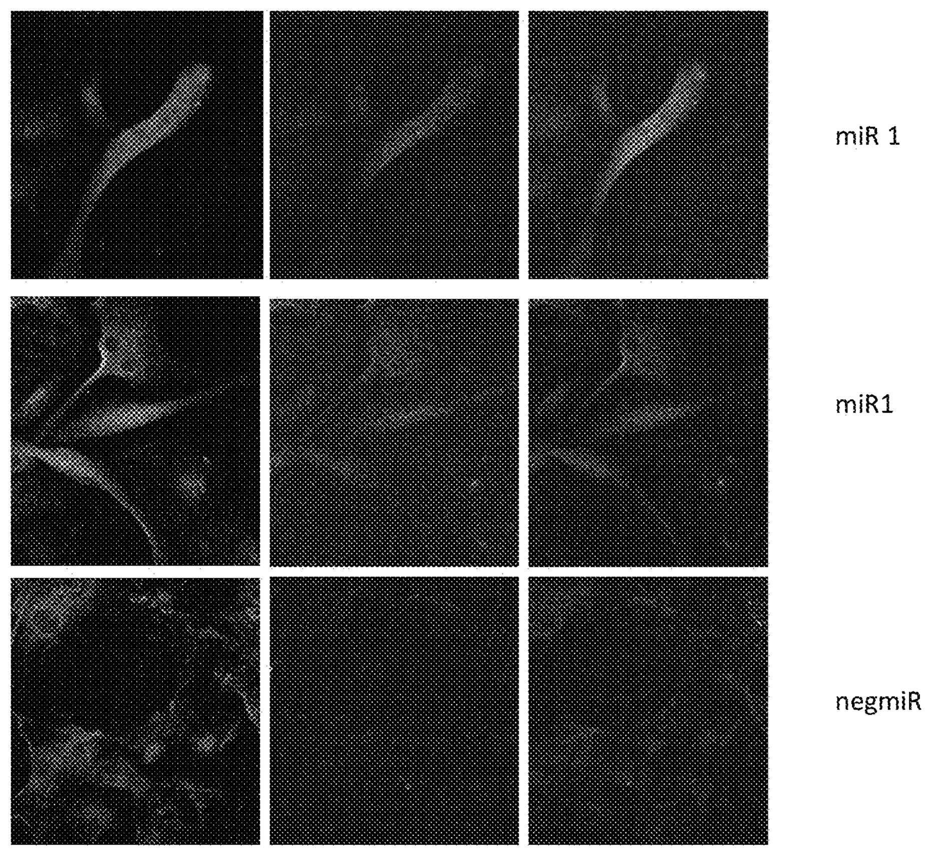
FIG. 4 is a series of photomicrographs showing the results of an experiment wherein cardiac fibroblasts were isolated and cultured from transgenic mice expressing Myosin heavy chain-driven CFP. Myosin heavy chain expression is restricted to muscle cells and therefore is turned on once reprogramming has been accomplished. Representative images of cardiac fibroblasts transfected with miR1 and costained with an antibody recognizing CFP 7 days following the initial transfection are shown. Confocal images were obtained of anti-CFP staining (red channel) and endogenous CFP expression (blue channel).

MicroRNAs (miR) are small (about 22-nucleotide) RNAs that are derived from larger pre-mirs. MiRs act as repressors of target mRNAs by promoting their degradation, when their sequences are perfectly complementary, or inhibiting translation when their sequences contain mismatches. Micro (mi)RNAs are emerging as important regulators of cellular differentiation, their importance underscored by the fact that they are often dysregulated during carcinogenesis Reprogramming Reprogramming is process by which cells change phenotype, state of differentiation, or function. For example, the cellular process governs the transformation of a somatic cell into a pluripotent stem cell. This process is exploited as a tool for creating patient-specific pluripotent cells that are useful in cell replacement therapies. In "direct reprogramming", the differentiated state of a specialized somatic cell is reversed to another type (e.g., endocrine cells to exocrine cells or fibroblasts to neurons or, as described herein, cardiomyocytes). This process useful for creating patient-specific pluripotent cells for cell replacement therapies. Suitable starting populations for reprogramming include adipocytes, $CD34^+$ cord blood cells, and fibroblasts.

Adipocytes are an exemplary population for reprogramming. Adipocytes, also known as lipocytes and fat cells, are the cells that primarily compose adipose tissue, specialized in storing energy as fat. Although the lineage of adipocytes is still unclear, preadipocytes are undifferentiated fibroblasts that can be stimulated to form adipocytes. $CD34^+$ cord blood cells are also an exemplary population for reprogramming. CD34+ cells are hematopoietic stem cells present in umbilical cord blood.

Optionally, fibroblasts are the starting population for reprogramming. Fibroblasts are traditionally defined as cells of mesenchymal origin that produce interstitial collagen (in contrast to myocytes that form collagen type IV as part of their basement membrane, fibroblasts also produce types I, III and VI). In general, fibroblasts lack a basement membrane and tend have multiple processes or sheet-like extensions. They contain an oval nucleus (with 1 or 2 nucleoli), extensive rough endoplasmic reticulum, a prominent Golgi apparatus, and abundant cytoplasmic granular material. Specific markers are scarce; however, DDR2 is useful as a marker. This marker is expressed in fibroblasts and other cells but not other cardiac cells. The mesenchymal cells that form the cardiac fibroblast population are believed to be derived from two principal sources: (1) the pro-epicardial organ, and (2) the epithelial-mesenchymal transformation during the formation of cardiac valves. Differentiation to cardiac fibroblasts is regulated by programmed sequences of growth factors, including FGF and PDGF.

Cardiac Fibroblast Differentiation and Heart Disease

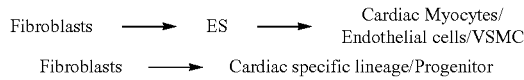

As described herein, factors, e.g., microRNA sequences, have been defined that lead to reversal of fibrosis. These microRNA compositions induce the process of direct reprogramming and lead to enhancement of cardiac tissue repair/regeneration procedures as well as better efficiency for cell therapy.

Fibroblast to Cardiovascular Cell Type

The process of direct reprogramming is carried out as follows. Fibroblasts, e.g., cardiac fibroblasts, skin or other type of fibroblasts are isolated using known methods. Factors were screened to determine which ones reverse the fibroblast to cardiovascular cell lineage. A miRNA/siRNA approach was chosen. Protocols for transfection and viral over-expression are known in the art. Following reprogramming, the treated cells are assay to determine the level of expression of cardiac cell markers.

Genes Involved with Cardiac Myocyte Specification

Markers of multipotent cardiovascular progenitors/cardiac myocytes include early mesodermal markes such as Brachyury, early cardiovascular progenitor cell markers such Flk1, markers of early commited cardiomyocyte progenitors such as Nkx2-5, Islet1, Mesp1, Gata4, Mef2c, Hand2, and mature cardiomyocyte markers such Troponin T2, Actinin, and alpha Myosin heavy chain. As described in detail below, TBX5 also plays a role in heart development. Gene sequences are provided below.

Direct Reprogramming of Cardiac Fibroblasts to Cardiac Myocyte Fate by Employment of miRNA Mimics or Antagonists Somatic cells have been reprogrammed to an embryonic-like state via viral transfection of four pluripotency factors (Takahashi et al., 2006, Cell 126, 663-676). Transcription factors have also been used to induce cellular reprogramming. A specific combination of three transcription factors (Zhou et al., 2008, Nature 455, 627-632) was employed to reprogram adult exocrine pancreatic cells in vivo to insulin-producing 13-cells representing the potential for switching gene expression in living organisms. Another study demonstrated that two cardiac transcription factors Gata4 and Tbx5 along with the chromatin-remodeling complex Baf60c, are capable of inducing programming and transdifferentiation of embryonic mouse mesoderm (Takeuchi et al., 2009, Nature 459, 708-711) to beating heart tissue. The central premise underlying the majority of these studies is the use of key transcription factors overexpression to redirect or control cell fate. The methods described herein preferably do not involve the use of transcription factors.

Prior to the invention, the possibility that a switch in gene expression induced by the introduction of key microRNAs as an alternative to transcription factors for direct reprogramming has heretofore not been reported. MicroRNAs are 21-23 nucleotide-long RNA molecules that represent an integral component of the regulatory machinery driving gene expression at the post-transcriptional level. Individual microRNAs are capable of modulating the expression of hundreds of genes (Zhao et al., 2007, Trends Biochem Sci 32, 189-197) and are rapidly being regarded as powerful regulators of both developmental and pathological processes (Judson et al., 2009, Nature Biotechnology 27:459-461; Cordes et al., 2009, Nature 460:705-711). Since microRNAs are capable of regulating the expression of several more gene targets, they are potent at switching gene expression and inducing cellular reprogramming.

Specific tissues and progenitor cell populations express distinct microRNA profiles, thereby suggesting a role for microRNAs in governing and/or directing cell fate decisions. Thus, studies were undertaken to elucidate the role for microRNAs as a therapeutic to activate key molecular programs inducing tissue regeneration. This approach is particularly suitable for treatment of cardiovascular conditions where there is a significant need to improve cardiac repair and remodeling in acquired heart disease. For example, one application of the cardiac specific miRNAs described herein is administration of a mirRNA mimic alone or combination of mimics for different miRNAs in the fibrotic heart and reversion of the fibrosis by direct reprogramming of the fibroblasts to a cardiac myocyte fate and thus a replacement of the scar tissue by new functional myocytes.

Reprogramming Efficiency-Enhancing Molecules

Optionally, the microRNA or combination of microRNAs is administered with a small molecule or other agent (e.g., an recombinant protein) to increase reprogramming efficiencies. Small molecules suitable for increasing the efficiency of conversion to cardiac myocytes include valproic acid, bone morphogenetic protein 4 (BMP4), Janus protein tyrosine kinase (JAK) inhibitor 1, RG108, R(+)Bay K 8644, PS48, and A83-01. These agents are delivered (e.g., infused or injected) to the subject before, after, or together with miR oligonucleotides or microRNA-expressing viral constructs. In the case of ex vivo reprogramming, the agents are added to the cell culture media.

Valproic acid (VPA; 2-propylpentanoic acid; $C_8H_{16}O_2$) is a chemical compound that has found clinical use as an anticonvulsant and mood-stabilizing drug, primarily in the treatment of epilepsy, bipolar disorder, and major depression. Valproic acid also blocks the voltage-gated sodium channels and T-type calcium channels. These mechanisms make valproic acid a broad spectrum anticonvulsant drug. Serum or plasma valproic acid concentrations are generally in a range of 20-100 mg/L during controlled therapy.

Valproic acid (VPA; 2-propyl-pentanoic acid) has been used for mood stabilization and the treatment of epilepsy for several decades (Perucca E CNS Drugs 2002, 16:695-714). VPA is a histone deacetylase (HDAC) inhibitor and plays a role in modifying chromatin structure and gene expression (Hsieh J, et al., Proc Natl Acad Sci USA 2004, 101:16659-64; Jenuwein T, Allis CD: Science 2001, 293:1074-80). VPA has also been found to affect various signaling systems, including the extracellular signal-regulated kinase (ERK), protein kinase C (PKC), and the Wnt/β-catenin pathways (Blaheta R A et al., Curr Med Chem 2002, 9:1417-33; Gurvich N, Klein PS: Pharmacol Ther 2002, 96:45-66; Rosenberg G: Cell Mol Life Sci 2007, 64:2090-103). VPA alters the Wnt/β-catenin signaling by directly or indirectly (Gould T D et al., Neuropsychopharmacology 2004, 29:32-8; Gould T D, Manji H K: Neuroscientist 2002, 8:497-511) inhibiting the activity of glycogen synthase kinase 3β (GSK3β). VPA also regulates the differentiation and proliferation of various cells, including mesenchymal and hematopoietic stem cells, neuroblastoma cells, primary neurons, and neural progenitor cells (NPCs).

Valproic acid, which has been utlilized as a drug for treating certain seizure disorders, is administered locally at the site of desired location, e.g., the site of fibrotic tissue or the site at which reprogramming is induced by miR delivery or systemically. A therapeutic range for the drug is currently established at 50-120 μg/mL and is taken as a tablet, slow release tablet, a liquid, or sprinkled on soft food. For example, valproic acid can be administered intravenously daily (3 g/24 hours) (Mink et al., 2011, Clin Neurol Neurosurg. Jun 22).

Valproic acid is available from Stemgent, and used at a final concentration of about 0.01 mM to about 10 mM, e.g., about 0.1 mM to about 5 mM or about 1 mM to about 3 mM. Preferably, valproic acid is used at a final concentration of about 2 mM. Valproic acid is administered in about one dose to about 5 doses, e.g., about 1 dose, about 2 doses, about 3 doses, about 4 doses, or about 5 doses. Preferably, valproic acid is administered in 2 doses. Valproic acid is administered about 1 hour to about 96 hours prior to miR transfection and about 1 hour to about 96 hours after miR transfection, e.g., about 12 hours to about 72 hours or about 24 hours to about 60 hours prior to and after miR transfection. Preferably, valproic acid is administered in two doses: one dose at 48 hours prior to miR transfection and one dose at 48 hours post-transfection.

Bone morphogenetic proteins (BMPs) are a group of growth factors also known as cytokines and as metabologens. Originally discovered by their ability to induce the formation of bone and cartilage, BMPs are now considered to constitute a group of pivotal morphogenetic signals, orchestrating tissue architecture throughout the body. Signal transduction through BMPRs results in mobilization of members of the SMAD family of proteins. The signaling pathways involving BMPs, BMPRs and Smads are important in the development of the heart, central nervous system, and cartilage, as well as post-natal bone development. BMP4 plays an important role in the onset of endochondral bone formation in humans. It is involved in muscle development, bone mineralization, and uteric bud development. BMP4 is also of crucial importance for cardiac development and differentiation.

BMP-4 is available from Stemgent, and used at a final concentration of about 0.1 ηg/mL to about 100 ηg/mL, e.g., about 1 ηg/mL to about 50 ηg/mL or about 10 ηg/mL to about 30 ηg/mL. Preferably, BMP-4 is used at a final concentration of about 20 ηg/mL. BMP-4 is administered every day beginning about 1 day to about 14 days before or after transfection of miRs, e.g., BMP-4 is administered about 2 days to about 13 days or about 5 days to about 10 days before or after transfection of miRs. Preferably, BMP-4 is administered 7 days post-transfection of miRs. Subsequently, BMP-4 is administered once/day for about 1 day, about 2 days, about 3 days, about 4 days, about 5 days, about 6 days, about 7 days, about 8 days, about 9 days, or about 10 days. Preferably, BMP-4 is administered every day for cells in culture.

JAK inhibitor 1(2-(1,1-Dimethylethyl)-9-fluoro-3,6-dihydro-7H-benz[h]-imidaz[4,5-f]isoquinolin-7-one, Pyridone 6, P6, DBI (420099 JAK Inhibitor I); $C_{18}H_{16}FN_3O$) is a potent, reversible, cell-permeable, and ATP-competitive inhibitor of Janus protein tyrosine kinases (JAKs). This molecule displays potent inhibitory activity against JAK1 (IC50=15 nM for murine JAK1), JAK2 (IC50=1 nM), JAK3 (Ki=5 nM), and Tyk2 (IC50=1 nM), and also inhibits other kinases at much higher concentrations. JAK inhibitor 1 also inhibits IL-2- and IL-4-dependent proliferation of CTLL cells and blocks the phosphorylation of STATS. This molecule also induces the growth inhibition of multiple myeloma cells expressing activated JAKs and STAT3.

The JAK inhibitor 1 is available from EMD Biosciences, and used at a final concentration of about 0.001 μM to about 10 μM, e.g., about 0.01 μM to about 5 μM or about 0.1 μM to about 1 μM. Preferably, the JAK inhibitor 1 is used at a final concentration of about 0.5 μM. The JAK inhibitor 1 is administered about 1 hour to about 96 hours before or after transfection of miRs, e.g., the JAK inhibitor 1 is administered once/day beginning about 12 hours to about 72 hours or about 24 hours to about 60 hours before or after transfection of miRs. Preferably, the JAK inhibitor 1 is administered 48 hours post-transfection of miRs. The JAK Inhibitor 1 is administered once/day for about 1 day, about 2 days, about 3 days, about 4 days, about 5 days, about 6 days, about 7 days, about 8 days, about 9 days, or about 10 days. Preferably, the JAK inhibitor 1 is administered every day for 5 days.

Small molecule inhibitors of JAK-1 such as (INCB018424 (Ruxolitinib) and INCB028050; Incyte Corp.) have been shown to be effective in rheumatoid arthritis models when administered orally. For example INCB028050 is used at a dosage of 10 mg/kg in rodents. Both these inhibitors as well as JAK Inhibitor I (2-(1,1-Dimethylethyl)-9-fluoro-3,6-dihydro-7H-benz[h]-imidaz[4,5-f]isoquinolin-7-one, Pyridone 6, P6, DBI (catalog #420099 from EMD biosciences) have $IC_{50}$ values in the nanomolar range. In the case of #420099, the $IC_{50}$ values against JAK1 and JAK2 are reported to be 15 nM and 1 nM respectively. In the case of INCB018424, the reported $IC_{50}$ values for JAK1 and JAK2 are 3 and 5 nM respectively. INCB018424 and INCB028050 are currently being utilized in clinical trials (Fridman J. S. et al., (2010) Selective Inhibition of JAK1 and JAK2 Is Efficacious in Rodent Models of Arthritis: Preclinical Characterization of INCB028050. J. Immunol. 184 (9) 5298-5307).

RG108 (2-(1,3-Dioxo-1,3-dihydro-2H-isoindol-2-yl)-3-(1H-indol-3-yl)propionic acid, N-Phthalyl-L-tryptophan; $C_{19}H_{14}N_2O_4$) is a potent and specific DNA methyltransferase (DNMT) inhibitor. It causes demethylation and reactivation of tumor suppressor genes and can be used to enhance reprogramming. RG108 has been found to inhibit human tumor cell line proliferation and increases doubling time in culture. This molecule is soluble to 100 mM in DMSO and to 100 mM in ethanol.

RG108 is available from Stemgent, and used at a final concentration of about 0.001 μM to about 10 μM, e.g., about 0.001 μM to about 5 μM or about 0.01 μM to about 0.1 μM. Preferably, RG108 is used at a final concentration of about 0.04 μM. RG108 is administered in about one dose to about 5 doses, e.g., about 1 dose, about 2 doses, about 3 doses, about 4 doses, or about 5 doses. Preferably, RG108 is administered in 2 doses. RG108 is administered about 1 hour to about 96 hours prior to miR transfection and about 1 hour to about 96 hours after miR transfection, e.g., about 12 hours to about 72 hours or about 24 hours to about 60 hours prior to and after miR transfection. Preferably, RG108 is administered in two doses: one dose at 48 hours prior to miR transfection and one dose at 48 hours post-transfection.

R(+)Bay K 8644 (R-(+)-1,4-Dihydro-2,6-dimethyl-5-nitro-4-[2 -(trifluoromethyl)phenyl]-3-pyridinecarboxylic acid methyl ester; $C_{16}H_{is}F_3N_2O_4$) is a L-type $Ca^{2+}$-channel blocker with negative inotropic and vasodilatatory effects in vivo. This enantiomer has opposite effects to the racemate (±)-Bay K 8644 and (S)-(−)-enantiomer. In combination with BIX-01294, this molecule helps generate induced pluripotent stem cells (iPSCs) from mouse embryonic fibroblasts (MEFs). This molecule is soluble to 100 mM in ethanol and to 100 mM in DMSO.

R(+)Bay K 8644 is available from Stemgent, and used at a final concentration of about 0.01 μM to about 10 μM, e.g., about 0.1 μM to about 5 μM or about 1 μM to about 3 Preferably, R(+)Bay K 8644 is used at a final concentration of about 2 R(+)Bay K 8644 is administered in about one dose to about 5 doses, e.g., about 1 dose, about 2 doses, about 3 doses, about 4 doses, or about 5 doses. Preferably, R(+)Bay K 8644 is administered in 2 doses. R(+)Bay K 8644 is administered about 1 hour to about 96 hours prior to miR transfection and about 1 hour to about 96 hours after miR transfection, e.g., about 12 hours to about 72 hours or about 24 hours to about 60 hours prior to and after miR transfection. Preferably, R(+)Bay K 8644 is administered in two doses: one dose at 48 hours prior to miR transfection and one dose at 48 hours post-transfection.

PS48 (5-(4-Chloro-phenyl)-3-phenyl-pent-2-enoic acid; $C_{17}H_{15}ClO_2$) is a PDK1 (phosphoinositide-dependent protein kinase 1) activator which binds to the HM/PIF binding pocket rather than the ATP-binding site. PS48 is one of only a few truly allosteric compounds targeting a regulatory binding site on a protein kinase catalytic domain that is not adjacent to or overlapping with the ATP-binding site. This molecule is soluble in DMSO>20 mg/ml.

PS48 is available from Stemgent, and used at a final concentration of about 0.01 μM to about 10 μM, e.g., about 0.1 μM to about 8 μM or about 4 μM to about 6 Preferably, PS48 is used at a final concentration of about 5 PS48 is administered in about one dose to about 5 doses, e.g., about 1 dose, about 2 doses, about 3 doses, about 4 doses, or about 5 doses. Preferably, PS48 is administered in 2 doses. PS48 is administered about 1 hour to about 96 hours prior to miR transfection and about 1 hour to about 96 hours after miR transfection, e.g., about 12 hours to about 72 hours or about 24 hours to about 60 hours prior to and after miR transfection. Preferably, PS48 is administered in two doses: one dose at 48 hours prior to miR transfection and one dose at 48 hours post-transfection.

A83-01 (3-(6-Methyl-2-pyridinyl)-N-phenyl-4-(4-quinolinyl)-1H-pyrazole-1-carbothioamide; $C_{25}H_{19}N_5S$) is a TGFβ kinase/activin receptor like kinase (ALK5) inhibitor. It blocks the phosphorylation of Smad2 and inhibits TGFIβ-induced epithelial-to-mesenchymal transition. A83-01 is more potent than small molecule SB431542, and inhibits differentiation of rat induced pluripotent stem cells (iPSCs) and increases clonal expansion efficiency. Small molecule A83-01 helps maintain homogeneity and long-term in vitro self-renewal of human iPSCs. This molecule is soluble in DMSO to 100 mM.

A83-01 is available from Stemgent, and used at a final concentration of about 0.01 μM to about 10 μM, e.g., about 0.1 μM to about 5 μM or about 0.4 μM to about 0.6 μM. Preferably, A83-01 is used at a final concentration of about 0.5 μM. A83-01 is administered in about one dose to about 5 doses, e.g., about 1 dose, about 2 doses, about 3 doses, about 4 doses, or about 5 doses. Preferably, A83-01 is administered in 2 doses. A83-01 is administered about 1 hour to about 96 hours prior to miR transfection and about 1 hour to about 96 hours after miR transfection, e.g., about 12 hours to about 72 hours or about 24 hours to about 60 hours prior to and after miR transfection. Preferably, A83-01 is administered in two doses: one dose at 48 hours prior to miR transfection and one dose at 48 hours post-transfection.

EXAMPLE 1

Reprogramming of Cardiac Fibroblasts

Mouse cardiac fibroblasts were transfected with specific combinations of distinct microRNAs significant to cardiac and/or muscle tissue. Quantitative real-time PCR (QRT-PCR) and immunocytochemistry (ICC) were employed to assess a switch in gene expression as early as 3 days following transfection. These techniques make use of specific primers (QRT-PCR) and antibodies (ICC) to detect the expression/upregulation of cardiac differentiation markers. Such markers include MADS box transcription enhancer factor 2, polypeptide C (MEF2C), NK2 transcription factor related, locus 5 (NKX2.5), GATA binding protein 4 (GATA4), heart and neural crest derivatives expressed 2 (HAND2), ISL1 transcription factor, LIM homeodomain (ISL1), troponin I type 3 (cardiac) (TNNI3). Sequences provided below.

Figure 5:
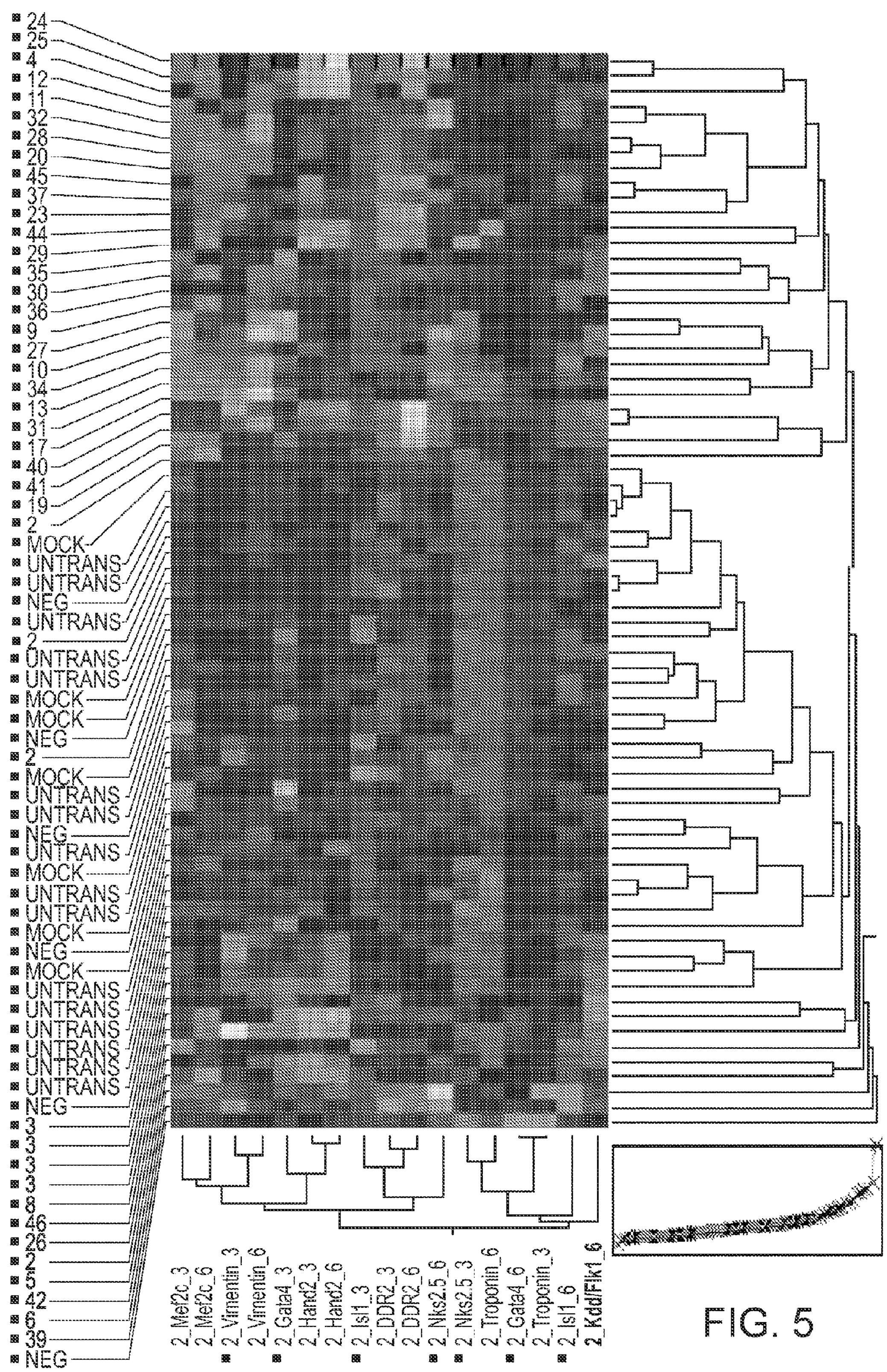
FIG. 5 is a heat map showing results of a two-way clustering analysis of candidate microRNA combinations and negative controls versus cardiac differentiation marker expression (obtained using QR-PCR).
Figure 6:
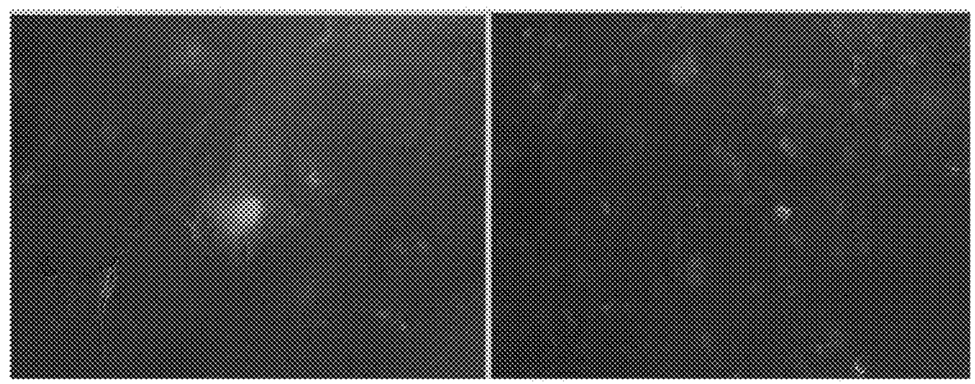
FIG. 6 is a photomicrograph showing immunostaining 6 days post-transfection with microRNA oligonucleotides. The figure shows a merged display of (A) cardiac fibroblasts transfected with mir138, mir208 and (B) mock-treated cardiac fibroblasts stained 6 days post-transfection for expression of cardiac troponin I (AlexaFluor, green) and DAPI (red).

The specific combinations of particular microRNAs required to induce cellular reprogramming were initially identified from two screens using all candidate microRNAs transfected individually as well as in all possible double and triple combinations with each other. FIG. 5 shows a two-way clustering of cardiac differentiation marker upregulation (from QRT-PCR) against a series of different microRNA combinations and negative controls from one such screen. Analyses such as this one facilitated the elucidation of gene regulation patterns by candidate microRNAs either individually or when specifically combined with other microRNAs. Combinations selected were identified as those that mediated cardiac differentiation marker upregulation at both the RNA and protein levels 3 days and 6 days post-transfection (FIG. 6).

A total of 65 microRNAs and combinations were tested. Exemplary microRNA combinations capable of inducing cellular reprogramming are listed below.

1. mir1
2. mir133
3. mir138
4. mir206
5. mir208
6. mir1, mir133
7. mir1, mir138
8. mir1, mir206
9. mir1, mir208
10. mir133, mir138
11. mir133, mir206
12. mir133, mir208
13. mir138, mir206
14. mir138, mir208
15. mir206, mir208
16. mir1, mir138, mir208
17. mir1, mir206, mir208
18. mir138, mir206, mir208
19. mir1, mir133, mir206
20. mir1, mir133, mir208
21. mir1, mir138, mir206
22. mir133, mir138, mir208
23. mir133, mir138, mir206
24. mir126
25. mir1, mir138, mir108
26. mir1, mir133a, mir208, mir499-5p
27. mir1, mir133a, mir206, mir499-5p
28. mir499-5p

EXAMPLE 2

Utilization of Specific microRNAs to Direct Reprogramming of Cardiac Fibroblasts to Cardiac Myocytes As described in detail below, because of their plasticity and presumed higher propensity for cell conversion, neonatal cardiac fibroblasts were reprogrammed into cardiac myocytes. Immunostaining methods were used to further investigate whether the microRNA-transfected cell populations express markers that are characteristic of cardiomyocytes. The organization of the expression of these proteins was also determined.

Figure 7:
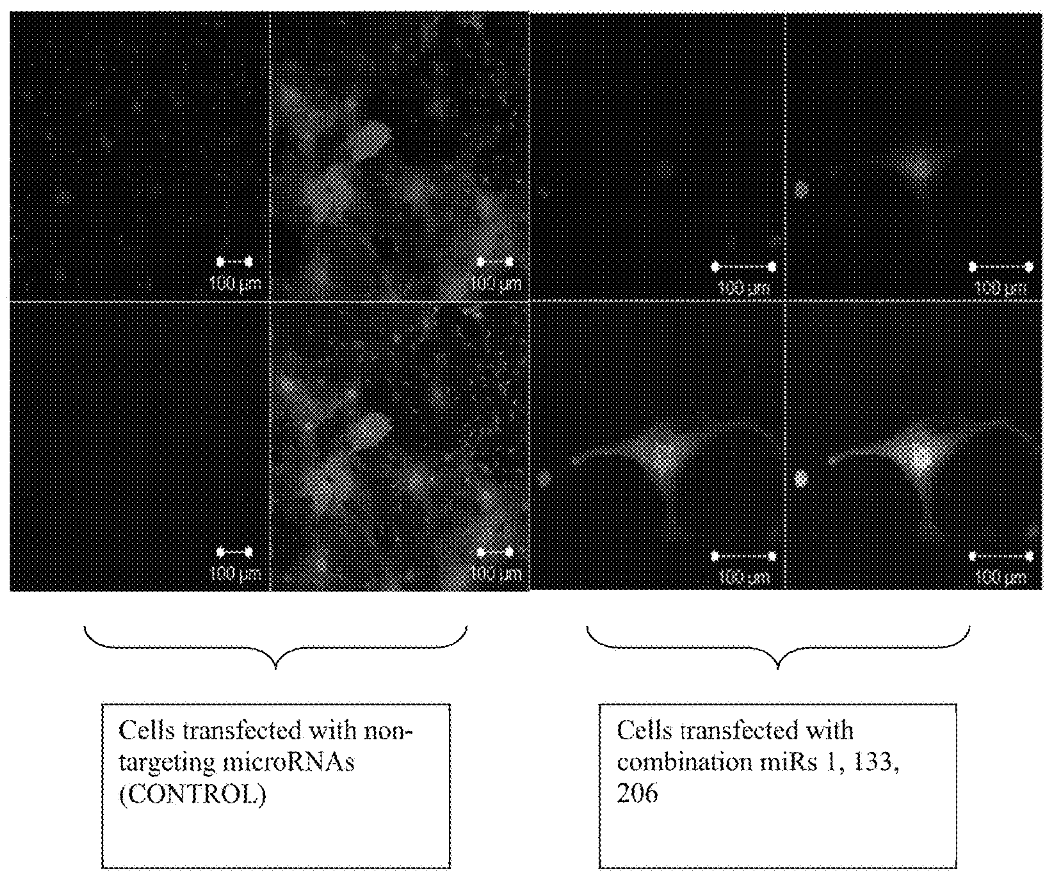
FIG. 7 is a series of photomicrographs showing immunostained cardiac fibroblasts after transfection with a combination of miR1, miR133, and miR206. The nucleus of cells was stained blue with 4',6-diamidino-2-phenylindole (DAPI). Cells that have been fibroblasts at some point in their lifetime were stained red with Fsp1Cre. Cardiomyocytes were stained green with cardiac troponin, a marker not expressed in fibroblasts.

The results presented in FIG. 7 show examples of cardiac markers that are "turned on" in microRNA-transfected neonatal cardiac fibroblasts two weeks post-transfection. As shown in FIG. 7, cardiac fibroblasts were immunostained two weeks after transfection with a combination of miR1, miR133, and miR206. The nucleus of cells was stained blue with 4',6-diamidino-2-phenylindole (DAPI). Cells that have been fibroblasts at some point in their lifetime were stained red with Fsp1Cre. Cardiomyocytes were stained green with cardiac troponin, a marker not expressed in fibroblasts. The results presented in FIG. 7 show that the combination of miR1, miR133, and miR206 induces cardiac fibroblasts to express cardiac myocytes markers. Specifically, this combination of microRNAs induced the expression of cardiac troponin, sarcomeric actinin and the L-type Calcium channel.

Genetic tools and cell sorting methods were utilized to determine the efficiencies of microRNA-induced cell conversion in both neonatal cardiac fibroblasts and tail tip fibroblasts. The efficiency of converting cardiac fibroblasts and tail tip fibroblasts to cardiac myocytes using the methods described herein is between 3-5% of the overall cell population. Specifically, cardiac fibroblasts were isolated from a transgenic model where the cyan fluorescent protein (CFP) reporter is driven by the myosin heavy chain alpha (alphaMHC) reporter, which is specifically "turned on" in cardiac myocytes. Thus, the starting cell population of cardiac fibroblasts is CFP negative. Seven days post-transfection with miRs (and small molecules) the CFP positive cell population was sorted, and this percentage was subtracted from the negative control. Therefore, this overall percentage is the efficiency of conversion to a cardiac myocyte-like phenotype, e.g., between 3-5% of the overall cell population. The efficiency of conversion to cardiac myocytes was increased to >30-50% by the addition of efficiency-enhancing molecules such as JAK inhibitor 1 to the combination of miRs.

Transfection rate efficiencies were measured 48 hours post-transfection, and range between 70-90% depending on the miR and combination. Specifically, to determine transfection rate efficiencies, a small fraction of cells that were transfected were removed, and RNA was isolated from them. Downregulation of known target genes of the miRs used in the study is then assessed using quantitative PCR.

In some cases, microRNA or a combination of microRNAs is administered with a small molecule to increase reprogramming efficiencies. Small molecules suitable for increasing the efficiency of conversion to cardiac myocytes include valproic acid, bone morphogenetic protein 4 (BMP4), JAK inhibitor 1, RG108, R(+)Bay K 8644, PS48, and A83-01.

The microRNA-transfected and subsequently reprogrammed cell populations have been isolated using genetic tools. Spontaneous contractile events have been observed in these cells maintained in culture. This functional property of the cells indicates that they have been reprogrammed into cardiac myocytes.

In a separate set of experiments, the microRNAs or microRNA combinations described herein are delivered (in lentiviral form) into a transgenic mouse model to determine whether these microRNAs convert cardiac fibroblasts into cardiac myocytes in vivo.

Exemplary sequences for use in compositions and methods of the invention include the following: Human HAND2 (NC_000004.11; SEQ ID NO: 22), Human Isl-1 (NC_000005.9; SEQ ID NO: 23), Human MEF2C (NC_000005.9; SEQ ID NO: 24), Human MYH6 (AC_000057.1; SEQ ID NO: 25), Human Nkx2.5 (NG_013340.1; SEQ ID NO: 26), Human Tnni3 (NG_007866.1; SEQ ID NO: 27), Human-Gata4 (SEQ ID NO: 28), Human TBX5 (AB051068.1; SEQ ID NO: 31).

The sequences identified by the Genbank accession numbers provided below are incorporated herein by reference.

| Marker | Genebank Number | Genome Reference |
|---|---|---|
| Human HAND2 | GI:12545384 | NC_000004.11 |
| Human Isl-1 | GI:115387114 | NC_000005.9 |
| Human MEF2C | Isoform 1: GI:19923215<br>Isoform 2: GI:196114945 | NC_000005.9 |
| Human MYH6 | GI:156104908 | AC_000057.1 |
| Human Nkx2.5 | Isoform 1: GI:4758090<br>Isoform 2: GI:260898750<br>Isoform 3: GI:260898752 | NG_013340.1 |
| Human Tnni3 | GI:151101270 | NG_007866.1 |
| Human - Gata4 | GI:33188461 | NG_008177.1 |
| Human TBX5 | GI:14041801 | AB051068.1 |

EXAMPLE 3

Reprogramming of Cardiac Fibroblasts into Cardiac Myocytes In Vivo

The microRNAs or microRNA combinations described herein were delivered (in lentiviral form) into a transgenic mouse model to determine whether the microRNAs convert cardiac fibroblasts into cardiac myocytes in vivo.

MicroRNA-expressing lentivirus constructs were purchased from Thermo Scientific (formerly Open Biosystems) in purified form. The following miRIDIAN shMIMIC microRNAs (followed by the catalog #) were used:

1. Non-silencing control—HMR5872
2. miR-499-5p—VSH5841-101207453
3. miR-133a—VSH5841-101208056
4. miR1—VSH5841-101208392
5. miR208a—VSH5841-101207644

MicroRNA/miRNA oligonucleotides or a combination of microRNA oligonucleotides are optionally delivered utilizing a lentivirus. In addition to Thermo Scientific, microRNA delivery systems are available from other suppliers such as BioSettia (San Diego, Calif. USA). For example, human microRNA (hsa-miRNA) precursors and approximately 100 bp of upstream and downstream flanking genomic sequences are PCR amplified and cloned into a self-inactivated (SIN) lentiviral vector to generate a lenti-miRNA collection. The miRNA lentivirus is a ready-to-use lentiviral stock. For example, each individual miRNA in the human lentiviral collection was cloned from its native context, including the stem-loop precursor sequence and approximately 100 bp of upstream and downstream flanking sequences to ensure that the miRNA is properly expressed and processed, and that it would function similarly to its endogenous form. Lentiviral transduction is one of the most effective delivery systems to express miRNA, shRNA, and cDNA. Unlike the retroviral system, the lentiviral integration is cell cycle independent. The genetic materials encoded by the lentivirus are efficiently delivered into both dividing and non-dividing cells. The lenti-miRNA viral genome is integrated into the host chromosome, thereby stably expressing the miRNA in transduced cell lines.

Figure 8:
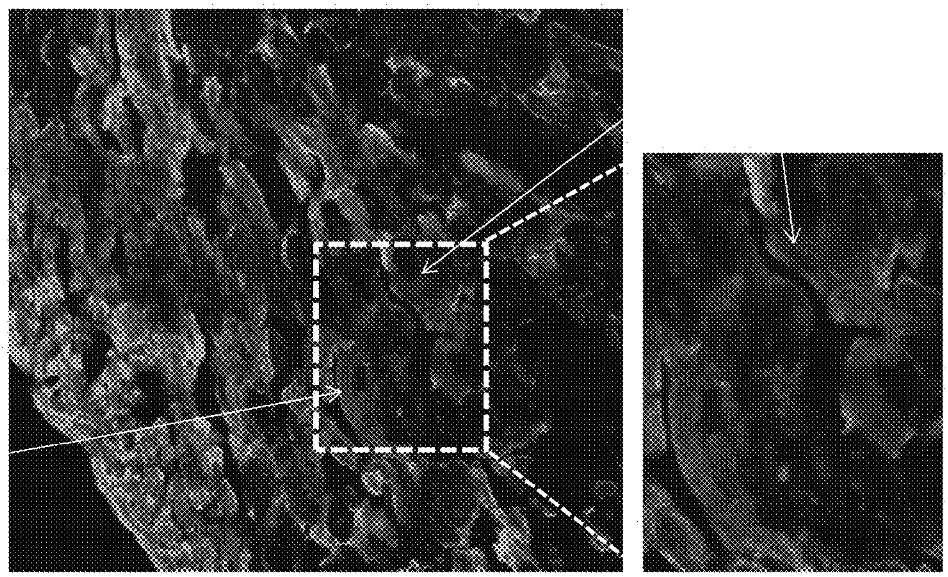
FIG. 8 is a series of photomicrographs showing an immunostained neonatal heart that was injected with lentivirus expressing miR-1. The neonate was injected at age 3-4 days old. Two weeks later, the hearts was harvested, fixed, and stained. The neonates are from a transgenic line where the red (tomato) reporter is a marker of cells derived from the fibroblastic lineage. Cells expressing red/tomato are/were a fibroblast at some point during their lifetime. Cardiac myocyte-specific marker cardiac troponin is shown in green. The arrows point to co-localization of red and green, and demonstrate in vivo evidence of miR-induced reprogramming.

The miR-expressing lentivirus were injected intramyocardially or infused at a dose of $2\times10^6$ pfu per mouse. FIG. 8 shows an exemplary image from a miR-1 injected heart. Heart tissue of a neonatal mouse was injected with lentivirus expressing miR-1. The neonate was injected at age 3-4 days old and two weeks later, the heart was harvested, fixed and stained. These neonates are from a transgenic line where the red (tomato) reporter is a marker of cells derived from the fibroblastic lineage. If a cell expresses red/tomato, it is/has been a fibroblast at some point during its developmental lineage. The green is from staining of the section with the cardiac myocyte-specific marker cardiac troponin. FIG. 8 demonstrates in vivo evidence of miR-induced direct reprogramming as shown by co-localization of red and green (the arrows are pointing to co-localization of red and green in the boxed area of the image).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method for promoting the direct reprogramming of cells into cardiomyocytic cells or tissue comprising contacting said cells with a microRNA oligonucleotide or a combination of microRNA oligonucleotides selected from the group consisting of mir1; mir138; mir206; mir208; mir1, mir133; mir1, mir138; mir1, mir206; mir1, mir208; mir133, mir138; mir133, mir206; mir133, mir208; mir138, mir206; mir138, mir208; mir206, mir208; mir1, mir138, mir208; mir1, mir206, mir208; mir138, mir206, mir208; mir1, mir133, mir206; mir1, mir133, mir208; mir1, mir138, mir206; mir133, mir138, mir208; mir133, mir138, mir206; mir1, mir133, mir208, mir499-5p; mir1, mir133, mir206, mir499-5p; and mir499-5p, or a corresponding miR-expressing delivery construct, wherein said cells comprise cardiac fibrotic tissue or fibroblasts, and wherein contacting comprises local administration at the site of fibrotic tissue.

2. The method of claim 1, wherein said microRNA oligonucleotide or combination thereof comprises a combination of mir1, mir133, and mir206; the combination of mir1, mir133, and mir208; the combination of mir1, mir206, and mir208; the combination of mir1, mir133, mir208, mir499-5p; the combination of mir1, mir133, mir206, and mir499-5p; mir1; mir206; or the combination of mir1, mir138, and mir108.

3. The method of claim 1, wherein said cell is directly reprogrammed into cardiomyocytic tissue without a stem cell intermediary state.

4. The method of claim 1, wherein said cardiomyocytic tissue is characterized by an increased expression of a cardiomyocyte marker protein after said contacting step compared to the level of said marker protein before said contacting step.

5. The method of claim 4, wherein said marker protein is selected from the group consisting of sarcomeric actinin, L-type calcium channel, brachyury, Flk1, Islet1, Mesp1, Gata4, Mef2c, Hand2, and TroponinT2.

6. The method of claim 1, wherein said fibrotic tissue is present in a heart diagnosed as comprising myocardial infarction, ischemic heart disease, hypertrophic cardiomyopathy, valvular heart disease, or congenital cardiomyopathy.

7. The method of claim 1, wherein local administration at the site of fibrotic tissue comprises direct injection into cardiac tissue.

8. The method of claim 1, further comprising contacting said cells with a reprogramming efficiency-enhancing molecule.

9. The method of claim 8, wherein said molecule is selected from the group consisting of valproic acid, bone morphogenetic protein 4 (BMP4), JAK inhibitor 1, RG108, R(+)Bay K 8644, PS48, and A83-01.

10. The method of claim 7, wherein direct injection into cardiac tissue is by stent or catheter.

11. A method for promoting the direct reprogramming of cells into cardiomyocytic cells or tissue comprising a) contacting said cells with a microRNA oligonucleotide or a combination of microRNA oligonucleotides selected from the group consisting of mir1; mir133; mir138; mir206; mir208; mir126; mir1, mir133; mir1, mir138; mir1,mir206; mir1, mir208; mir133, mir138; mir133, mir206; mir133, mir208; mir138, mir206; mir138, mir208; mir206, mir208; mir1, mir138, mir208; mir1, mir206, mir208; mir138, mir206, mir208; mir1, mir133, mir206; mir1, mir133, mir208; mir1, mir138, mir206; mir133, mir138, mir208; mir133, mir138, mir206; mir1, mir133, mir208, mir499-5p; mir1, mir133, mir206, mir499-5p; and mir499-5p, or a corresponding miR-expressing delivery construct, wherein said cells comprise adipocytes or CD34+ umbilical cord blood cells; and b) administering the adipocytes or CD34+ umbilical cord blood cells to fibrotic cardiac tissue.

12. The method of claim 11, wherein said microRNA oligonucleotide or combination thereof comprises a combination of mir1, mir133, and mir206; the combination of mir1, mir133, and mir208; the combination of mir1, mir206, and mir208; the combination of mir1, mir133, mir208, mir499-5p; the combination of mir1, mir133, mir206, and mir499-5p; mir1; mir206; or the combination of mir1, mir138, and mir108.

13. The method of claim 11, wherein said cell is directly reprogrammed into cardiomyocytic tissue without a stem cell intermediary state.

14. The method of claim 11, wherein said cardiomyocytic tissue is characterized by an increased expression of a cardiomyocyte marker protein after said contacting step compared to the level of said marker protein before said contacting step.

15. The method of claim 14, wherein said marker protein is selected from the group consisting of sarcomeric actinin, L-type calcium channel, brachyury, Flk1, Islet1, Mesp1, Gata4, Mef2c, Hand2, and TroponinT2.

16. The method of claim 11, wherein said fibrotic tissue is present in a heart diagnosed as comprising myocardial infarction, ischemic heart disease, hypertrophic cardiomyopathy, valvular heart disease, or congenital cardiomyopathy.

17. The method of claim 11, wherein local administration at the site of fibrotic tissue comprises direct injection into cardiac tissue.

18. The method of claim 11, further comprising contacting said cells with a reprogramming efficiency-enhancing molecule.

* * * * *